(12) United States Patent
Irazoqui et al.

(10) Patent No.: US 11,524,161 B2
(45) Date of Patent: Dec. 13, 2022

(54) SYSTEM FOR WIRELESS RECORDING AND STIMULATING BIOELECTRIC EVENTS

(71) Applicant: Purdue Research Foundation, West Lafayette, IN (US)

(72) Inventors: Pedro Irazoqui, Lafayette, IN (US);
Gabriel Omar Albors, West Lafayette, IN (US); Daniel Pederson, Lafayette, IN (US); Christopher John Quinkert, Dyer West Lafayette, IN (US); Muhammad Abdullah Arafat, West Lafayette, IN (US); Jack Williams, Lafayette, IN (US); Zhi Wang, West Lafayette, IN (US); John G. R. Jefferys, Oxford (GB); Thelma Anderson Lovick, Birmingham (GB); Terry L. Powley, West Lafayette, IN (US); Rebecca Anne Bercich, Terre Haute, IN (US); Henry Mei, Vadnais Heights, MN (US); Jesse Paul Somann, West Lafayette, IN (US); Quan Yuan, West Lafayette, IN (US); Hansraj Singh Bhamra, San Jose, CA (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

(21) Appl. No.: 16/308,355

(22) PCT Filed: Jun. 12, 2017

(86) PCT No.: PCT/US2017/037079
§ 371 (c)(1),
(2) Date: Dec. 7, 2018

(87) PCT Pub. No.: WO2017/214638
PCT Pub. Date: Dec. 14, 2017

(65) Prior Publication Data
US 2019/0247664 A1 Aug. 15, 2019

Related U.S. Application Data

(60) Provisional application No. 62/348,405, filed on Jun. 10, 2016.

(51) Int. Cl.
*A61N 1/36* (2006.01)
*A61N 1/05* (2006.01)
(Continued)

(52) U.S. Cl.
CPC ............ *A61N 1/36135* (2013.01); *A61B 5/01* (2013.01); *A61B 5/08* (2013.01); *A61B 5/14539* (2013.01);
(Continued)

(58) Field of Classification Search
CPC ... A61B 5/113; A61B 5/0205; A61B 5/02055; A61B 5/087; A61B 5/14539;
(Continued)

(56) References Cited

U.S. PATENT DOCUMENTS

| 10,044,227 B2 | 8/2018 | Chappell et al. |
| 2002/0127144 A1 | 9/2002 | Mehta |

(Continued)

FOREIGN PATENT DOCUMENTS

| WO | WO 2016/059556 | 4/2016 |

OTHER PUBLICATIONS

EP Extended European Search Report in EP Appln. No. EP17811170, dated May 22, 2019, 7 pages.
(Continued)

*Primary Examiner* — Jon Eric C Morales
(74) *Attorney, Agent, or Firm* — Fish & Richardson P.C.

(57) ABSTRACT

Systems and techniques for wireless implantable devices, for example implantable biomedical devices employed for
(Continued)

biomodulation. Some embodiments include a biomodulation system including a non-implantable assembly including a source for wireless power transfer and a data communications system, an implantable assembly including a power management module configured to continuously generate one or more operating voltage for the implantable assembly using wireless power transfer from the non-implantable assembly, a control module operably connected to at least one communication channel and at least one stimulation output, the control module including a processor unit to process information sensed via the at least one communication channel and, upon determining a condition exists, to generate an output to trigger the generation of a stimulus.

13 Claims, 83 Drawing Sheets

(51) Int. Cl.
    *A61N 1/372* (2006.01)
    *A61N 1/378* (2006.01)
    *A61B 5/01* (2006.01)
    *A61B 5/08* (2006.01)
    *A61B 5/145* (2006.01)
(52) U.S. Cl.
    CPC ......... *A61N 1/0531* (2013.01); *A61N 1/0534* (2013.01); *A61N 1/0548* (2013.01); *A61N 1/0551* (2013.01); *A61N 1/3605* (2013.01); *A61N 1/36007* (2013.01); *A61N 1/3611* (2013.01); *A61N 1/36053* (2013.01); *A61N 1/36064* (2013.01); *A61N 1/3787* (2013.01); *A61N 1/37211* (2013.01); *A61N 1/37223* (2013.01)
(58) Field of Classification Search
    CPC ............ A61B 5/14542; A61B 5/14551; A61B 5/4211; A61N 1/0556; A61N 1/3601; A61N 1/0517; A61N 1/0548; A61N 1/0551; A61N 1/36017; A61N 1/36157; A61N 1/36171; A61N 1/36178
    See application file for complete search history.

(56) References Cited

U.S. PATENT DOCUMENTS

| | | | |
|---|---|---|---|
| 2005/0070987 A1 | 3/2005 | Erickson | |
| 2006/0122660 A1 | 6/2006 | Birinder et al. | |
| 2007/0027494 A1 | 2/2007 | Martin | |
| 2007/0255364 A1 | 11/2007 | Gerber et al. | |
| 2008/0269833 A1 | 10/2008 | Scott et al. | |
| 2010/0222686 A1 | 9/2010 | Fisher et al. | |
| 2010/0228079 A1 | 9/2010 | Peter | |
| 2012/0253249 A1* | 10/2012 | Wilson | A61N 1/36057 601/154 |
| 2013/0293025 A1 | 11/2013 | Xu et al. | |
| 2014/0074186 A1 | 3/2014 | Faltys et al. | |
| 2014/0194058 A1* | 7/2014 | Lee | H02J 7/025 455/41.1 |
| 2014/0243714 A1 | 8/2014 | Ward et al. | |
| 2015/0148878 A1* | 5/2015 | Yoo | A61N 1/0556 607/118 |
| 2018/0296845 A1* | 10/2018 | Baumgartner | A61N 1/3787 |

OTHER PUBLICATIONS

Akay, "Long-term measurement of muscle denervation and locomotor behavior in individual wild-type and ALS model mice," Journal of Neurophysiology, Feb. 2014, 111:694-703.

Bernardi et al, "Specific absorption rate and temperature increases in the head of a cellular-phone user," Microwave Theory and Techniques, 2000, 48:1118-1126.

Brown et al, "Stimulus-artifact elimination in a multi-electrode system," Biomed Circuits Syst, Mar. 2008, 2:10-21.

Ghovanloo & Najafi, "A Compact Large Voltage-Compliance High Output-Impedance Programmable Current Source for Implantable Microstimulators," Biomedical Engineering, 2005, 52:97-105.

International Commission on Non-Ionizing Radiation, "Guidelines for limiting exposure to time-varying electric and magnetic fields (1 Hz to 100 kHz)," Health Phys, Dec. 2010, 99:818-36.

Jefferys et al, "Chronic focal epilepsy induced by intracerebral tetanus toxin," The Italian Journal of Neurological Sciences, 1995, 16:27-32.

Loeb & Peck, "Cuff electrodes for chronic stimulation and recording of peripheral nerve activity, " J Neurosci Methods, Jan. 1996, 64:95-103.

Mei et al, "Optimal Wireless Power Transfer to Systems in an Enclosed Resonant Cavity," IEEE Antennas and Wireless Propagation Letters, 2015, 4 pages.

Mei et al., "Cavity Resonator Wireless Power Transfer System for Freely-Moving Animal Experiments," IEEE Transactions on Biomedical Engineering, 2015.

PCT International Preliminary Report on Pattentability in Appln. No. PCT/US2017/037079, dated Dec. 11, 2018, 18 pages.

PCT International Search Report and Written Opinion in International Appln. No. PCT/US2017/37079, dated Nov. 13, 2017, 30 pages.

Pearson et al, "A new electrode configuration for recording electromyographic activity in behaving mice," J Neurosci Methods, Oct. 15, 2005, 148:36-42.

Shahrokhi et al, "The 128-ehannel fully differential digital integrated neural recording and stimulation interface," Biomedical Circuits and Systems, 2010, 4:149-161.

\* cited by examiner

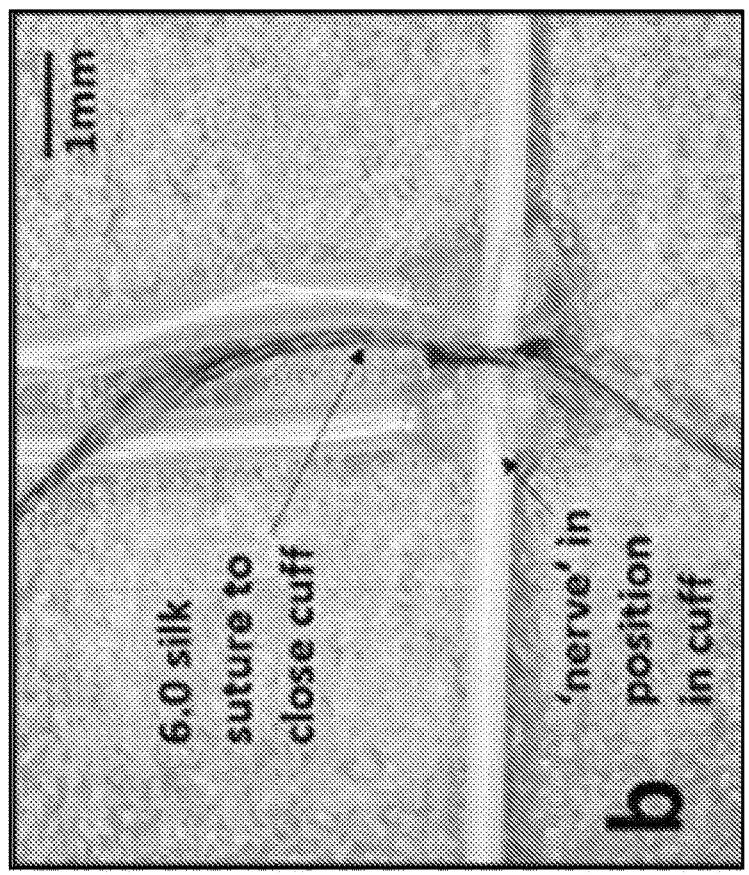
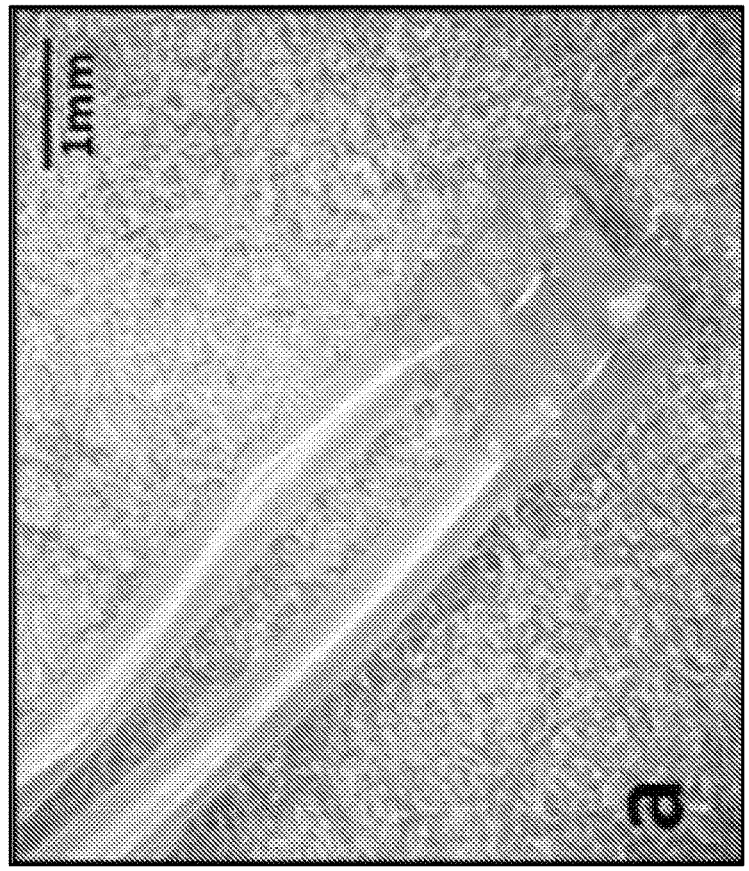
FIG. 24

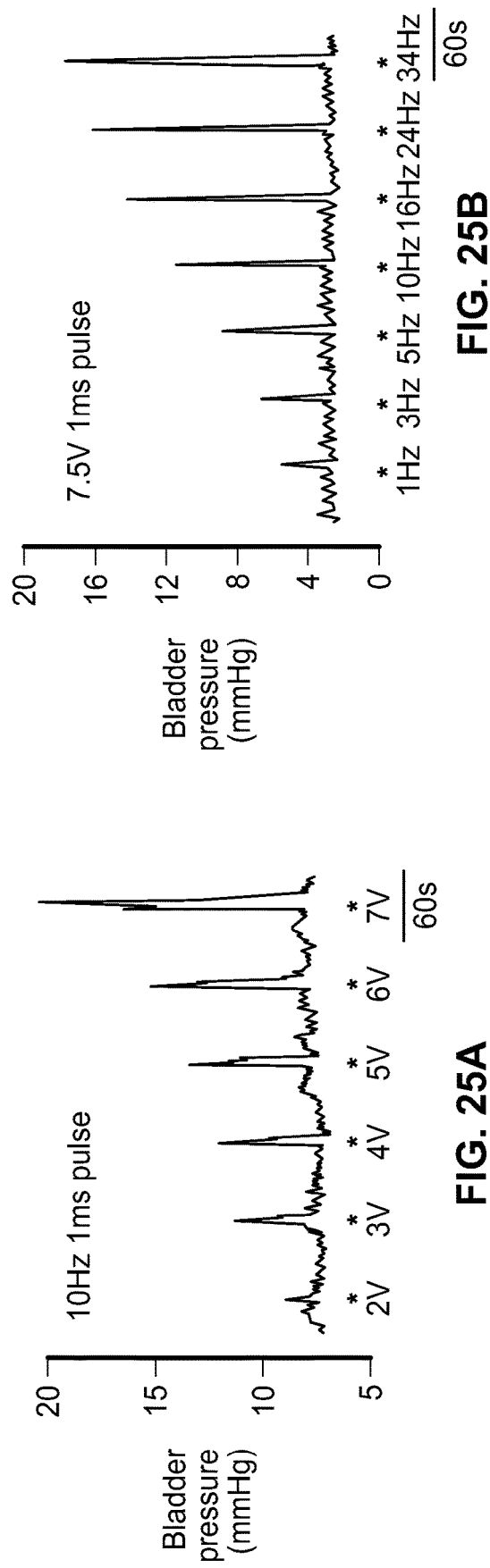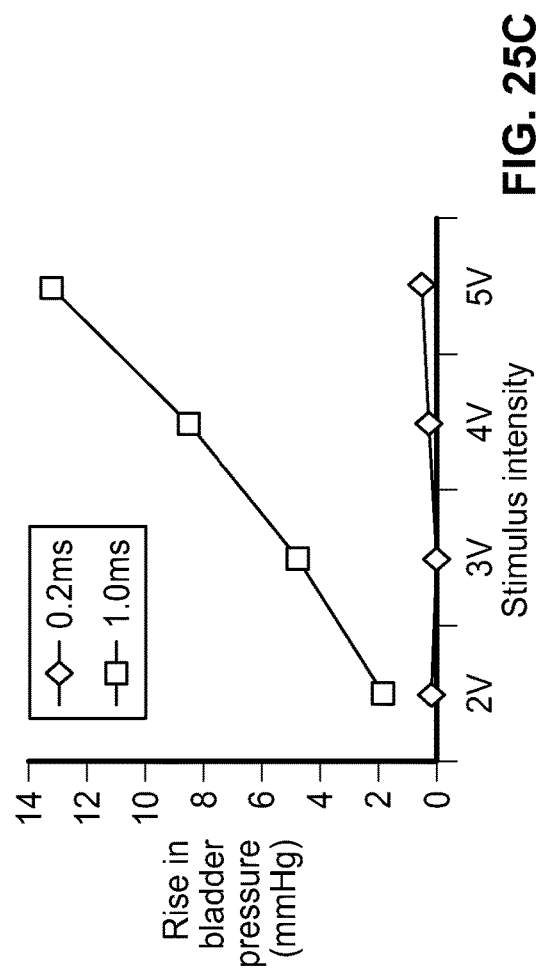
FIG. 25A
FIG. 25B
FIG. 25C

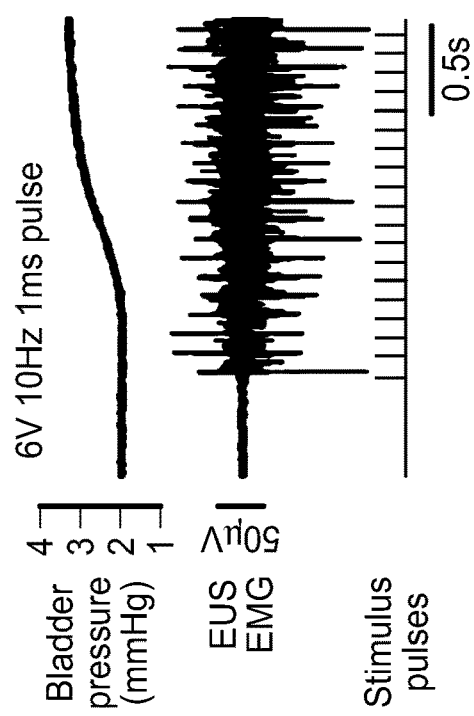
FIG. 25D
FIG. 25E
FIG. 25F

A. Electrode on whole nerve bundle. Possibly a very weak response during the rise in bladder pressure when the rat voids.
B. Divide nerve into two bundles. Bundle B shows a clear increase in activity when bladder pressure rises.
C. No change in activity in bundle C

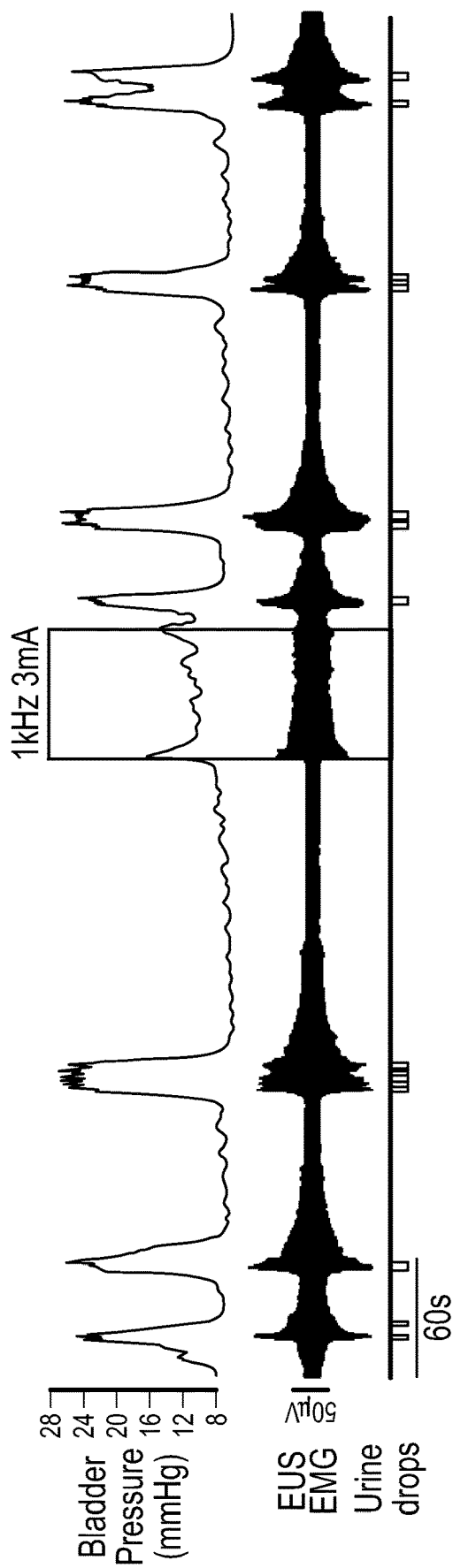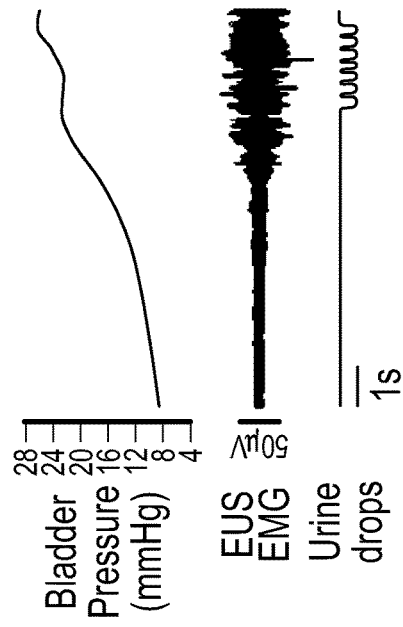
FIG. 29A
FIG. 29B

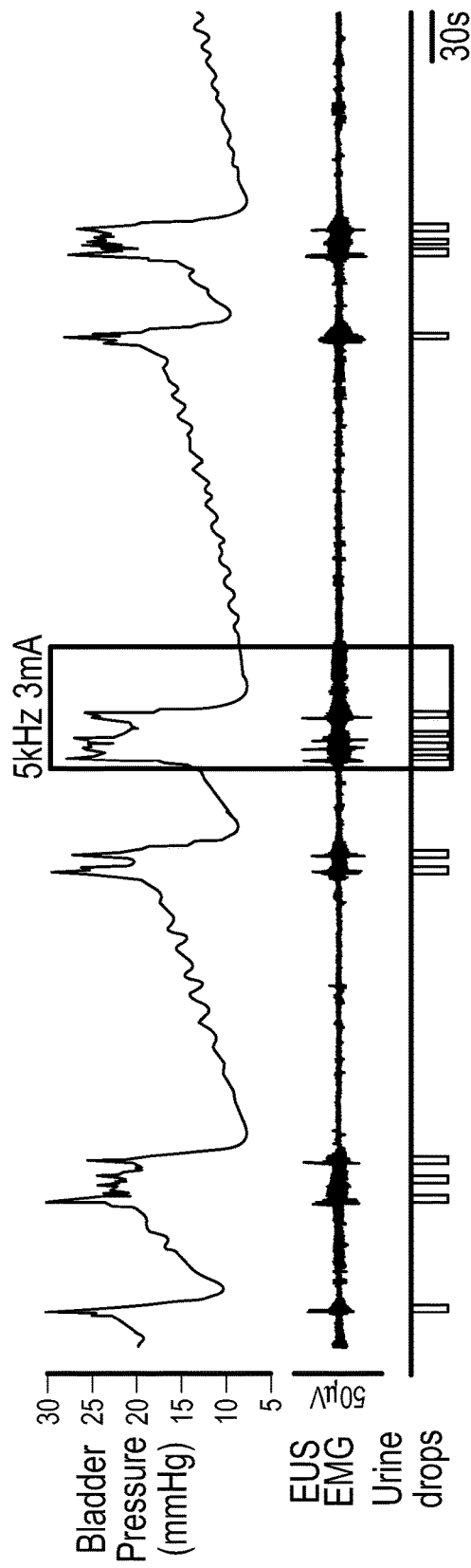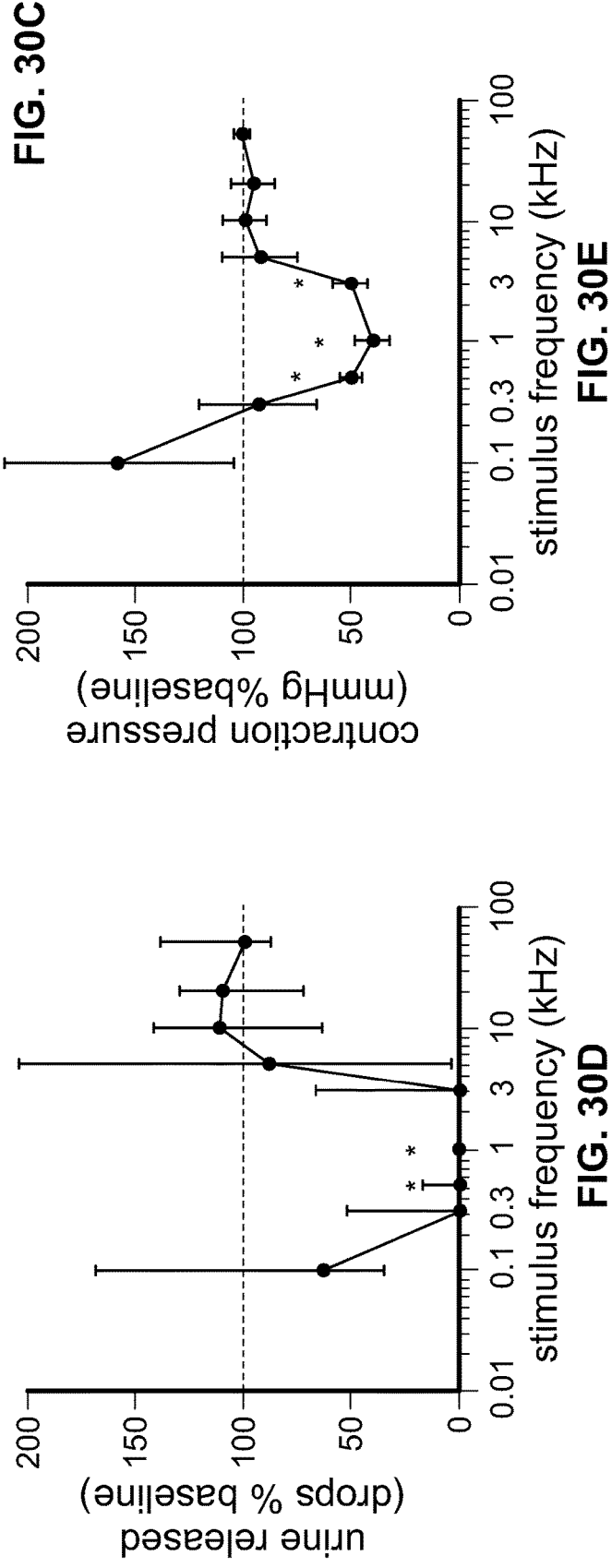
FIG. 30C
FIG. 30E
FIG. 30D

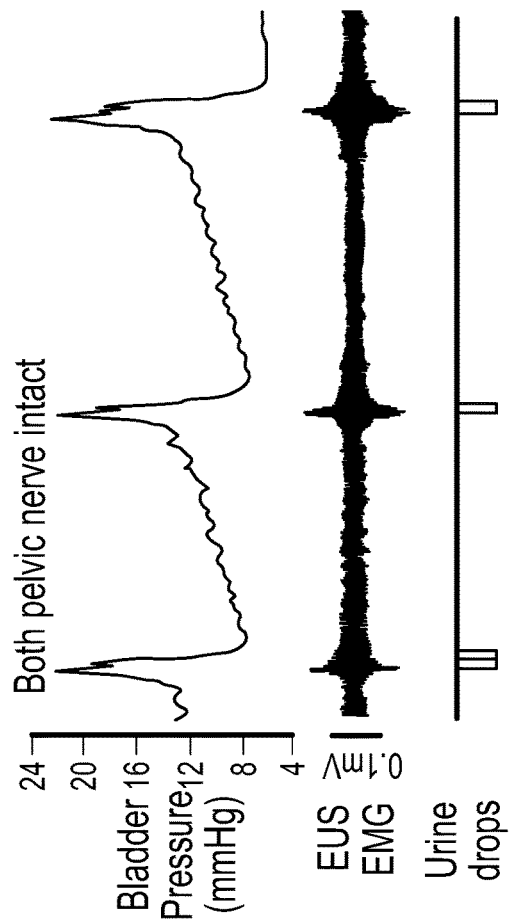
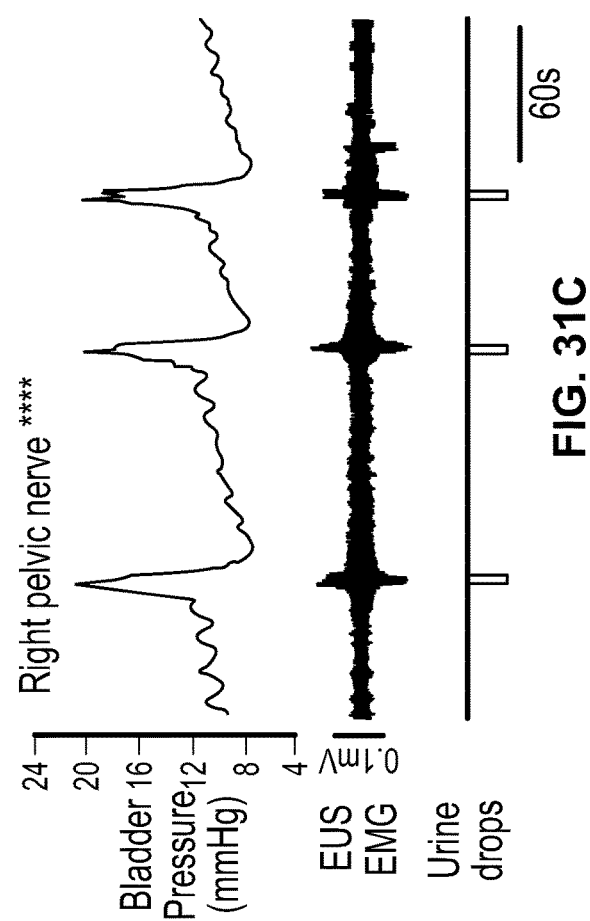
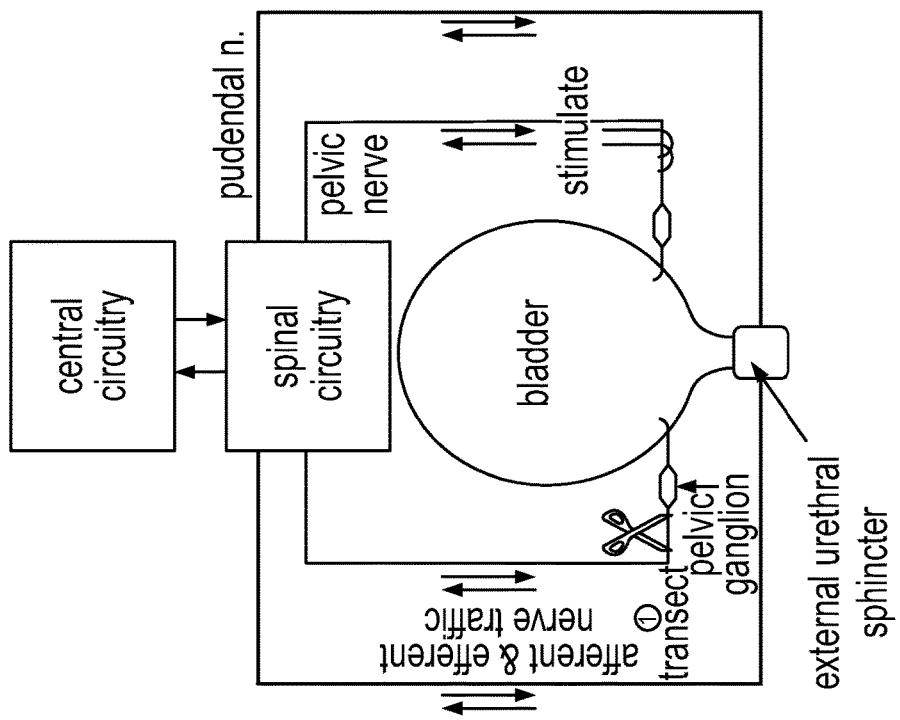
FIG. 31B
FIG. 31C
FIG. 31A

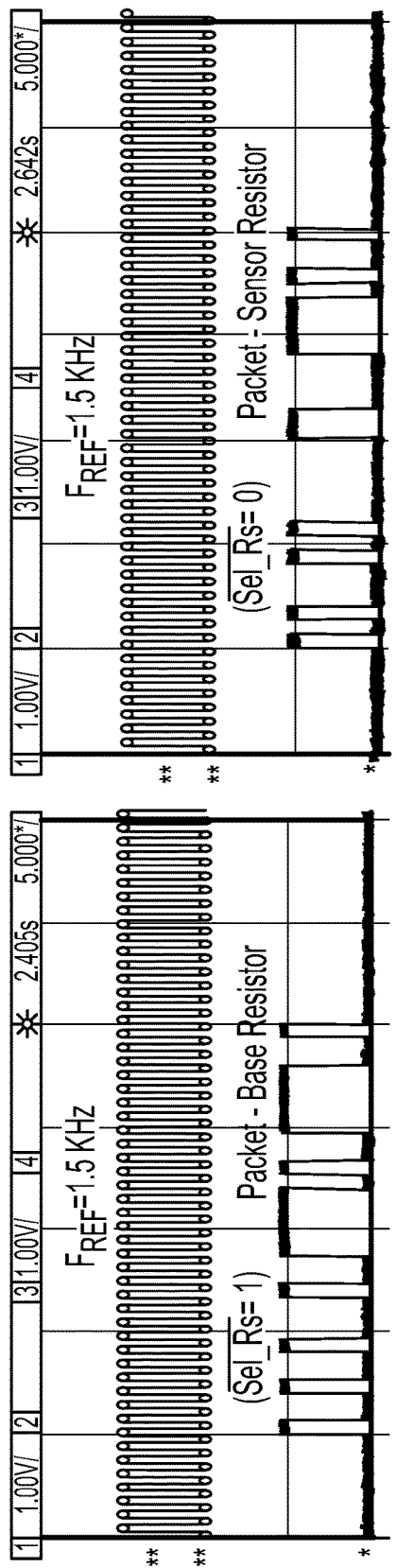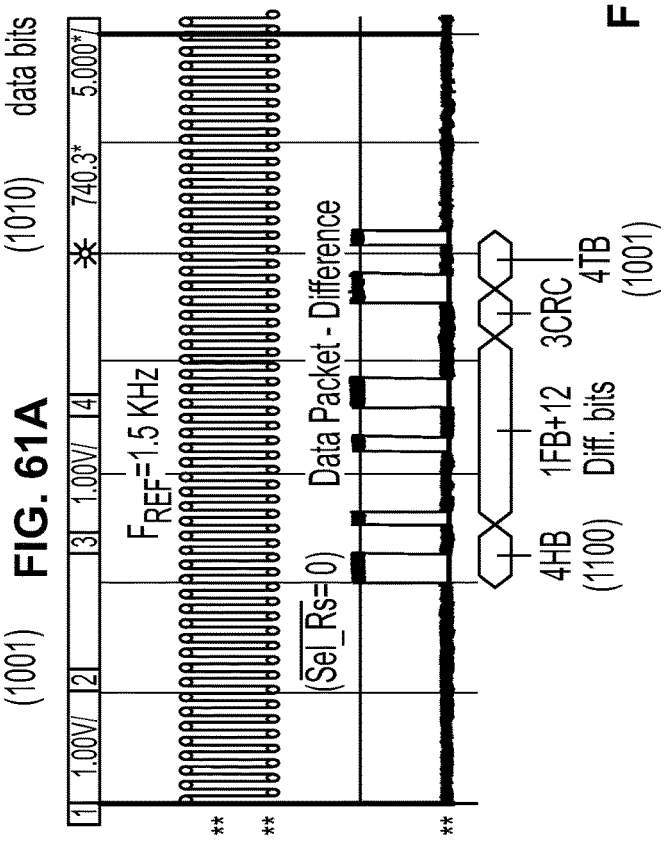

SYSTEM FOR WIRELESS RECORDING AND STIMULATING BIOELECTRIC EVENTS

CROSS-REFERENCE TO RELATED APPLICATIONS

This application is a National Stage Application under 35 U.S.C. § 371 and claims the benefit of International Application No. PCT/US2017/037079, filed Jun. 12, 2017, which claims the benefit under 35 U.S.C. § 119(e) of U.S. Patent Application No. 62/348,405 entitled "SYSTEM FOR WIRELESS RECORDING AND STIMULATING OF BIOELECTRIC EVENTS", filed Jun. 10, 2016, which is incorporated herein by reference in its entirety.

STATEMENT OF FEDERALLY SPONSORED RESEARCH

This invention was made with government support under Grant no. NS085762, awarded by the National Institutes of Health, and Grant No. N66001-12-1-4029 and N66001-14-2-4056 awarded by the Defense Advanced Research Projects Agency. The government has certain rights in the invention.

BACKGROUND

This specification relates to systems and techniques for wireless implantable devices, for example implantable biomedical devices employed for biomodulation, including but not limited to neuromodulation (nerves), myomodulation (muscles) and the modulation of any other biological functions.

Wireless implantable devices for behavior modulation in subjects, such as humans, are of great interest in the scientific community. As open loop and feedback based electrical simulators continue to expand in clinical impact, it may be desirable to increase availability of robust freely behaving data, such as biopotential recordings, from subjects, such as animals, for optimized stimulated parameters and control algorithms. It may be desirable to leverage various device-based technologies for implementing biomodulation. A platform of miniature implantable technology for human subjects can be utilized as a systematic and object approach to address emerging questions from the clinical community. Additionally, employing implantable wireless technologies may allow for treatment of patients with certain biological and physiological disorders (e.g., epilepsy and depression), and for use in increasingly complex chronic behavioral experiments by allowing them to be performed with continuous monitoring.

In addition, advances in wireless powering, ultralow power integrated circuits (IC) and microprocessors, and IC packaging, may make it desirable to further incorporate the use of wireless technology for biomedical research and treatment. Early wireless devices provided separate and/or distinct functionality, for example either functioning for biopotential acquisition or for electrical stimulation. In some instances, powering for these wireless devices was achieved with batteries or wireless inductive coupling. The emergence of optogenetics inspired the development of several wireless optical stimulators, each with unique features. Nonetheless, use of these devices presented some drawbacks related to their size, including difficulties being implantable comfortably in subjects. In addition, it may be difficult to use a single device in multiple capacities, for example providing biopotential recording with electrical stimulation, as the early devices are not configured to support multiple functions.

Vagus nerve stimulation (VNS) is approved by the Food and Drug Administration (FDA) as an adjunctive treatment option for patients with epilepsy or depression that is resistant to pharmacological therapies. Contemporary VNS treatments are implemented by the surgical implantation of a pacemaker-like device with electrodes that make contact with the vagus nerve in the neck. The implanted battery common to all contemporary VNS devices accounts for the majority of the device volume and, as battery functionality declines with age, demands repeated surgeries to replace the entire device at intervals spanning years. While research is being performed to develop entirely non-invasive systems that provide VNS therapy without the need for surgery, these systems lack the spatial specificity of implanted devices.

Therefore, it may be desirable to leverage wireless implantable devices employable for medical treatments, such as VNS, that provides spatial specificity and stimulus waveform definition and reliability comparable or superior to contemporary implanted VNS devices while eliminating active circuitry and batteries from the implant.

SUMMARY

This document discloses a biomodulation platform for use in humans and animals. As used herein, "biomodulation" includes but is not necessarily limited to neuromodulation (nerves), myomodulation (muscles) and the modulation of any other biological functions. This may be accomplished by: a) monitoring any of a host of parameters induced by the biomodulation platform, including but not limited to thermal, pressure, other mechanical changes, bioelectric changes, chemical changes (e.g. such as neurotransmitter levels, cytokines, pH), and other biomarkers; and/or b) actuating via the biomodulation platform using any of a variety of suitable techniques (e.g. electrically, optically, mechanically, thermally, ultrasonically, or otherwise) a particular biological system or outcome of interest. The platform utilizes wireless power transfer techniques to transfer power from an external device to an implanted device on a continuous basis, thus enabling further design flexibility in the implantable component design such as a smaller size and different and smaller physical configurations.

Generally, the platform enables the implantable components to be implanted in human and animal research biomodulation anatomical locations and enables biomodulation applications that would otherwise not be possible. For example, using platform design features described in this document, the main implantable component of the platform may be implanted in anatomical locations within a human not feasible with prior systems, and/or may be implanted in animal model anatomical locations not feasible with prior systems. In addition, the platform enables use scenarios with implantable power requirements that may be unsupportable with systems using batteries to power implantable components. As such, the platform enables biomodulation research and use scenarios not previously possible.

In one aspect, the biomodulation system includes a non-implantable assembly comprising a source for wireless power transfer and a data communications system. The biomodulation system further comprises an implantable assembly that includes a power management module configured to continuously generate operating voltage for the implantable assembly using wireless power transfer from the non-implantable assembly. The implantable assembly further includes a control module operably connected to at least one recording channel and at least one stimulation output, the control module including a processor unit to process information sensed via the at least one recording channel and, upon determining a condition exists, to generate an output to trigger the generation of a stimulation pulse. In such a biomodulation system, the power management module generates operating voltage to supply, for example, analog front-end circuitry for the at least one recording channel, the processor unit, a bi-directional telemetry component to communicate data to and from the non-implantable assembly, and/or stimulation generation circuitry.

In some cases, advantages of the techniques and systems disclosed herein can include a wireless platform that includes active implants (e.g., controller implants) and entirely passive implants (e.g., passive electrodes) coupled by magnetic fields to an active external generator device worn by the patient. Thus, the disclosed system can realize advantages of implants employable in various techniques for the treatment of humans, such as VNS, having a reduced volume and complexity in comparison to some contemporary systems. Moreover, the use of wireless implantable devices in therapeutic procedures like VNS can require reduced surgery, while providing robust forward-compatibility with evolving external generators.

The wireless platform also enables chronic freely behaving experiments for the study of neurological disease and functional, interventional therapies in clinical subjects. Moreover, the disclosed implementation achieves critical design objects such as a miniature footprint for minimal mechanically induced biological impact, modularity for rapid customization to a specific need or application, and low power consumption to extend operational range and minimize heating for biological safety. Other benefits are potentially realized in association with the system's capabilities to monitor the thermal, pressure, and other mechanical changes, bioelectric changes, chemical changes (e.g., neurotransmitter levels, cytokines, pH), and other biomarkers induced by the device. Other benefits are potentially realized by the system's capabilities to actuate electrically, optically, mechanically, thermically, ultrasonically, or otherwise, a particular biological system or outcome of interest. The devices can monitor electrode impedance due to changes induced by inflammatory cascades or mechanical electrode fatigue. In some cases, commercially available, or off-the-shelf, components are used in the design to promote access and repeatability. The selection of each integrated circuit (IC) component can be based on an assessment of performance with respect to size, thus leveraging the design tradeoff for increased suitability for its intended use. Additionally, the disclosed wireless implantable devices can have IC packaging, utilizing quad flat no-leads and a ball grid array packaging, for example, that permits the form factor of the wireless implantable device to achieve a substantially reduced size. The disclosed system can also utilize passive components, thereby providing the benefits a small footprint, for example a 0201, smaller, or larger footprint. In another example, the platform can be used to test and validate preclinical trials and other testing undergoing evaluation.

As a general description, the wireless platform consists of three core hardware units 1) the wireless implantable device, referred to hereinafter as a Bionode assembly, or simply, a Bionode for short; 2) a base station, which can be used to enable wireless bidirectional communication, such as telemetry; and 3) active external generator device for wireless powering. The Bionode assembly has two modules: 1) the power module, configured to support power related capabilities such as to receive the provide continuous energy and 2) the control module to perform command, control, and communication related capacities such as from acquired data, for neuromdodulation parameters, and with possibly wireless telemetry to possibly include sensing to track biomarkers and/or signals of interest and stimulation to control biological systems or outcomes of interest. The modules of the Bionode are capable of being implemented as separate PCBs or separate ICs, that are stacked to minimize the footprint, or singly on one PCB or one IC. As an example, a Bionode can have a footprint of 7×16×6 mm, another Bionode device has a footprint of 750×750×250 m. Some are larger, some smaller depending on the application, needs, and sophistication required.

Some embodiments described herein include a biomodulation system including a non-implantable assembly including a source for wireless power transfer and a data communications system, an implantable assembly including a power management module configured to continuously generate one or more operating voltage for the implantable assembly using wireless power transfer from the non-implantable assembly, a control module operably connected to at least one communication channel and at least one stimulation output, the control module including a processor unit to process information sensed via the at least one communication channel and, upon determining a condition exists, to generate an output to trigger the generation of a stimulus.

In some implementations, the system including include one or more of the following features, including each combination and subcombination of features. The power management module may generate operating voltage to supply (1) analog front-end circuitry for the at least one communication channel, (2) the processor unit, (3) bi-directional telemetry component to communicate data to and from the non-implantable assembly, and (4) stimulation generation circuitry. The power management module may generate two or more different operating voltages including one or more first operating voltages at a first voltage level and one or more second operating voltages having a second voltage level that is independent of the first voltage level, wherein the operating voltages supply (1) different portions of the analog front-end circuitry for the at least one communication channel, (2) the processor unit, (3) the bi-directional telemetry component to communicate data to and from the non-implantable assembly, and (4) the stimulation generation circuitry. The wireless power transfer may be accomplished using magnetic resonance coupling. The wireless power transfer may be accomplished using near-field magnetic inductive coupling. The output to trigger the generation of a stimulus may be generated at least in part based on a measured condition of the subject. The measured condition may be measured by an implantable electrode located remote from the implantable assembly. The measured condition may be measured by an electrode of the implantable assembly. The output may be generated at least in part based on a closed-loop control algorithm that uses the measured condition of the subject as a feedback input. The output may be generated at least in part by a measured response of the subject to a stimulation delivered by an electrode. The at least one communication channel may be a wired lead. The at least one communication channel may be a wireless communication channel. The system may include an electrode configured to deliver the stimulus to a subject. The implantable assembly may be implanted in the chest of a subject. The system may include a lead configured for wireless communication with the control module of the implantable assembly. The control module and lead may be located within a subject remote from one another. The control module may be located within a chest of a subject, and the implantable electrode may be remote from the chest. The electrode may be located within the subject to deliver a stimulus to the bladder. The electrode may be located within the subject to deliver a stimulus to the vagus nerve. The electrode may be located within the subject to deliver a stimulus to a branch of the vagus nerve associated with the gastric system. The electrode may be located within the subject to deliver a stimulus to the subject's stomach. The electrode may be located within the subject to deliver a stimulus to the cortex. The electrode may be located within the subject to deliver a stimulus to the brainstem. The electrode may be located within the subject to deliver a stimulus to the stomach. The electrode may be located within the subject to deliver a stimulus to the pelvic nerve. The electrode may be located within the subject to deliver a stimulus to one or more of: nerves projecting to the esophagus, the larynx, and the sphincter. The electrode may be configured to measure a condition of the subject. The electrode may include a hormone sensing optrode. The electrode may include a pressure sensor. The electrode may be configured to measure bladder pressure. The electrode may include a sensor configured to measure a cytokine level. The electrode may include an electrode selected from the group consisting of a single neuron measurement electrode, a local field potential (LFP) electrode, an electroencephalogram (EEG) electrode, electromyography electrode (EMG), and compound nerve action potential electrode (CNAP). The electrode may be wirelessly powered by the implantable assembly. The electrode may not include a power source housed locally within the electrode.

Some embodiments described herein include biomodulation system including an implantable assembly including: a control module operably connected to at least one communication channel and at least one stimulation output, the control module including a processor unit to process information sensed via the at least one communication channel and, upon determining a condition exists, to generate an output to trigger the generation of a stimulus, and a pressure sensor located within a subject to measure a pressure of the subject's bladder, and a first electrode configured to deliver the stimulus to the subject's pelvic nerve in response to the output.

In some implementations, the system including include one or more of the following features, including each combination and subcombination of features. The condition may be at least partially based on a pressure measurement of the subject's bladder. The stimulus may be configured to generate a urinary tract clamping response that prevents urinary voiding of the subject in response to the condition. The implantable assembly may be configured to remove the stimulus in response to a user input. The system may include a non-implantable assembly including a data communications system configured to transmit the user input to the implantable assembly. The system may include a non-implantable assembly including a data communications system. The non-implantable assembly may include a source for wireless power transfer to a power management module of the implantable assembly. The wireless power transfer may be accomplished using magnetic resonance coupling. The wireless power transfer is accomplished using far-field radio frequency (RF) powering. The implantable assembly may include a power management module configured to continuously generate operating voltage or voltages for the implantable assembly. The power management module may generate operating voltage to supply (1) analog front-end circuitry for the at least one communication channel, (2) the processor unit, (3) bi-directional telemetry component to communicate data to and from the non-implantable assembly, and (4) stimulation generation circuitry. The power management module may generate two or more different operating voltages including one or more first operating voltages at a first voltage level and one or more second operating voltages having a second voltage level that is independent of the first voltage level, wherein the operating voltages supply (1) different portions of the analog front-end circuitry for the at least one communication channel, (2) the processor unit, (3) the bi-directional telemetry component to communicate data to and from the non-implantable assembly, and (4) the stimulation generation circuitry. The pressure sensor may include a piezoresistive differential pressure sensor. The pressure sensor may include a receiver powering coil. The pressure sensor may not include a battery. The pressure sensor may include an active transmitter.

Some embodiments described herein include a method of biomodulation for reducing urinary incontinence symptoms, including measuring a bladder pressure by an electrode including a pressure sensor, wirelessly transmitting the bladder pressure to a control module of an implantable assembly, the control module implanted within the subject remote from the electrode and operably connected to at least one communication channel configured to receive the bladder pressure measurement, the control module including a processor unit to process bladder pressure sensed via the at least one communication channel, determining a condition exists based at least in part on the bladder pressure measurement, and delivering an electrical stimulation configured to generate a urinary tract clamping response in the subject to prevent urinary voiding.

In some implementations, the method including include one or more of the following features, including each combination and subcombination of features. Delivering an electrical stimulation may include delivering an electrical stimulation to the subject's pelvic nerve. The method may include wirelessly transferring the bladder pressure measurement to a non-implantable assembly, processing the bladder pressure measurement by the non-implantable assembly, and transmitting a command to the implantable assembly to generate an output to deliver the electrical stimulation. The method may include transferring power wirelessly to a power management module of the implantable assembly. Transferring power may include charging a rechargeable battery of the implantable assembly. The method may include transferring power wirelessly to the electrode, the wireless power transfer sufficient for the electrode to generate the electrical stimulation. The at least one communication channel may include a wired lead. The at least one communication channel may include a wireless communication channel. The pressure sensor may include a piezoresistive differential pressure sensor. The pressure sensor may include a receiver powering coil. The pressure sensor may not include a battery. The pressure sensor may include an active transmitter.

Some embodiments described herein include a method of biomodulation, including measuring a patient condition by an implanted electrode, communicating the measurement to a control module of an implanted assembly, the implanted assembly located within the subject remote from the electrode, the control module having at least one stimulation output, the control module including a processor unit to process the measurement, generating an output to trigger the generation of a stimulus, and delivering a first stimulus according to a first set of stimulation parameters in response to the output, the first set of stimulation parameters determined based at least in part on the measurement of the patient condition.

In some implementations, the method including include one or more of the following features, including each combination and subcombination of features. The method may include delivering a second electrical stimulation according to a second set of stimulation parameters different than the first set of stimulation parameters. The first set of stimulation parameters and the second set of stimulation parameters may be calculated to deliver a constant dose of neural activity. The first electrical stimulation and the second electrical stimulation may be delivered at a predetermined interval. Measuring the patient condition may include measuring the patient condition in response to a prior electrical stimulation delivered before the first electrical stimulation.

Some embodiments described herein include a biomodulation system including an implantable assembly including a control module operably connected to at least one communication channel and at least one stimulation output, the control module including a processor unit to process information sensed via the at least one communication channel and, upon determining a condition exists, to generate an output to trigger the generation of a stimulus, a sensor located within a subject to obtain a condition measurement of a physiological pathway of the subject, the condition measurement a cytokine level, and a first electrode configured to deliver the stimulus to the subject based at least on part on the condition measurement, the stimulus configured to affect an inflammation reflex when a seizure occurs.

In some implementations, the system including include one or more of the following features, including each combination and subcombination of features. The sensor may include an optical sensor configured to measure the cytokine level. The first electrode may be configured to deliver the stimulus to a location selected from the group consisting of the brain stem, cortex, and vagus nerve. The electrical stimulation may include deep brain stimulation (DBS). The system may include a non-implantable assembly including a data communications system configured to transmit the user input to the implantable assembly. The non-implantable assembly may include a source for wireless power transfer to a power management module of the implantable assembly. The wireless power transfer may be accomplished using magnetic resonance coupling. The wireless power transfer may be accomplished using near-field magnetic inductive coupling. The implantable assembly may include a power management module configured to continuously generate operating voltage for the implantable assembly. The power management module may generate operating voltage to supply (1) analog front-end circuitry for the at least one communication channel, (2) the processor unit, (3) bi-directional telemetry component to communicate data to and from the non-implantable assembly, and (4) stimulation generation circuitry. The power management module may generate two or more different operating voltages including one or more first operating voltages at a first voltage level and one or more second operating voltages having a second voltage level that is independent of the first voltage level, wherein the operating voltages supply (1) different portions of the analog front-end circuitry for the at least one communication channel, (2) the processor unit, (3) the bi-directional telemetry component to communicate data to and from the non-implantable assembly, and (4) the stimulation generation circuitry.

Some embodiments described herein include a method of biomodulation for reducing symptoms of epilepsy, including monitoring a physiological pathway by an electrode to obtain a condition measurement including a cytokine level, wirelessly transmitting the condition measurement to a control module of an implantable assembly, the control module implanted within the subject remote from the electrode and operably connected to at least one communication channel configured to receive the condition measurement, the control module including a processor unit to process the condition measurement sensed via the at least one communication channel, determining a condition exists based at least in part on the condition measurement, and delivering an electrical stimulation configured to affect an inflammation reflex when a seizure occurs.

In some implementations, the method including include one or more of the following features, including each combination and subcombination of features. The electrode may include an optical sensor configured to measure the cytokine level. Delivering an electrical stimulation may include delivering an electrical stimulation to a location selected from the group consisting of the brain stem, cortex, and vagus nerve. The method may include wirelessly transferring the condition measurement to a non-implantable assembly, processing the condition measurement by the non-implantable assembly, and transmitting a command to the implantable assembly to generate an output to deliver the electrical stimulation. The method may include transferring power wirelessly to a power management module of the implantable assembly. Transferring power may include charging a rechargeable battery of the implantable assembly. The method may include transferring power wirelessly to the electrode, the wireless power transfer sufficient for the electrode to generate the electrical stimulation. The at least one communication channel may include a wired lead. The at least one communication channel may include a wireless communication channel. The electrical stimulation may include deep brain stimulation (DBS).

Some embodiments described herein include a biomodulation system including an implantable assembly including a control module operably connected to at least one communication channel and at least one stimulation output, the control module including a processor unit to process information sensed via the at least one communication channel and, upon determining a condition exists, to generate an output to trigger the generation of a stimulus, one or more sensors located within a subject to obtain a pH level, a temperature, and a respiratory condition, and a first electrode configured to deliver the stimulus to the subject based at least in part on one or more of the pH level, temperature, and respiratory condition, wherein the stimulus is configured to affect a reflex when a seizure occurs.

In some implementations, the system including include one or more of the following features, including each combination and subcombination of features. The first electrode may be configured to deliver the stimulus to a location selected from the group consisting of the brain stem, cortex, vagus nerve, sympathetic nerves, upper esophageal sphincter, and larynx. The electrical stimulation may be deep brain stimulation (DBS). The system may include including a non-implantable assembly including a data communications system configured to transmit the user input to the implantable assembly. The non-implantable assembly may include a source for wireless power transfer to a power management module of the implantable assembly. The wireless power transfer may be accomplished using magnetic resonance coupling. The wireless power transfer may be accomplished using near-field magnetic inductive coupling. The implantable assembly may include a power management module configured to continuously generate operating voltage for the implantable assembly. The power management module may generate operating voltage to supply (1) analog front-end circuitry for the at least one communication channel, (2) the processor unit, (3) bi-directional telemetry component to communicate data to and from the non-implantable assembly, and (4) stimulation generation circuitry. The power management module may generate two or more different operating voltages including one or more first operating voltages at a first voltage level and one or more second operating voltages having a second voltage level that is independent of the first voltage level, wherein the operating voltages supply (1) different portions of the analog front-end circuitry for the at least one communication channel, (2) the processor unit, (3) the bi-directional telemetry component to communicate data to and from the non-implantable assembly, and (4) the stimulation generation circuitry, and wherein the second operating voltage supplies the stimulation generation circuitry.

Some embodiments described herein include a method of biomodulation for reducing symptoms of epilepsy, including, monitoring a physiological pathway by an electrode to obtain a condition measurement including a pH level, temperature, and respiratory level, wirelessly transmitting the condition measurement to a control module of an implantable assembly, the control module implanted within the subject remote from the electrode and operably connected to at least one communication channel configured to receive the condition measurement, the control module including a processor unit to process the condition measurement sensed via the at least one communication channel, determining a condition exists based at least in part on the condition measurement, and delivering an electrical stimulation configured to affect a reflex when a seizure occurs.

In some implementations, the method including include one or more of the following features, including each combination and subcombination of features. Delivering an electrical stimulation may include delivering an electrical stimulation to a location selected from the group consisting of the brain stem, cortex, vagus nerve, sympathetic nerves, upper esophageal sphincter, and larynx. The method may include wirelessly transferring the condition measurement to a non-implantable assembly, processing the condition measurement by the non-implantable assembly, and transmitting a command to the implantable assembly to generate an output to deliver the electrical stimulation. The method may include transferring power wirelessly to a power management module of the implantable assembly. Transferring power may include charging a rechargeable battery of the implantable assembly. The method may include transferring power wirelessly to the electrode, the wireless power transfer sufficient for the electrode to generate the electrical stimulation. The at least one communication channel may include a wired lead. The at least one communication channel may include a wireless communication channel. The electrical stimulation may include deep brain stimulation (DBS).

Some embodiments described herein include a biomodulation system including an implantable assembly including a control module operably connected to at least one communication channel and at least one stimulation output, the control module including a processor unit to process information sensed via the at least one communication channel and, upon determining a condition exists, to generate an output to trigger the generation of a stimulus, one or more sensors located within a subject configured to obtain a cytokine level, and a first electrode configured to deliver the stimulus to the subject based at least in part on the cytokine level, the stimulus configured to cause a vagally mediated reduction in lymphocyte release from post-synaptic cites of the vagus nerve in the gastrointestinal tract.

In some implementations, the system including include one or more of the following features, including each combination and subcombination of features. The first electrode may be configured to deliver the stimulus to the vagus nerve. The system may include a non-implantable assembly including a data communications system configured to transmit the user input to the implantable assembly. The non-implantable assembly may include a source for wireless power transfer to a power management module of the implantable assembly. The wireless power transfer may be accomplished using magnetic resonance coupling. The wireless power transfer may be accomplished using near-field magnetic inductive coupling. The implantable assembly may include a power management module configured to continuously generate operating voltage for the implantable assembly. The power management module may generate operating voltage to supply (1) analog front-end circuitry for the at least one communication channel, (2) the processor unit, (3) bi-directional telemetry component to communicate data to and from the non-implantable assembly, and (4) stimulation generation circuitry. The power management module may generate two or more different operating voltages including one or more first operating voltages at a first voltage level and one or more second operating voltages having a second voltage level that is independent of the first voltage level, wherein the operating voltages supply (1) different portions of the analog front-end circuitry for the at least one communication channel, (2) the processor unit, (3) the bi-directional telemetry component to communicate data to and from the non-implantable assembly, and (4) the stimulation generation circuitry, and wherein the second operating voltage supplies the stimulation generation circuitry.

Some embodiments described herein include a method of biomodulation for reducing symptoms of inflammation, including monitoring a physiological pathway by an electrode to obtain a condition measurement that includes a cytokine level, wirelessly transmitting the condition measurement to a control module of an implantable assembly, the control module implanted within the subject remote from the electrode and operably connected to at least one communication channel configured to receive the condition measurement, the control module including a processor unit to process the condition measurement sensed via the at least one communication channel, determining a condition exists based at least in part on the condition measurement, and delivering an electrical stimulation of the vagus nerve configured to cause a vagally mediated reduction in lymphocyte release from post-synaptic cites of the vagus nerve in the gastrointestinal tract.

In some implementations, the method including include one or more of the following features, including each combination and subcombination of features. The method may include wirelessly transferring the condition measurement to a non-implantable assembly, processing the condition measurement by the non-implantable assembly, and transmitting a command to the implantable assembly to generate an output to deliver the electrical stimulation. The method may include transferring power wirelessly to a power management module of the implantable assembly. Transferring power may include charging a rechargeable battery of the implantable assembly. The method may include transferring power wirelessly to the electrode, the wireless power transfer sufficient for the electrode to generate the electrical stimulation. The at least one communication channel may include a wired lead. The at least one communication channel may include a wireless communication channel.

Some embodiments described herein include a biomodulation system including an implantable assembly including a control module operably connected to at least one communication channel and at least one stimulation output, the control module including a processor unit to process information sensed via the at least one communication channel and, upon determining a condition exists, to generate an output to trigger the generation of a stimulus and one or more electrodes configured to deliver the stimulus to the subject, the stimulus configured to cause reversible inactivation of the nucleus accumbens shell (AcbSh).

In some implementations, the method including include one or more of the following features, including each combination and subcombination of features. The system may include one or more electrodes configured to deliver the stimulation to a location selected from the group consisting of midbrain dopaminergic system, such as the ventral tegmental area, nucleus accumbens, olfactory tubercle, frontal cortex, and amygdala. The system may include a non-implantable assembly including a data communications system configured to transmit the user input to the implantable assembly. The non-implantable assembly may include a source for wireless power transfer to a power management module of the implantable assembly. The wireless power transfer may be accomplished using magnetic resonance coupling. The wireless power transfer may be accomplished using near-field magnetic inductive coupling. The implantable assembly may include power management module configured to continuously generate operating voltage for the implantable assembly. The power management module may generate operating voltage to supply (1) analog front-end circuitry for the at least one communication channel, (2) the processor unit, (3) bi-directional telemetry component to communicate data to and from the non-implantable assembly, and (4) stimulation generation circuitry. The power management module may generate two or more different operating voltages including one or more first operating voltages at a first voltage level and one or more second operating voltages having a second voltage level that is independent of the first voltage level, wherein the operating voltages supply (1) different portions of the analog front-end circuitry for the at least one communication channel, (2) the processor unit, (3) the bi-directional telemetry component to communicate data to and from the non-implantable assembly, and (4) the stimulation generation circuitry, and wherein the second operating voltage supplies the stimulation generation circuitry. The system may include an electrode configured to monitor the subject's cortex in response to the stimulation.

Some embodiments described herein include a method of biomodulation for reducing symptoms of alcoholism, including, monitoring a physiological pathway by an electrode to obtain a condition measurement, wirelessly transmitting the condition measurement to a control module of an implantable assembly, the control module implanted within the subject remote from the electrode and operably connected to at least one communication channel configured to receive the condition measurement, the control module including a processor unit to process the condition measurement sensed via the at least one communication channel, and delivering an electrical stimulation based at least in part on the condition measurement, wherein the electrical stimulation includes deep brain stimulation configured to cause reversible inactivation of the nucleus accumbens shell (AcbSh).

In some implementations, the method including include one or more of the following features, including each combination and subcombination of features. Monitoring a physiological pathway may include monitoring the cortex. The method may include wirelessly transferring the condition measurement to a non-implantable assembly, processing the condition measurement by the non-implantable assembly, and transmitting a command to the implantable assembly to generate an output to deliver the electrical stimulation. The method may include transferring power wirelessly to a power management module of the implantable assembly. Transferring power may include charging a rechargeable battery of the implantable assembly. The method may include transferring power wirelessly to the electrode, the wireless power transfer sufficient for the electrode to generate the electrical stimulation. The at least one communication channel may include a wired lead. The at least one communication channel may include a wireless communication channel.

Some embodiments described herein include a biomodulation system including an implantable assembly including a control module operably connected to at least one communication channel and at least one stimulation output, the control module including a processor unit to process information sensed via the at least one communication channel and, upon determining a condition exists, to generate an output to trigger the generation of a stimulus; and one or more electrodes configured to deliver the stimulus to a subject's cortex, the stimulus configured to deliver deep brain stimulation to the subject's cortex.

In some implementations, the system including include one or more of the following features, including each combination and subcombination of features. The system may include a non-implantable assembly including a data communications system configured to transmit the user input to the implantable assembly. The non-implantable assembly may include a source for wireless power transfer to a power management module of the implantable assembly. The wireless power transfer may be accomplished using magnetic resonance coupling. The wireless power transfer may be accomplished using near-field magnetic inductive coupling. The implantable assembly may include a power management module configured to continuously generate operating voltage for the implantable assembly. The power management module may generate operating voltage to supply (1) analog front-end circuitry for the at least one communication channel, (2) the processor unit, (3) bi-directional telemetry component to communicate data to and from the non-implantable assembly, and (4) stimulation generation circuitry. The power management module may generate two or more different operating voltages including one or more first operating voltages at a first voltage level and one or more second operating voltages having a second voltage level that is independent of the first voltage level, wherein the operating voltages supply (1) different portions of the analog front-end circuitry for the at least one communication channel, (2) the processor unit, (3) the bi-directional telemetry component to communicate data to and from the non-implantable assembly, and (4) the stimulation generation circuitry, and wherein the second operating voltage supplies the stimulation generation circuitry. The system may include an electrode configured to monitor the subject's cortex in response to the stimulation.

Some embodiments described herein include a method of biomodulation for reducing symptoms of alcoholism, including monitoring a physiological pathway by an electrode to obtain a condition measurement, wirelessly transmitting the condition measurement to a control module of an implantable assembly, the control module implanted within the subject remote from the electrode and operably connected to at least one communication channel configured to receive the condition measurement, the control module including a processor unit to process the condition measurement sensed via the at least one communication channel, and delivering an electrical stimulation based at least in part on the condition measurement, wherein the electrical stimulation includes deep brain stimulation of the cortex.

In some implementations, the method including include one or more of the following features, including each combination and subcombination of features. Monitoring a physiological pathway may include monitoring the cortex. The method may include wirelessly transferring the condition measurement to a non-implantable assembly, processing the condition measurement by the non-implantable assembly, and transmitting a command to the implantable assembly to generate an output to deliver the electrical stimulation. The method may include transferring power wirelessly to a power management module of the implantable assembly. Transferring power may include charging a rechargeable battery of the implantable assembly. The method may include transferring power wirelessly to the electrode, the wireless power transfer sufficient for the electrode to generate the electrical stimulation. The at least one communication channel may include a wired lead. The at least one communication channel may include a wireless communication channel.

Some embodiments described herein include a biomodulation system including an implantable assembly including a control module operably connected to at least one communication channel and at least one stimulation output, the control module including a processor unit to process information sensed via the at least one communication channel and, upon determining a condition exists, to generate an output to trigger the generation of a stimulus, a sensor located within a subject to obtain a condition measurement of a physiological pathway of the subject, the condition measurement including a hormone level, and a first electrode configured to deliver the stimulus to the subject based at least on part on the condition measurement, the stimulus configured to affect a gastric condition.

In some implementations, the system including include one or more of the following features, including each combination and subcombination of features. The sensor may include an optical sensor configured to measure the hormone level. The hormone level may be selected from the group consisting of ghrelin, PYY, somatostatin, gastrin, nesfatin, leptin and 5-HT (e.g. in the stomach), and/or CCK, secretin, 5-HT, GIP, GLP-1, PYY and neurotensin. The first electrode may be configured to deliver the stimulus to a location selected from the group consisting of a branch of the vagus nerve associated with the stomach, a branch of the vagus nerve associated with stomach sphincters, a distal esophagus, the stomach muscle, and a proximal duodenum. The system may include a non-implantable assembly including a data communications system configured to transmit the user input to the implantable assembly. The non-implantable assembly may include a source for wireless power transfer to a power management module of the implantable assembly. The wireless power transfer may be accomplished using magnetic resonance coupling. The wireless power transfer may be accomplished using near-field magnetic inductive coupling. The implantable assembly may include a power management module configured to continuously generate operating voltage for the implantable assembly. The power management module may generate operating voltage to supply (1) analog front-end circuitry for the at least one communication channel, (2) the processor unit, (3) bi-directional telemetry component to communicate data to and from the non-implantable assembly, and (4) stimulation generation circuitry. The power management module may generate two or more different operating voltages including one or more first operating voltages at a first voltage level and one or more second operating voltages having a second voltage level that is independent of the first voltage level, wherein the operating voltages supply (1) different portions of the analog front-end circuitry for the at least one communication channel, (2) the processor unit, (3) the bi-directional telemetry component to communicate data to and from the non-implantable assembly, and (4) the stimulation generation circuitry, and wherein the second operating voltage supplies the stimulation generation circuitry.

Some embodiments described herein include a method of biomodulation for reducing symptoms of a gastric disorder, including monitoring a physiological pathway by an electrode to obtain a condition measurement including a hormone level, wirelessly transmitting the condition measurement to a control module of an implantable assembly, the control module implanted within the subject remote from the electrode and operably connected to at least one communication channel configured to receive the condition measurement, the control module including a processor unit to process the condition measurement sensed via the at least one communication channel, determining a condition exists based at least in part on the condition measurement, and delivering an electrical stimulation configured to affect a gastric condition.

In some implementations, the method including include one or more of the following features, including each combination and subcombination of features. The electrode may include an optical sensor configured to measure the hormone level. The hormone level may be selected from the group consisting of ghrelin, PYY, somatostatin, gastrin, nesfatin, leptin and 5-HT (e.g. in the stomach), and/or CCK, secretin, 5-HT, GIP, GLP-1, PYY and neurotensin. Delivering an electrical stimulation may include delivering an electrical stimulation to a location selected from the group consisting of a branch of the vagus nerve associated with the stomach, a branch of the vagus nerve associated with stomach sphincters, a distal esophagus, the stomach muscle, and a proximal duodenum. The method may include wirelessly transferring the condition measurement to a non-implantable assembly, processing the condition measurement by the non-implantable assembly, and transmitting a command to the implantable assembly to generate an output to deliver the electrical stimulation. The method may include transferring power wirelessly to a power management module of the implantable assembly. Transferring power may include charging a rechargeable battery of the implantable assembly. The method may include transferring power wirelessly to the electrode, the wireless power transfer sufficient for the electrode to generate the electrical stimulation. The at least one communication channel may include a wired lead. The at least one communication channel may include a wireless communication channel.

Some embodiments described herein include a biomodulation system, including a non-implantable means for wireless power transfer and data communications, and an implantable means for generating operating voltage for an implantable assembly using wireless power transfer, and means for receiving an measurement related to a patient condition and generating an output to trigger the generation of a stimulus based at least in part on the measurement.

Some embodiments described herein include a biomodulation system including a resonant cavity including a source for wireless power transfer, an implantable assembly including, a power management module configured to continuously generate one or more operating voltage for the implantable assembly using wireless power transfer from the non-implantable assembly, and a control module operably connected to at least one communication channel and at least one stimulation output, the control module including a processor unit to process information sensed via the at least one communication channel and, upon determining a condition exists, to generate an output to trigger the generation of a stimulus.

In some implementations, the system including include one or more of the following features, including each combination and subcombination of features. The implantable assembly may be inserted into a subject that is located within the resonant cavity. The subject may be a non-human mammal. The non-human mammal may be a rodent. The resonant cavity may include a cage for the non-human mammal, with the walls of the cage including antennae for the wireless power transfer. The biomodulation system may be configured for use in pre-clinical testing.

The biomodulation systems and methods described herein may include wireless power transfer that serves to charge or re-charge a rechargeable power supply. The biomodulation systems and methods described herein may include wireless power transfer accomplished using far-field radio frequency (RF) powering. The biomodulation systems and methods described herein may be used with a patient that is a human. The biomodulation systems and methods described herein may be used with a patient that is a non-human mammal.

The details of one or more embodiments of the subject matter described in this specification are set forth in the accompanying drawings and the description below. Other features, aspects, and advantages of the invention will become apparent from the description, the drawings, and the claims.

DRAWING DESCRIPTIONS

Figure 17A:
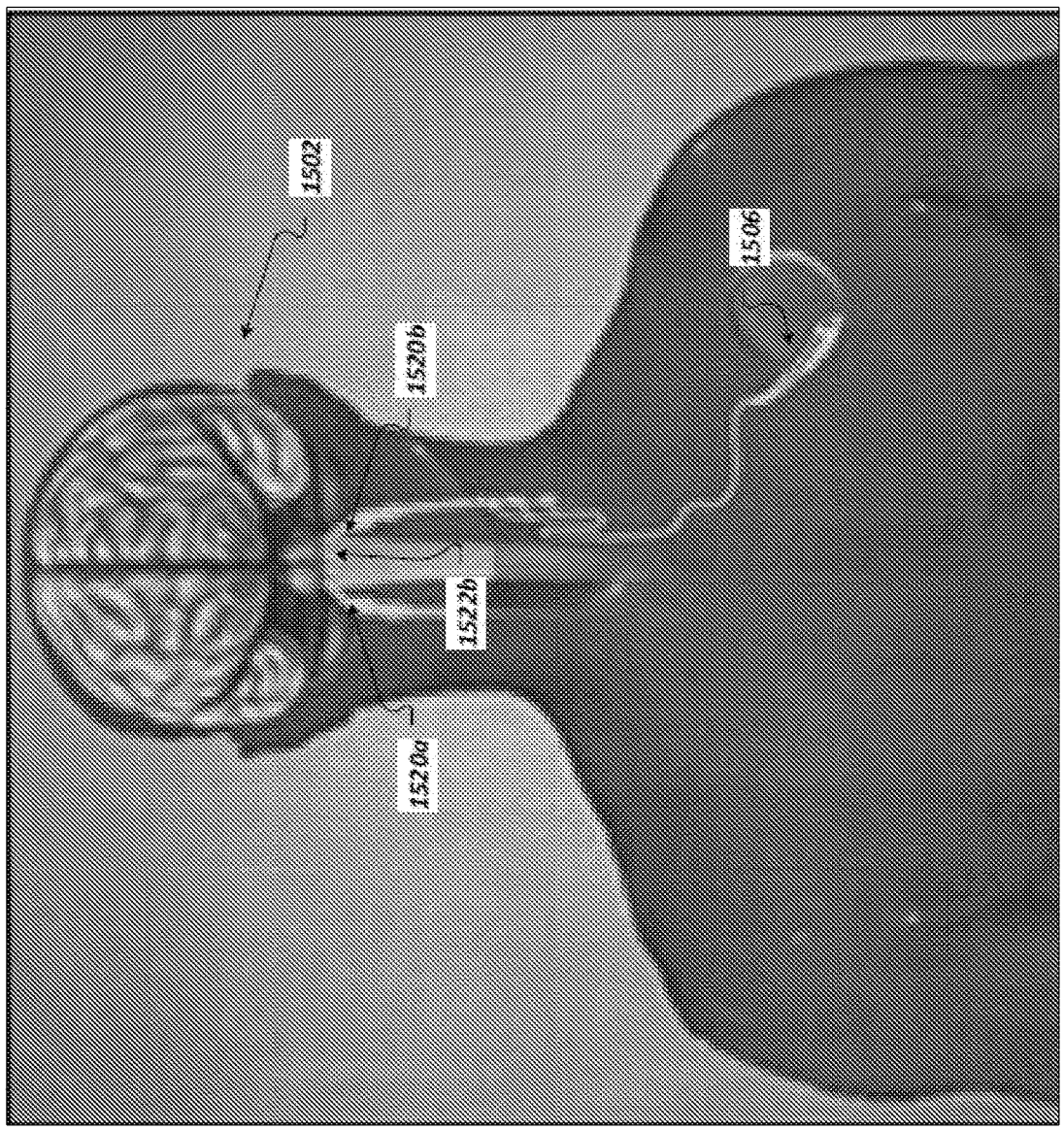
Figure 17B:
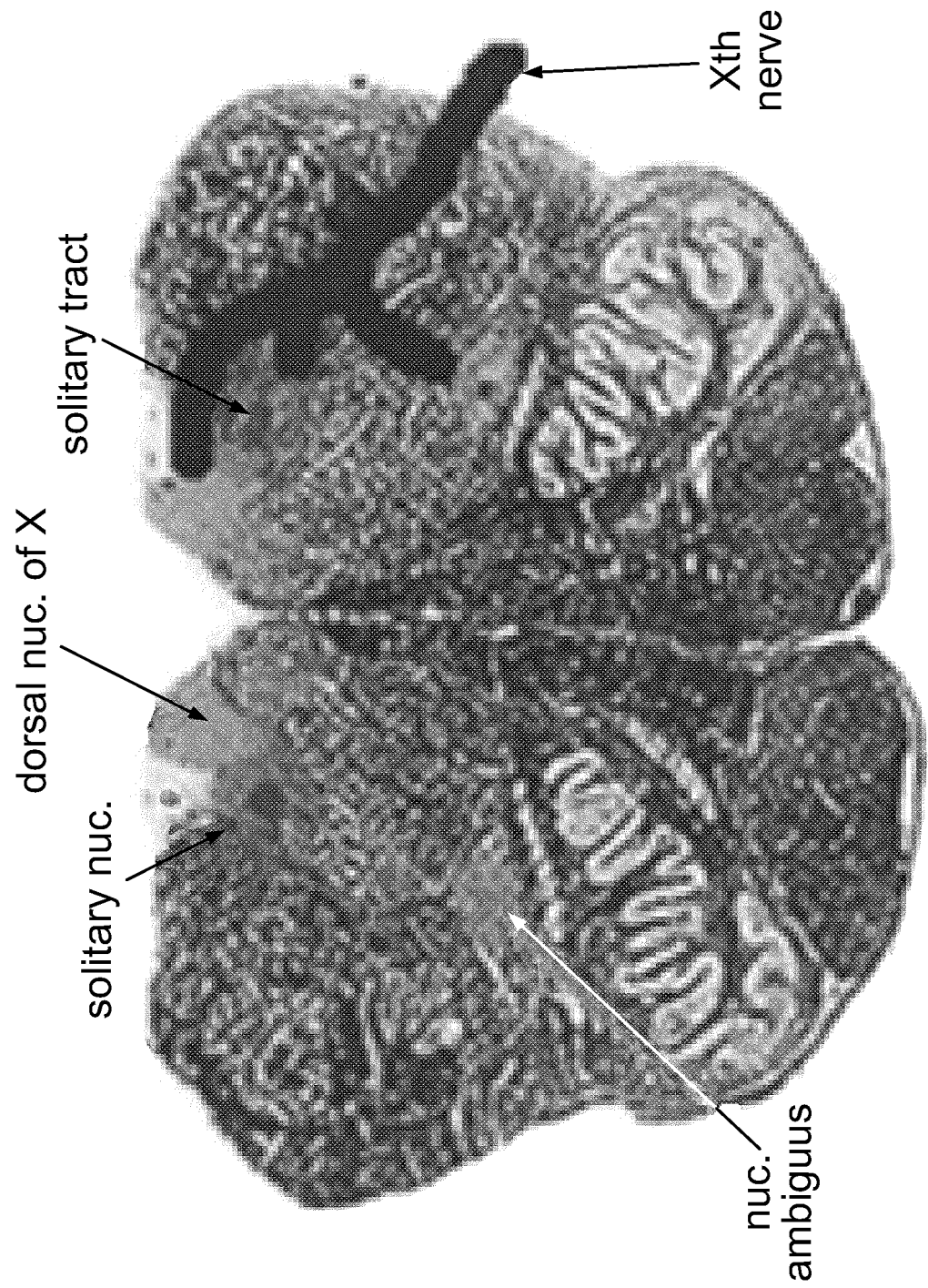
Figure 17C:
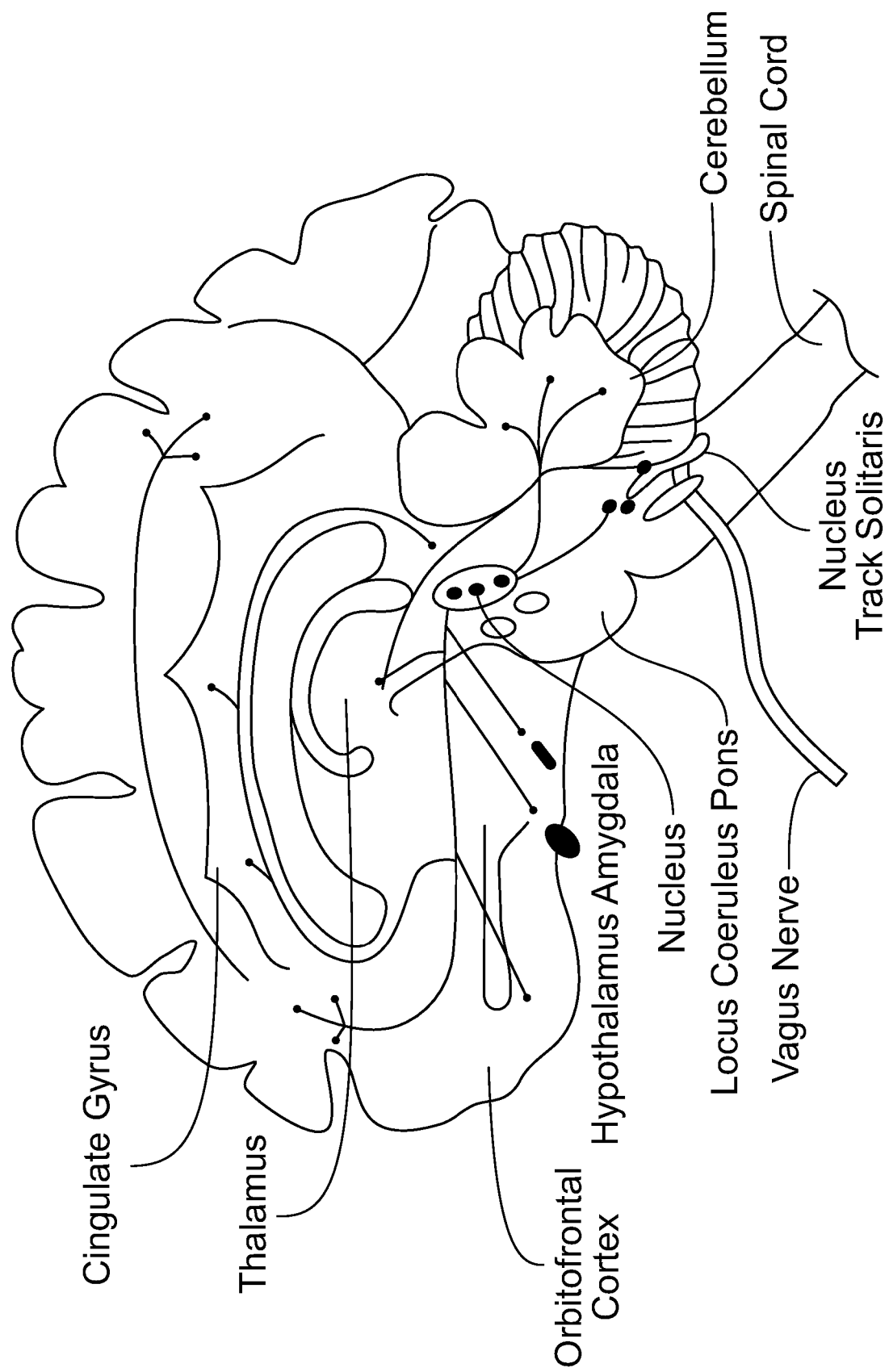

FIGS. 17A-C depict the anatomy and projections of the vagus nerve, and the implant locations of for the system.

Figure 18:
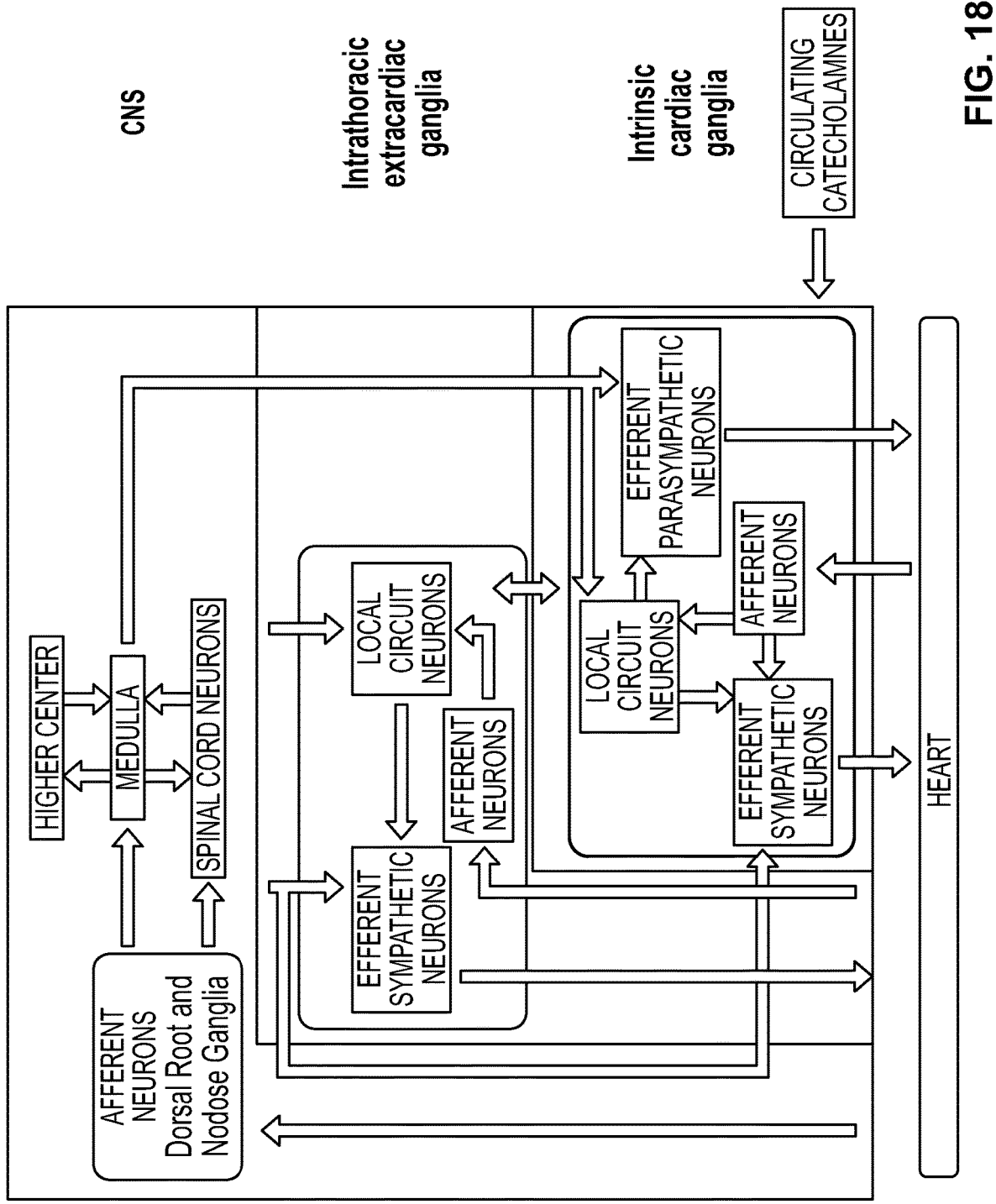

FIG. 18 depicts a cardiocentric view of the autonomic neuronal hierarchy that coordinates regional cardiac indexes as they related to the CNS.

Figure 19:
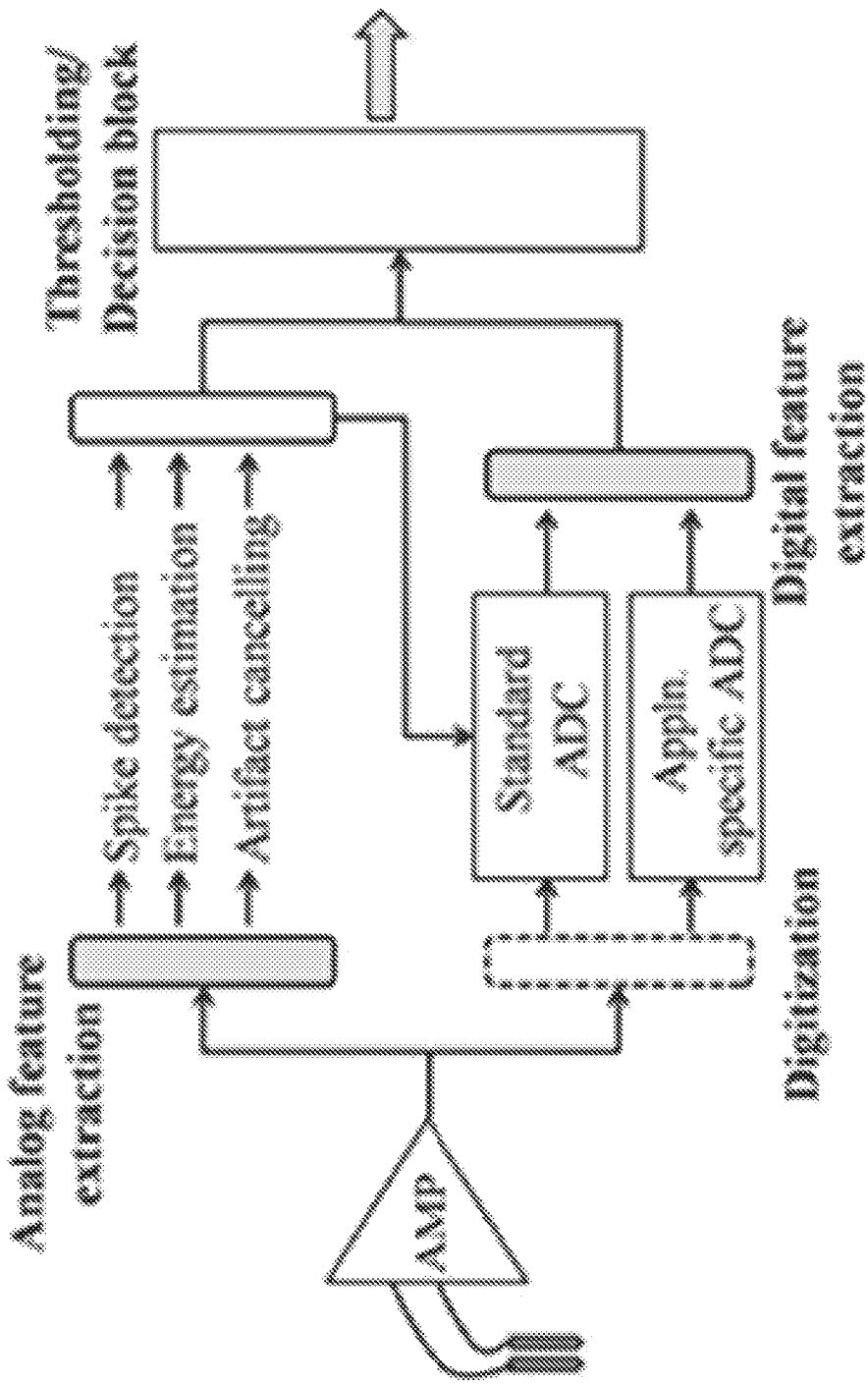

FIG. 19 shows a block diagram of the possible feature extraction schemes that can be applied to implantable medical devices.

Figure 20:
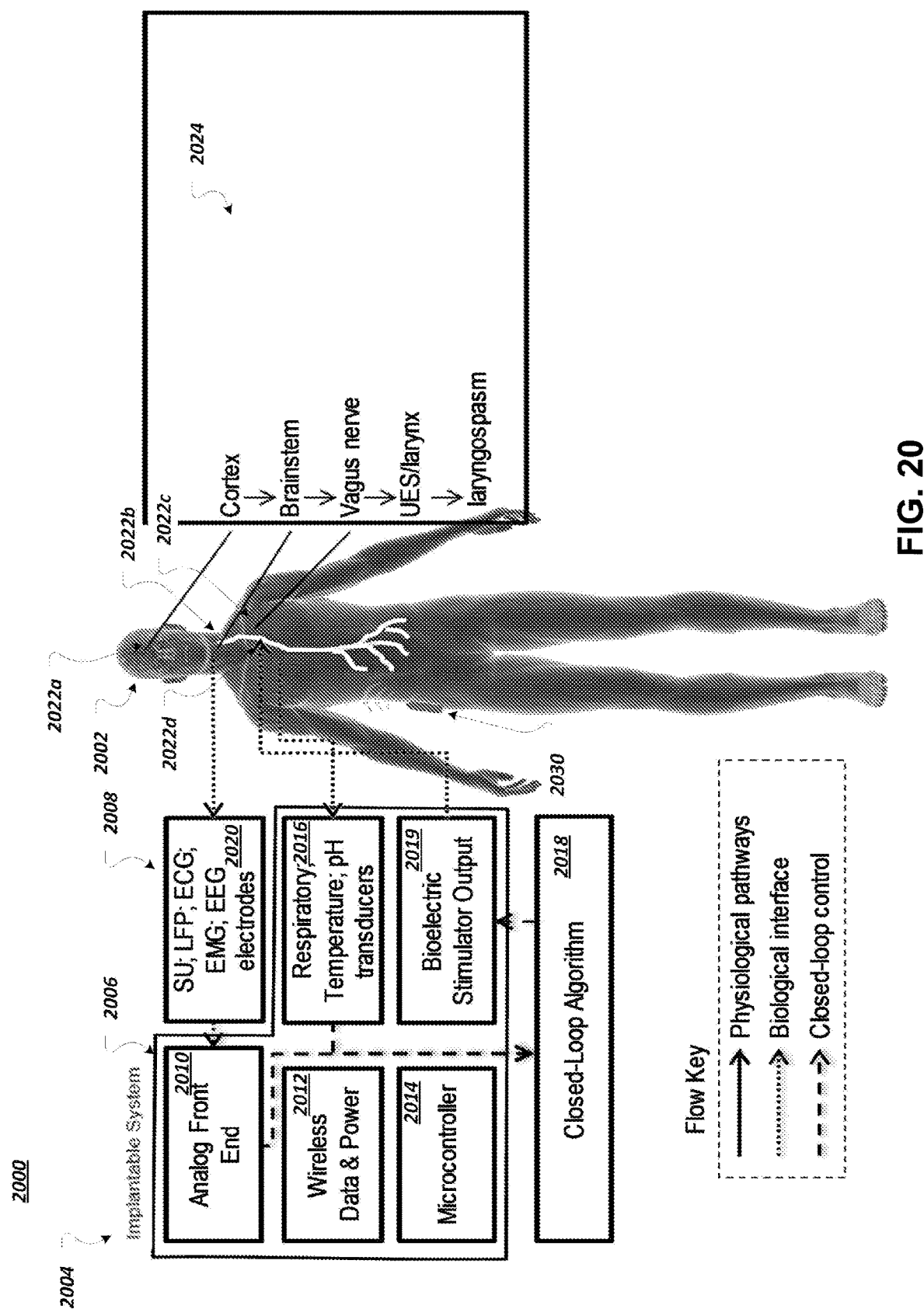

FIG. 20 depicts an example system in which an implantable system is configured for the treatment of epilepsy in a patient.

Figure 21:
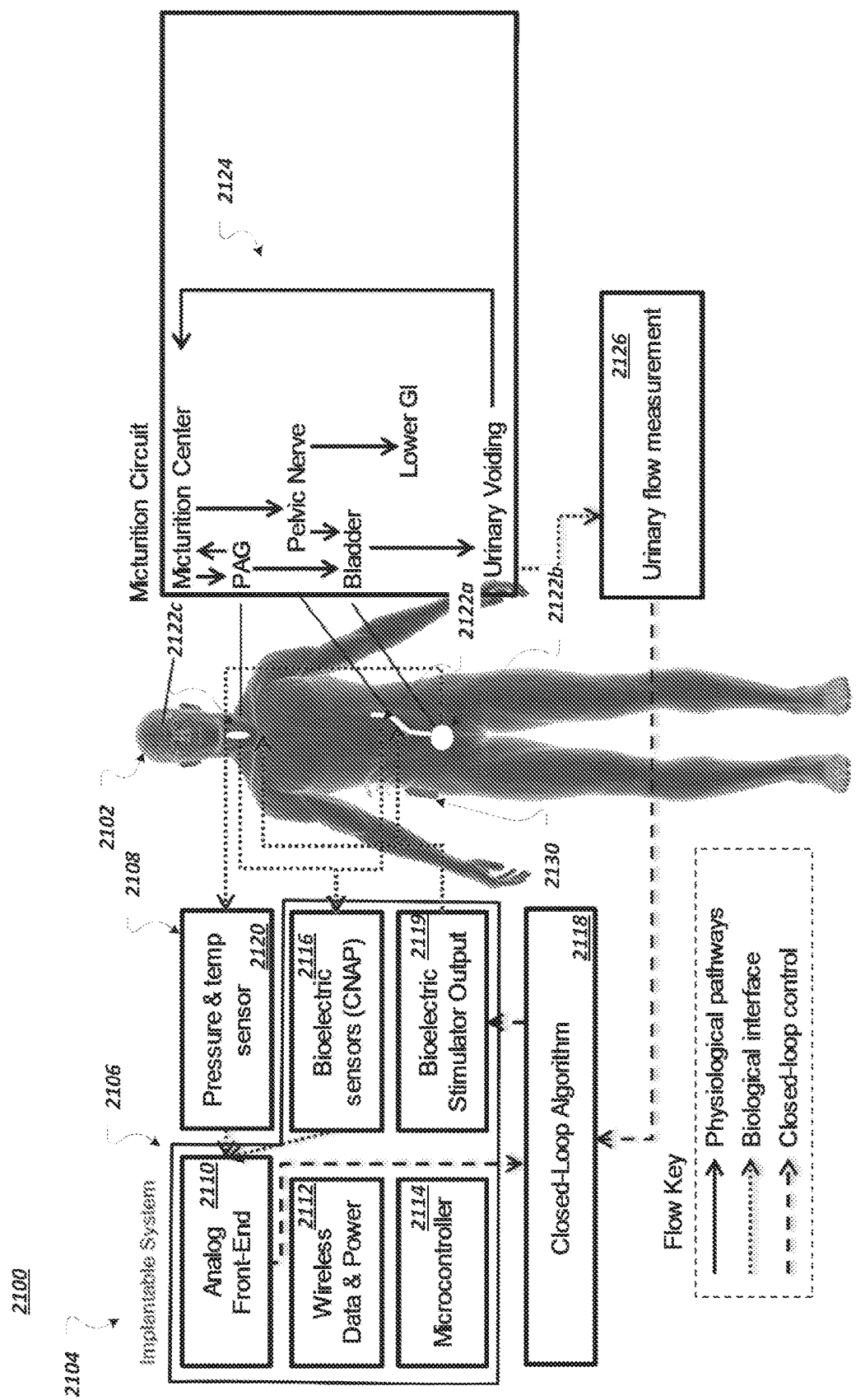

FIG. 21 depicts an example system in which an implantable system is configured for the treatment of urinary incontinence in a patient.

Figure 22:
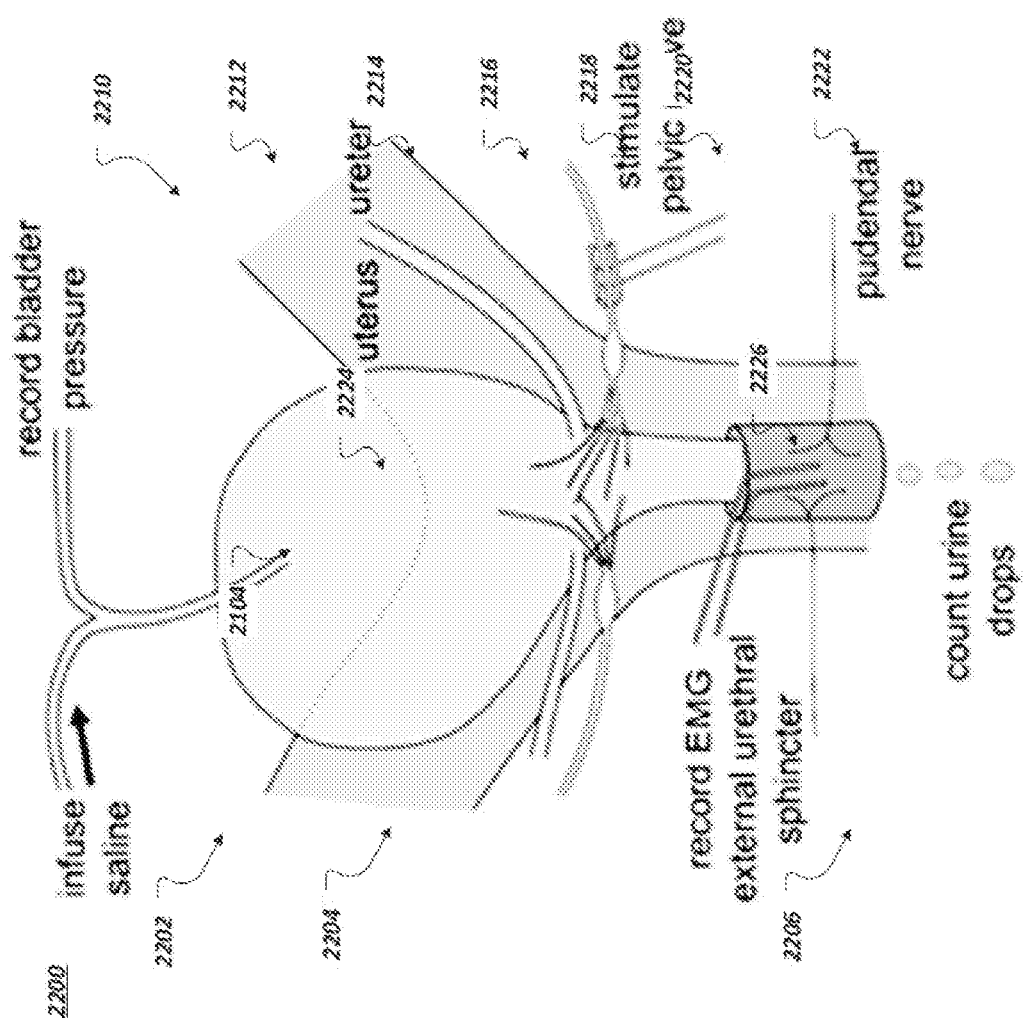

FIG. 22 shows the anatomical relationship between pelvic nerve and bladder and the localization of sensors and electrodes placed in the bladder, external urethral sphincter and pelvic nerve.

Figure 23:
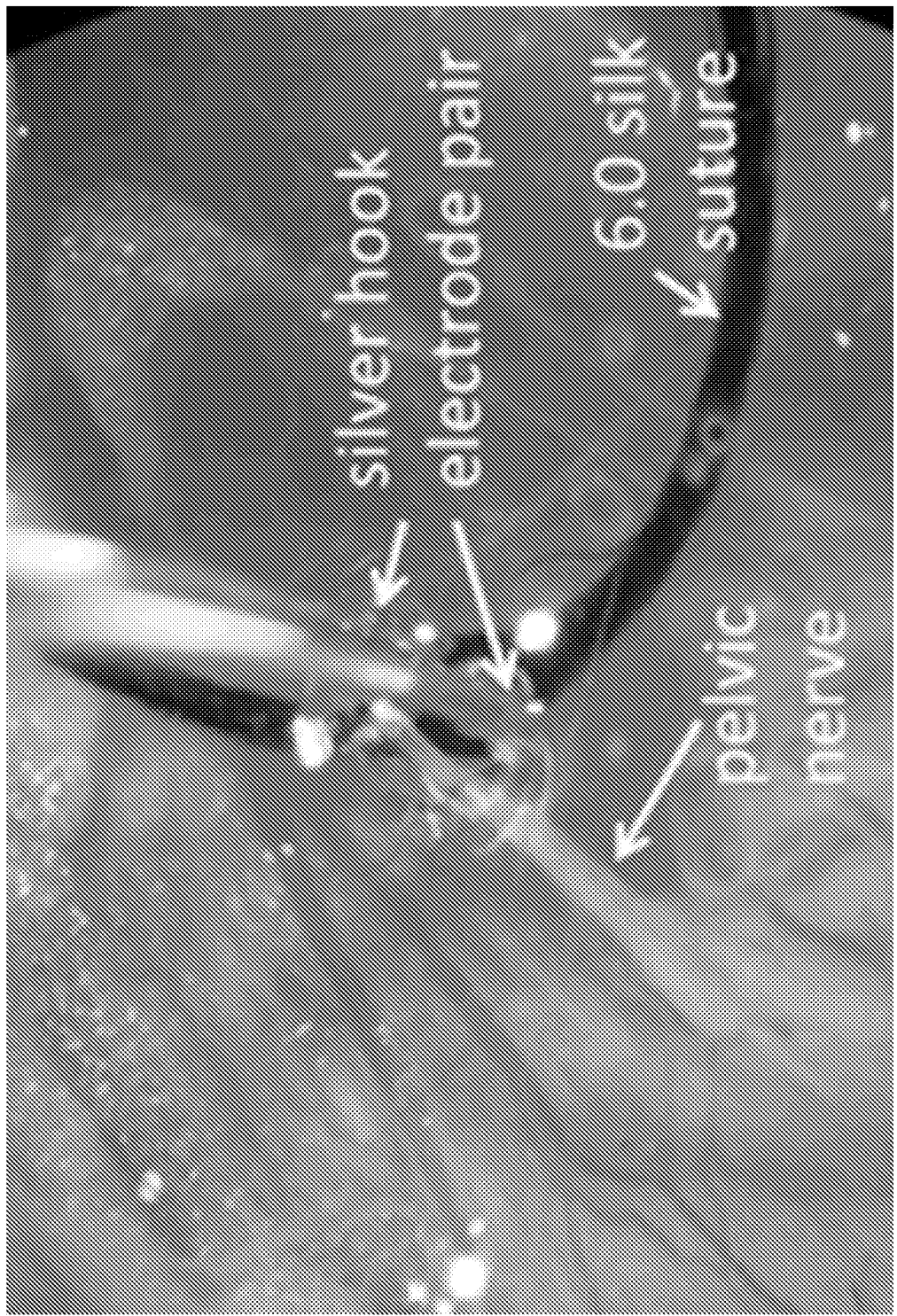

FIG. 23 shows example silver hook electrode assemblies used for stimulation and recording from the pelvic nerve.

FIG. 24 shows an example of cuff electrodes used for stimulation and recording from the pelvic nerve.

FIG. 25 depicts example testing results of pelvic nerve stimulation.

Figure 26A:
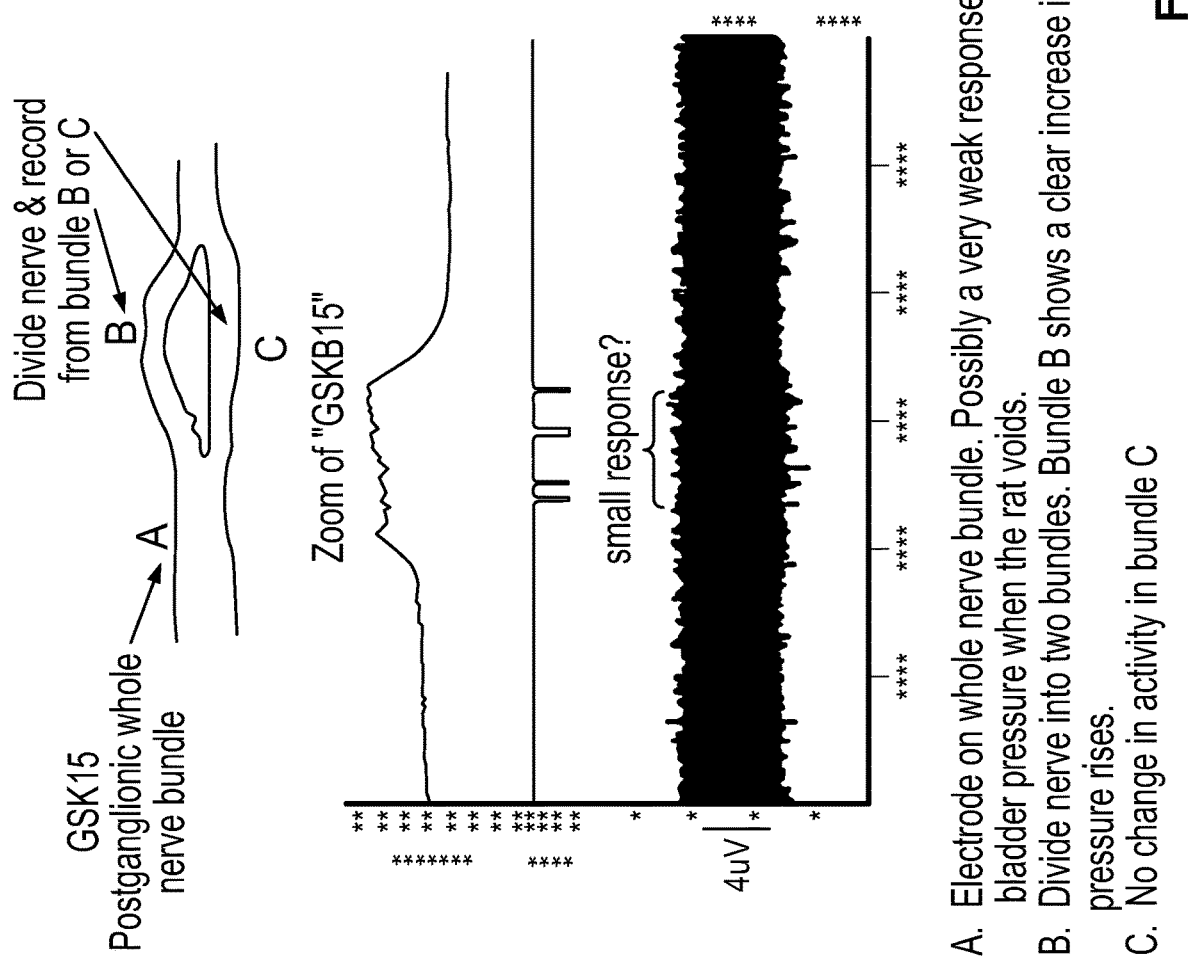
Figure 26C:
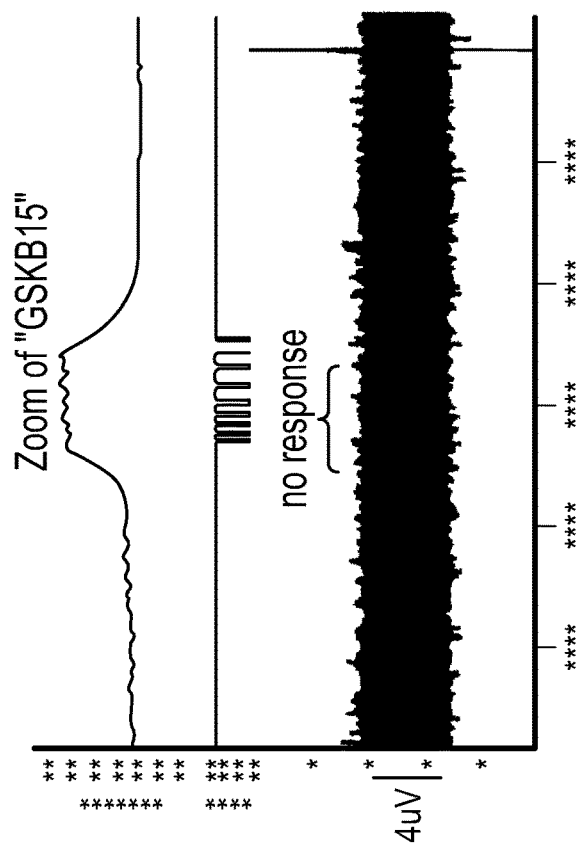

FIG. 26 depicts example testing results from monitoring the whole pelvic nerve bundle and portions thereof.

Figure 27:
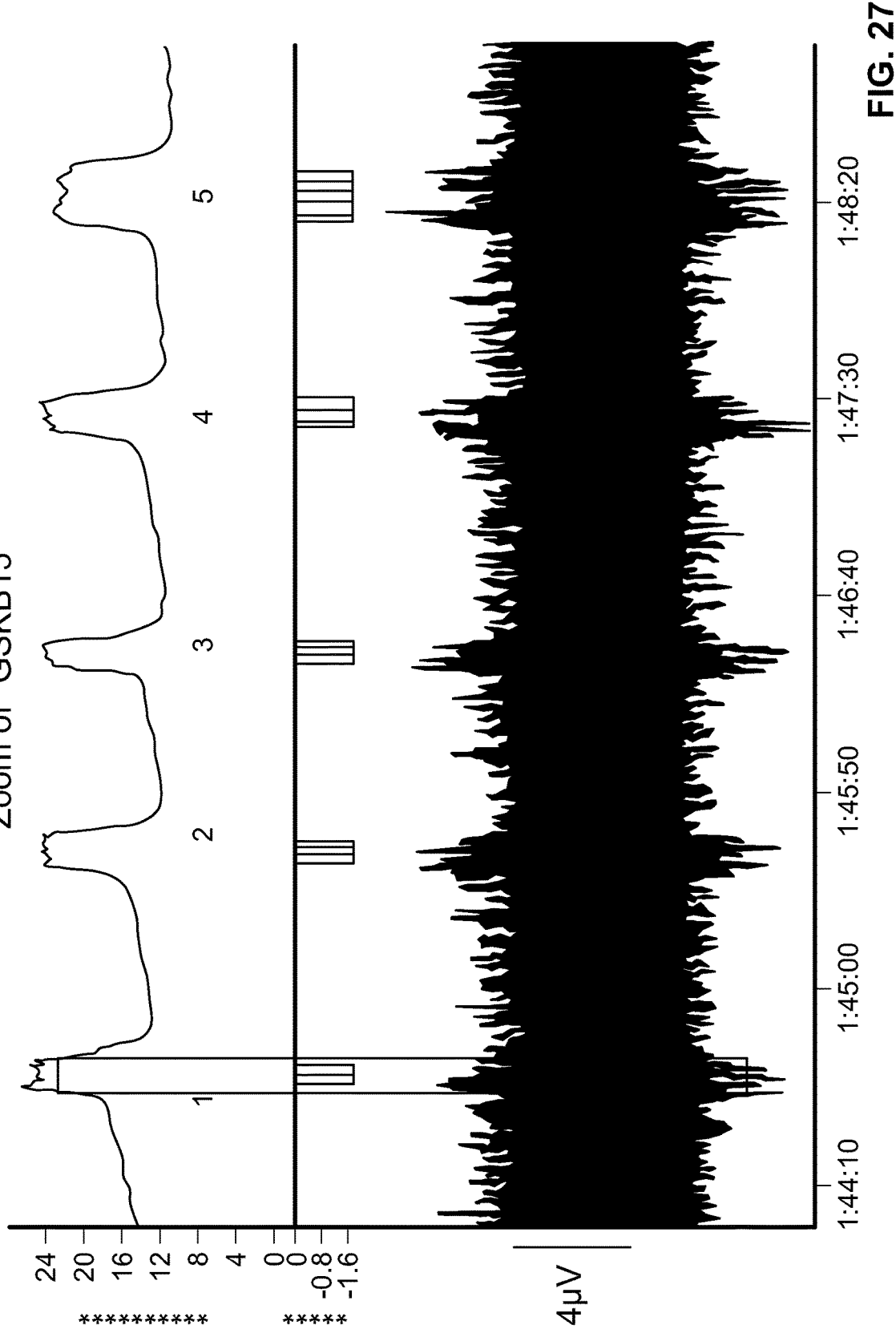

FIG. 27 depicts example testing results from monitoring portions of the whole pelvic nerve bundle.

Figure 28:
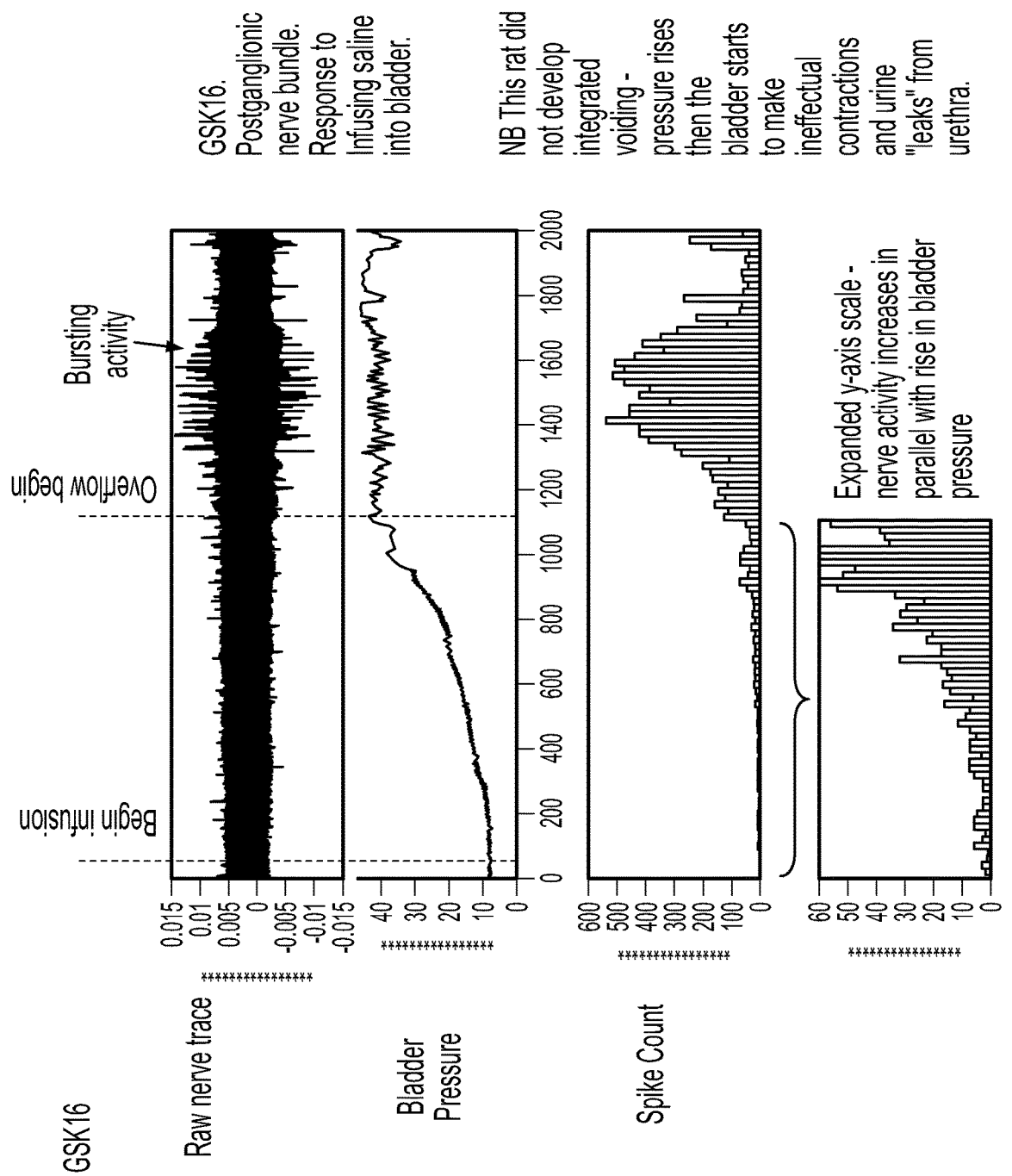

FIG. 28 depicts example testing results correlating bladder pressure and nerve activity.

FIG. 29 depicts example testing results from stimulation of the pelvic nerve using high frequency charge balanced alternating current as it relates to bladder pressure signaling an imminent void.

Figure 30A:
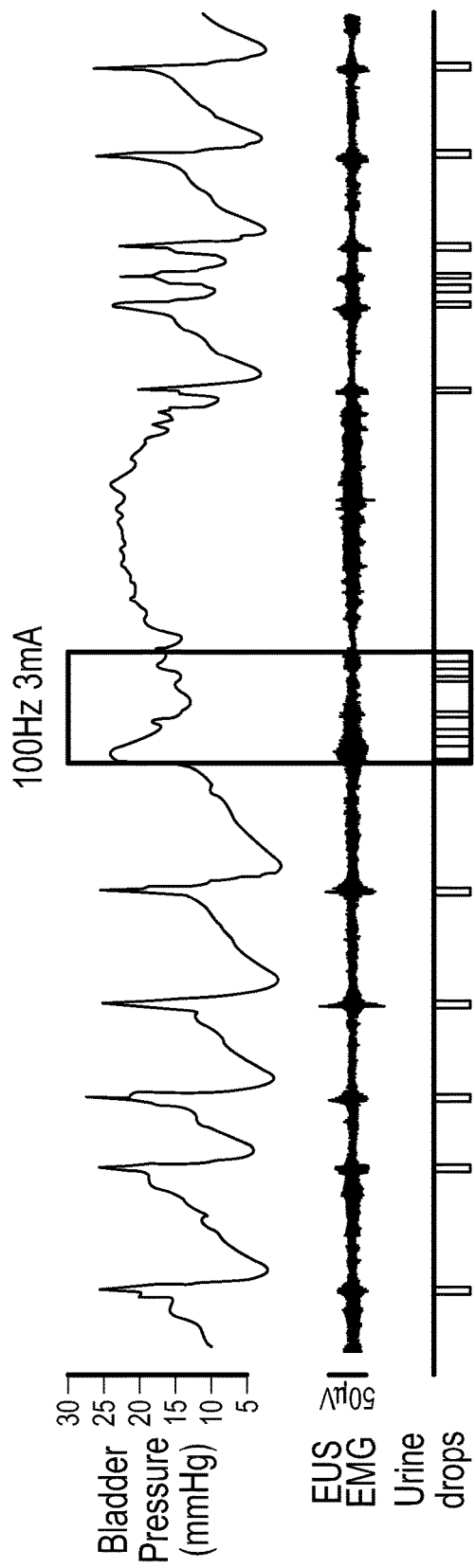
Figure 30B:
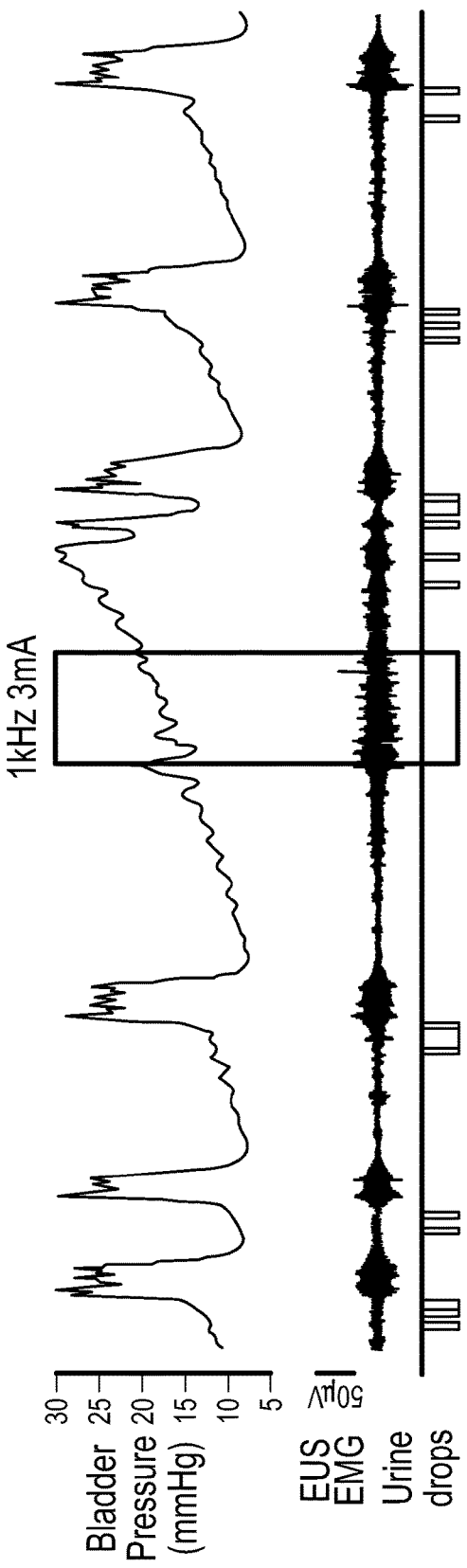

FIG. 30 depicts example testing results showing the frequency dependence between the effect of pelvic nerve stimulation on voiding.

FIG. 31 depicts example results of an experiment testing a mechanism underlying pelvic nerve-evoked suppression of voiding.

FIG. 32 depicts an example results of experiments testing ligating the pelvic nerve distal to the stimulating electrode.

Figure 33:
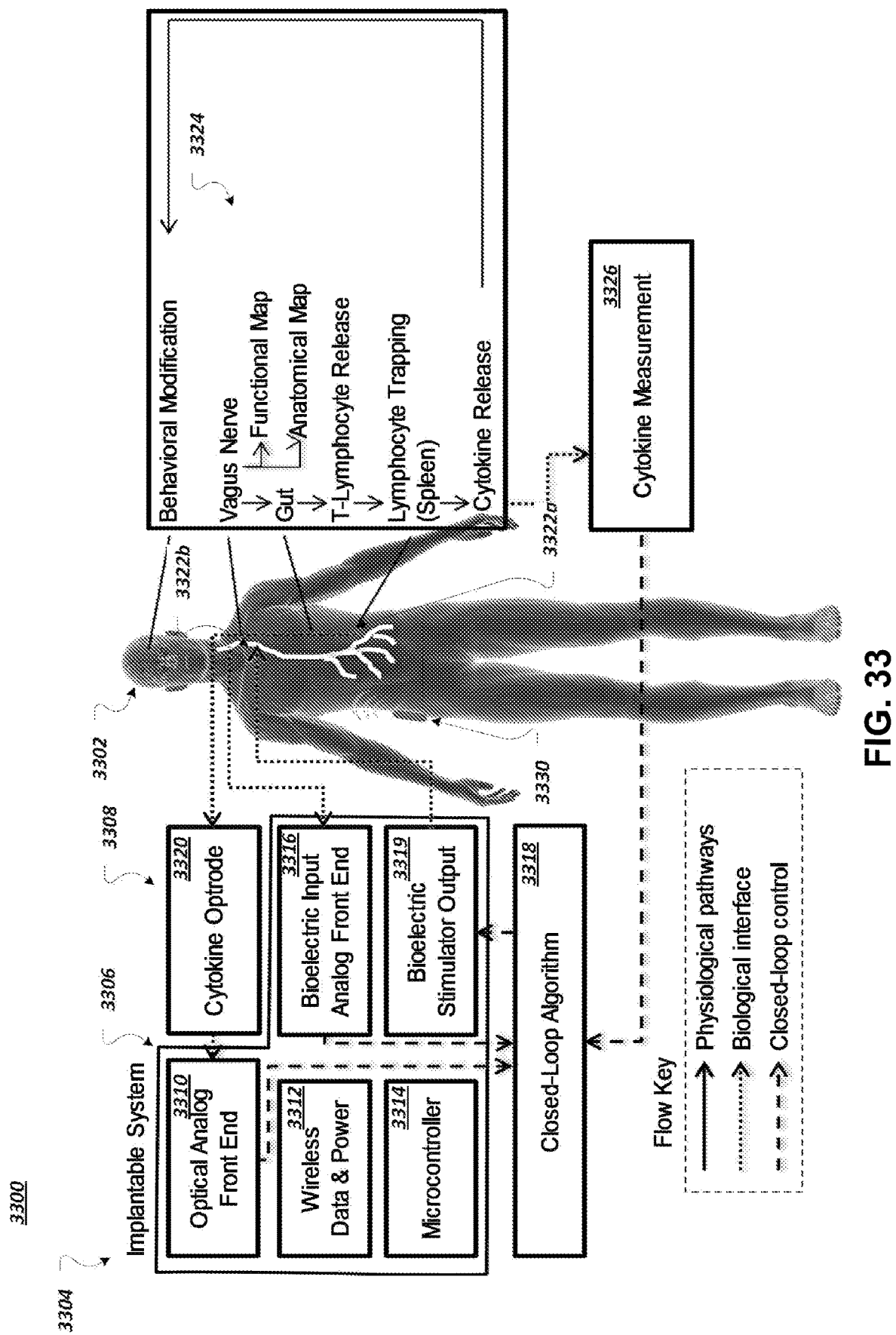

FIG. 33 depicts an example system in which an implantable system is configured for the treatment of inflammation reflex in a patient.

Figure 34:
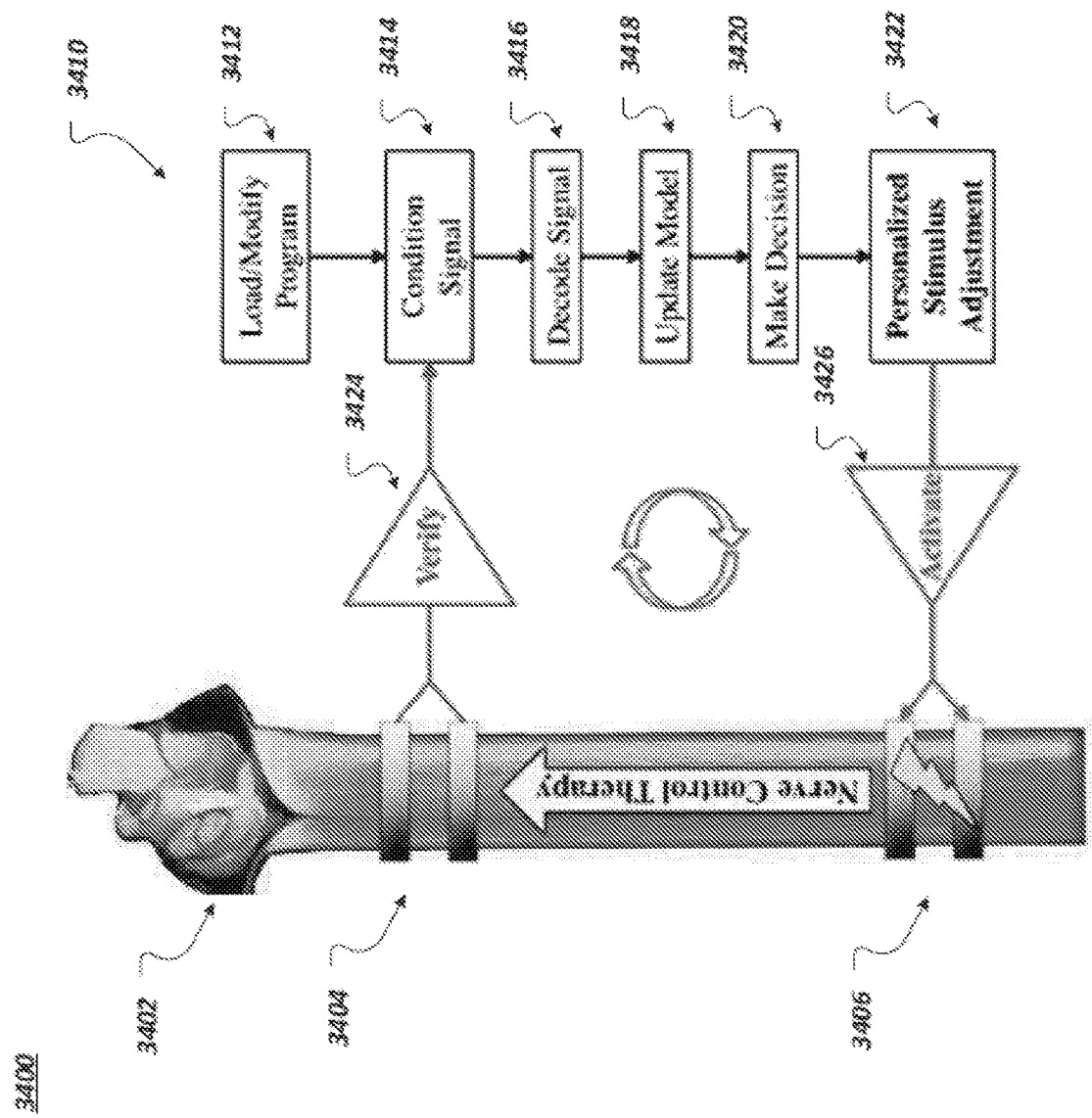

FIG. 34 depicts an example system in which the control device provides simultaneous stimulation and readings on a nerve as part of a closed loop control algorithm.

Figure 35:
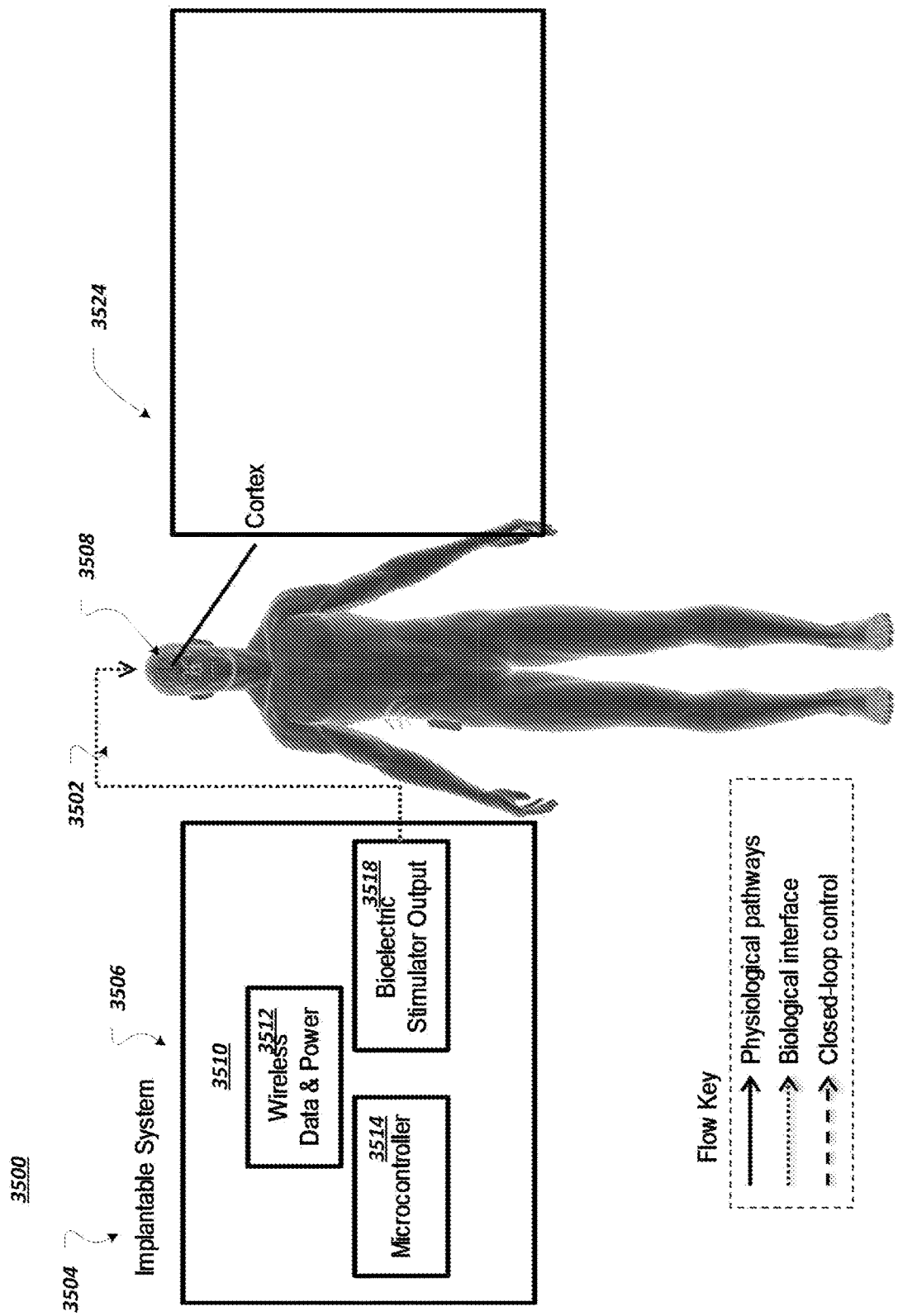

FIG. 35 depicts an example system in which an implantable system is configured for the treatment of alcoholism in a patient.

Figure 36:
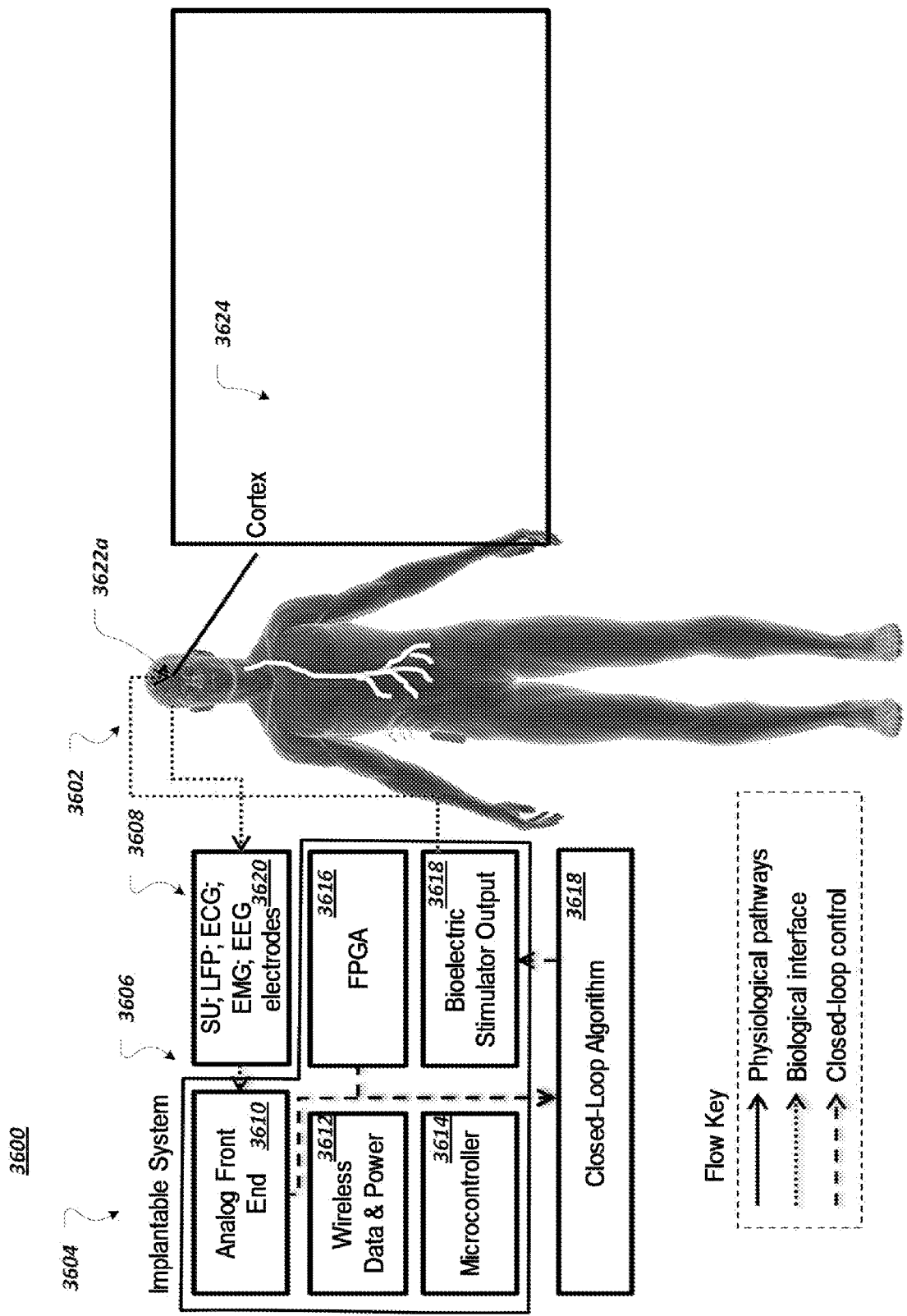

FIG. 36 depicts an example implantable system configured for preclinical trials related to subjects with Parkinson's disease in a patient.

Figure 37:
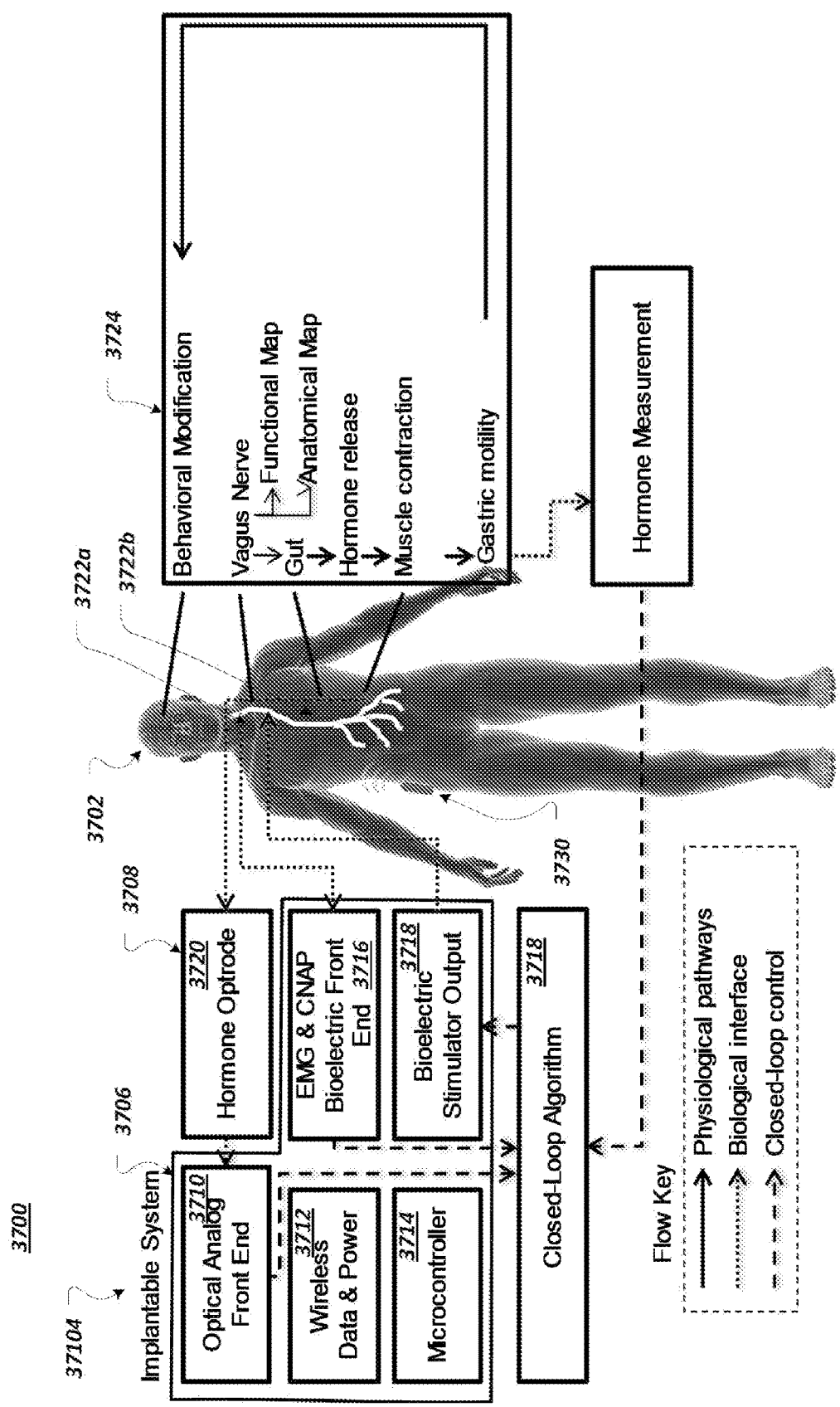

FIG. 37 depicts an example system to treat gastric disorders.

Figure 38:
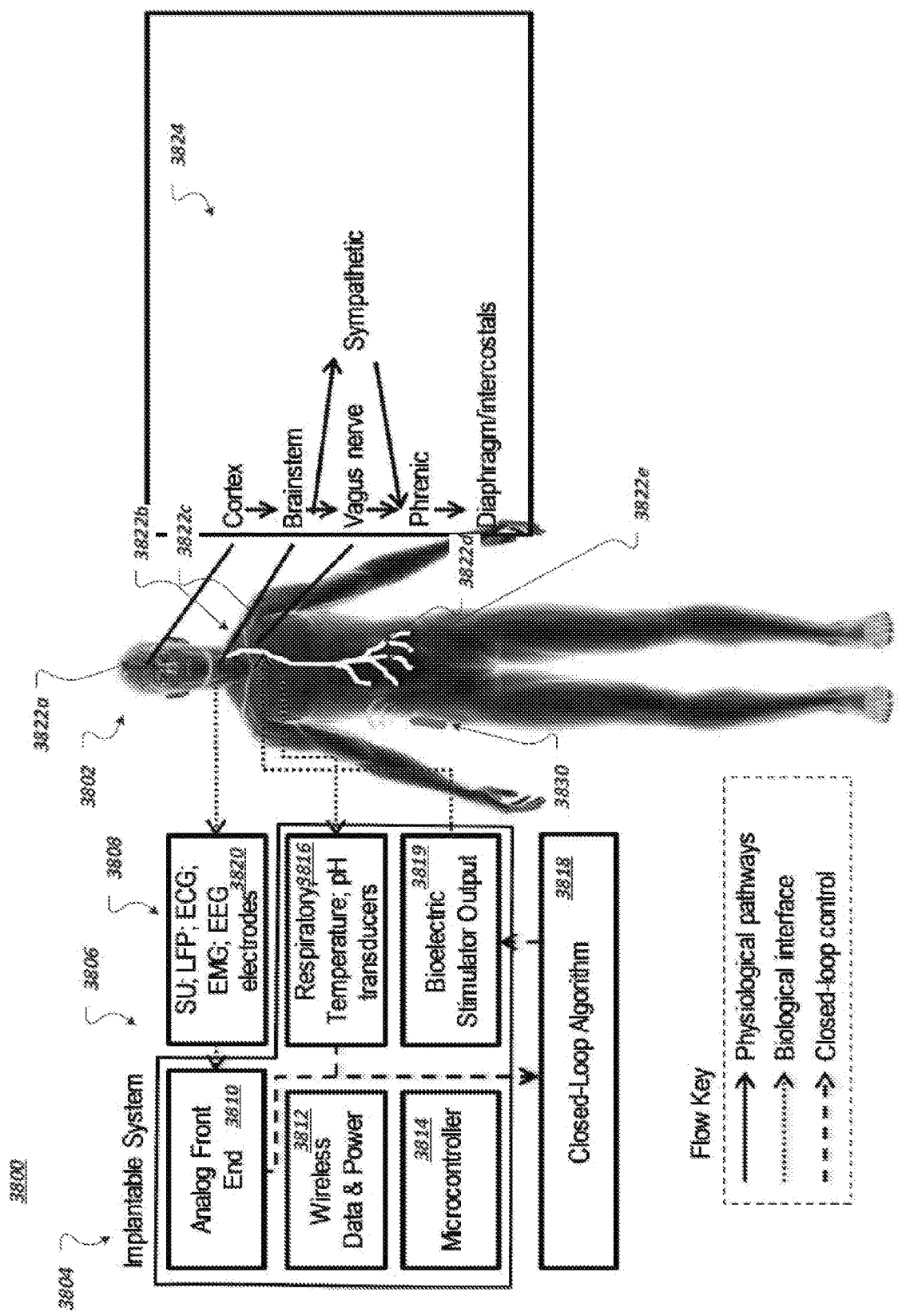

FIG. 38 depicts an example system in which an implantable system is configured for the treatment of addiction in a patient.

Figure 39A:
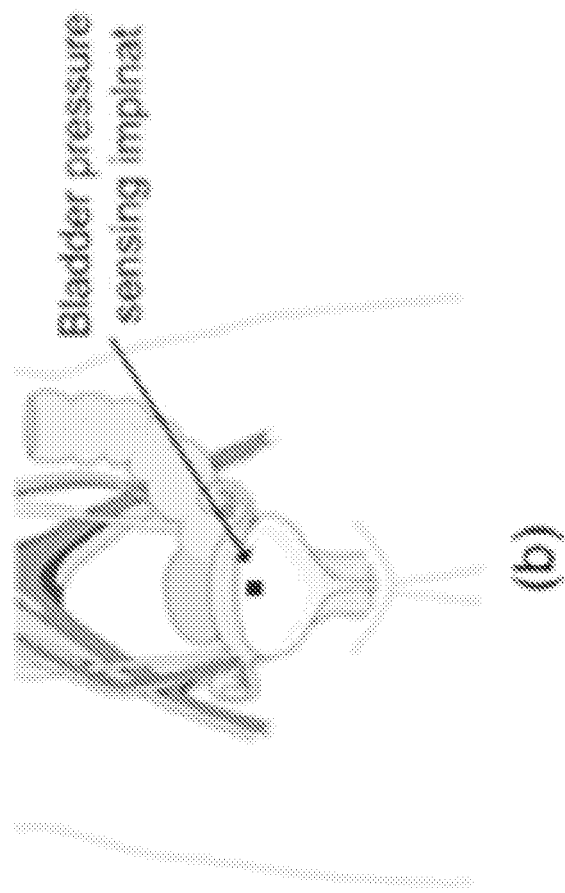
Figure 39B:
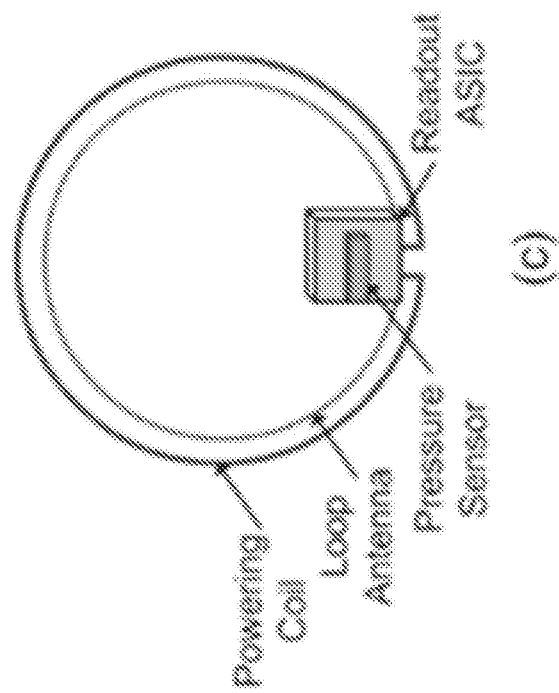

FIGS. 39A-B are conceptual diagrams of the target implant location and the readout ASIC: (A) Bladder pressure monitor system. (B) Readout full system implant comprises a readout ASIC, an antenna and a powering coil.

Figure 40:
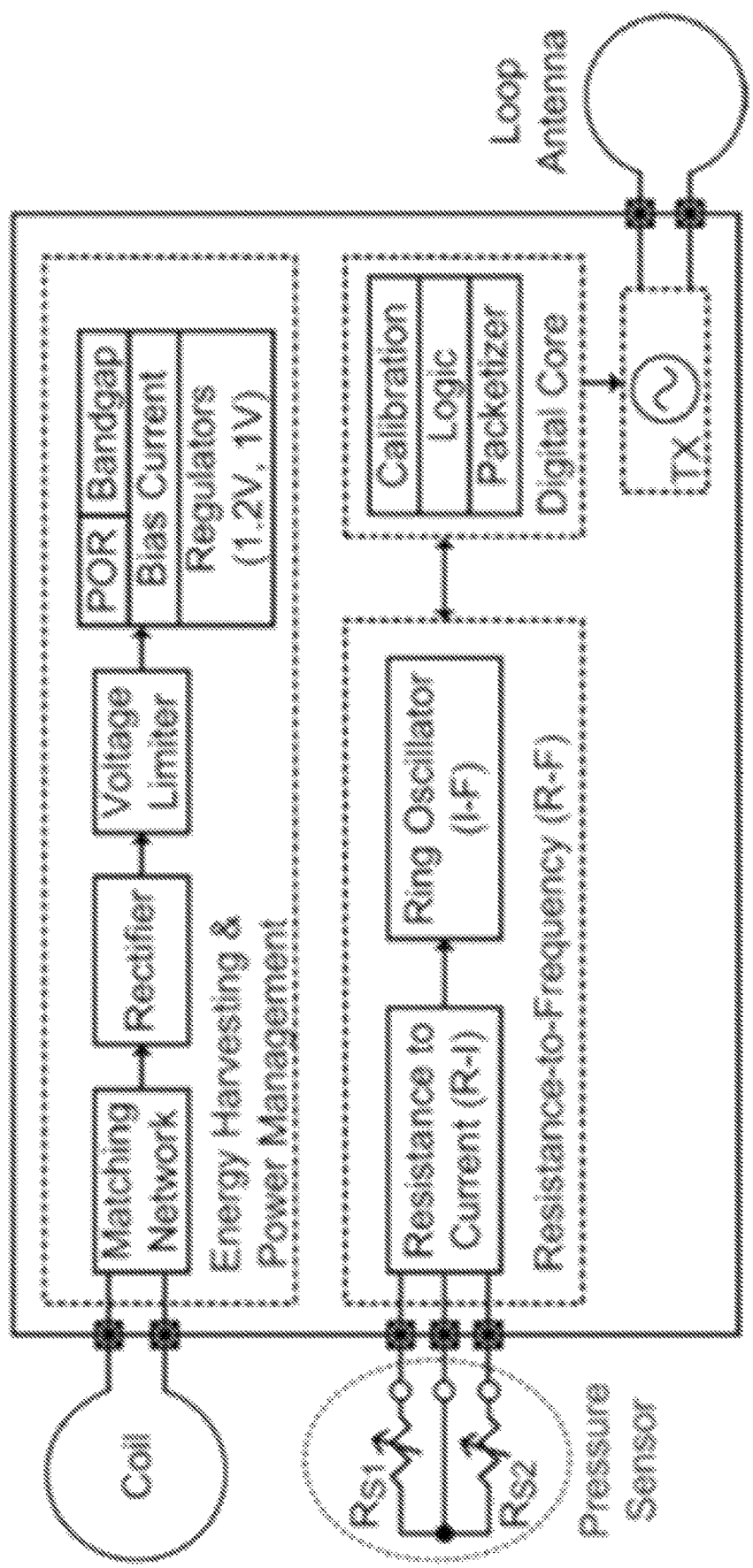

FIG. 40 is a block diagram of the pressure-sensing system on a chip (SoC).

Figure 41:
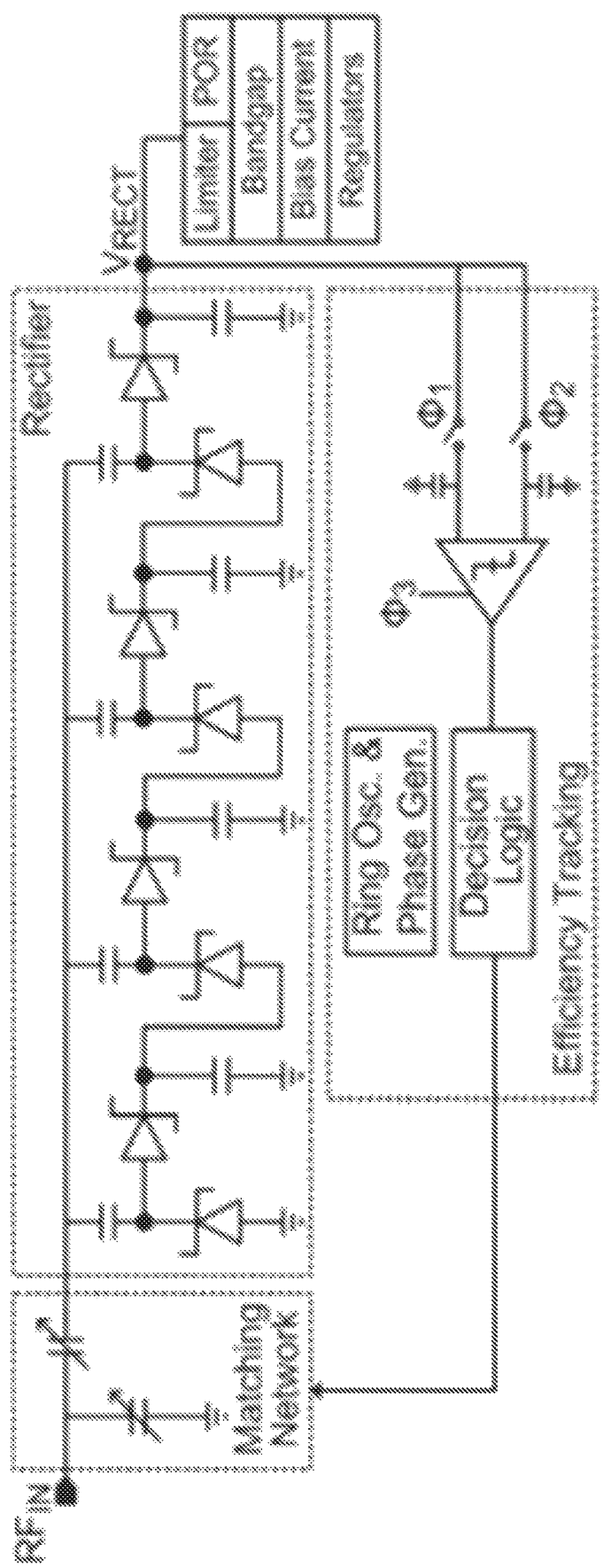

FIG. 41 is a block diagram of energy harvesting (EH) and power management subsystems.

Figure 42:
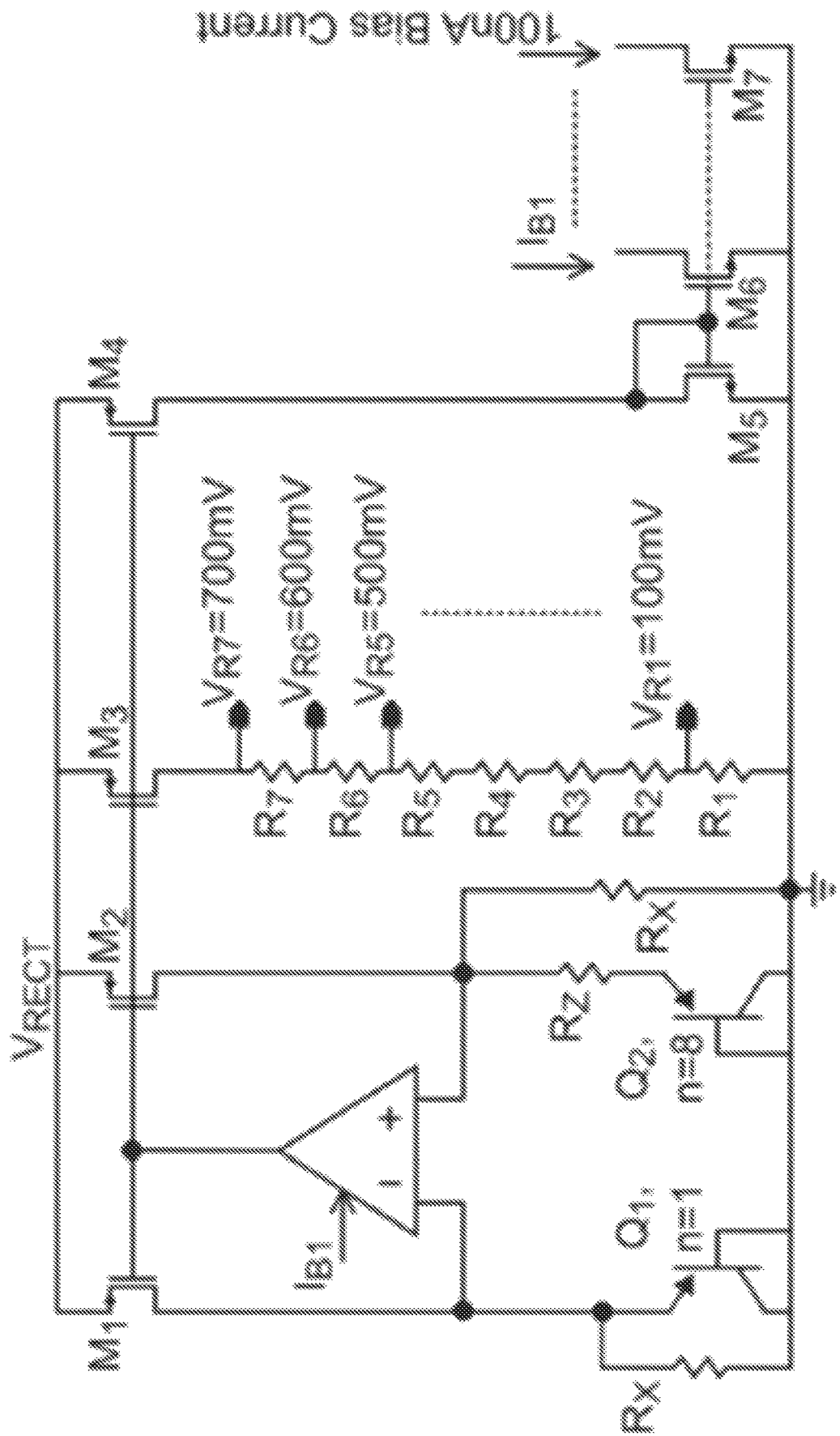

FIG. 42 is a schematic diagram of the bandgap reference to generate pseudo-differential reference voltages and bias currents for the SoC chip.

Figure 43:
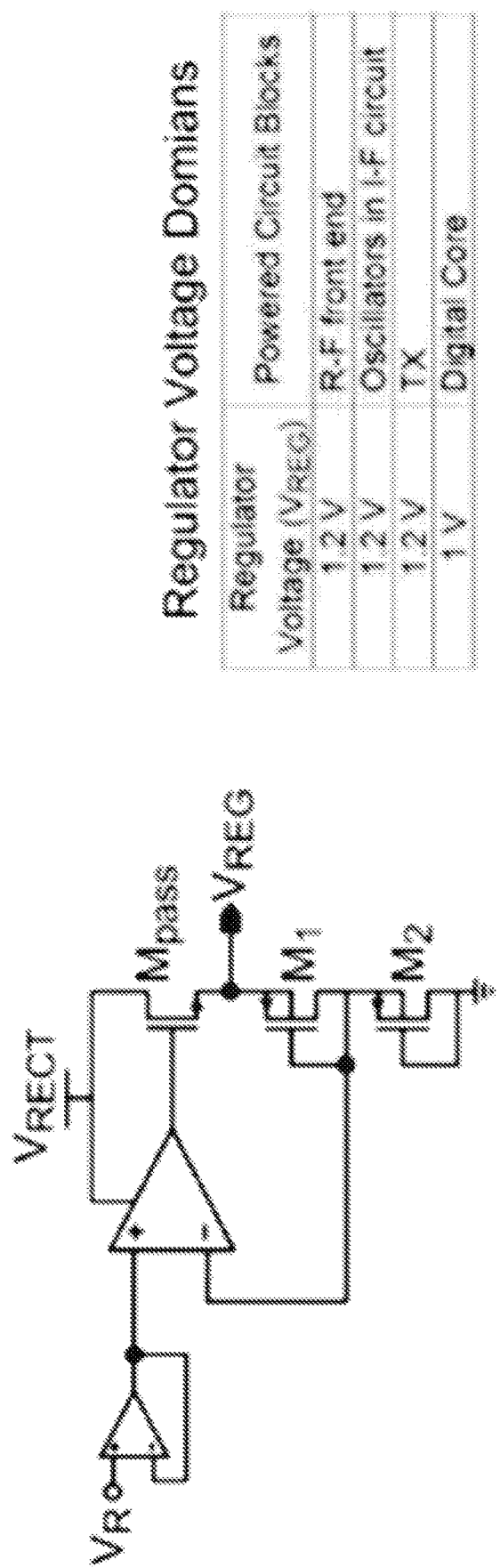

FIG. 43 is a schematic diagram of one of the four voltage regulators and their supply domains.

Figure 44:
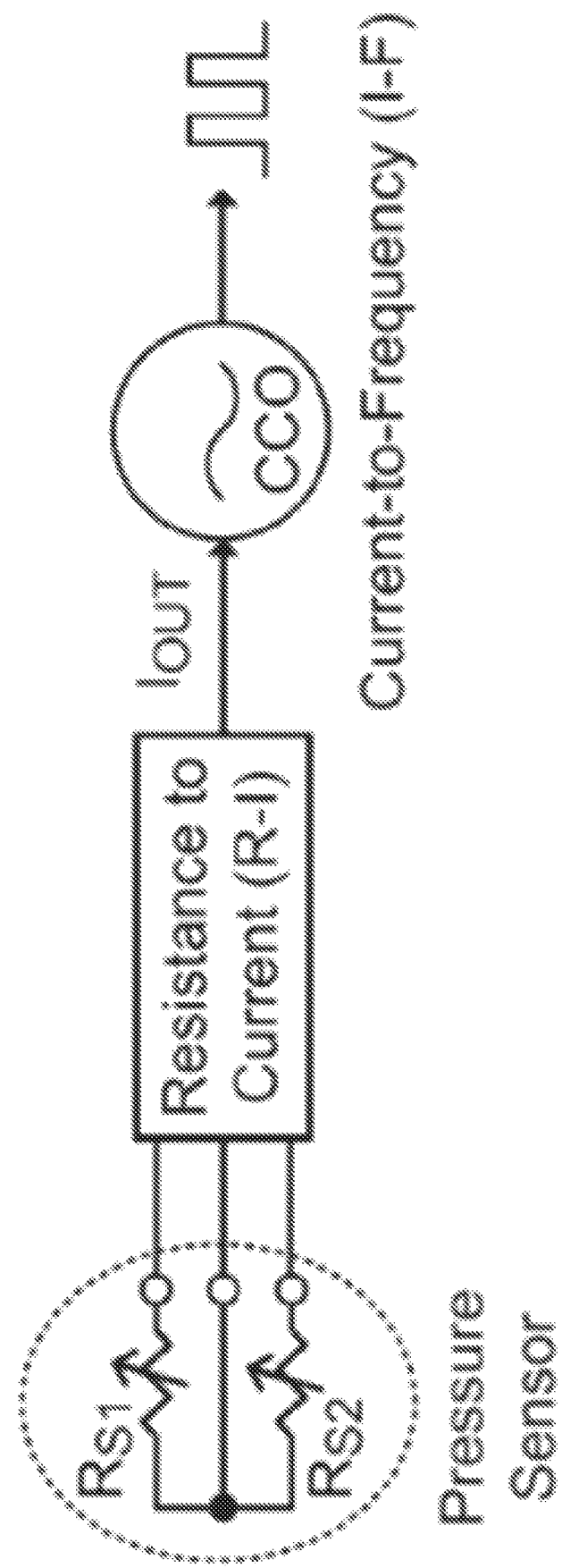

FIG. 44 is a concept diagram of the implemented R-F converter.

Figure 45:
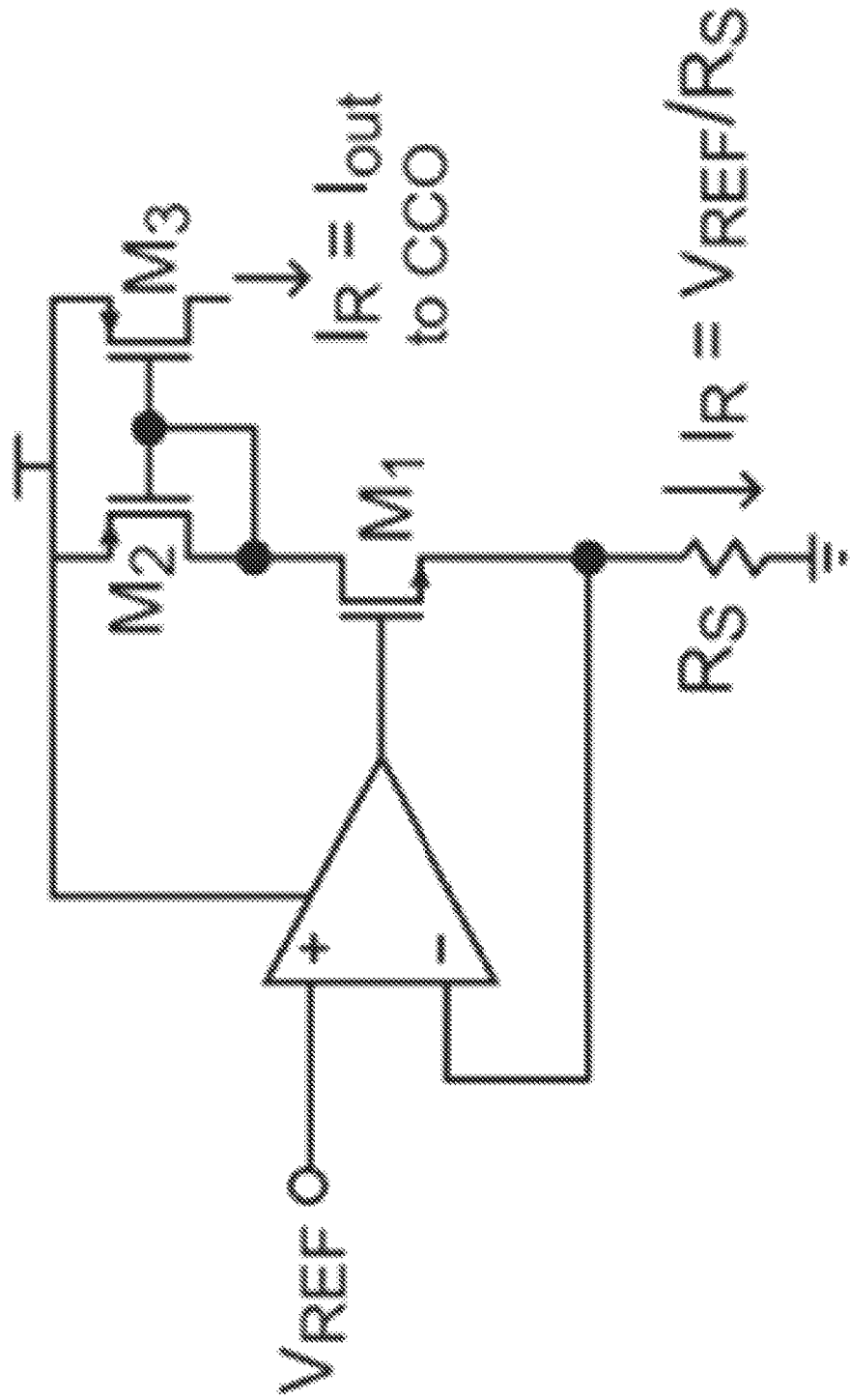

FIG. 45 is a schematic diagram of a conventional R-I converter.

Figure 46:
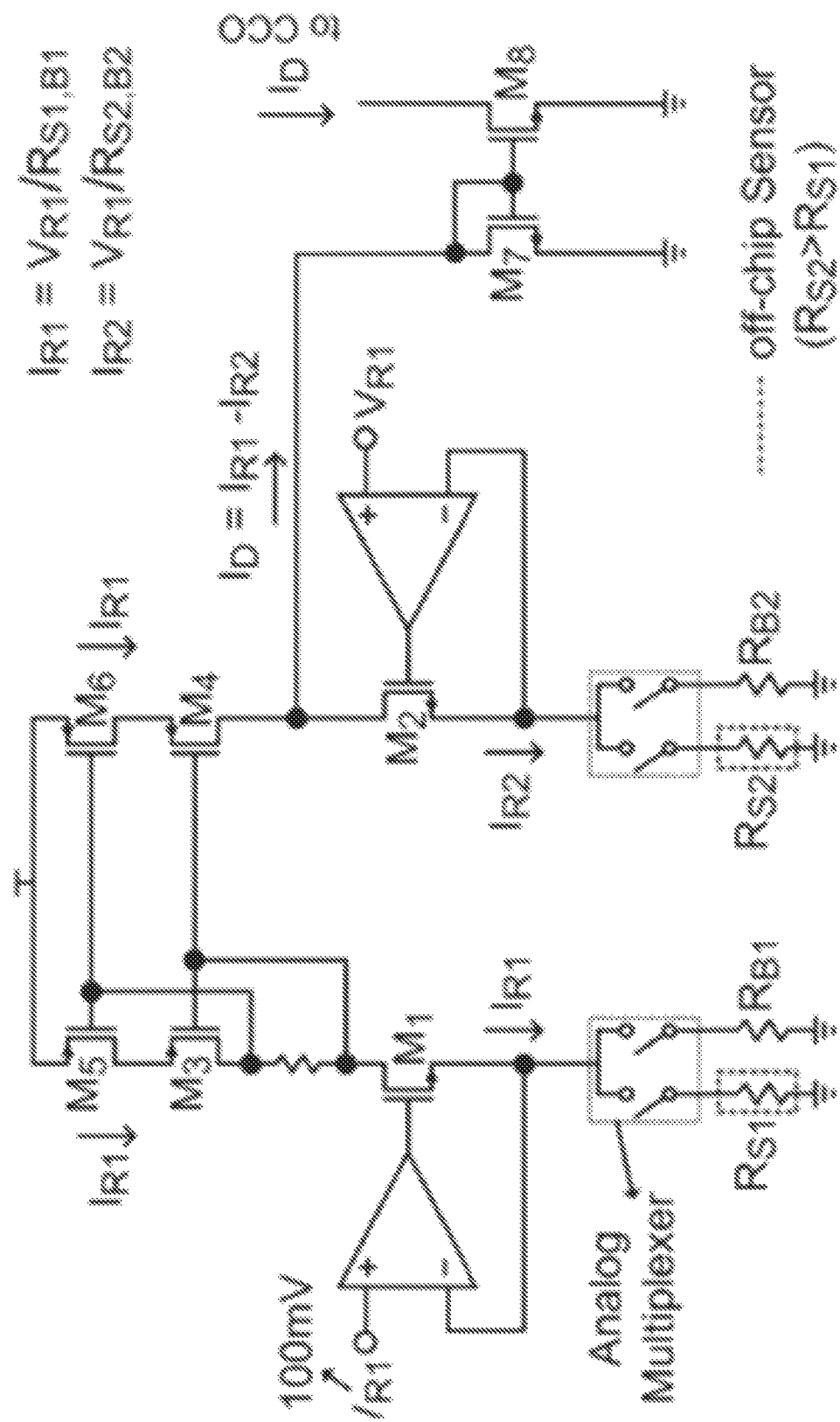

FIG. 46 is a schematic diagram of first differential R-I (R-I1) converter.

Figure 47:
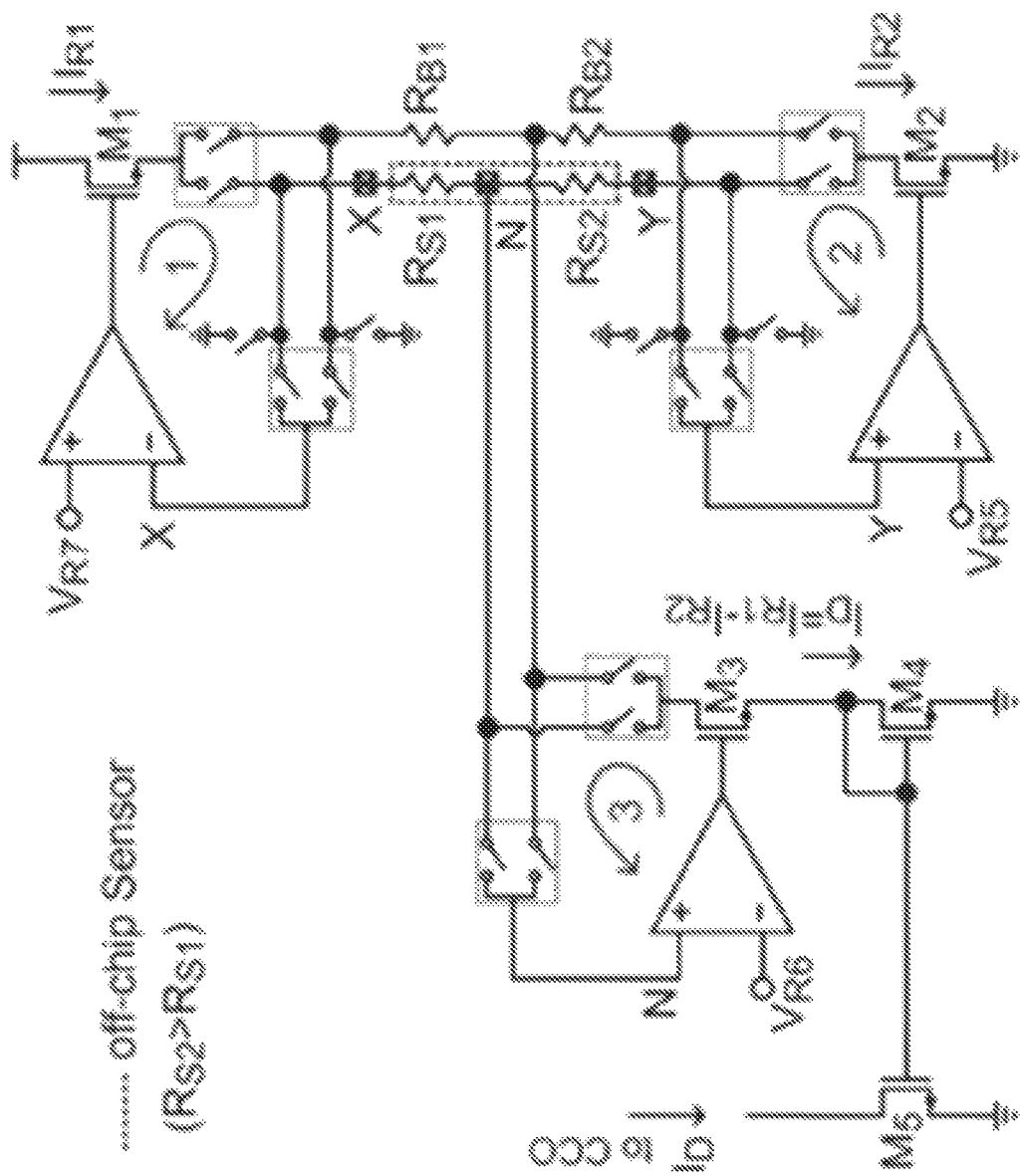

FIG. 47 is a schematic diagram of second differential R-I (R-I2) converter.

Figure 48:
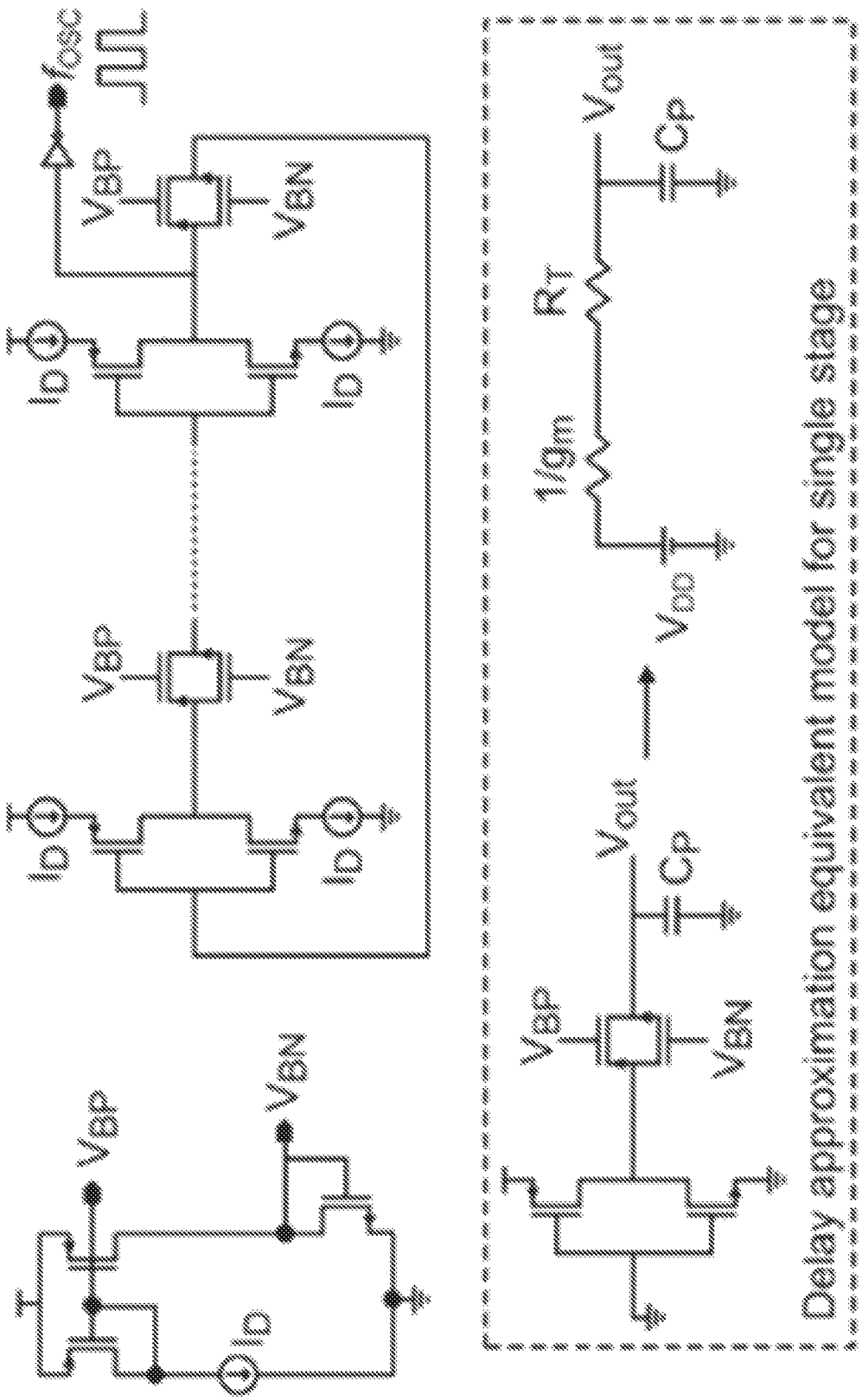

FIG. 48 is a schematic diagram of the ring oscillator, providing I-F conversion.

Figure 49:
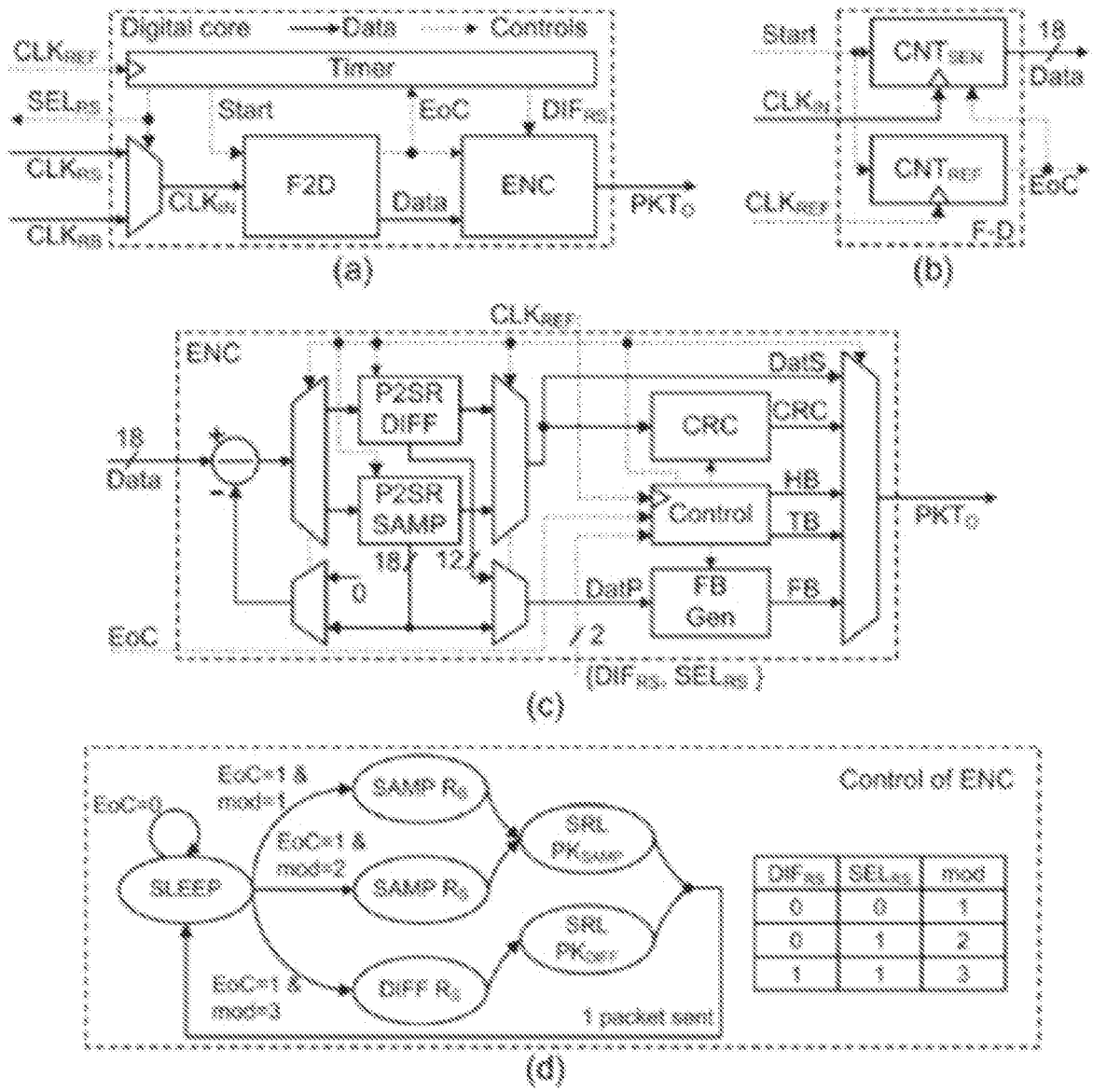

FIG. 49 is a digital Core: (a) Block diagram. (b) F-D converter. (c) Block diagram of encoder (ENC). (d) State diagram of ENC.

Figure 50:
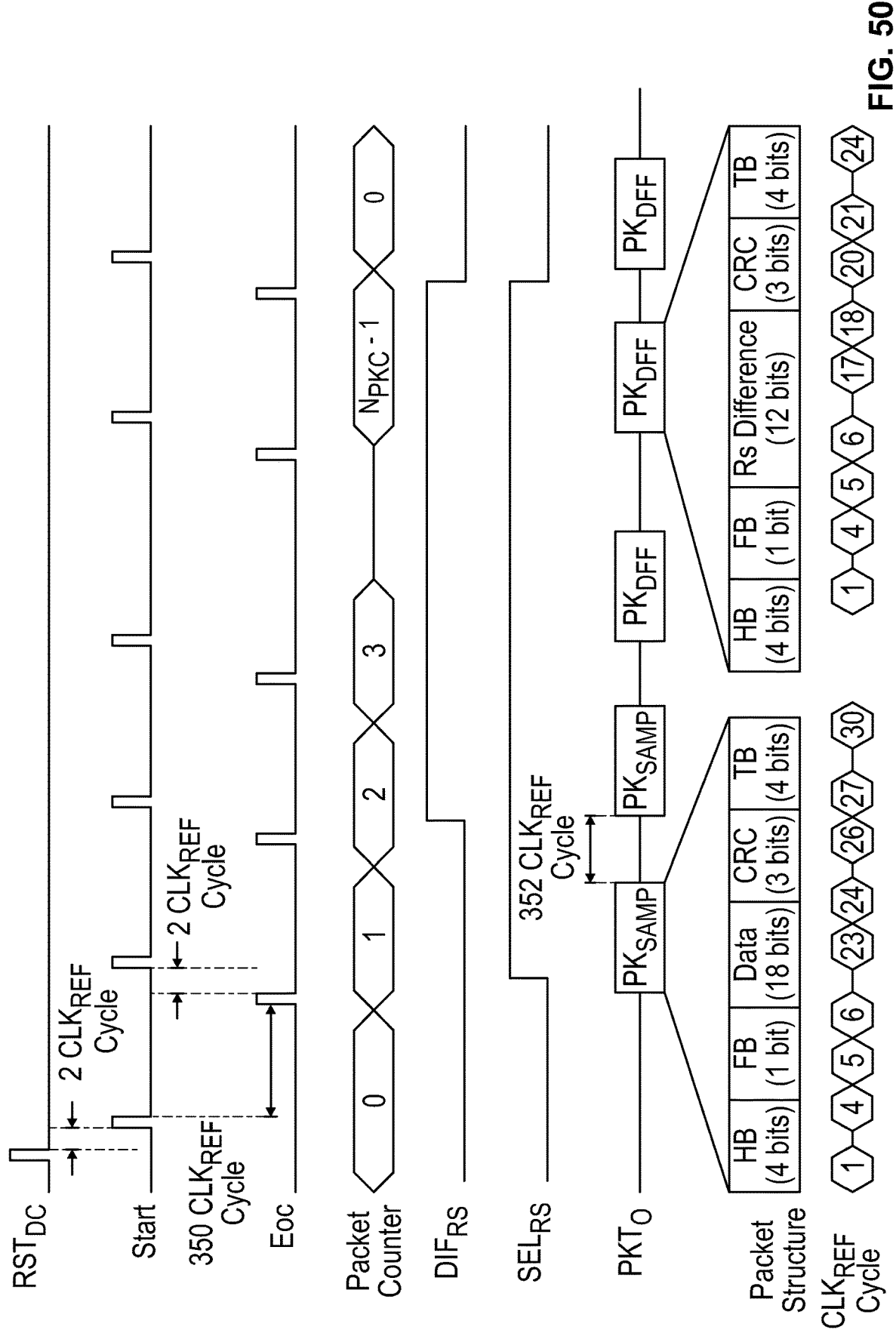

FIG. 50 is a timing diagram of digital core and the packet structure.

Figure 51:
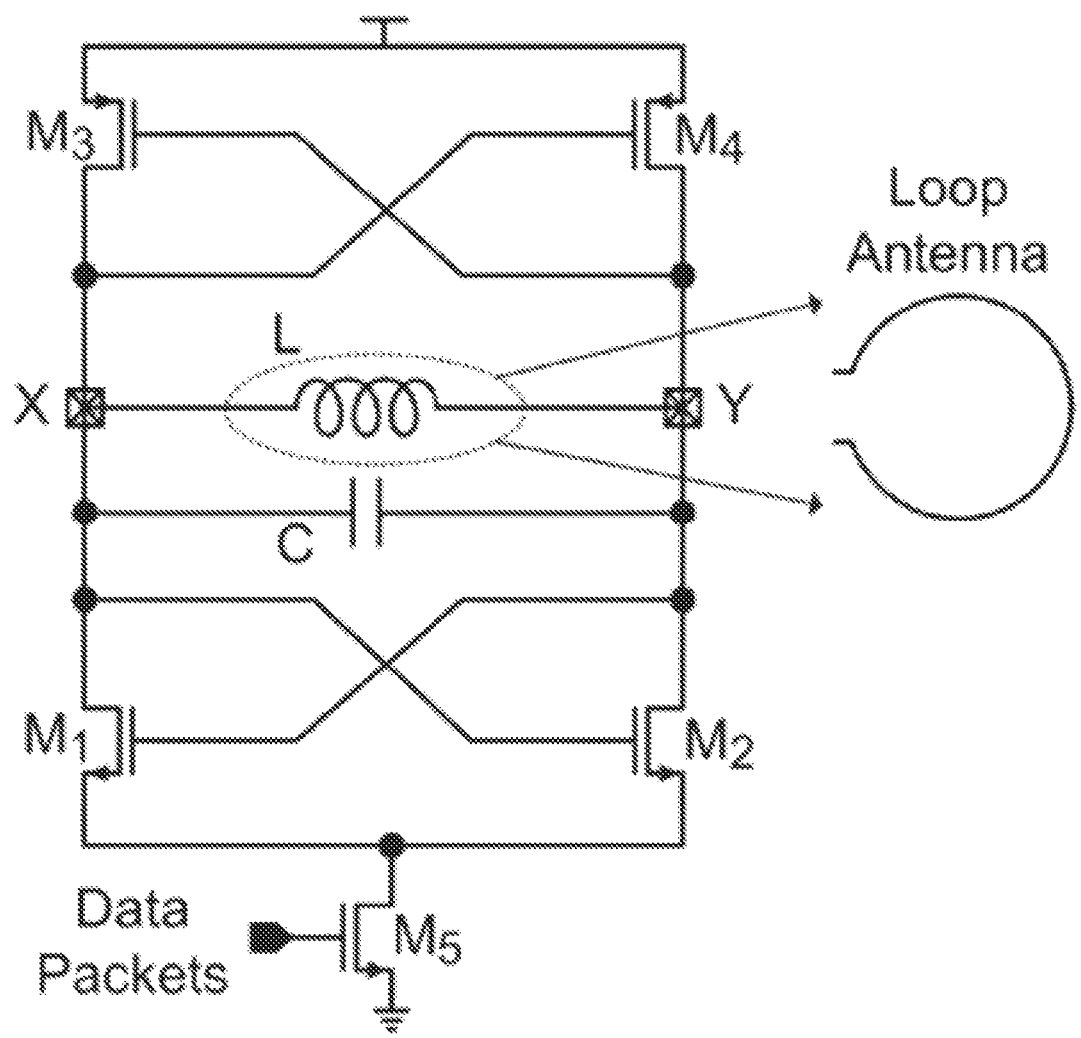

FIG. 51 is a schematic diagram of the 2.45 GHz ISM band transmitter, comprising a voltage-controlled power oscillator (VCPO) and an off-chip loop antenna.

Figure 52:
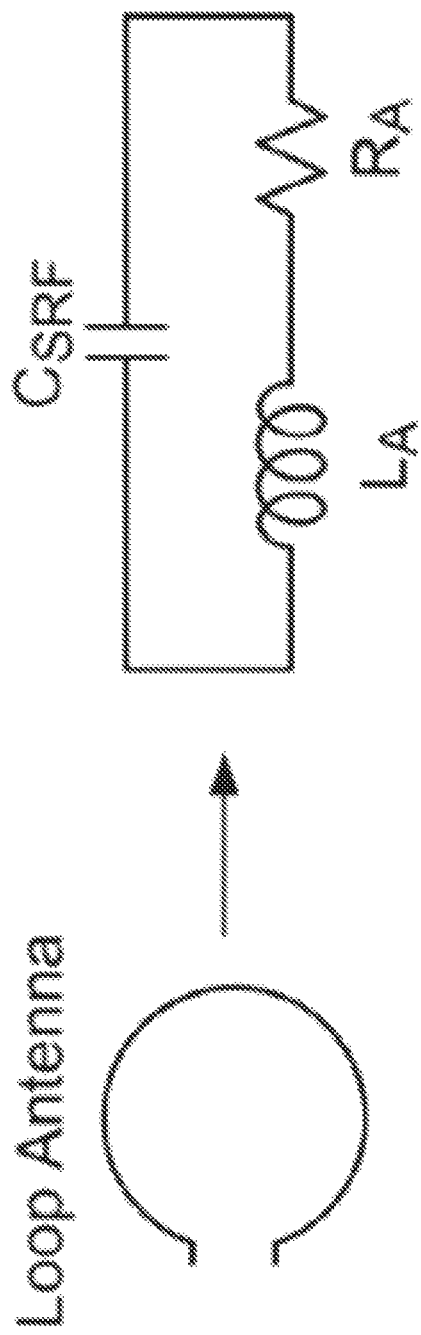

FIG. 52 is an equivalent lumped circuit model of an electrically small loop antenna. The antenna can be modeled as a series combination of an inductor (LA) and a resistor (RA). CSRF models the self resonance frequency of the loop.

Figure 53B:
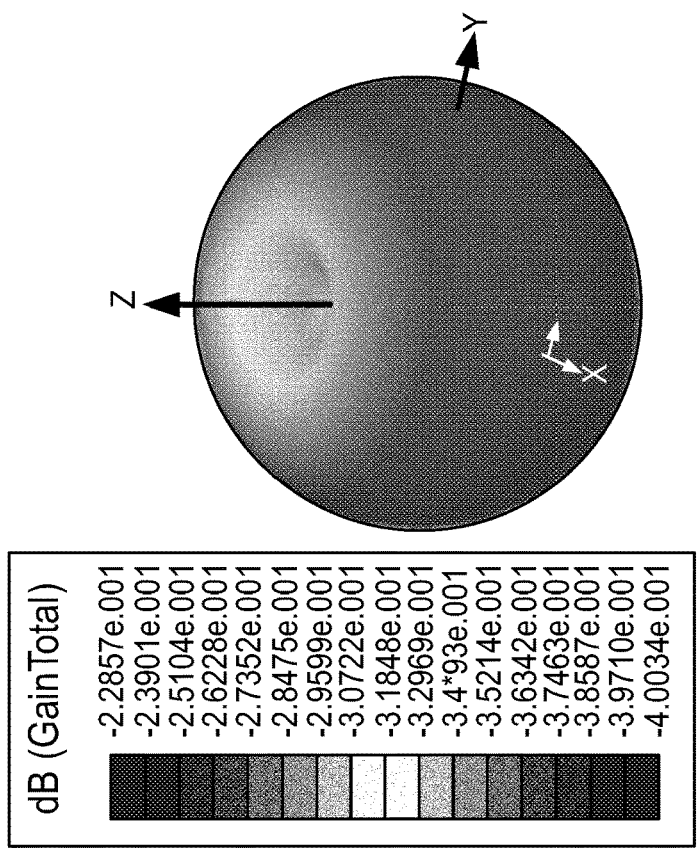

FIG. 53 is a simulated antenna radiation pattern: (a) on a FR-4 board (air). (b) gold trace on a 20 μm thick parylene substrate with a 20 μm parylene coating.

Figure 54:
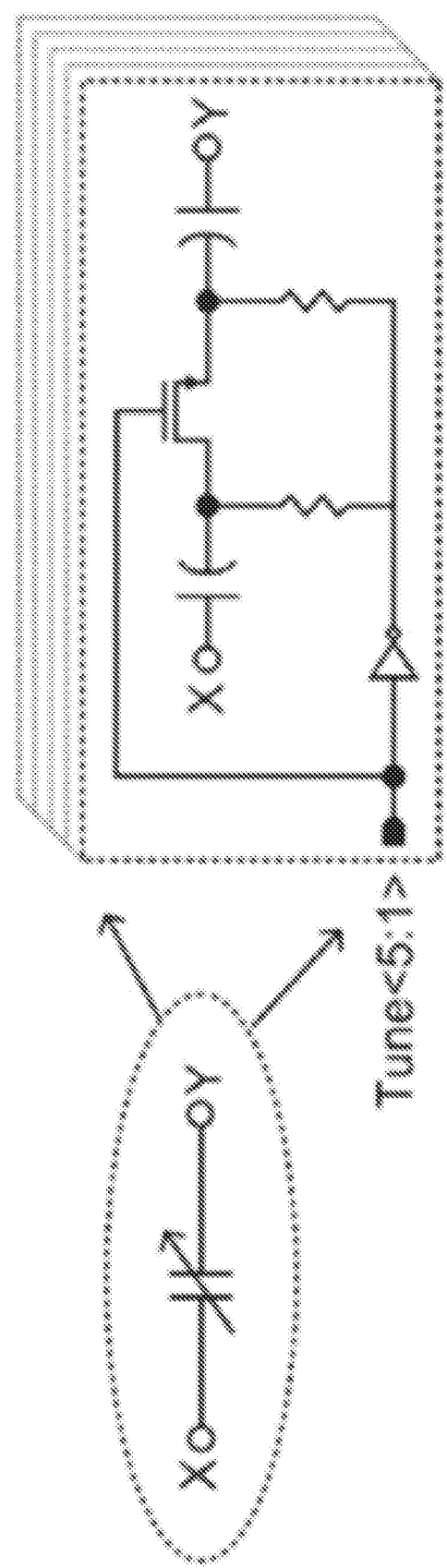

FIG. 54 is a simplified schematic diagram of 5-bit DAC, implemented by MIM capacitors to tune the resonance frequency of the LC tank.

Figure 55:
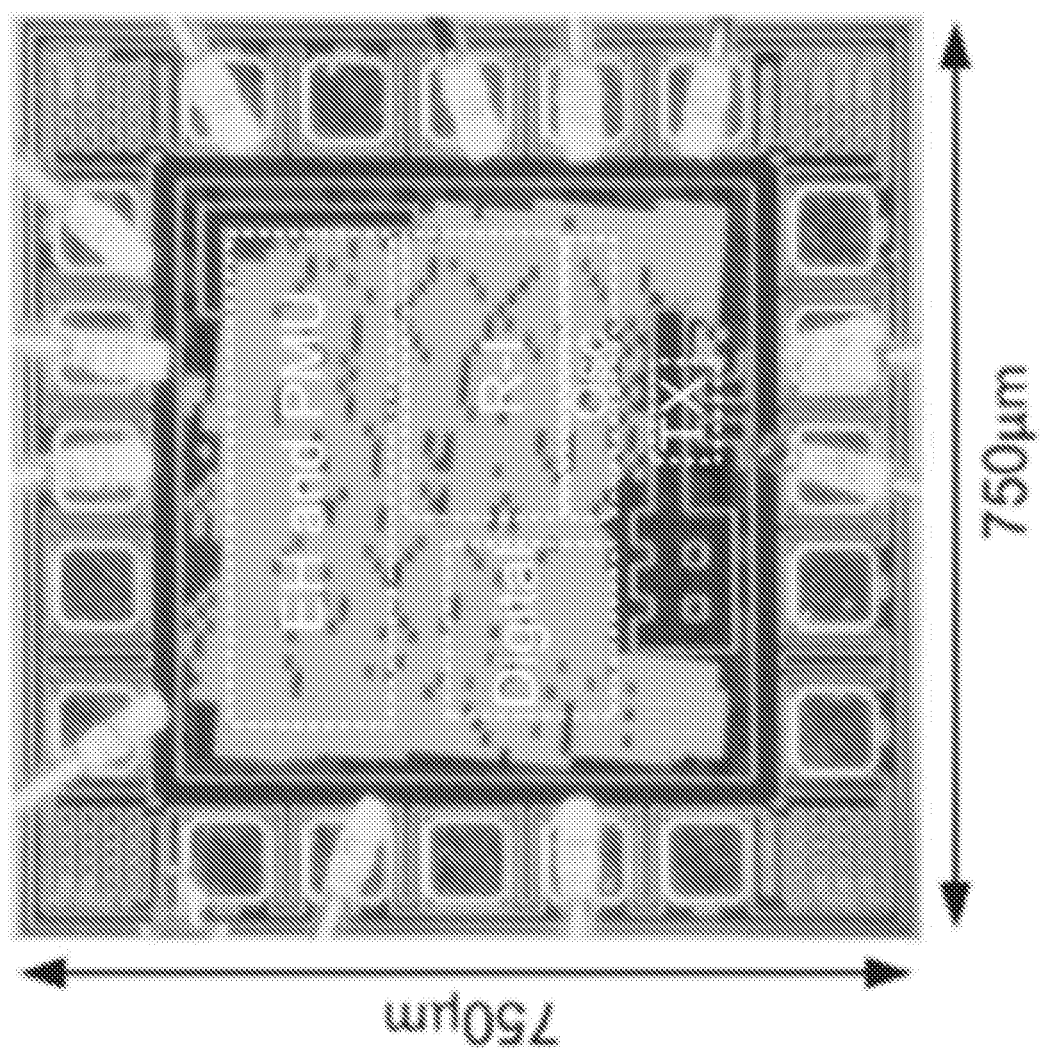

FIG. 55 illustrates a micro-photograph of the implemented chip.

Figure 56:
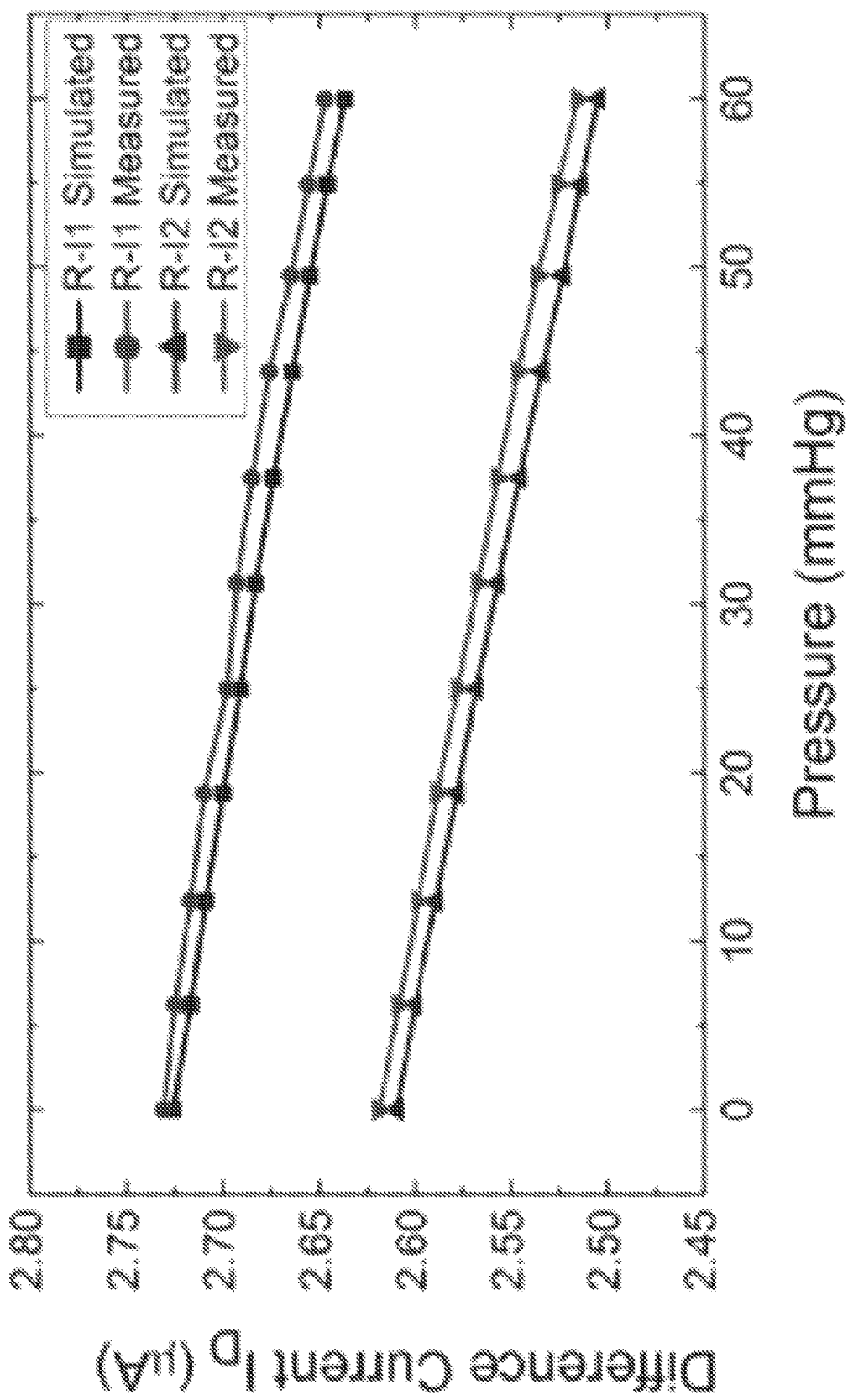

FIG. 56 illustrates a measured and simulated current for the R-I1 Converter.

Figure 57A:
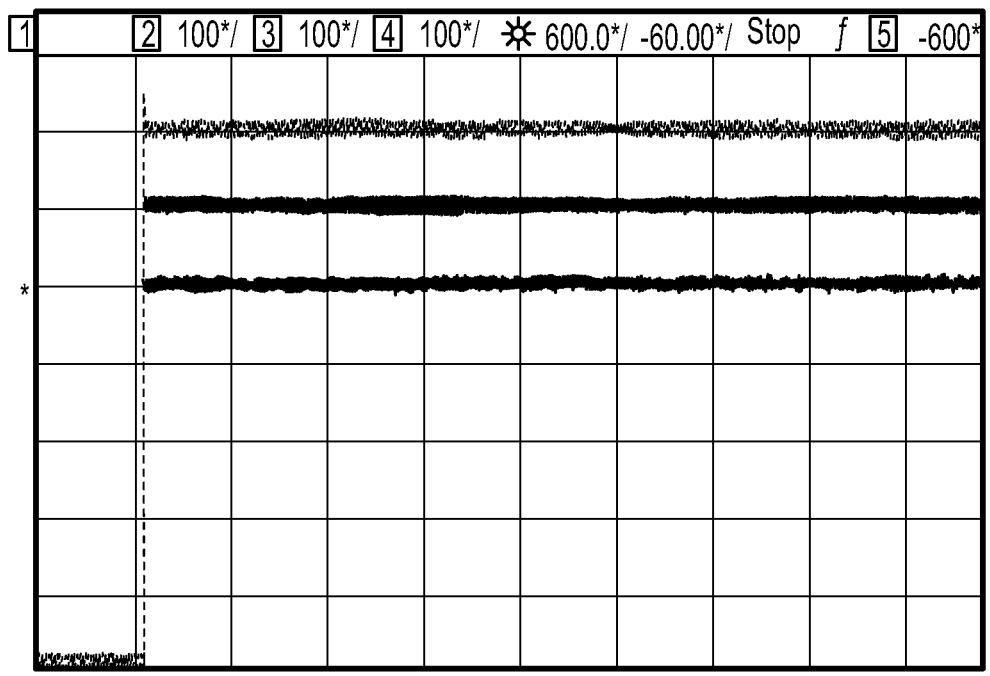
Figure 57B:
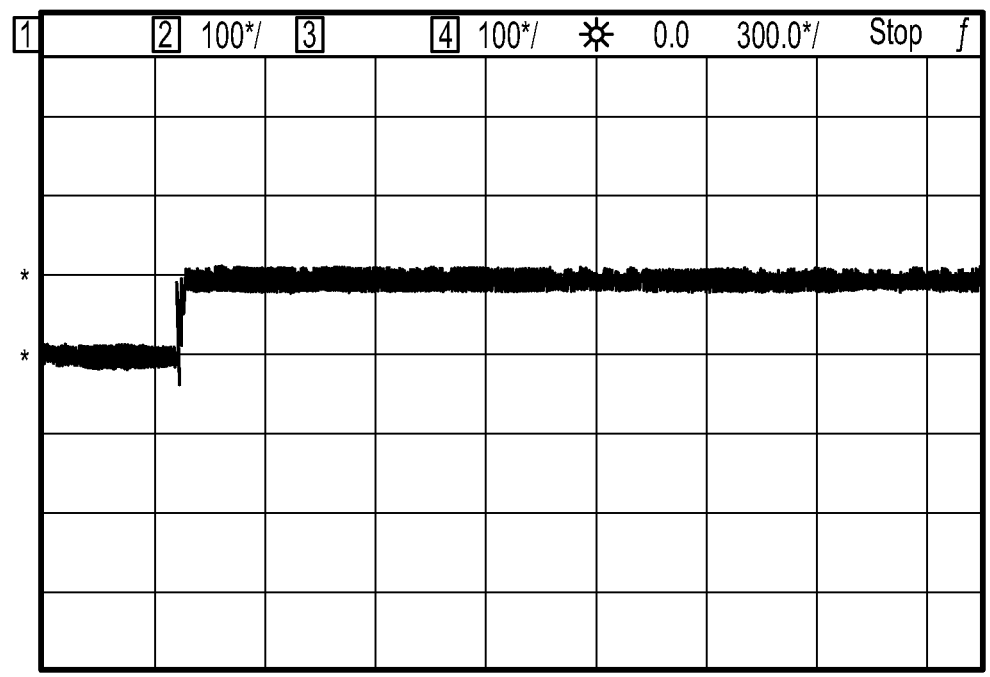

FIG. 57 illustrates a) a Pseudo-differential reference voltage across the sense resistors terminals in R-I2 converter, and (b) 100 mV reference voltage across the sensor resistors in R-I1 converter.

Figure 58:
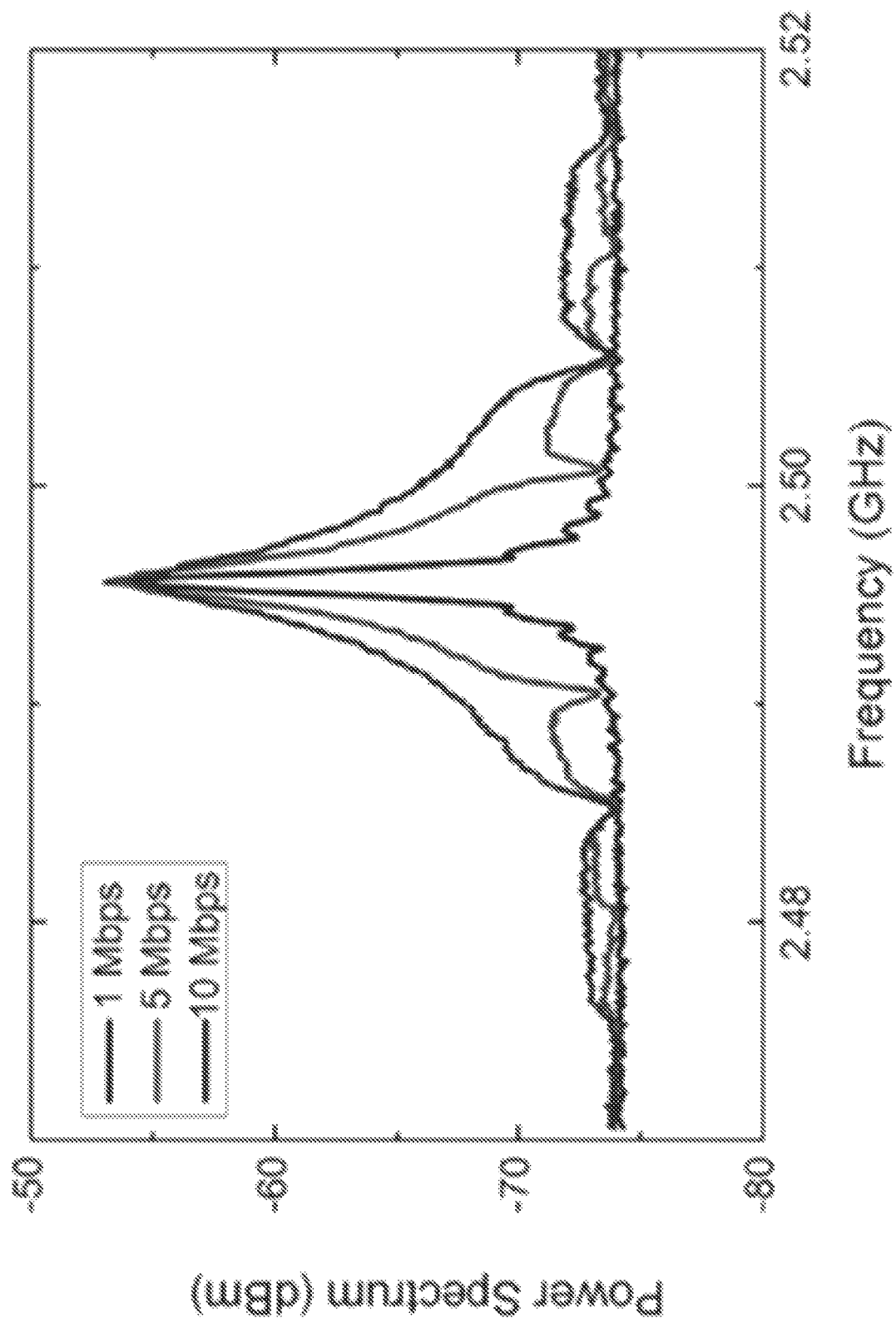

FIG. 58 illustrates a measured TX power spectrum, OOK modulated by the PRBS at various data rates.

Figure 59:
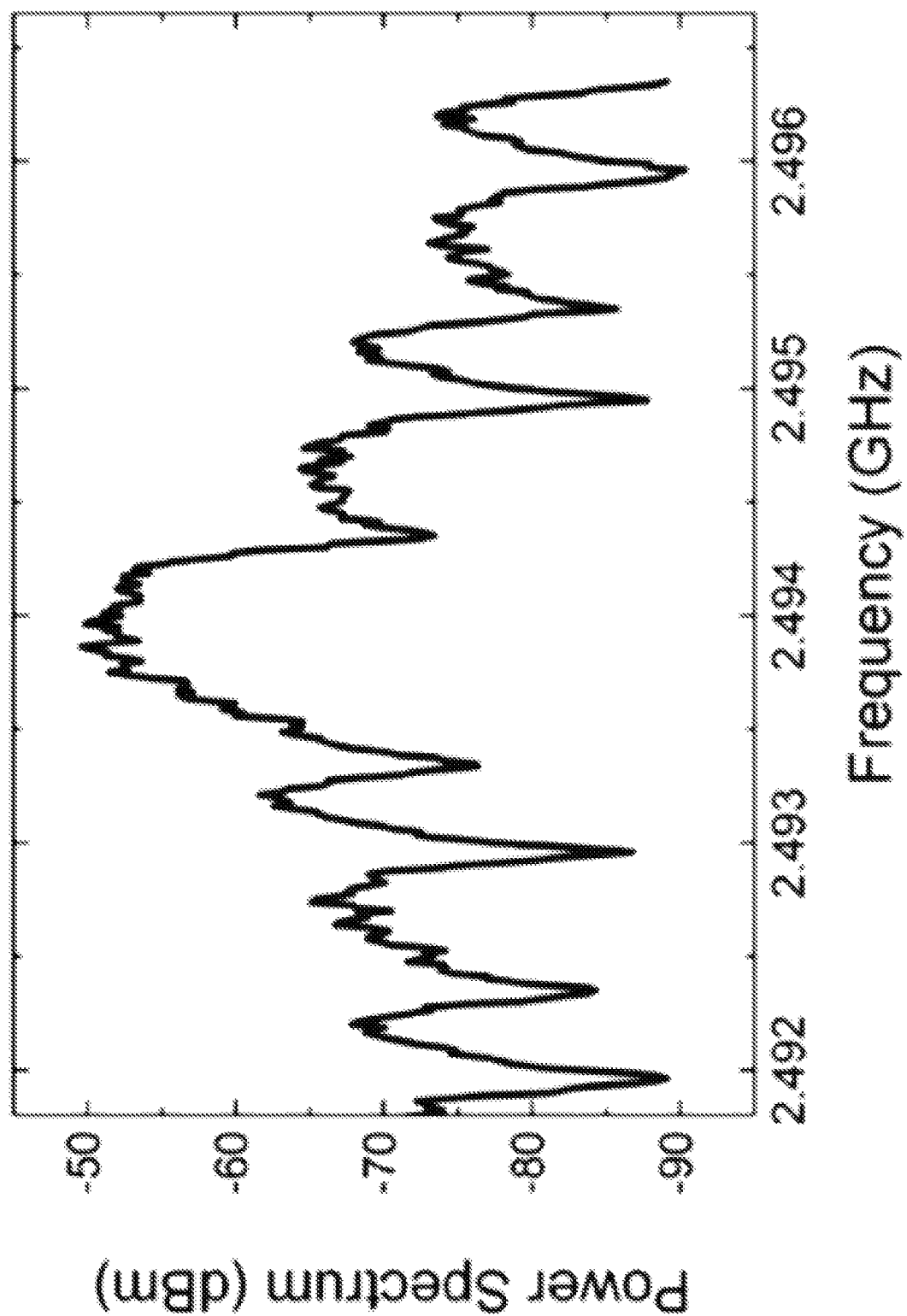

FIG. 59 illustrates a measured TX power spectrum, FSK modulated by 1 Mbps PRBS.

Figure 60:
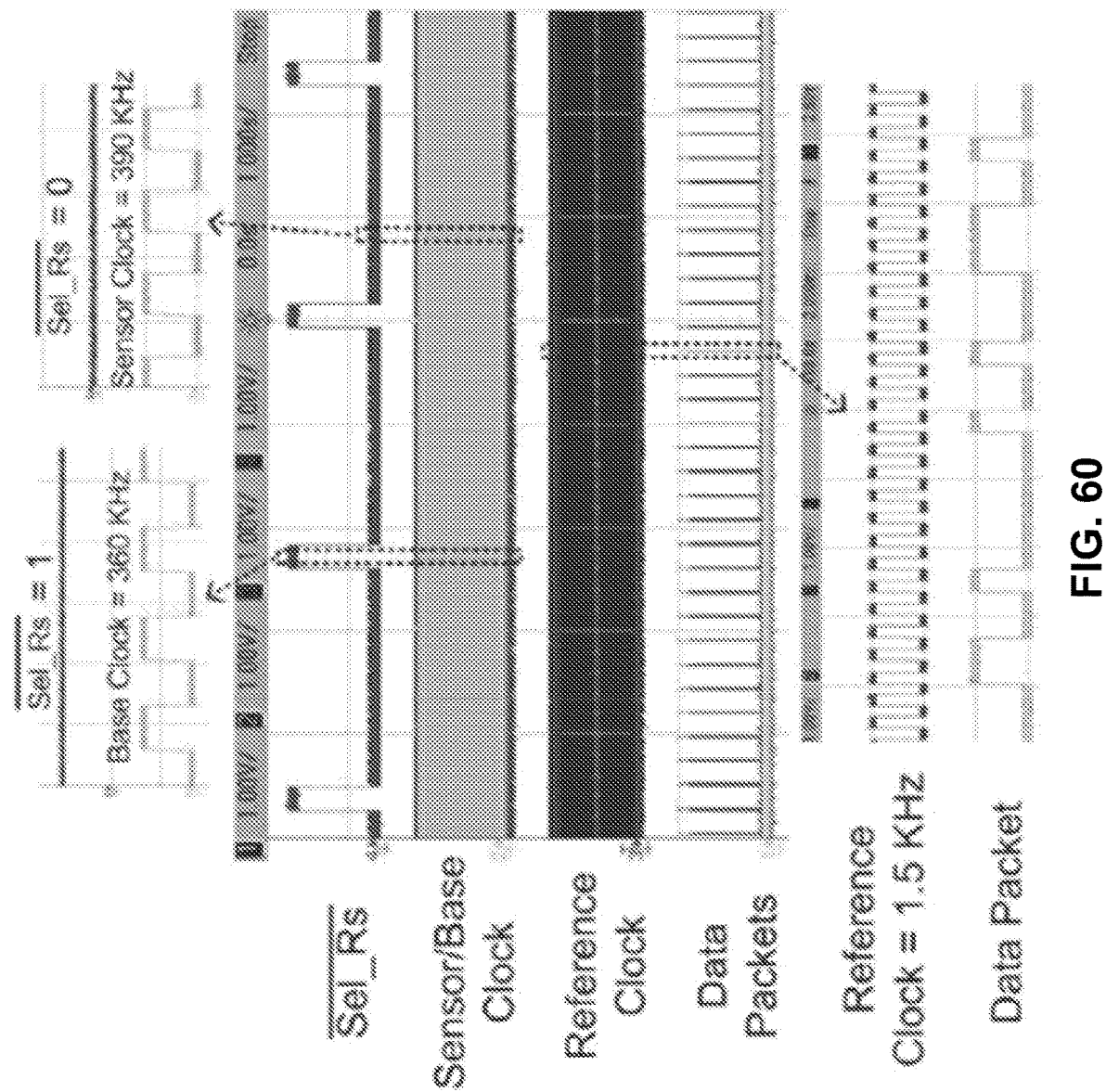

FIG. 60 illustrates a measured waveforms and data packet for the full system.

FIG. 61 illustrates measured data packets that correspond to: a) Base frequency, b) Sensor frequency and c) Difference between two sensor frequencies.

Figure 62:
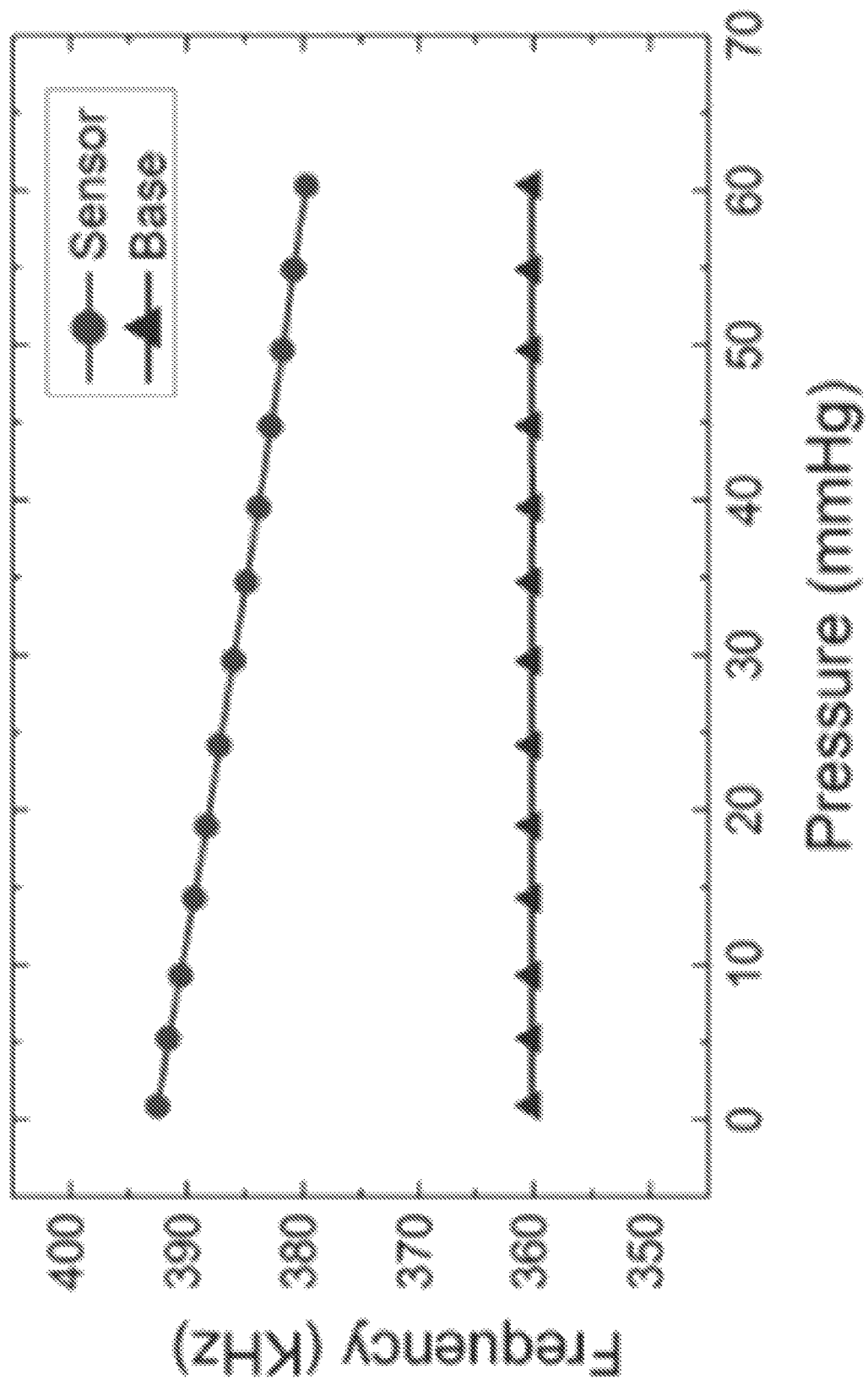

FIG. 62 illustrates measured change in the sensor frequency with pressure, where base frequency remains constant with applied pressure.

Figure 63:
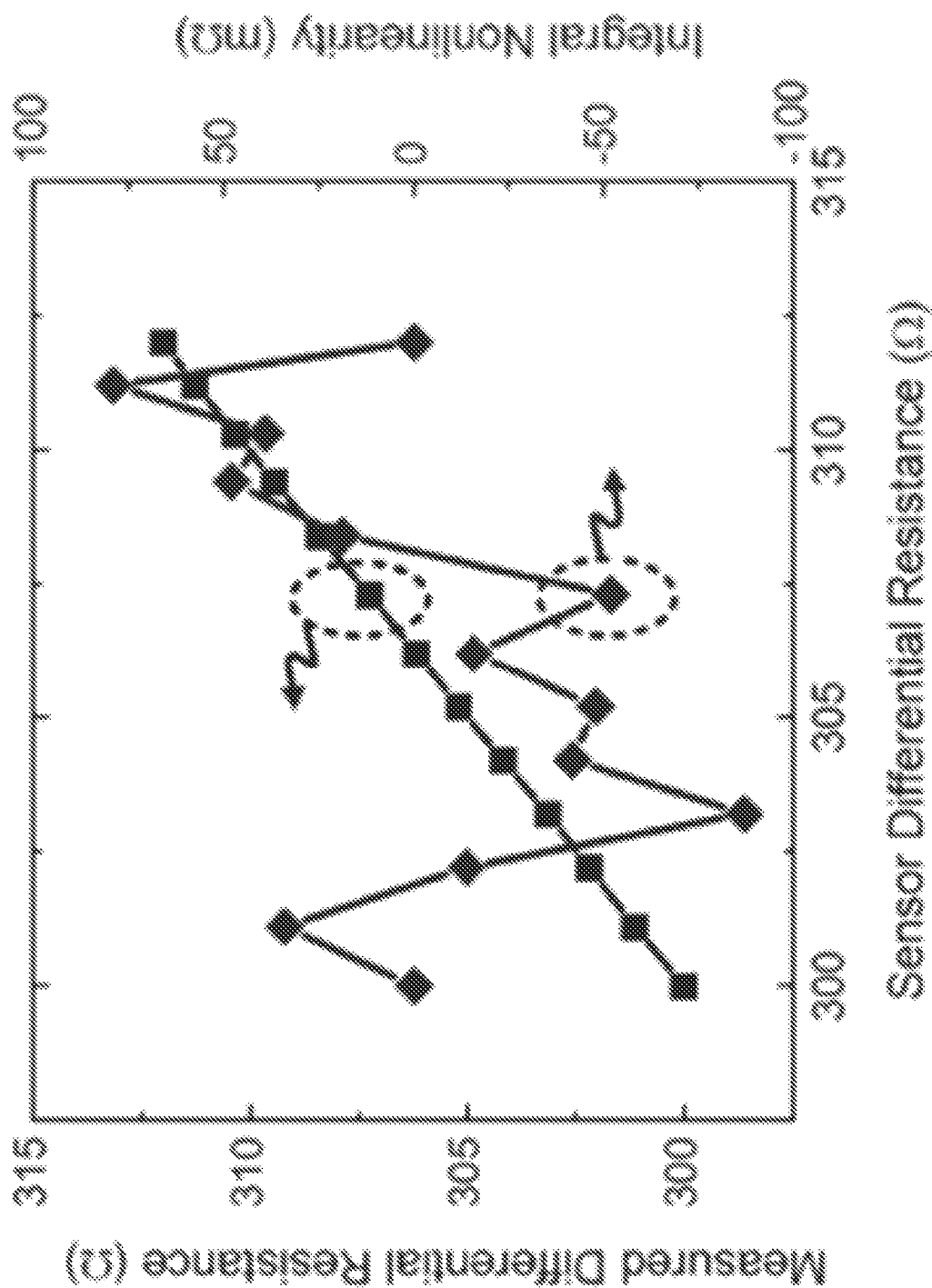

FIG. 63 illustrates measured difference in sensor resistances (RS1-RS2) and integral non-linearity.

Figure 64:
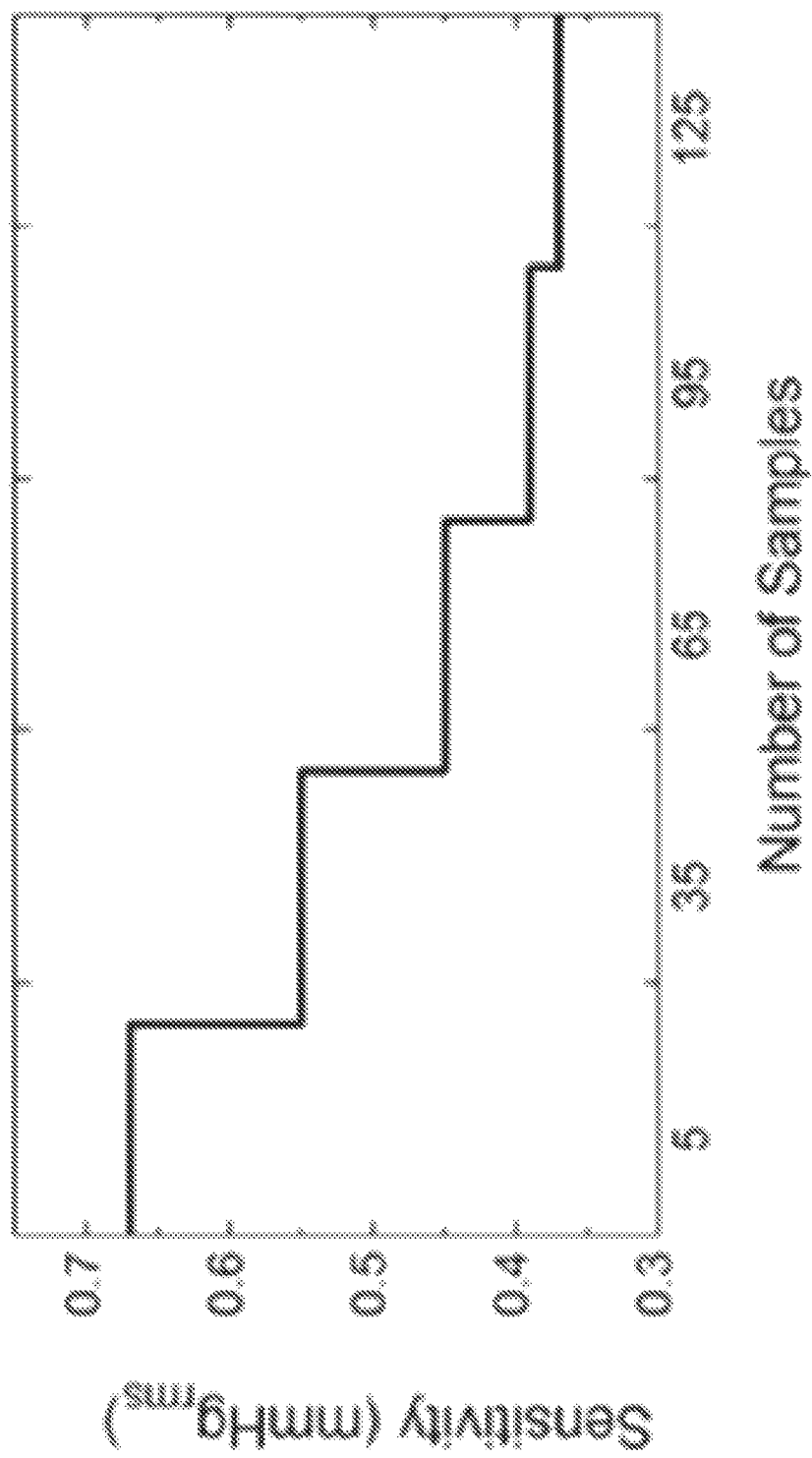

FIG. 64 illustrates measured sensitivity of the chip with number of averaged data samples (or conversion time)

Figure 65:
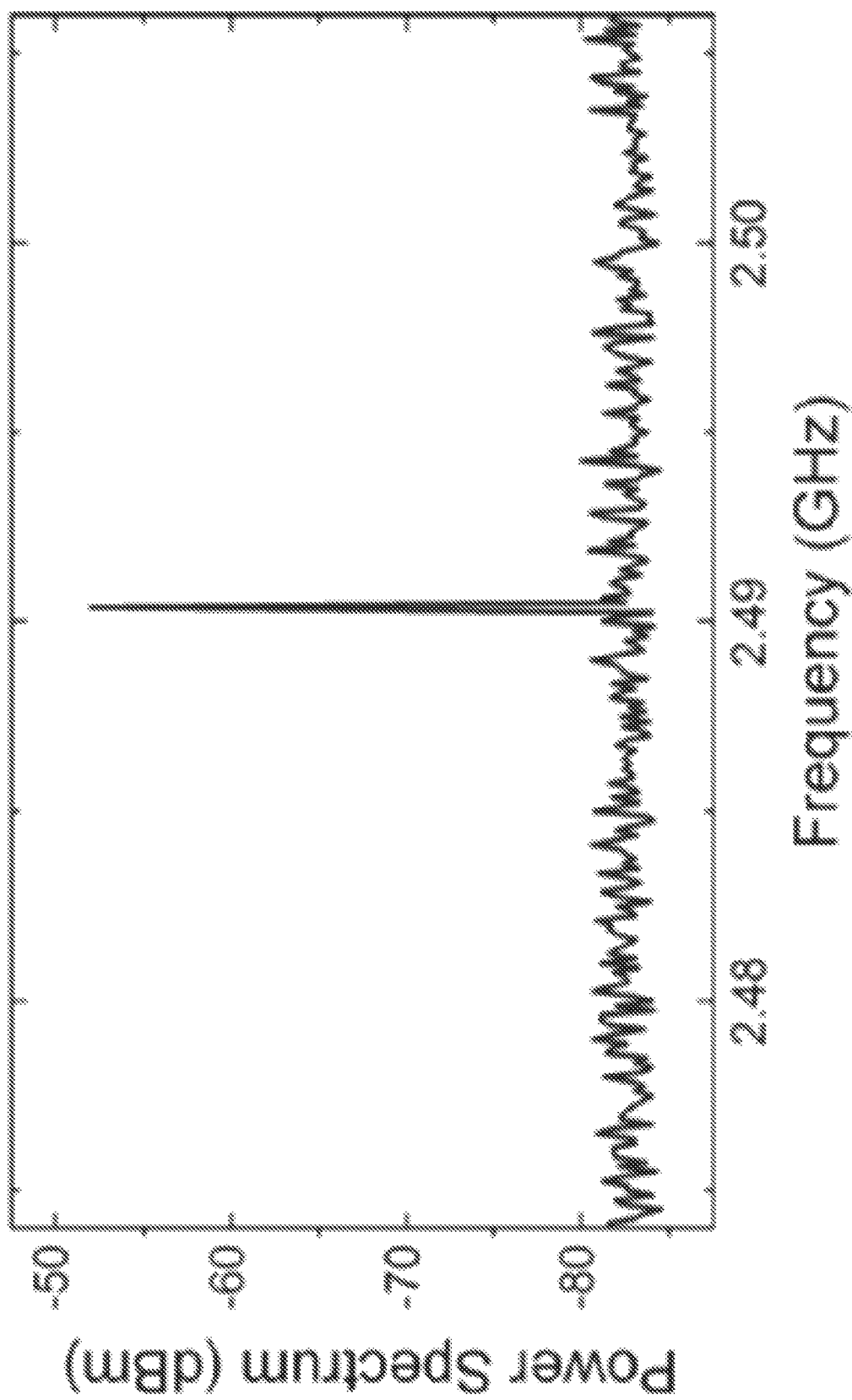

FIG. 65 illustrates measured power spectrum of the received data.

Figure 66:
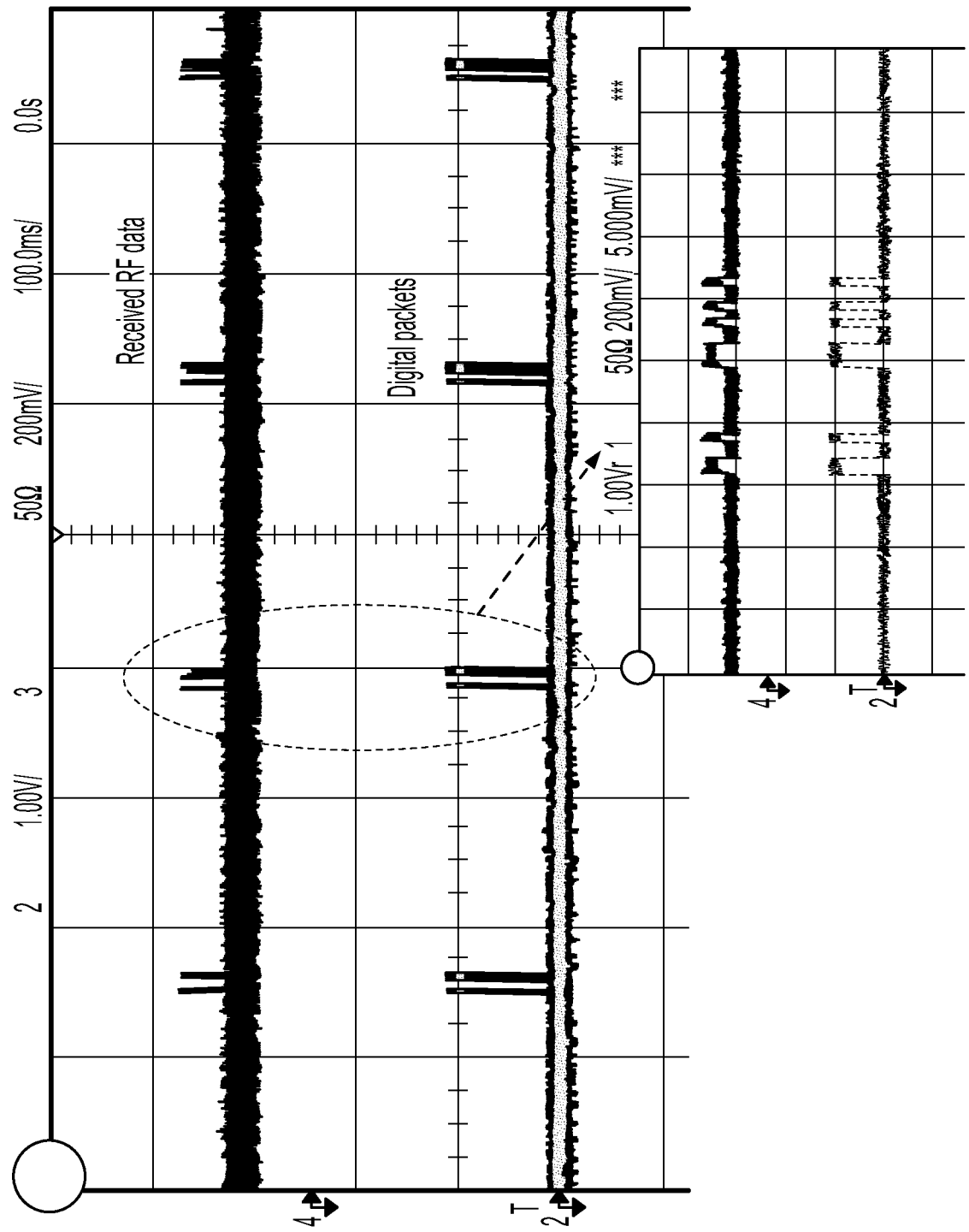

FIG. 66 illustrates received RF data and corresponding digital packets.

Figure 67:
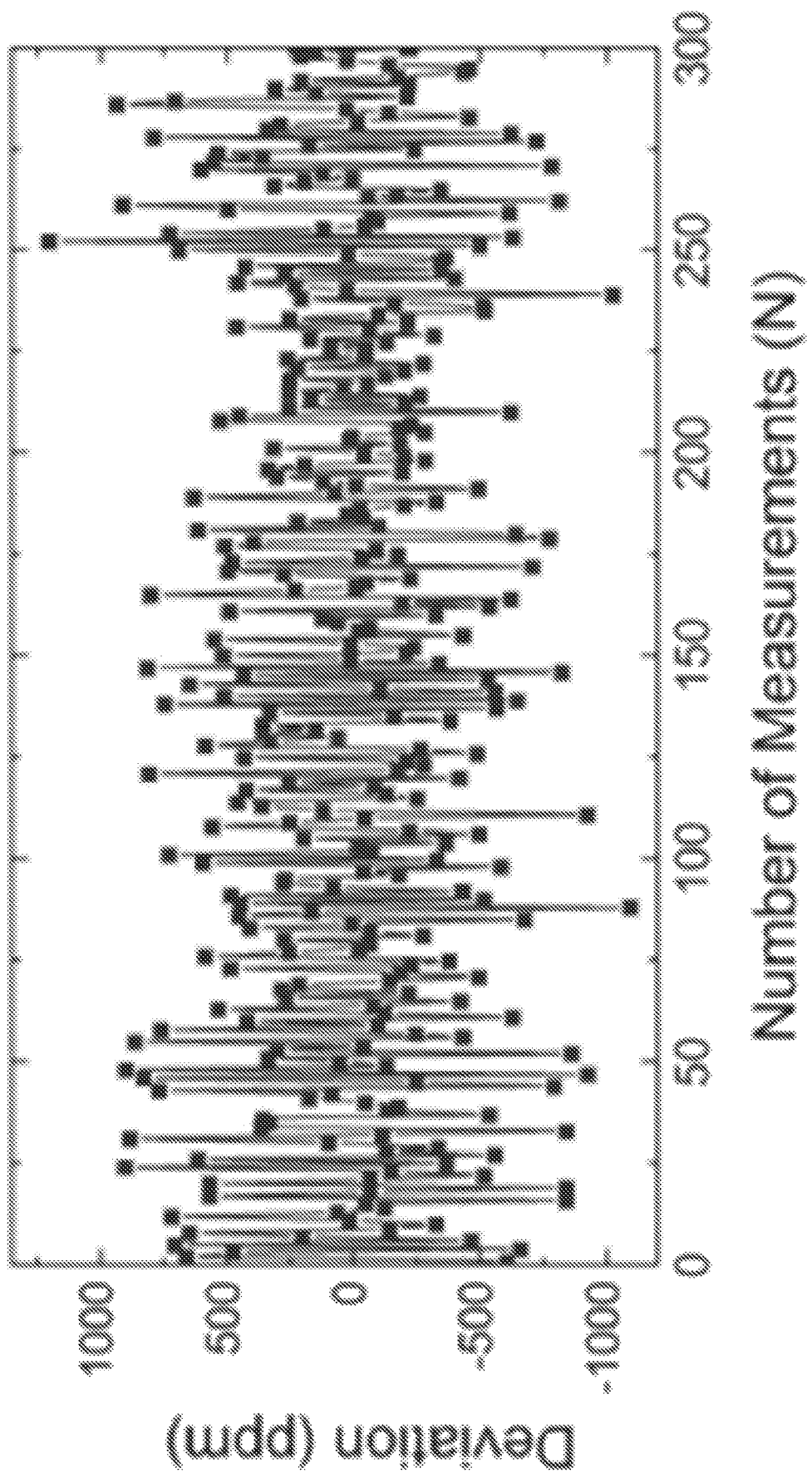

FIG. 67 illustrates a wirelessly measured noise floor for resistance sensing.

Figure 68:
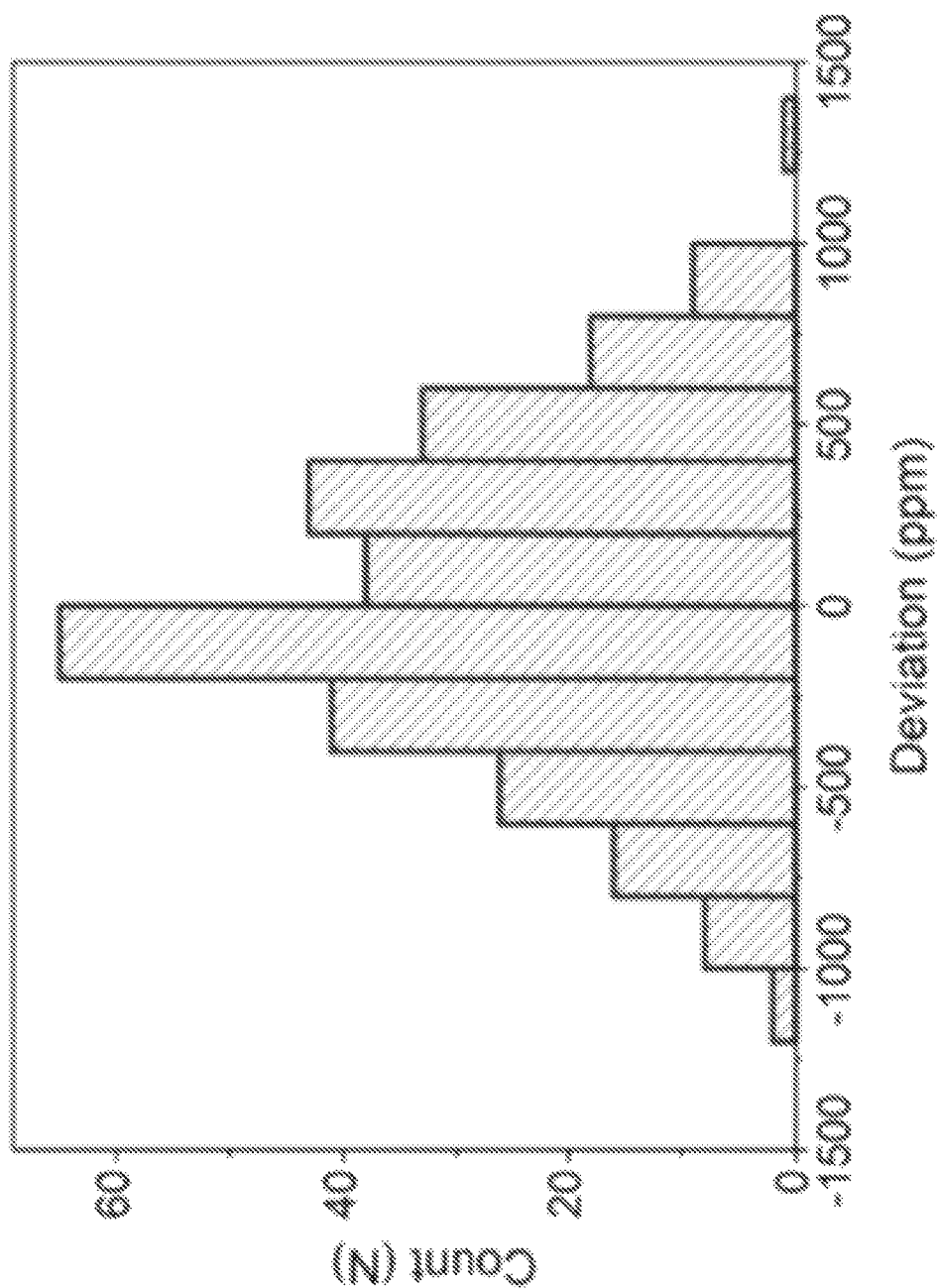

FIG. 68 illustrates a wirelessly measured noise histogram for resistance sensing.

Figure 69:
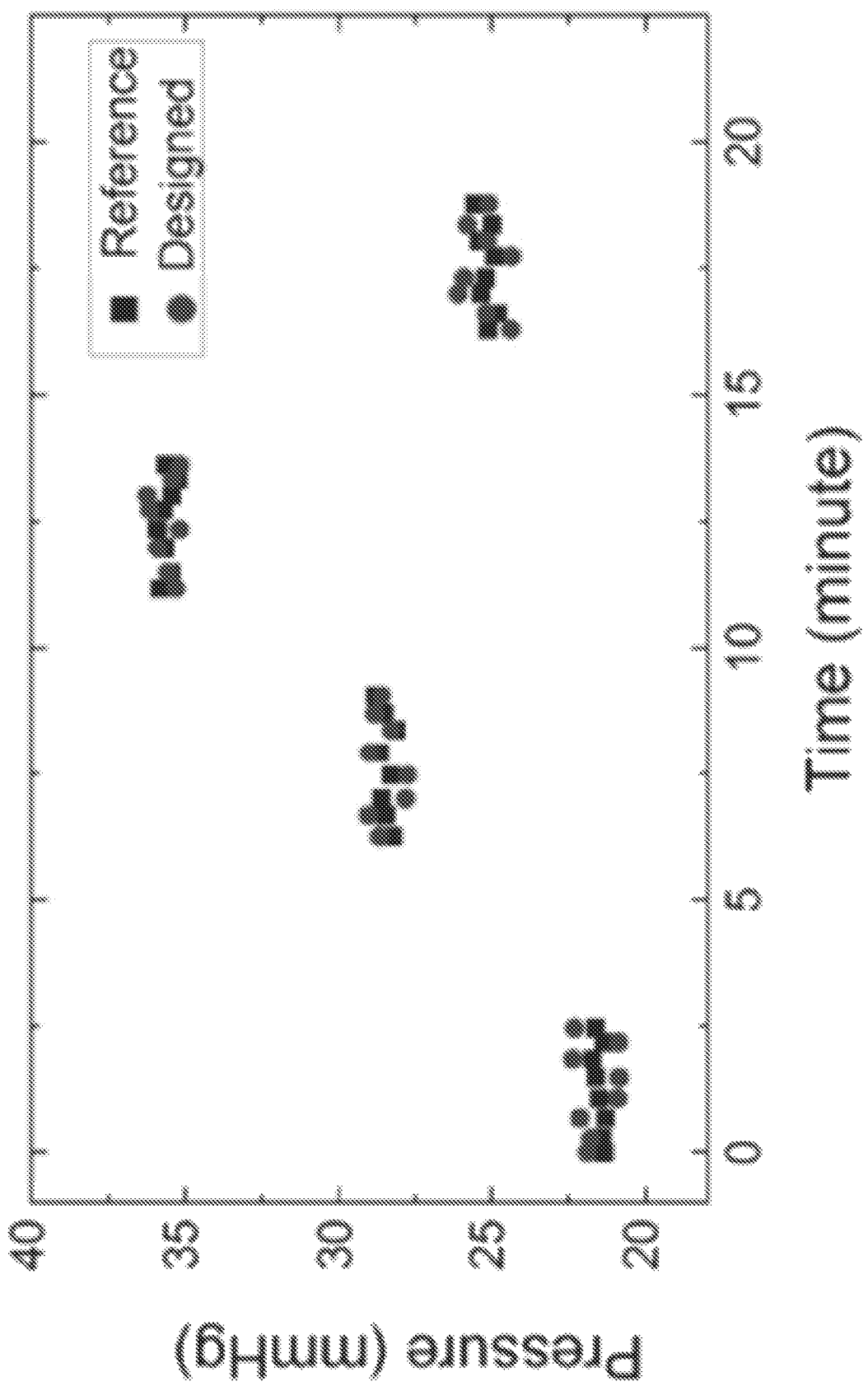

FIG. 69 illustrates a pressure measurement with time.

Figure 70:
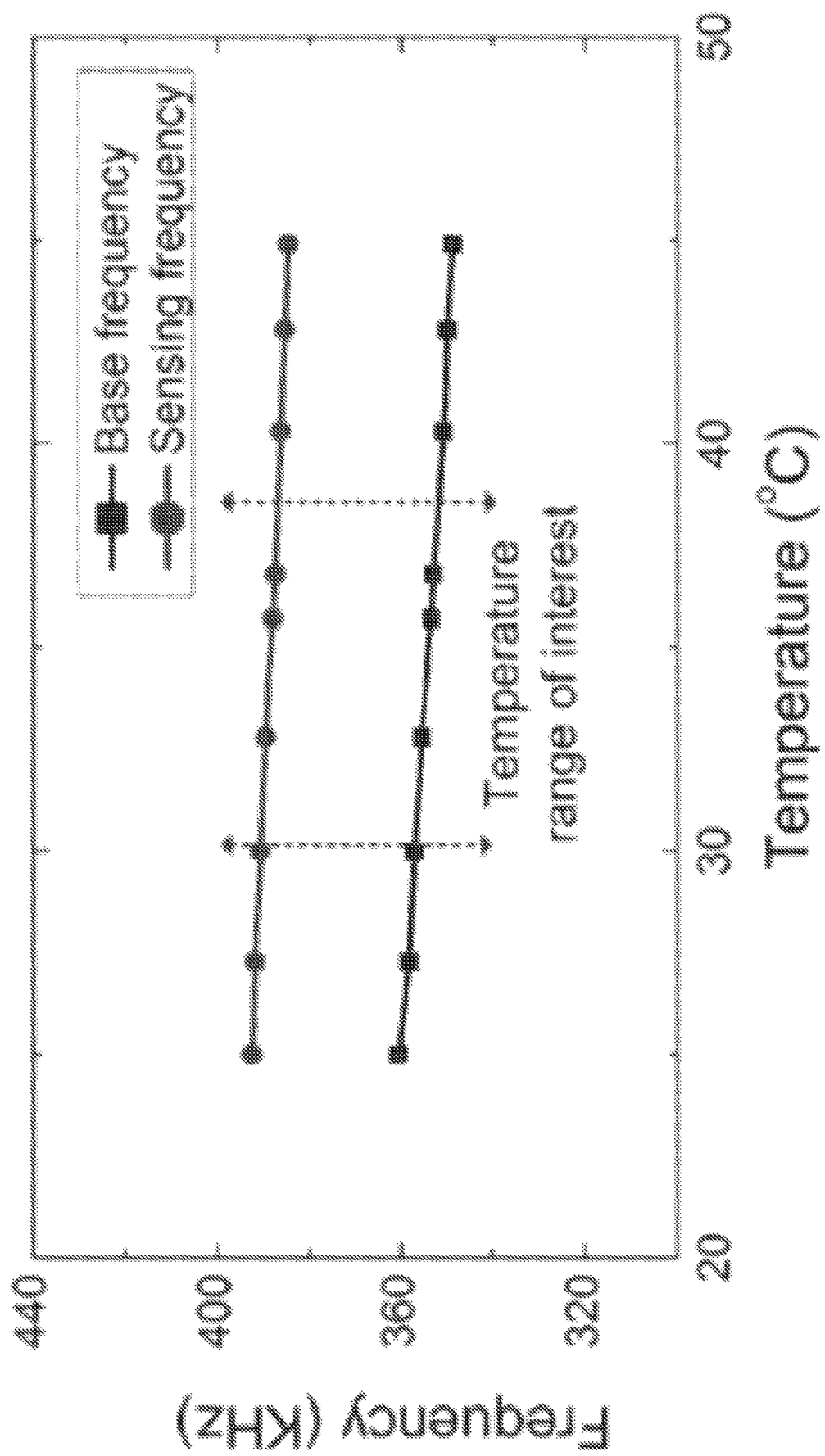

FIG. 70 illustrates measured temperature variation in sensing and base frequencies.

Figure 71:
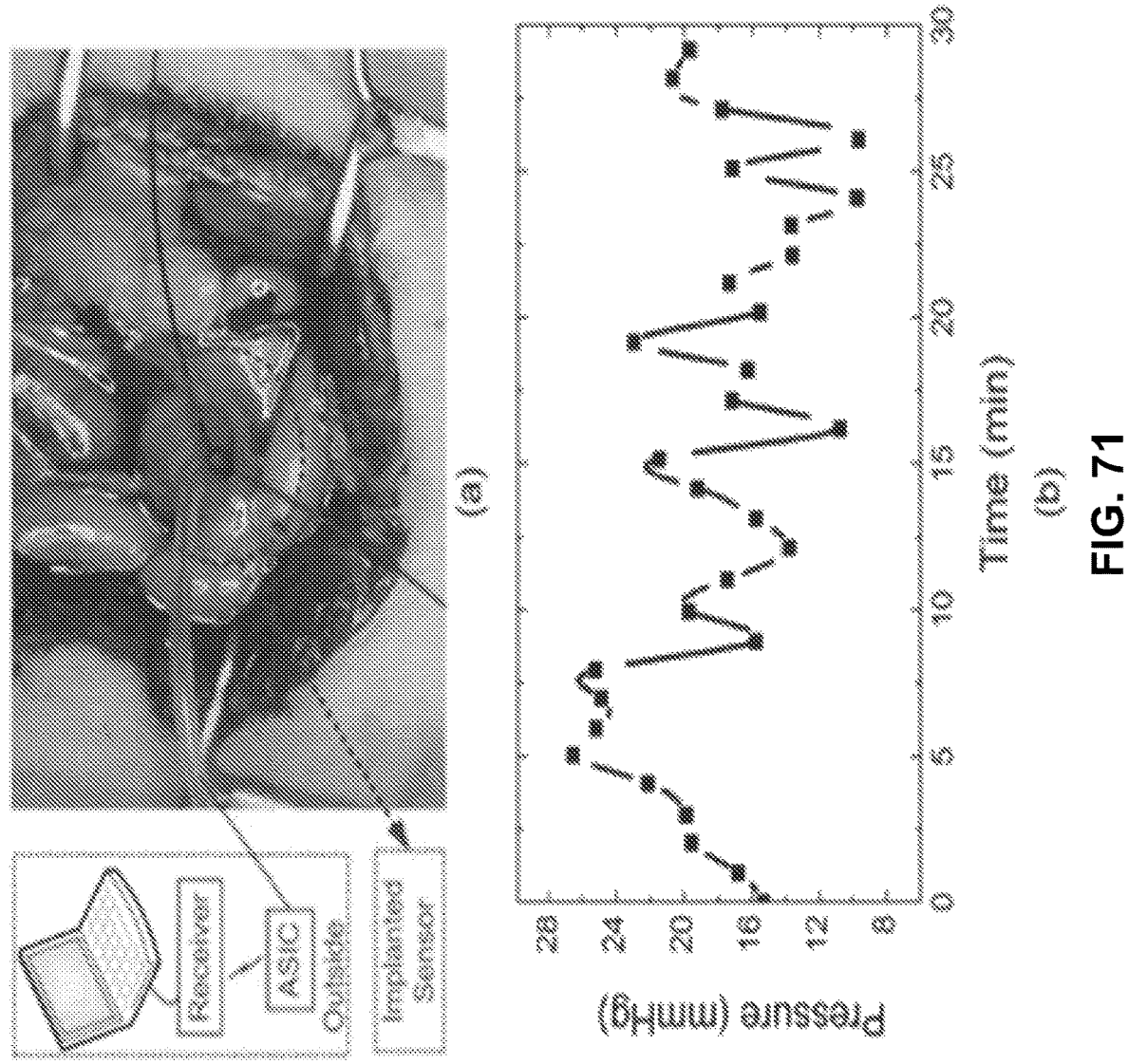

FIG. 71 illustrates in-vivo experiments including: a) Experimental setup, and b) Bladder pressure recording.

Figure 72:
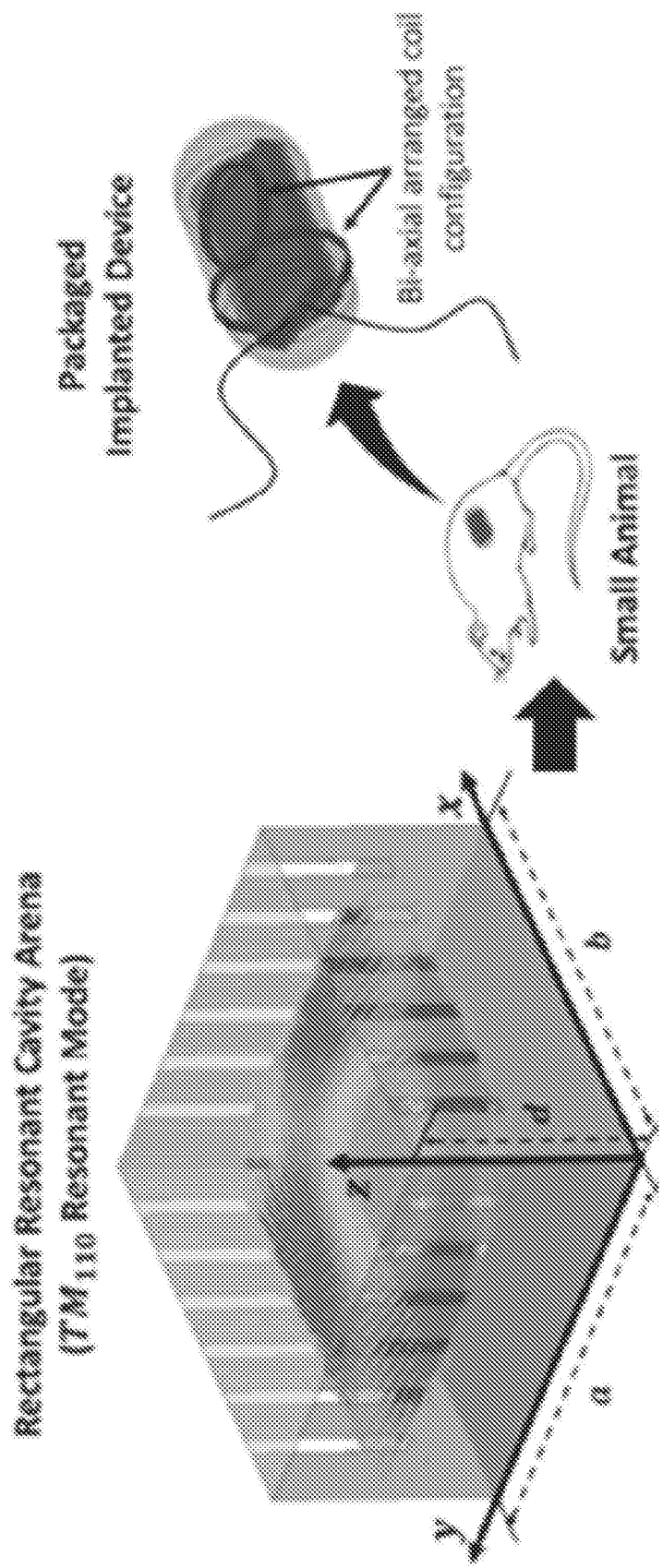

FIG. 72 is a cavity resonator forming part of the wireless power transfer system for use in pre-clinical biomedical research involving non-human mammals (such as a rat) with a Bionode implanted.

Figure 73:
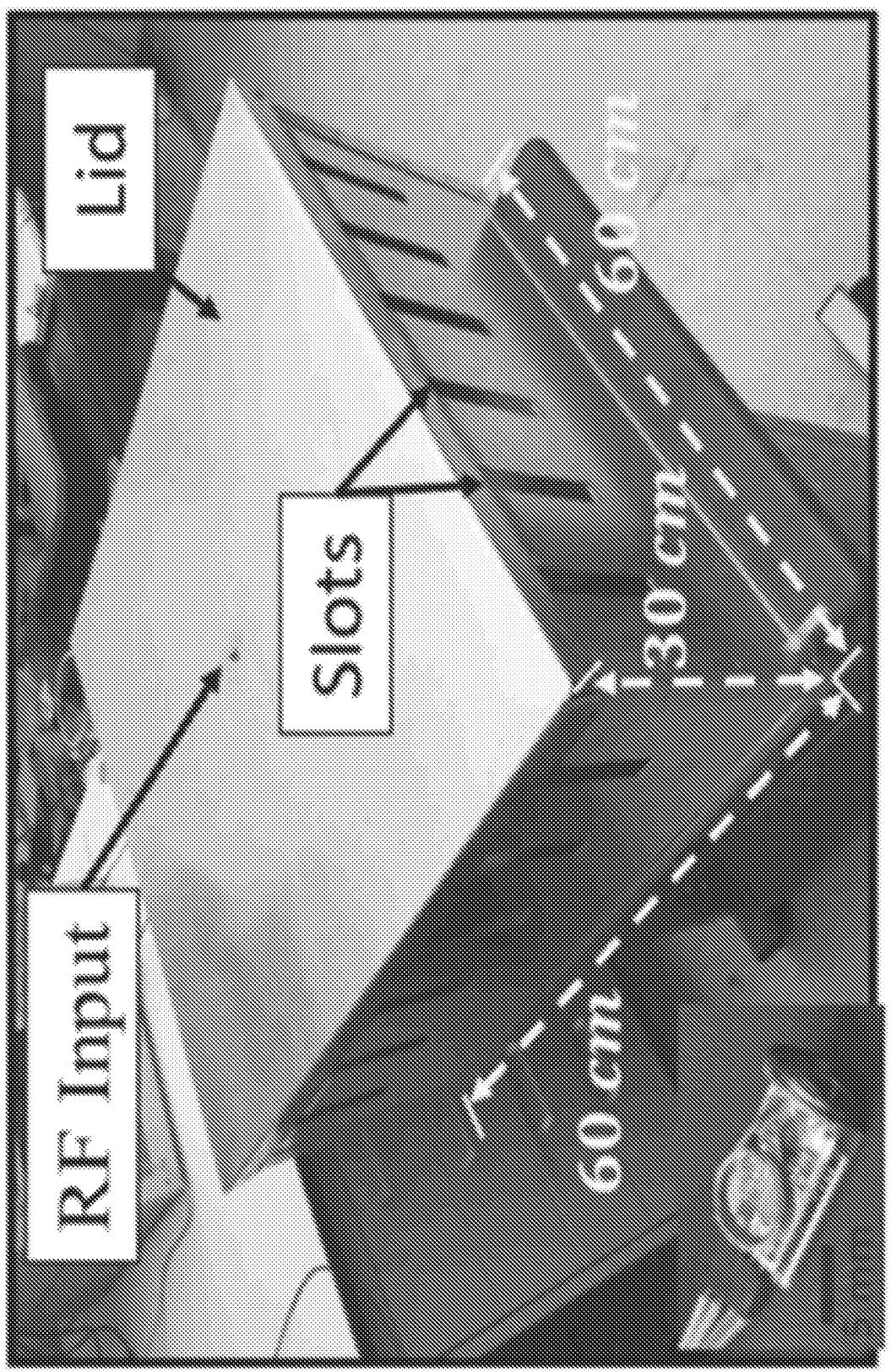

FIG. 73 is a constructed cavity resonator and fully assembled device with Bionode microelectronics platform, power management board, and receive coil assembly according to the present disclosure.

Figure 74:
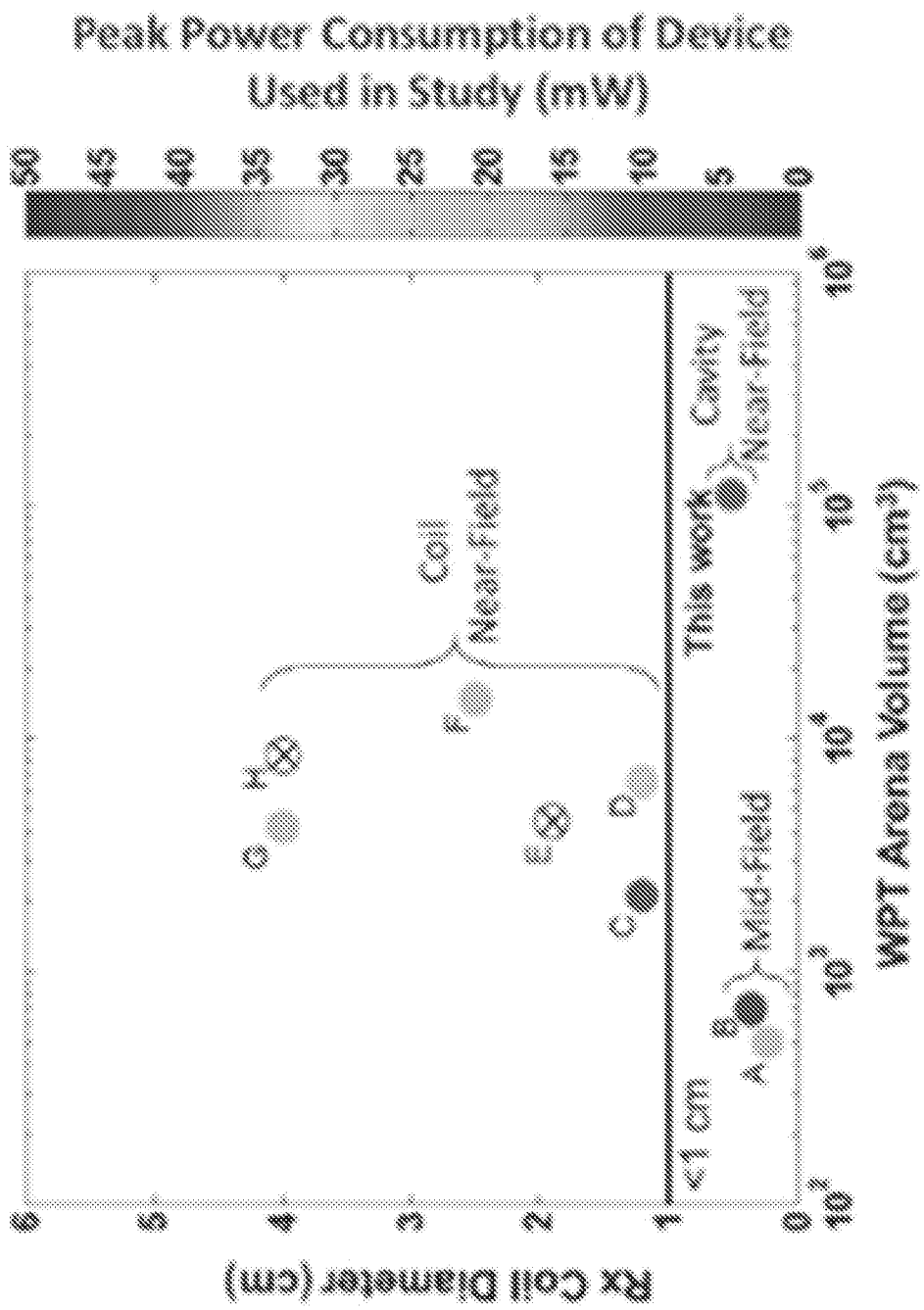

FIG. 74 is a chart comparing the system performance when employing wireless power transfer with the resonant cavity system relative to other types of wireless power transfer.

Like reference, numbers and designations in the various drawings indicate like elements.

DETAILED DESCRIPTION

Disclosed herein are techniques and systems related to a biomodulation system including a main wireless implantable device, referred to herein as a Bionode assembly or Bionode for short, which in some implementations is powered without an implanted battery or implanted active circuitry, thereby allowing a design to have minimal possible volume, complexity, and sensitivity to variations in operating conditions. Additionally, the biomodulation system (which also may be referred to as the Bionode platform) achieves these advantages, while providing the spatial specificity and stimulation waveform definition provided by some existing biomodulation systems.

The biomodulation system utilizing the Bionode can provide distinct advantages over some existing technologies, by realizing a high level of functionality, adaptability, and compatibility (e.g., with external testing environment). The operating conditions for the implantable Bionode can be configurable through its use of reprogrammable firmware, bidirectional communication (e.g., enabling immediate updates), and selectable hardware components. The system can also be enabled with functions beyond biological recording and stimulating, for instance device temperature sensing and electrode impedance measurements, (both of which provide valuable feedback to the user once the device is implanted and inaccessible). Moreover, the integrated stimulator of the Bionode can be used as an instrument for calibration. As discussed throughout, the Bionode platform implements extensive functionality and multi-tasking ability. Thus, the Bionode platform has utility as a possibly battery-less, fully implantable wireless solution in the biomedical field, for instance being employable in a wide range of electrophysiological and behavior treatments and studies.

Figure 1A:
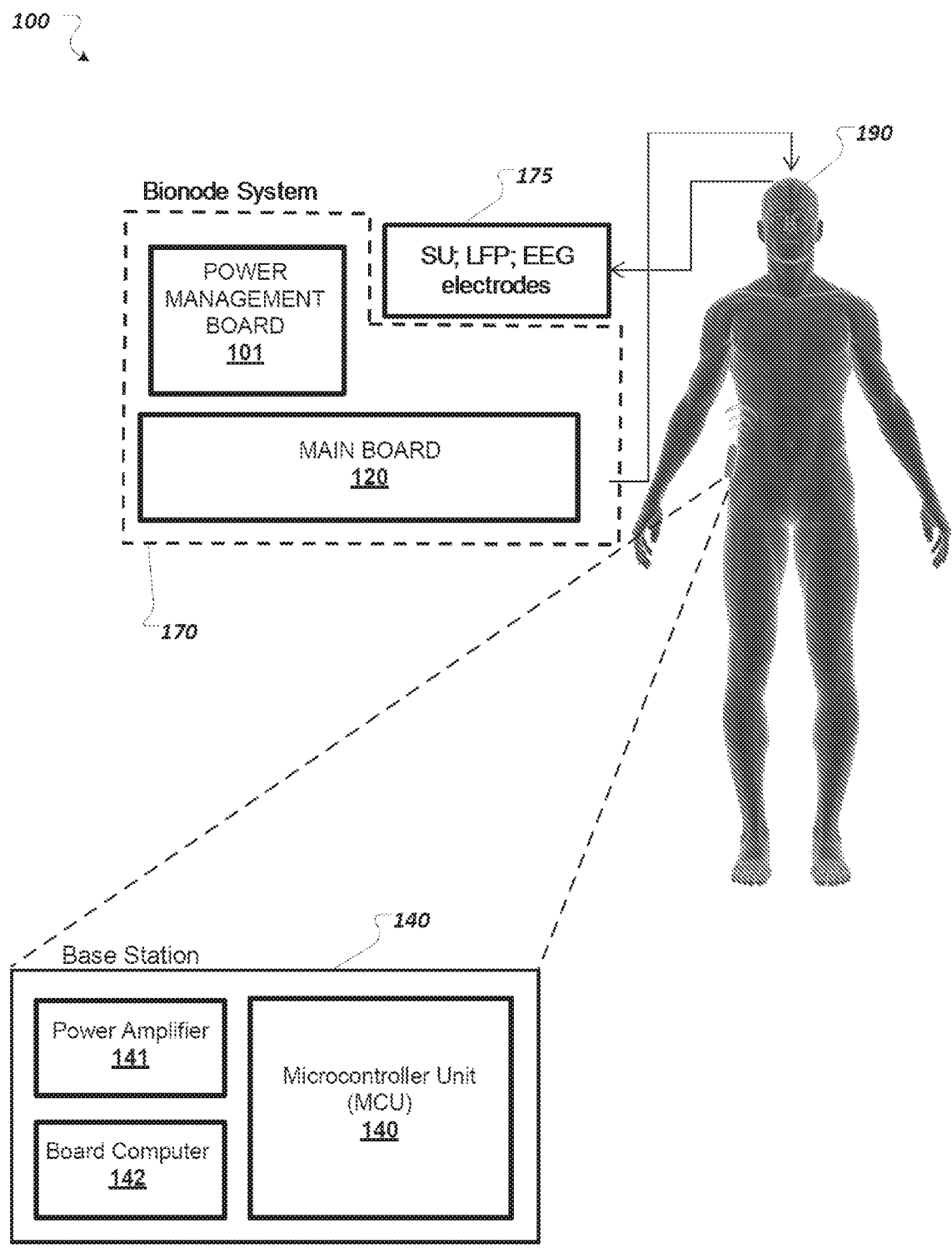
FIGS. 1A-1B shows a diagram of an example of the wireless platform system, including a wireless implantable device, for implementing wireless recording and stimulating of bioelectric events.

FIG. 1A shows an embodiment of a biomodulation platform system 100 including an implantable wireless device employing wireless power transfer. The wireless platform system 100 is designed for monitoring and actuating biological sites, and therefore enabling targeted and controlled activation of the biological pathway of a desired therapy of a patient 190, shown in FIG. 1A as a human. It should be appreciated that while applicable to human patients, as illustrated in FIG. 1A, the wireless platform system 100 can be utilized in treatments and biomedical research involving non-human patients, such as other mammals. For example, the system 100 can be employed in chronic behavioral experiments performed in rodents. The wireless platform system 100 is configured to perform biomodulation in a human patient 190, and can be applicable to a wide range of medical conditions including, but not limited to: epilepsy; glaucoma; inflammation; incontinence; gastroparesis; addiction; alcoholism; Parkinson's (e.g., preclinical trials); and the like. Various embodiments of the wireless platform system 100 that are each configured for suitable use in the specialized treatment of a respective condition are addressed in detail herein.

FIG. 1A shows the wireless platform system 100 includes an implantable assembly, namely, a Bionode assembly 170, or simply, the Bionode; and a non-implantable, and in many use cases wearable, base station assembly 140. The system 100 utilizes wireless power transfer (WPT) 195 to transfer power wirelessly from the non-implantable base station 140 to the implantable Bionode 170, to provide operating voltage for the Bionode 170 on a continuous basis. The system 100 can be used for various treatments by surgical implantation with electrodes 175 operatively connected to the Bionode 170 that make contact with the desired biological site of the patient 190, while excluding the use of an implanted battery. Thus, the smaller size and implantable nature of the Bionode 170 supports precise targeting, dosing, and monitoring of neural activation within the patient 190. FIG. 1A also illustrates various sub-elements of the Bionode 170 and the base station 140 devices. The Bionode 170 is shown as including the power management board 101 and main board 120, configured for performing the capabilities of the implantable device, as discussed in detail herein. The base station 140 is shown as including a power amplifier 141 utilized in the wireless power transfer process; board computer 142 (e.g., computing platform with modifiable hardware and software modules, such as Raspberry Pi platforms); and microcontroller unit (MCU) 145. The sub-elements for the Bionode 170 and the base station 140 are discussed in detail in reference to FIG. 1B below.

Electrodes 175 are electrical conductors used to make contact with a nonmetallic part of a circuit, such as human tissue, which can be configured for performing recording of bioelectric events in accordance with the disclosed techniques. In some embodiments, the electrodes 175 can be optionally implemented as components of the Bionode 170. According to this embodiment, the electrodes 175 have a wired coupling to the main board 101 of the Bionode 170 via a feedthrough board.

In accordance with the disclosed techniques, driving the Bionode 170, without an internal battery, involves the use of a wireless powering mechanism illustrated generally as 195. In an embodiment, the wireless powering aspects of the system 100 are embodied in part in a non-implanted base station component 140 that can be worn comfortably by the patient. Wireless power transfer 195 from the base station 140 to the implantable Bionode 170 may, in some embodiments, be accomplished using enhanced magnetic inductive coupling techniques utilizing metal coils on the power management board 101 of the Bionode 170 to a magnetic field generated by the base station 195. According to an implementation, wireless powerless transfer conducted between the base station 195 and the Bionode 170 involves conveying low frequency magnetic fields to the Bionode 170 via magnetic fields oscillating at low frequencies (e.g., 960 kilocycles-1,060 kilocycles) to interact less with human tissue than compared to electromagnetic fields oscillating at higher frequencies.

In some cases, the power transfer aspects may be accomplished according to the magnetic resonance coupling techniques described in related U.S. patent application Ser. No. 14/728,976 entitled "MAGNETIC RESONANCE COUPLING", filed Jun. 2, 2015, which is incorporated herein by reference in its entirety. Moreover, in another embodiment, wireless powering can be accomplished using near-field inductive coupling techniques. For instance, in some cases, the Bionode 170 is implanted proximate to the skin's surface of the patient 190, thus allowing for short-range coupling in a low-powered magnetic field generated between the non-implanted base station 195 and the implanted Bionode 170. Various other mechanisms employable for wireless power transfer may be utilized, as deemed necessary and/or appropriate.

In some cases, the non-implanted base station 195 supplies a time-varying magnetic field with time-dependent behavior and magnitude designed to elicit the desired stimulation current waveform in the Bionode 170. The design of the optimal current waveform at the output of a current generator in the base station 195 to produce the desired stimulation waveform in the implanted system. Generation of current waveforms at the output of the base station's generator can involve producing waveforms that are identical in shape and time-dependence to the waveform intended to be delivered to the biological site, in order to obtain the desired ranges of implant current stimulation waveform characteristics. In some instances, the system 100 is designed to deliver a biphasic rectangular pulse train stimulation waveform to the desired biological site with waveform characteristics including frequencies from 1 Hz to 150 Hz, pulse widths from 50 μSec to 1000 μSec, and pulse magnitudes of 0.25 mA to 12 mA. Moreover, the waveform characteristics supported by the system 100 can be generated to surpass the ranges of typical VNS waveform characteristics to provide maximum values in the ranges approved by the United States Food and Drug Administration, employing frequencies between 10 Hz to 60 Hz, pulse widths from 100 µSec to 500 µSec, and current magnitudes of 0.25 mA to 7 mA.

In another embodiment, wireless power transfer capabilities are realized through magnetic resonance coupling of the power management board 101 of the Bionode 170 with a cavity resonator (e.g., a cage that acts as an antenna and that also houses an animal into which the Bionode 170 has been implanted). In this case, the implanted Bionode 170 is wirelessly powered using a resonator based wireless power transfer system, in which the cavity resonator delivers power to the Bionode 170 inside of a chamber. Accordingly, the microelectronics of the power management board 101 is configured to provide power to the Bionode 170 transferred from energy of a magnetic field that is generated by the cavity resonator while the implantable device is appropriately oriented inside of the chamber. The WPT system, including the cavity resonator, can be strategically designed to: 1) maximize power transfer efficiency (PTE) through optimal impedance matching, 2) minimize resonator orientation mismatch sensitivity with the biaxial resonators on the power module, and 3) allow patient housing, namely rodents such as mice and rats for experimental purposes. Energy is wirelessly delivered to the implanted device by coupling magnetic fields generated within a metallic rectangular cavity (e.g., $TM_{110}$ resonant mode; L×W×H, 60.96×60.96× 30 cm3) to the power management board 101 of the implant. The cavity resonator can be constructed from any suitable material that can then produce a magnetic field, such as various metals including aluminum, copper, and the like.

Figure 1B:
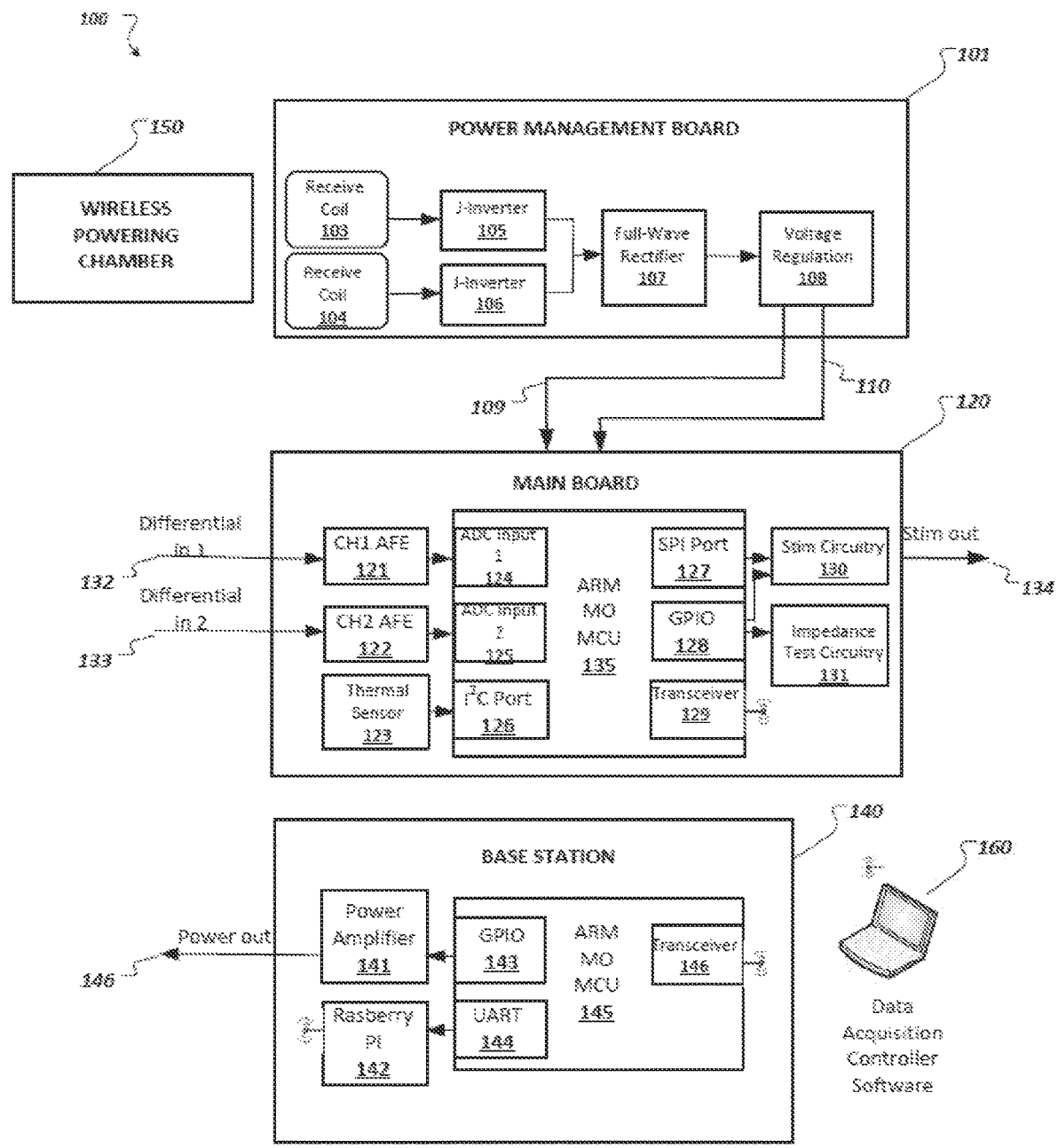

FIG. 1B is a block diagram illustrating an example of a wireless platform system 100 for implementing wireless recording and stimulating of bioelectric events, in accordance with the disclosed techniques. FIG. 1B illustrates the main sub-elements of the wireless Bionode 170, which includes the power management board 101 and the main board 120. In some cases, the power management board 101 can be stacked on top of the main board 120 to construct the implantable Bionode (as shown in FIG. 2C). Also shown in FIG. 1B are sub-elements of the base station 140.

The power management board 101 is illustrated as having various components configured to implement the power related aspects of the Bionode 170, including but not limited to: two receive coils 104 utilized in the wireless power transfer; two j-inverters 106; a full wave rectifier 107; and a voltage regulation 108 element. The power management board 101 can be configured to provide two different supply voltages 109 and 110 to run the microelectronics in the main board 120. The different supply voltages 109 and 110 may be of different levels, for example, 1.8 volts for supply voltage 109 to supply (1) analog front-end circuitry 121 and 122 for two recording channels, (2) the processor unit 135, and (3) a bi-directional telemetry component 129 to communicate data to and from the non-implantable base station assembly 140, and 11.2 volts for supply voltage 110 to supply the stimulation generation circuitry 130. According to the embodiments, the Bionode 170 is enabled with two-way telemetry involving transceiver 129 with the external base station 140, also having a transceiver 146. The base station 140 can use a single board computer (SBC) 142 that can be used to relay the data via a wireless network connection, such as Wi-Fi, to a computer, such as computer 160 shown in FIG. 1B having data acquisition controller software. For example, the SBC 142 may be implemented using Raspberry Pi along with custom circuitry. For example, the base station 140 can use Raspberry Pi along with a custom-made PCB that has the amplifiers and waveform generators for powering along with the radio DSP components for telemetry.

FIG. 1B illustrates the computer in communication with the base station 140, as a laptop 160. Generally, the computer 160 may be used by a user to program operation of the base station 140 and Bionode 170, and receive data regarding the operation of those components. Although shown as a laptop 160, various other personal computing device can be utilized, such as a desktop computer, tablet, or smartphone. The laptop 160 includes a processor, which can be one or more hardware processors, which can each include multiple processor cores. Also, the laptop 160 can include a memory, such as volatile and non-volatile memory, for example Random Access Memory (RAM) and Flash RAM.

Furthermore, laptop 160 (or any computing device communicatively coupled with the Bionode 170 and the base station 140) is configured to execute software related to the capabilities of the Bionode 170, such as the recording and stimulating of bioelectric events. In some implementations, data acquisition controller software can be installed on the laptop 160. As an example, the data acquisition controller software is written in a high level programming language, such as Python3. Moreover, the software can be used to display data in a user visible format on the display device of the computer, for instance as real-time data plots. This software running on laptop 160 can also serve as a user interface (UI) for controlling functional parameters of the system, such as sampling rate, ADC resolution, and stimulus waveform settings, features particularly useful in research settings involving, for example, an animal subject.

Additionally, users of the system 100 can communicate with the Bionode system 170 through the base station 140 using a software application called Bionode DataView. In some instances, the system software can be written for portability to various computing platforms, such as Macintosh, Windows, and Linux operating systems, which allows the application to be built for and deployed to a wide range of computing devices. To further increase the ease of deployment, the base station 140 creates its own Wi-Fi connection, allowing any device with Wi-Fi capabilities to communicate with the base station 140 without the need of additional hardware drivers. The Bionode application can also provide a graphical user interface that displays all acquired data and current Bionode 170 and base station 140 settings in real time. The user interface allows the user to set Bionode stimulation parameters as well as initiate and terminate stimulation sessions. Moreover, data packets can be recorded through the Bionode application into a desired file format, such as a binary data file. Subsequently, these raw binary files can be either analyzed directly, or exported as .wav files, which are easily importable, by multiple data analysis tools (i.e. MATLAB, Spike 2, etc.)

The power management board 101 can be employed to realize wireless power transfer (WPT) with a cavity resonator (as shown in FIG. 1B, which can be a cage that houses an animal and also acts as an antenna to wirelessly power the Bionode) or with a wearable base station device (shown in FIG. 1A). The pairing of the cavity resonator and each coil 104 in the power management board 101 can be operatively described as functioning in the manner of a 2-port band-pass filter. For instance, power transfer efficiency (PTE) is optimized by impedance matching and maximizing the unloaded Q, Q0, and the powering frequency.

The power management board 101 can act as a power supply by coupling RF energy and rectifying the induced current to DC. Orientation mismatch of the transmitter can introduce challenges in some cases, such as in the case of freely behaving experiments. While use of the resonant cavity can yield improved performance in comparison to some conventional WPT systems, it is not immune to non-optimal performance. For better WPT robustness, with respect to device orientation, two perpendicular copper coils with separate impedance matching J-inverter 105 topologies and a single full-wave rectifier 107 can be implemented for biaxial RF-to-DC conversion, as shown in FIG. 1B. The output of the rectifier 107 is shown as being fed to a voltage regulation element 108, that can be a low-dropout (LDO) linear regulator, to produce a voltage supply (e.g., 1.8 V) to the main board 120 components, such as the analog front ends (AFEs) 121, 122, thermal sensor 123, the MCU 135, and stimulation circuitry 130.

Also, the power management board 101 can provide a voltage supply, (e.g., 11.2 V) to a current controlled stimulator (CCS), illustrated in FIG. 1B as the stimulation ("stim") circuitry 130. An unregulated supply voltage can be buffered with a 47 µF storage capacitor and surge protected by a 5.6 V Zener diode, for example. As an example, the power management board 101 may have a 7×12 mm footprint and be fabricated with a 2 layer FR-4 PCB. In an implementation, the power management board 101 and the main board 120 connect at the two regulated outputs and device ground.

To accommodate the powering requirements of the Bionode system 170, the power management board 101 can be designed to provide a specified amount of power, for example, 16 milliwatts of average power. In some cases, the power management board 101 can be configured with the ability to produce up to 60 milliwatts of peak power, for example. This power is transferred to the Bionode 170 through voltage rails (109 and 110) that are used by the Bionode's acquisition circuitry 121, 122, and 123, microcontroller 135, and stimulation circuitry 130.

The power management board 101 can use two secondary coils oriented orthogonally to each other (or a single coil bent 90 degrees) to collect energy from a circulating magnetic field inside of the chamber housing of the resonator. The orthogonal orientation of these two coils allows the power management module 101 to more consistently collect energy while the implant is in varying orientations within the WPT chamber. The power transferred to each coil can be maximized via an impedance-matching admittance inverter network on the power management board 101 tuned to the resonant frequency of the chamber (e.g., approximately 340 MHz). The power management board 101 can include circuitry implementing an impedance matching network. As an example, the impedance matching network includes two capacitors, which initially have values predicted by bandpass filtering theory. These capacitor values are further tuned based off of measured resonant responses of the system. The circuitry utilized for implementing the impedance matching aspects of the power management board 101 are discussed in detail in reference to FIG. 9 below.

The control module, implemented as the main board 120, can be generally described as the brain of the Bionode. FIG. 1B illustrates the main board 120 as including, but not limited to: analog front ends (AFEs) for each of the two channels, namely CH1 AFE 121, and CH2 AFE 122; thermal sensors 123; microcontroller unit (MCU) 135; stimulation circuitry 130; and impedance test circuitry 131. Furthermore, the MCU 135 is shown as including internal elements, including: an analog-to-digital (ADC) input 1 124; ADC input 2 125; inter-integrated circuit i²C port 126; serial peripheral interface (SPI) port 127; general purpose input/output (GPIO) 128; and transceiver 129.

The main board 120 is configured to implement multiple operational functions of the Bionode 170, including but not limited to: biopotential acquisition, biomodulation, electrode impedance monitoring, thermal monitoring, and bidirectional telemetry. The main board 120 has the circuitry for the recording and stimulating channels, as well as a microcontroller 135, radio, and antenna for data transmission and reception (transceiver 129). The main board 120 is shown to produce an electrical output, stimulation output signal 134, which can be used to stimulate a nerve, for instance, at the implanted biological site of the patient, in the case of biomodulation.

A system-on-chip (SoC), (e.g., SoC, NordicnrF51822) may be utilized to run and coordinate the multiple protocols of the Bionode. In an implementation, the SoC may contain a 32-bit ARM Cortex-M0: a MCU 135 with 256 kB of flash memory, which allows for rapid changes to the device's functional protocol through reprogrammable firmware.

The main board 120, in some cases, may be a six-layer FR-4 (glass-reinforced epoxy) printed circuit board (PCB) (39.37 mil thickness) and fabricated for example by Advanced Circuits (Aurora, Colo.). The footprint of the main board 120 can be deigned at 7 mm×12 mm. Given close proximity of the mixed signal microelectronics, a design consideration for layout is to physically isolate the analog, digital, and radio frequency (RF) blocks of the Bionode.

Biopotential acquisition can require specific electrical features, such as high differential input impedance, low noise, high common-mode rejection ratio (CMRR), and sufficient gain and bandwidth. Accordingly, in an effort to achieve desirable features, the main board 120 is configured with two parallel AFEs, shown as CH1 AFE 121, and CH2 AFE 122. Each AFE can have a two-stage gain topology (shown in FIG. 3A). Each of the AFEs 121, 122 are shown as receiving differential inputs 132, 133 respectively. The inputs—differential inputs 132, 133—can be signals transmitted from a differential pair of electrodes that can be used for ECG recording, for example.

In some cases, the gain and bandwidth of the AFEs 121, 122 can be reconfigured individually through passive component selection but also may be limited by the gain bandwidth product of the second stage (200 kHz). The total gain for both channels is set to 60 dB, in an embodiment. The first stage (20 dB gain) of an AFE 121, 122 can use an amplifier (e.g., INA333 instrumentation amplifier, Texas Instruments) due to its characteristics, such as 100 GΩ differential input impedance and 50 µA power consumption. The second stage (40 dB gain) of the AFEs 121, 122 can be AC coupled with an inverting bandpass filter topology. The output of the second stage is then routed to an ADC, for instance a 10-bit analog-to-digital (ADC) embedded in the SoC. Also, low pass input filters can be used within the AFEs 121, 122 to decrease RF interference in WPT. Implementation of frontends can impact matching and differential input impedance, in some instances.

The Bionode system's AFEs 121, 122 can have a measured CMRR of >80 dB from DC to 60 Hz and a measured input-referred noise of 2.3 µV. For purposes of analyzing performance characteristics of the recording channel for the Bionode 170, input-referred noise, gain, and bandwidth measurements were performed using an Agilent 35670A dynamic signal analyzer.

According to some embodiments, the Bionode 170 is supported by various external systems. In this case, the wireless platform system 100 includes a Wireless Powering Transfer (WPT) chamber 150. The WPT chamber 150 can provide both power to the implanted Bionode and a living space for the implanted subject rodent. Data wirelessly transmitted to and/or from the Bionode 170 can pass through the base station 140 that provides a communication interface between the Bionode 170 and a computing device, illustrated as a laptop 160 in FIG. 1. The communication interface to the laptop 160 can be implemented via a wireless link using various wireless networking technologies, for example Wi-Fi. A custom designed cross-platform application for the system 100 can be configured to provide a graphical user interface, which can be displayed on the laptop 160 for example, and used to allow users to view and save data transmitted by the Bionode 170 as well as specify various settings (i.e., stimulation waveform parameters) on the Bionode 170. Expected values versus measured results for one implementation can be shown for the following parameters:

| Category | Specification | A/E | Value [Expected] | Measured |
|---|---|---|---|---|
| Stimulation and blocking | Number of channels and type (single-ended/ differential) | A | 1 Differential | 1 single-ended |
| | Pulse frequency range | A | 20 kHz | 0.01 to 20 kHz(Pulse frequency is measured from positive stim (rising)edge to negative stim (falling) edge) |
| | Pulse shape (rectangular, fixed pattern, arbitrary) | A | rectangular | rectangular |
| | Amplitude range of pulse control (for electrical stim/block) | A | 0 to 1 mA | 0 to 1.06 mA |
| | Compliance at maximal amplitude (for electrical stim/block) | E | 0.01 mA | 0.015 mA |
| | Range over which duty cycle can be configured | A | 0% to 100% | 0-100% |
| | Wireless stimulus monitoring rate and resolution (if available) | A | 25 kSps and 8 bit depth | Not implemented in BN4.1 |
| | Offset voltage build-up after continuous 50% duty cycle stim at 10 kHz over a low-leakage capacitor (e.g. ceramic, testing setup info available on request) | E | 0 mV | 1.2 V@1000 uA Pulse Amplitude, 50 us Pulse Width, 100 us Pulse Period |
| Nerve Recording | Number of channels and type (single-ended/ differential) | A | 2 Differential | 2 Differential |
| | Total input referred noise at relevant frequency band and gain | E | 1.77 µV RMS @ 1 kHz | 3.1 µV RMS @ 1 kHz |
| | Range of amplifier gains | A | 60 dB in 1 steps | 59.9 dB |
| | Input range | A | 1.2 mV | |
| | Analog channel bandwidth (HPF to LPF) (selectable during assembly, not after) | A | 10 Hz to 5 kHz | N/A |
| | ADC dynamic range and effective resolution | A | 10 bits | Not present in nRF51822 datasheet |
| | Simultaneous operation with stim/block | E | yes | yes |
| Power & telemetry | Battery type (primary or rechargeable) and capacity (if any) | A | None | Lithium Ion (LiR1220) 12 mAh |
| | Power transfer frequency (if rechargeable) (enclosed cavity volume) | A | 335 to 340 MHz | 335 to 345 MHz |
| | Average power transfer rate @ 5 cm in moving animals (if rechargeable) | A | N/A | N/A |
| | Average power budget for overall system at worst-case stimulation/ block | A | 19.28 mW | 18.52 mW(1 mA, 11 k, 50%) |
| | Average power budget for overall system while recording | A | 7.28 mW | 5.288 mW |
| | Maximal implant depth, number of data (and power) coils in the implant | E | 10 cm, 2 coils | |

-continued

| Category | Specification | A/E | Value [Expected] | Measured |
|---|---|---|---|---|
| | Data telemetry protocol and rate (up- and downstream) | A | Custom type, 250 kbps | Custom, 2 Mbps |
| | Base-station: Tx power, Rx sensitivity (At the input/output of the microcontroller) | A | TX: 4 dBm, RX: −85 dBm | −85 dBm per nRF51822 datasheet |
| | Implant: Tx power, Rx sensitivity (At the input/output of the microcontroller) | A | TX: 4 dBm, RX: −85 dBm | −85 dBm per nRF51822 datasheet |
| Implant packaging | Weight of the implantable device | E | 1.5 Gram | 9 Gram(10 Gram with bat) |
| | Size of the implantable device(s), L × W × H (cylindrical) | E | ~1 cm$^3$ (.5 r × 1.41) | 6.18 cm$^3$(.75 r × 3.51(4 cm with bat)) |
| | Insulation material for wires and implant (e.g. Teflon, epoxy, silicone) | A | Si wires, epoxy implant | Silicone, Epoxy and Glass |
| | Number of wires in the cable to electrodes (including ground) | A | 7 | 2-7, depending on application |
| | Cable connector and number of leads for recording, stimulation, and sensors | A | NA | NA |

Two major modalities of biomodulation are electrical and optical. Safety parameters for electrical stimulation have been extensively characterized, and protocols should be charge balanced with biphasic waveforms. Other stimulation parameters such as frequency, pulse width, and pulse pattern distribution are lesser studied and are of interest for biological efficacy and decreased power consumption. A current-controlled stimulator (that may be utilized in a Bionode) may use an op-amp constant current sink that draws charge from a 11.2 V supply (provided at voltage supply 110, shown in FIG. 1B, for example). Charge balanced biphasic stimulation is enabled by a dual-pole dual-throw (DPDT) switch at the electrode inputs. An on-board 12-bit digital-to-analog converter (DAC) provides the reference voltage. All stimulation parameters are controlled by protocols in the MCU 135. The performance of the stimulator is evaluated by connecting the stimulator outputs to a known load impedance (10 kΩ) and sweeping the stimulator's functional parameters (e.g. pulse width, current amplitude, and pulse repeat time/duty cycle). A sample of the biphasic stimulator output, illustrated as "stim out" 134, for a range of stimulus current amplitude settings at a 50% duty cycle is given in FIG. 4. The measured charge balance is 6 nC at a pulse width of 1 ms. The current controlled stimulator (CCS) can deliver up to 1.12 mA across a 10 kΩ load owing to its 11.2 V headroom.

Optical stimulation for use in optogenetic experiments can be configured by replacing the electrodes with an optical module for deep brain stimulation and disabling the biphasic stimulation. Of experimental interest, blue light emitting diodes (LEDs) typically have the highest forward voltage at 3.0-3.3 V. The 11.2 V headroom is more than sufficient to drive the LED.

Figure 2A:
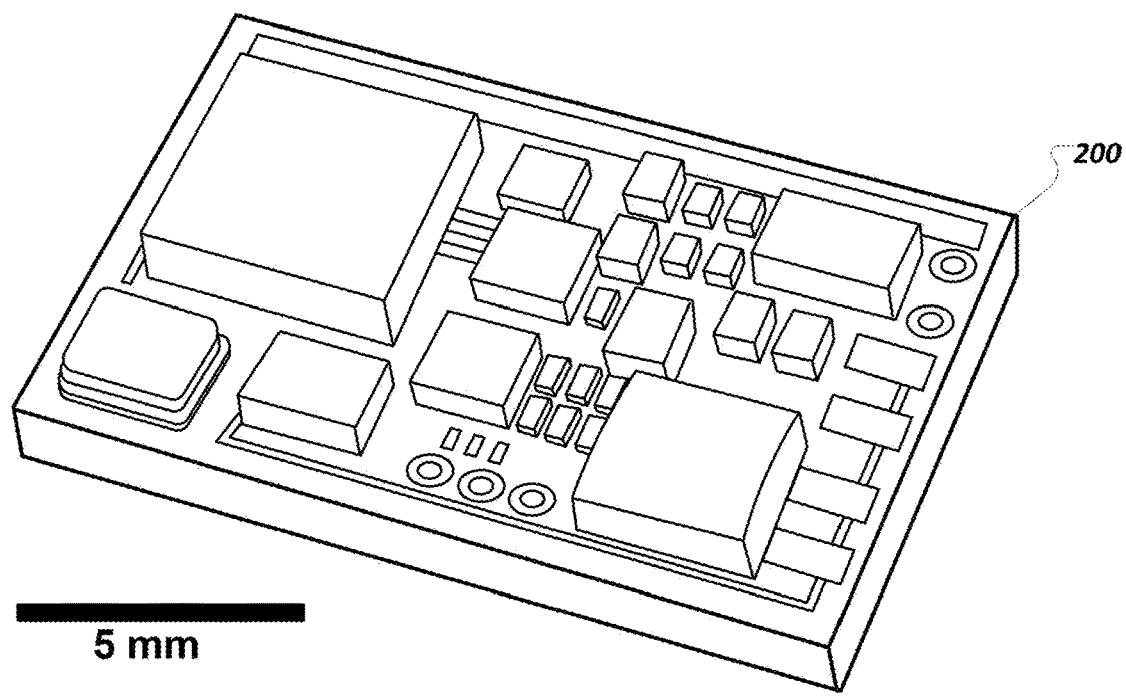
FIGS. 2A-2B show a top and bottom view, respectively, of an example of a main board for the wireless implantable device for implementing the disclosed techniques.
Figure 2B:
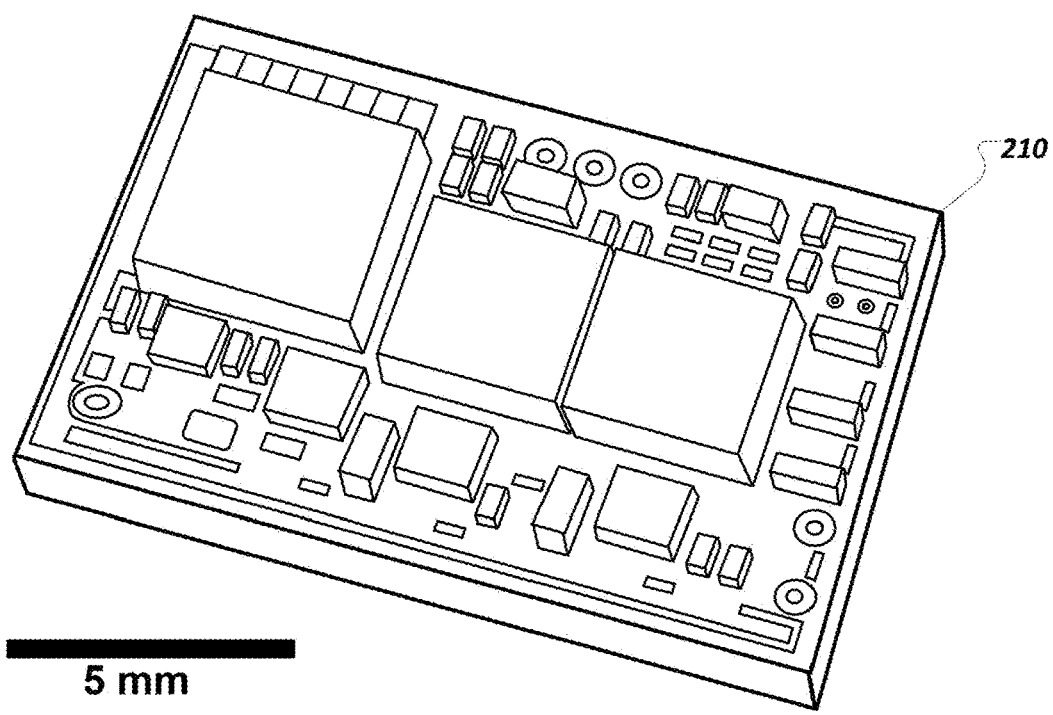
Figure 2C:
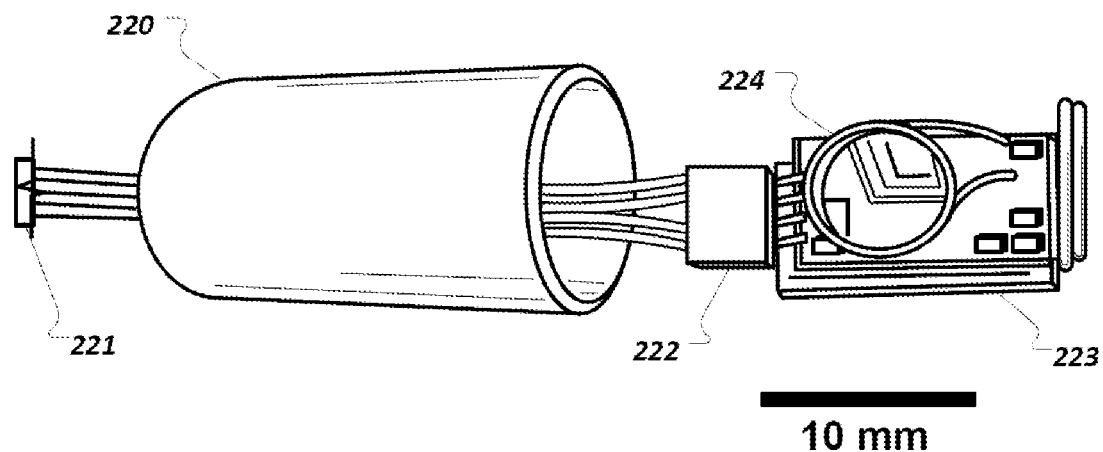
FIGS. 2C-2D show an example of a wireless implantable device for implementing the disclosed techniques.

FIG. 2A and FIG. 2B show a top and bottom view, respectively, of an example of a Bionode control module or main board 200, 210 (that is, an example physical configuration of the main board 120 shown in FIGS. 1A and 1B). As shown, the main board 200, 210 is a printed circuit board (PCB) assembly. In FIGS. 2A-2B, the main board 200, 210 is illustrated as fully populated with the microelectronics operating in concert to implement the various functions associated with the Bionode, namely the main board (shown in FIG. 1). The main board 200, 210 can be implemented using integrated circuit (IC) chips and passive components to achieve various aspects of the Bionode, such as the two differential recording channels, one current controller, biphasic stimulator, thermal sensing, electrode impedance measurement, and two-way telemetry. It should be appreciated from FIGS. 2A-2B that the Bionode's microelectronics fit within the main board 200, 210 having a characteristically small circuitry area, and similarly a small footprint. In some cases, the board 200, 210 can have a footprint measuring 7 mm×12 mm. A microcontroller can be included in the microelectronics of the main board 200, 210. In an implementation, the main board 200, 210 has installed thereon a microcontroller implemented as an Application Specific Integrated Circuit (ASIC), which is an integrated circuit (IC) programmed for a specific use. In some implementations, the ASIC can be powered wirelessly according to the wireless powering aspects described herein. For instance, the ASIC can be powered wirelessly at 13.56 MHz using a powering wand and a loop antenna on the circuit board 200, 210. Additionally, the main board 200,210 includes the electronics needed to convert an electromagnetic wave to a DC voltage, for example 1.8 V, to power the ASIC.

In an embodiment, maximum dimensions of the microelectronic platform shown in FIGS. 2A-2B, once populated, may be 12 mm (length)×7.5 mm(width)×2.5 mm (height). The circuit illustrated as main board 200,210 can be designed for optimal impedance matching of the receive coils, power rectification, and power management module placed on a twin board and stacked. Once integrated, main board 200, 210 plus the receive coil system can increase the total device form factor to 15 mm (length)×7.5 mm (width)×5 mm (height) for a total device volume of ~0.6 cc. The stimulator can be current controlled with a 12V headroom, for instance. In accordance with the microelectronic implemented in main board 200,210, the Bionode may be equipped with two differential recording channels, one stimulating channel, thermal sensing, and electrode impedance measurement. In an embodiment, the device logic may use off-shelf electrical components, for example an ARM CORTEX M0 microcontroller.

Figure 2D:
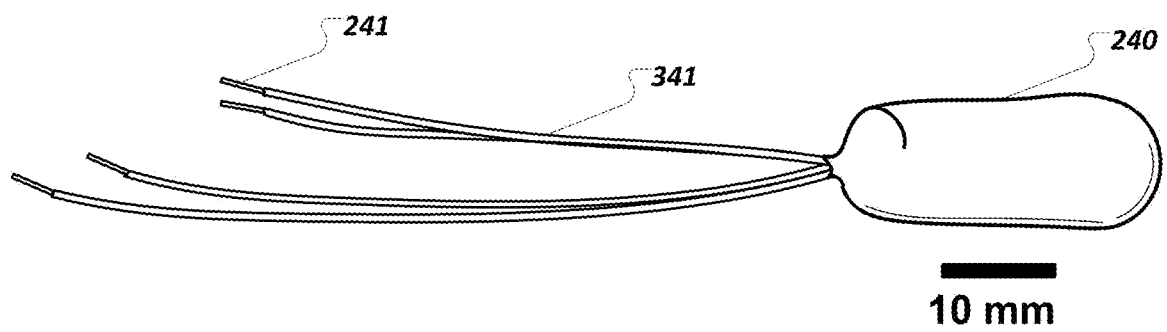

FIG. 2C shows an example of a wireless implantable device, or Bionode such as 170 shown in FIGS. 1A and 1B, for implementing the disclosed techniques. As shown in FIG. 2C, a power management board is stacked on top of a main board to create a fully assembled Bionode 223. FIG. 2C illustrates the Bionode 223 including a header 222 with crimp pins. In some embodiments, the header 222 is optionally used to remove and replace electrode leads 221, 241, 341. The Bionode 223 can be covered by a shell 220, which is depicted as being removed from the Bionode 223. In FIG. 2D, the Bionode 223 is illustrated as being encapsulated inside of a shell 240. In some cases, the shell 240 is a molded medical epoxy shell.

FIG. 2C also illustrates a loop antenna 224. The loop antenna 224 can be connected to the board of the Bionode 223. The loop antenna 224 can be used for wireless transmission of data to and/or from the Bionode 223. As an example, the data is transmitted to the loop antenna 224 at 3 GHz.

Figure 3A:
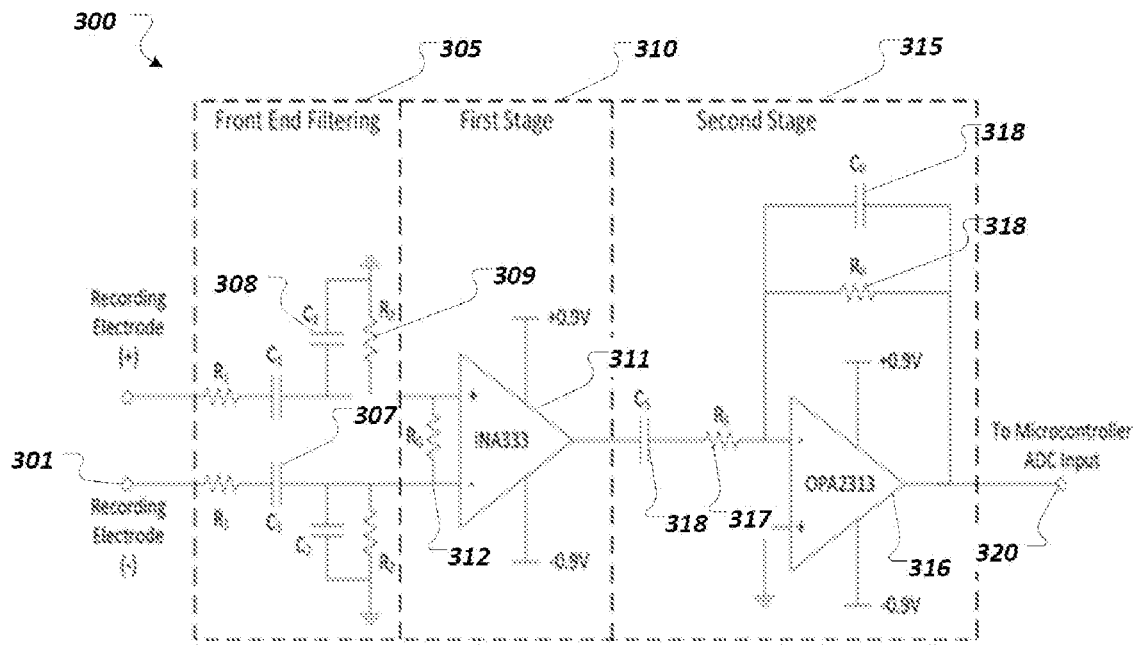
FIG. 3A shows a diagram of an example for circuitry implementing an analog front-end (AFE) aspect of the wireless implantable device for implementing the disclosed techniques.

FIG. 3A is a diagram of an example for circuitry implementing an analog front-end (AFE) for a recording channel of the Bionode, such as AFEs 121 and 122 of FIG. 1B. The circuitry 300 can be configured in a manner that implements various advantageous electrical design characteristics for the sensing aspects of the Bionode, such as a high differential input impedance, low noise, a high common mode rejection ratio (CMMRR), and sufficient gain and bandwidth. As a general description of the circuitry 300, the front-end filter 305 allows for passive bandpass filtering prior to amplification. The first stage 310 in capable of operating as an amplification stage, which differentially amplifies the signal. The amplification within the first stage 310 can be achieved using a precision instrumentation amplifier 311 with minimal gain, for example. The second stage 315 can also operate as an amplification stage. The second stage 315 can have a substantially higher gain in comparison to the first stage 310, and is configured to implement active bandpass filtering.

In some implementations, various electrical parameters can be adjusted, for example the gain and bandwidth can be set for each input channel in order to properly condition the various signals that may be sensed by the circuitry 300 (i.e., electrocardiogram (ECG), electrocorticogram (ECoG), electromyogram (EMG), local field potential (LFP), compound nerve action potential (CNAP), thermocouple sensor inputs, or pressure sensor inputs). While the circuitry 300 can filter out noise generated by the some sources (i.e., nearby-radiated signals, motion artifacts, and other biological signals), it can be configured to filter out high frequency noise, for example noise that is injected into the signal path from the wireless power transfer (WPT).

According to the embodiment of FIG. 3A, the Bionode has two parallel dual-ended AFEs, for instance one for each input channel. Each of the AFEs can be designed using the circuitry 300, which include passive front-end filtering 305 coupled with a first stage 310 and a second stage 315. The stages 310,315 are configured for gain amplification. The first stage 310 implements differential amplification and the second stage 315 can be a high-gain stage that also provides band-pass filtering. These parallel AFEs are dual-ended with rails, for example, +0.9V rails to allow the AFE to have a zero DC bias voltage. This can be utilized in the instances where the stimulation circuit requires that the negative stimulation electrode is connected to the Bionode's ground. If the AFE had a non-zero DC bias voltage, a static potential could exist between the recording electrodes 301 and the negative stimulation electrodes; which can potentially cause tissue damage, electrode erosion, and unintended stimulation performance.

Further, in alternative embodiments of the circuitry 300, the passive front-end filtering 305 can be configured to provide the option to include the passive high pass filter, low pass filter, or bandpass filter before the first stage differential amplifier. While adding these filters can reduce the CMRR and the differential input impedance of the AFE, it can be advantageous for the design to implement these filters in certain conditions. As an example, in the instance of directly sensing bio-signals with differential leads (i.e., ECG, ECoG, or EMG), a drifting DC offset voltage may be observed which can cause the inputs to the instrumentation amplifier 311 in the first stage 310 to drift out of the DC voltage input range of the instrumentation amplifier 311. To address this problem when measuring signals, such as biopotential signals, a passive high-pass filter can be populated in the front-end filtering stage of the AFE. A similar issue has also been observed related to high-frequency conditions, for example when providing power to the Bionode using a high frequency inductive link. High frequency radio frequency (RF) noise can couple onto the leads and traces of the Bionode when inductively powering. To compensate for noise, the circuitry 300 can be configured to remove the noise by populating a passive low-pass filter in the front-end filtering 305 stage of the AFE. If operating the Bionode under conditions where both of the aforementioned problems arise (i.e., wirelessly powering a Bionode while measuring ECG), a passive band-pass filter is populated in the front-end filtering 305 section of the AFE circuitry 300. In the case of operating void of the aforementioned problematic conditions, the front-end filtering 305 section can be bypassed by implementing a specific circuitry. As an example, the bypass is implemented by populating the R1 306 and C1 307 pads with zero ohm resistors and not populating the R2 308 and C2 309 pads; providing input channels with higher differential input impedance and CMRR.

Examples of performance characteristics for one AFE circuitry 300 of the Bionode can be shown for the following parameters:

| Parameter | Value | | |
| --- | --- | --- | --- |
| | No front-end filters | Low-pass front-end filter | Bandpass front-end filter |
| Gain | 60 dB | 60 dB | 59.9 dB |
| High-pass cut off | 10.47 Hz | 4.9 Hz | 6.0 Hz |
| Low-pass cut off | 1.410 kHz | 1.48 kHz | 1.46 kHz |
| CMRR | 100 dB | 43 dB | 72 dB |
| Input impedance | 100 GΩ | 3.61 MΩ | 2.03 MΩ |
| Input-referred noise | 51.85 nV/√Hz | 101 nV/√Hz | 97.3 nV/√Hz |

The first stage 310 can include a ground referenced instrumentation amplifier 311 that differentially amplifies its input signal. An amplifier 311 can be chosen as a design choice based on various component characteristics, such as its high input impedance (i.e., 100 GΩ), low power consumption (i.e., 50 µA), and low operating voltage (i.e., 1.8 V). The value of the RG 312 resistor can determine the gain of the instrumentation amplifier 311. For example, the gain for amplifier 311 can be set to 20 dB (RG=11 kΩ). This is comparatively smaller than the gain of the second stage 315, so as to reduce noise.

The second stage 315 is shown as implementing an inverting band-pass filter topology, using an operational amplifier 316. The amplifier 316 can be chosen because of various component characteristics, for instance sufficient gain bandwidth (1 MHz), low noise (25 nV/sqrt(Hz)), and rail-to-rail output. In some cases, an amplifier 316 has the added benefit of being available in a compact dual-package form factor which allows one IC to be used to implement both AFEs, thereby reducing circuit area. The gain and bandwidth of the second stage 315 can be reconfigured individually by adjusted by appropriate component values for RS 317, CS 318, RP 318, and CP 319. The gain for the second stage 315 can be set to between 20 and 50 dB, as an example.

The outputs 320 of the circuitry 300 for each of the AFEs are routed directly into two of the microcontroller's ADC inputs. A microcontroller for the Bionode system can be powered off of the same ±0.9V rails that power the AFEs, which can potentially remove the necessity for the outputs of the second stages 3 15 to be transformed into single-ended signals. This allows the outputs to be routed directly into the ADC inputs of the microcontroller. In some implementations, the microcontroller's ADC can be configured to acquire samples at either 8-bit or 10-bit resolution with a total sample rate of up to 25 kHz, which is selectable by the user via the bidirectional communication interface.

Figure 3B:
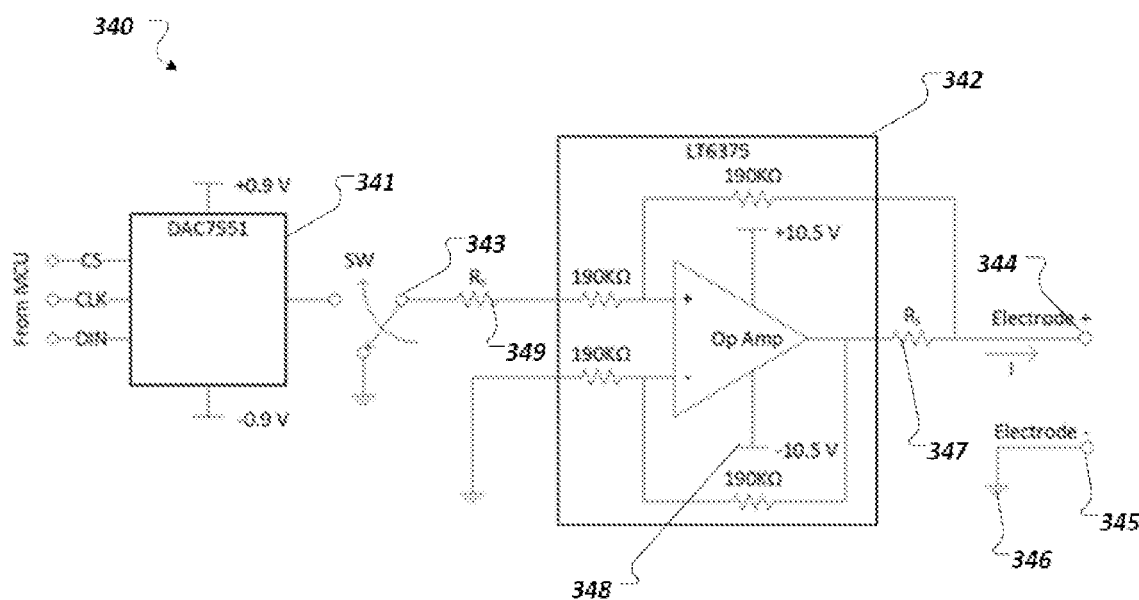
FIG. 3B shows an example of circuitry for implementing a constant current stimulation aspect of the wireless implantable device.

FIG. 3B shows an example of circuitry 340 for implementing constant current stimulation aspects of the wireless implantable device. In some implementations, a current stimulation waveform that is constant, or otherwise substantially constant, can be applied to the Bionode. As a general description of the circuitry 340, a constant current stimulation is generated via a current source 342. The output of the current source 342 can be set by the microcontroller of the Bionode via the digital-to-analog converter (DAC) 341. A normally grounded control switch 343 can be used to potentially prevent unintended stimulation from occurring, for example during a power on sequence. To enable bi-phasic stimulation, a positive stimulation electrode 344 can swing around the negative electrode 345 which shown as being tied directly to the Bionode's ground 346.

As discussed above, the current stimulation can be constructed using a current source 342, which is driven by the digital-to-analog converter (DAC) 341. FIG. 3B illustrates the current source 342 as a Howard current source (HCS) that converts a control voltage provided by the DAC 341 into a current waveform. The DAC 341 topology is shown, but other topologies like current mirroring or electrode polarity switching (where the positive and negative electrodes are physically switched) can be implemented. The configuration in FIG. 3B may realize advantages associated with a DAC generating reliable symmetric bipolar current pulses. Difficulties relating to achieving symmetric pulses can be experienced in cases where current mirroring topologies are used, for example due to part tolerances. Also, electrode polarity switching can sometimes create asymmetric responses in stimulated nerves, as an example due to the physical change in anodic and cathodic electrode placement.

In the current source 342 of circuitry 340, the output current I is related to the control voltage $V_{CTRL}$ by the following equation:

$$I = \frac{V_{CTRL}}{R_S} \quad (1)$$

In some implementations, $R_s$ 347 is a current limiting resistor configured such that the particular design requirements, such as specified stimulation current amplitude and precision, can be met. For example, a Bionode can be designed to provide a maximum stimulation current of 1 mA through a 10 kΩ electrode impedance. In some cases, because the output voltage range for the DAC which provides $V_{CTRL}$ is −0.9V to 0.9V, R_S was set to 800Ω, it allows for the current source 342 to provide current outputs ranging from −1.125 mA to 1.125 mA. In order to drive this current across a 10 kΩ electrode impedance, for example, the current source 342 is powered by a ±10.5 V supply 348 which can allow a maximum voltage of 10.5V to appear at the output terminal.

According to an embodiment, stimulation waveforms are created by a 12-bit DAC 341 which is controlled by the Bionode's on-board microcontroller via a serial peripheral interface (SPI). These stimulation waveforms are generally biphasic rectangular pulses, which may be defined by a user in terms of amplitude, pulse width (TPW), and pulse repeat time (TPRT).

As an example, a user may define these parameters using software supported by the platform, such as a Bionode application, which subsequently instructs the Bionode to set interrupt registers in its on-board microcontroller. These interrupt registers can define the stimulation waveform by specifying when DAC 341 output voltage updates must occur. To further increase the accuracy of the DAC 341 output, calibration registers may also be defined by the user which are used by the microcontroller to automatically compensate for static DC offset voltages that may be present on the output of the DAC 341. There can be a range of these DC offset voltages, and calibration values to compensate for these offsets can be obtained experimentally during the fabrication of each Bionode.

Additionally, the circuitry 340 illustrates a single pull double throw (SPDT) switch 343 is placed between the DAC 341 output and the current source 342. The switch 343 can be employed to avoid any start-up glitches on the output of the DAC 341, which can potentially be experience when the DAC 341 is first powered on. If not avoided, this glitch may cause the stimulator circuit 340 to output an unwanted stimulus pulse every time the Bionode is powered on.

The switch 343 is controlled by the on-board microcontroller and has a pull-down resistor 349 attached to the control line which can help ensure that the switch 343 is in position zero even when the microcontroller is powering on and not yet driving its voltage level. When at position zero, the switch 343 connects ground to the $V_{CTRL}$ line of the current source 341, causing the stimulator to not output any current. When at position one, the switch 343 connects the output of the DAC 341 to $V_{CTRL}$, allowing the DAC 341 to control the current output of the stimulator circuit 340. For safety reasons, it may be desirable to set the switch 343 to position one when the user has specified that stimulation should occur.

A list of the key performance specifications for the stimulator are shown for the following parameters:

| Parameter | Value | Units |
|---|---|---|
| Voltage headroom | 10.5 | V |
| Current amplitude[1] | 0.005-1.050 | mA |
| Current amplitude resolution | 4.4 | µA |
| Pulse width ($T_{PW}$) | 50-8.36e6 | µs |
| Pulse width resolution | 1 | µs |
| Pulse rate | 1e−5-20 | kHz |
| Charge balance error[2] | <0.5 | % |

Figure 4:
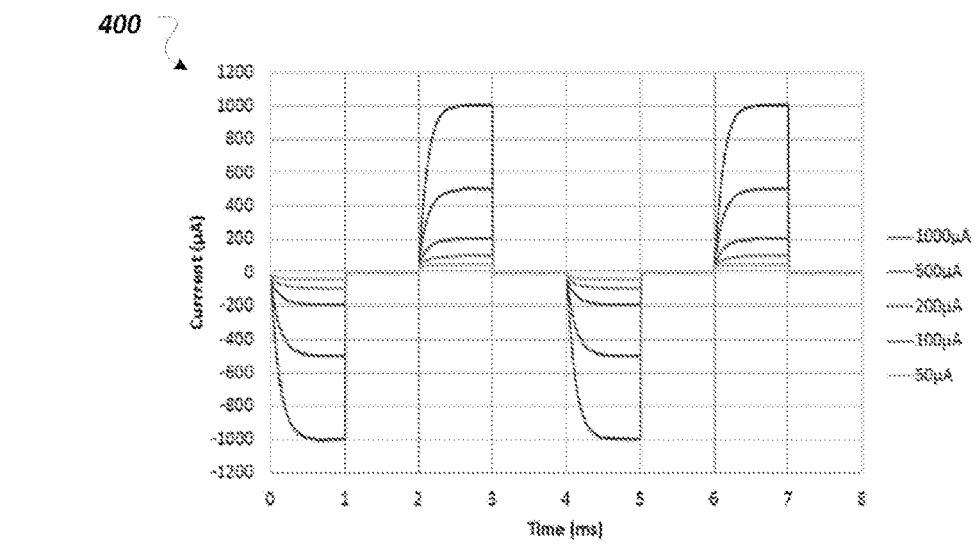
FIG. 4 shows an example graph displaying current-controlled, biphasic output measured from the stimulator outputs aspect of the wireless implantable device.

FIG. 4 is an example graph 400 displaying current-controlled, biphasic output measured from the stimulator outputs of a Bionode. In this example, the stimulator output is measured on a benchtop using a 10 kΩ load across the stimulator outputs. The graph 400 displays the output signal as a relationship between time (ms), along the X-axis, versus current (A) along the Y-axis. Pulse width, current amplitude, and duty cycle can be selectable parameters in real-time through reverse telemetry from the base station to the Bionode. A pulse width of 1 ms and a 50% duty cycle are used here to illustrate the current output for a range of amplitude settings.

Figure 5:
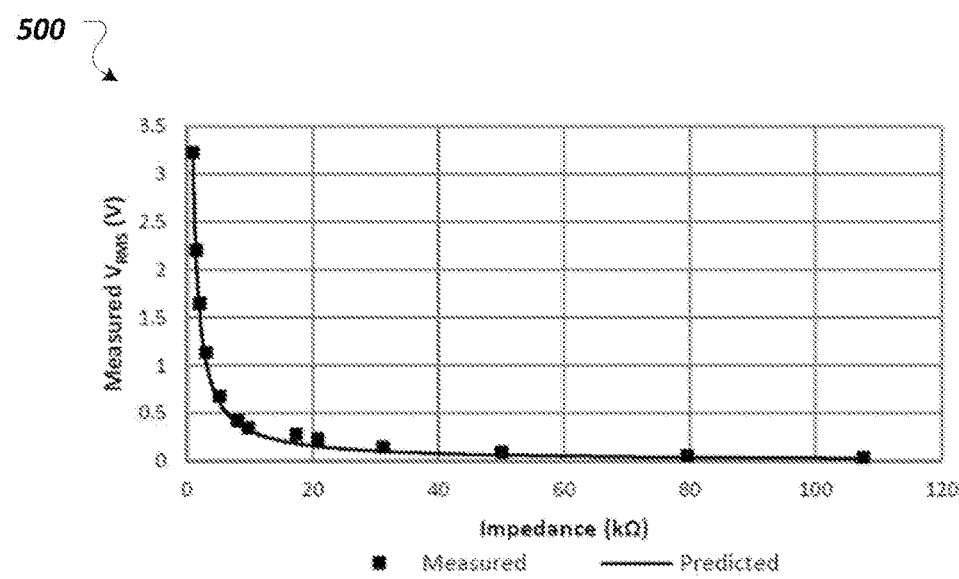
FIG. 5 shows an example of a graph displaying root-mean-square (RMS) voltage measured employing the electrode impedance measurement capabilities aspect of the wireless implantable device.

FIG. 5 is an example of a graph 500 displaying root-mean-square (RMS) voltage measured employing the electrode impedance measurement capabilities of the Bionode. For instance, the measured RMS voltage graphically represented in graph 500 can be recorded across a series of known load impedances, while running electrode impedance measurement circuitry. The graph 500 displays the RMS voltage signal as a relationship between impedance (kΩ), along the X-axis, versus the $V_{RMS}$ (V) along the Y-axis. A prediction curve can be calculated to fit to this data, and exhibit an R2 value of 0.994. Further, the prediction curve can be used to approximate the electrode impedance at a fixed frequency.

Figure 6:
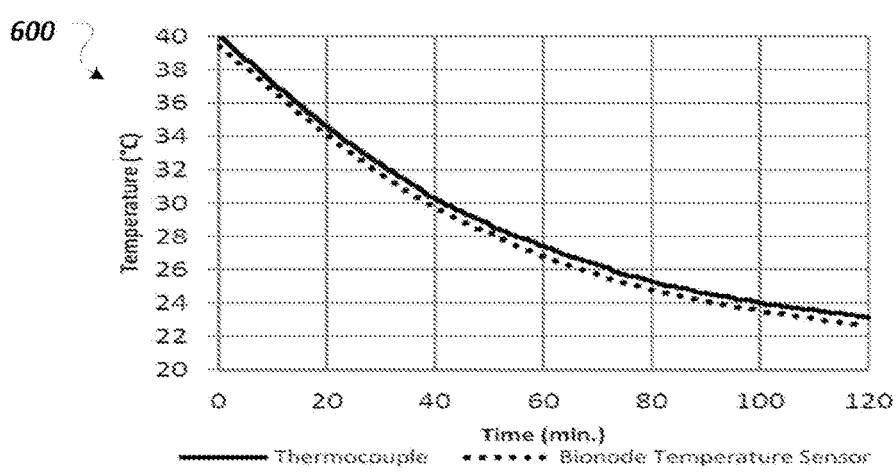
FIG. 6 shows an example of a graph displaying plotted points of temperature sensor measurements and curve of thermocouple change.

FIG. 6 is an example of a graph 600 displaying plotted points of temperature sensor measurements and curve of thermocouple change. The graph 600, as an example, is a graphical representation of a comparison of temperature IC and thermocouple tracking change in environment temperature. The graph 600 displays the relationship between time (min), along the X-axis and temperature (° C.) of the thermocouple and the temperature sensor measurements, along the Y-axis.

Figure 7:
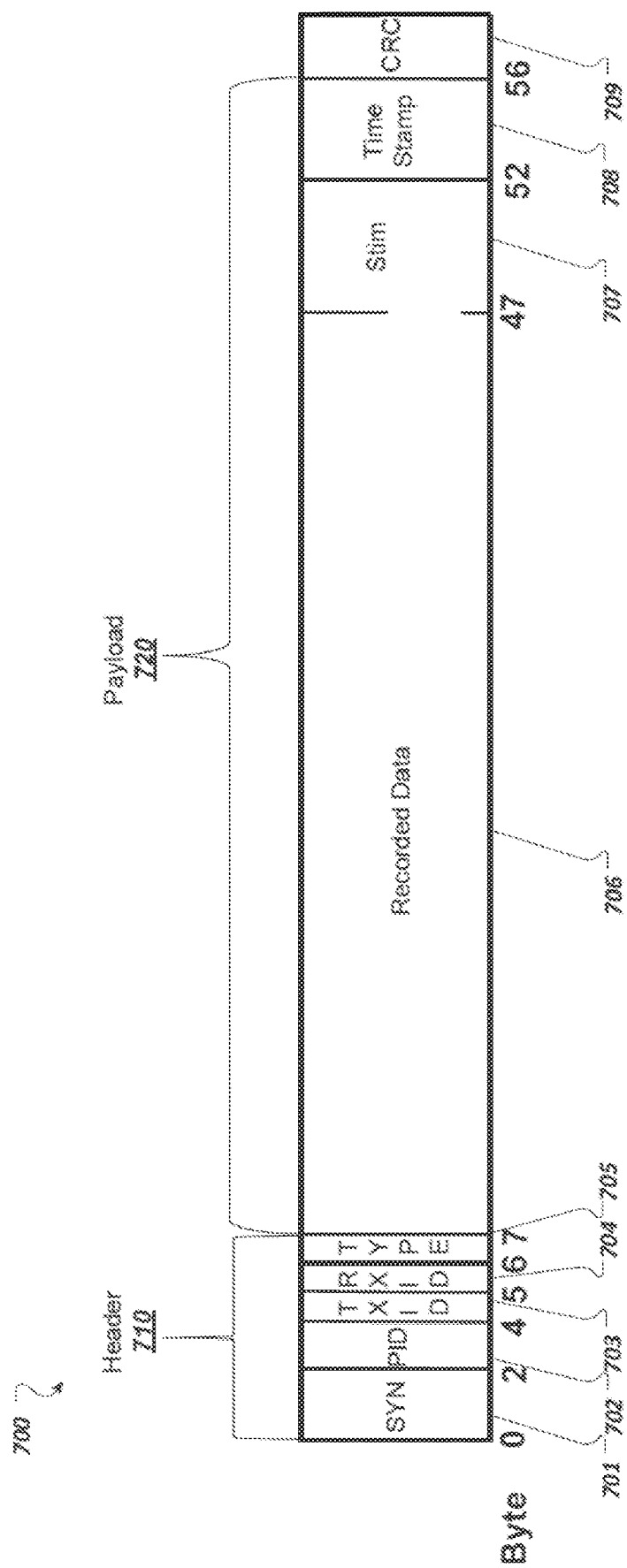
FIG. 7 shows an example of a format for a data packet structure, used in implementing a wireless communication protocol.

FIG. 7 shows an example of a format for a data packet structure, used in implementing a wireless communication protocol. For example, a data packet 700 having the format displayed in FIG. 7 can be transmitted, during wireless communication, from the Bionode to be received by a computer device running software for the Bionode platform. As illustrated, the data packet 700 is formatted in accordance with the Bionode's wireless communication protocol to include various fields that can be divided into three main segments: a header 710, a payload 720, and a CRC 709. The header 710 section of the data packet 700, includes one or more fields: Synchronization (SYN) 701; Packet ID (PID) 702; transmission ID (TXID) 703; receiver ID (RXID) 704; and TYPE 705. In the payload 720 section, the format has one or more fields including: recorded data 706; stim status 707; and time stamp 708.

Further, each the fields of the packet's format include information usable to support wireless communication aspects of the system. SYN 701: synchronization bytes equal to 0xA55A indicating the start of a packet. PID 702: packet ID generated by a running counter that indicates the number of packets sent since power on. TXID 703: indicates packet origin (PC, Base Station, or Bionode). RXID 704: indicates intended recipient (PC, base station, or Bionode). TYPE 705: packet type which categorizes the content of the payload section of the packet. Recorded Data 706: contains either 40 8-bit data samples or 32 10-bit data samples. Data resolution is defined by the preceding TYPE byte. Stim status 707: each bit indicates whether the stimulator was stimulating or not during the acquisition of each corresponding data sample in the recorded data segment of the payload. Time Stamp 708: a 4-byte time stamp added by the base station which can be used in tandem with the PID by the PC to determine the sampling rate of the data as well as the duration of any lost data. Lastly, CRC 709: a 16-bit cyclic redundancy check used to determine the validity of each packet.

The packets 700 that are transmitted to and from the personal computer, base station, and the Bionode (shown in FIG. 1) can contain the same header 710 and CRC 709 sections. In some embodiments, the payload 720 section varies depending on the type of data being transmitted in the packet 700. The header 710 section is used by the base station to properly route one or more packets 700 it receives, and the contents of the header 710 can also be analyzed to determine if a packet 700 has been routed incorrectly. The leading SYN bytes consist of the bytes 0xA55A. These bytes allow the beginning of a data packet 700 to be found in cases where partial packets may be missing from the data stream. This is likely to occur during a serial transmission that occurs between the base station's microcontroller and the base station's on-board Raspberry Pi (shown in FIG. 1). The next bytes in the data packet 700 contain an incrementing packet ID number. The packet ID number is set and incremented by the device that is transmitting, or otherwise sending, the data packet (i.e., personal computer, the base station, or the Bionode) and is used to determine if packets have been missed by the receiver. The next two bytes in the packet 700 contain the ID numbers of the transmitting device that sent the packet (0=PC, 1=Base Station, 2=Bionode, 3=Invalid), and the device that is the intended receiver. These bytes tell the base station where to route all incoming packets and inform the receiver of where the incoming data packet came from. The final byte of the header 710 contains the type ID of the packet 700 which indicates the type of data is contained in the payload 720. The types of payload data and their associated type IDs are shown in the table below:

| Type ID | Packet Type |
|---|---|
| 0 | 8-bit data sampled by the Bionode |
| 1 | 10-bit Data sampled by the Bionode |
| 2 | Lead impedance measurement |
| 3 | Thermistor reading from the Bionode |
| 4 | Bionode register configuration |
| 5 | Base station register configuration |
| 6 | Identification response |
| 7 | Identification ping |
| 8 | Invalid packet |
| 255 | Shutdown Base Station Command |

Figure 8:
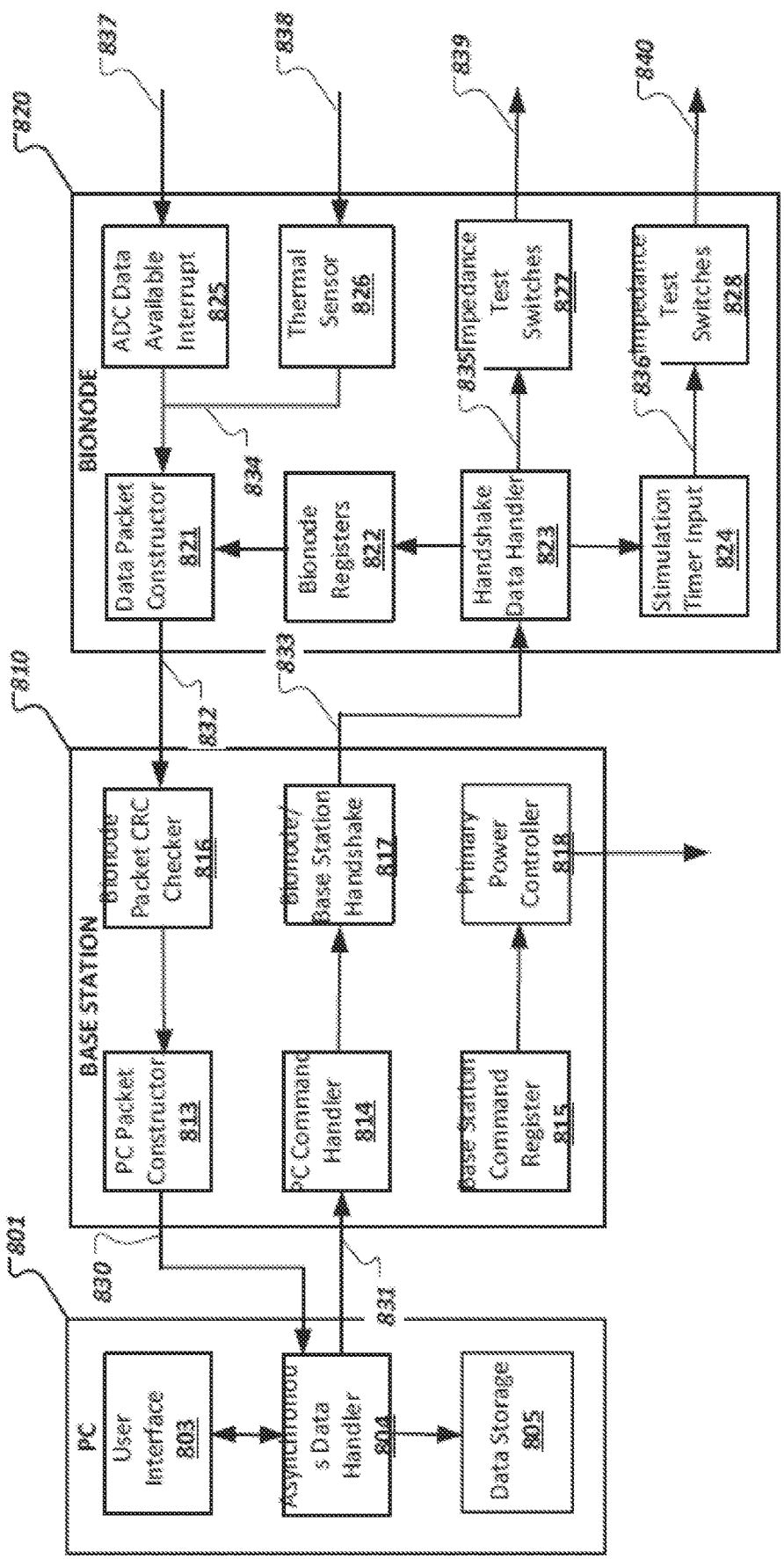
FIG. 8 shows a diagram depicting an example of the communication path between components of the wireless platform system.

FIG. 8 shows a diagram depicting the communication paths between the components of the wireless platform system, including the Bionode 820, the base station 810, and the personal computer 801. Bidirectional communication during use of the system can greatly increase the flexibility and possible application use of an implantable device. The ability to transmit data potentially removes the burden of on-board data storage from the implantable device, but it also allows the implantable device to communicate its current status and settings in real time; allowing for increased confidence in implant performance over time. Furthermore, the ability to receive data allows the implantable device to be configured, calibrated, and instructed before, during, and after implantation; increasing its adaptability to varying circumstances. An implantable device that can both receive and transmit data has the added benefit of allowing an external user or system to reactively send instructions to the implantable device based off of recorded data obtained by the implantable device; effectively creating a closed-loop system.

A potential challenge to implementing bidirectional communication in an implantable device is handling the increase power consumption introduced by radio communication circuitry. In many cases, including that of the Bionode 820, the most power-hungry system on implantable device is the transmit and/or receive radio. Power consumption on the Bionode 820 can be greatly reduced while transmitting and receiving data by tightly coordinating when data transmissions occur.

The microcontroller on the Bionode 820 is configured to communicate data telemetry coming into and out of the device. The microcontroller for the Bionode 820 can be selected to achieve desirable component characteristics, such as low-power sleep states, small size, on-board radio, and on-board analog to digital converter (ADC). For example, a microcontroller can be utilized that only draws 2 µA of current when it is in sleep mode, and draws 20 mA of current when the radio is activated, an interrupt-driven firmware design was developed in order to keep the microcontroller in sleep mode with the radio deactivated as much as possible.

Bidirectional communication can be performed, as illustrated in FIG. 8, by enforcing a coordinated handshake protocol with a custom designed external base station 810 which facilitates all communication between the Bionode 820 and any outside user. After the Bionode 820 acquires a specific number of samples, for example 40 data samples, from its ADC, the microcontroller of Bionode 820 initiates a data-packet transmission to the base station 810 using the on-board radio. Data packets can be constructed, for instance using conventional packetization techniques, to include recoded data, and subsequently communicated via transmission signal 832 from the data packet constructor 821.

In some cases, the radio is a 2.4 GHz ISM band radio. This is illustrated as transmission signal 837 to ADC Data available interrupt 825, for example. In some cases, a transmission signal 838 received by the thermal sensor 826 can initiate data-packet transmission from the Bionode 820. In most cases, the radio is activated during this transmission which lasts approximately 1 millisecond.

However, after a successively transmitting multiple packets, for instance the 100th data packet, Bionode 820 initiates a hand-shake with the base station 810. The handshake can be performed between the Bionode/base station handshake 817 unit of the base station 810 and the handshake data handler 823 of the Bionode 820.

After transmitting a specified data packet, or a data packet otherwise deemed as the end of communication (e.g., 100th data packet), the Bionode 820 sets its radio to receive mode, and listens for a data packet from the base station 810 for a time, typically not exceeding 10 milliseconds. This gives the base station 810 an opportunity to send a single data packet to the Bionode 820. The data packet can contain a 45-byte long payload, which is used to set firmware registers in the Bionode 820 microcontroller that store data acquisition, stimulation, and communication settings. The registers are shown in FIG. 8 as Bionode registers 822. Because the payload contains values for writeable firmware Bionode registers 822, the Bionode can be fully configured and instructed during this single data transmission.

In some cases, the handshake driven communication scheme allows the Bionode 820 to transmit acquired data rapidly, while maintaining the ability to receive data from an outside source with minimal radio activation time. For example, given a total data acquisition sample frequency of 5 kHz, the Bionode's radio will transmit 125 data packets per second and initiate a handshake once every 800 milliseconds. Given the radio on-time described above, bidirectional communication is achieved with the radio being deactivated at least 86.7% of the time.

Another challenge in a wireless communication scheme is increasing data robustness. In order to properly analyze any data recorded by the Bionode 820, the ability to identify when data has been corrupted or lost may be desired. Data can be corrupted or lost during wireless transmission in various conditions, including: if it is obstructed by a blockage that can absorb RF energy; if a nearby device communicating on the same frequency creates interference; and if the distance between the Bionode 820 and the base station 810 exceeds the transmission range of the Bionode 820. Furthermore, data can be lost in the scenario if the Bionode 820 suddenly loses power during data acquisition or transmission.

The Base Station 810 can be configured to employ methods to detect both corrupted and lost data packets. For example, before sending data packets to the base station 810, the Bionode 820 can append a 2-byte cyclic redundancy check (CRC) to the end of the packet (shown in FIG. 7). The base station 810 uses this CRC to determine the validity of all incoming data packets. The capability to perform redundancy checking can be implemented by Bionode packet CRC Checker 816. Corrupted data packets failing this CRC are discarded by the base station 810, and not passed on to other users. Additionally, to make lost data packets detectable, the base station 810 can append a 4-byte time stamp at the end of incoming packets. These time stamps can be used to determine if data samples are missing from the acquired data stream, and how many data samples are missing, which can improve accuracy for later data analysis and improve the overall performance of the Bionode platform.

Figure 9:
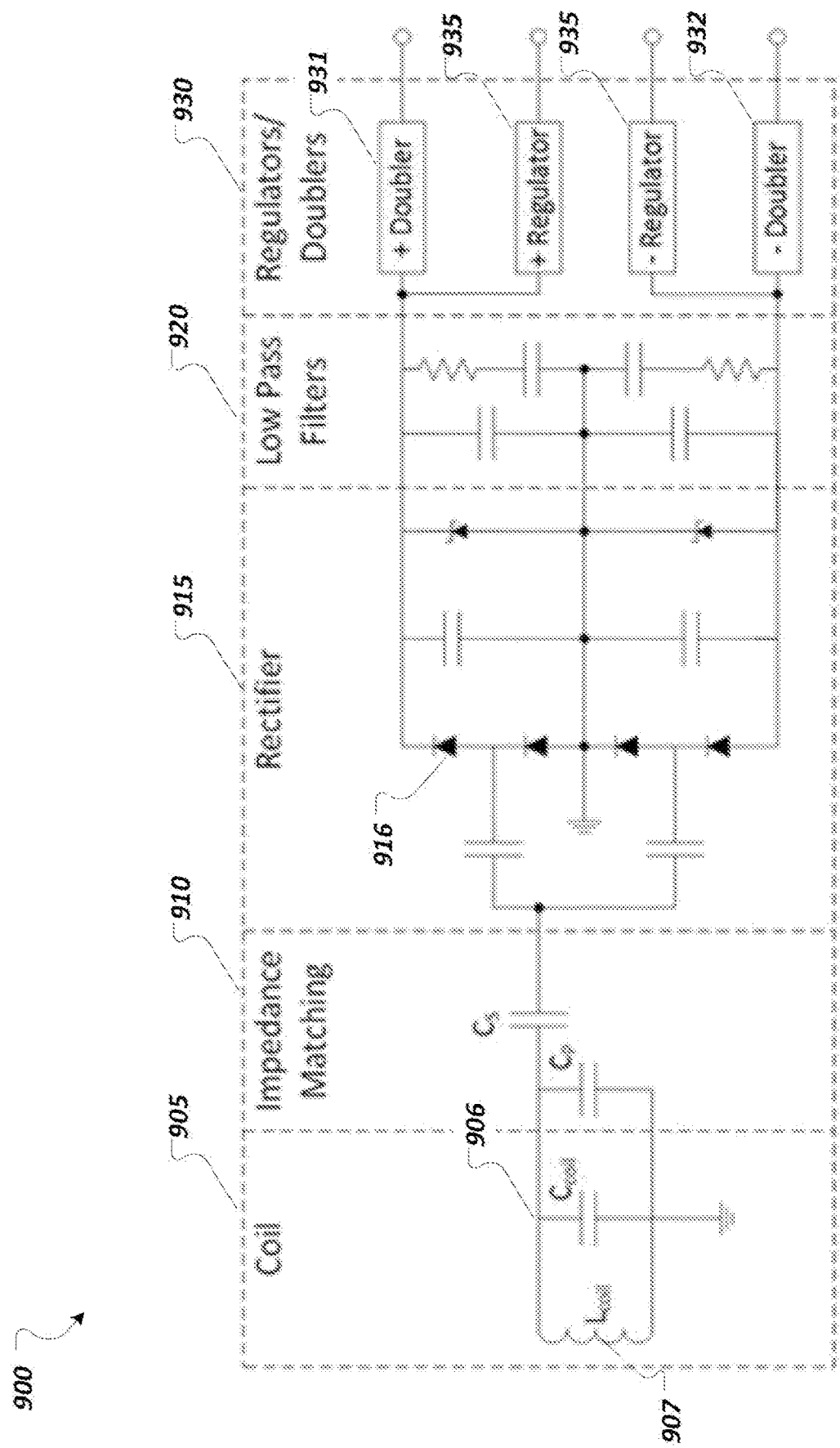
FIG. 9 shows a diagram of an example of circuitry implementing impedance matching aspects of the wireless implantable device.

FIG. 9 shows a diagram of an example for circuitry 900 implementing impedance matching aspects of the wireless implantable device. The impedance-matching circuitry 900 can be employed to maximize the amount of power that is transferred to receiving coils of the power management board (shown in FIG. 1B). For instance, each coil—represented in FIG. 9 as a coil stage 905 including a capacitor $C_{coil}$ 906 and an inductor Lcoil 907 coupled in parallel—is connected directly to an impedance matching stage 910 which maximizes its power transfer efficiency. Acquired AC signals are then rectified using a dual-ended rectifier 915 to produce positive and negative DC voltages. Both the positive and negative rectifier outputs are then passed through passive low pass filters 920 to remove high frequency RF noise. Positive and negative power rails for the Bionode can be generated by regulating the filtered outputs of the rectifier 915 circuit. Higher voltages that may be needed by the Bionode stimulation circuit can be generated by passing the filtered rectifier outputs through positive and negative voltage doubler circuits 930.

The AC voltages coupled onto each coil 905 are capable of being converted into both positive and negative DC voltages using the full wave rectifier 915. Subsequently, high amplitude voltages coming out of the rectifier 915 are clamped using diodes 916, so as to protect low-voltage circuitry on the Bionode. Furthermore, to provide stable voltage rails to the Bionode, resistor-capacitor-based low-pass filters 920 are implemented on both the positive and negative rectifier outputs to reduce coupled AC noise from non-idealities present in the rectifier 915. The rectified voltages are then fed into regulators 935, 936 to provide the digital and recording circuitry on the Bionode with accurate, low ripple voltage supplies. To supply the higher headroom voltage that may be required by the Bionode's stimulation circuitry, both outputs of the full wave rectifier can be doubled using a boost converter for the positive output, illustrated as doubler 931, and an inverting charge pump for the negative output, illustrated as doubler 932. The outputs of these doubler circuits provide the voltages required by the Bionode's stimulation circuitry to drive its constant current stimulation output.

Figure 10:
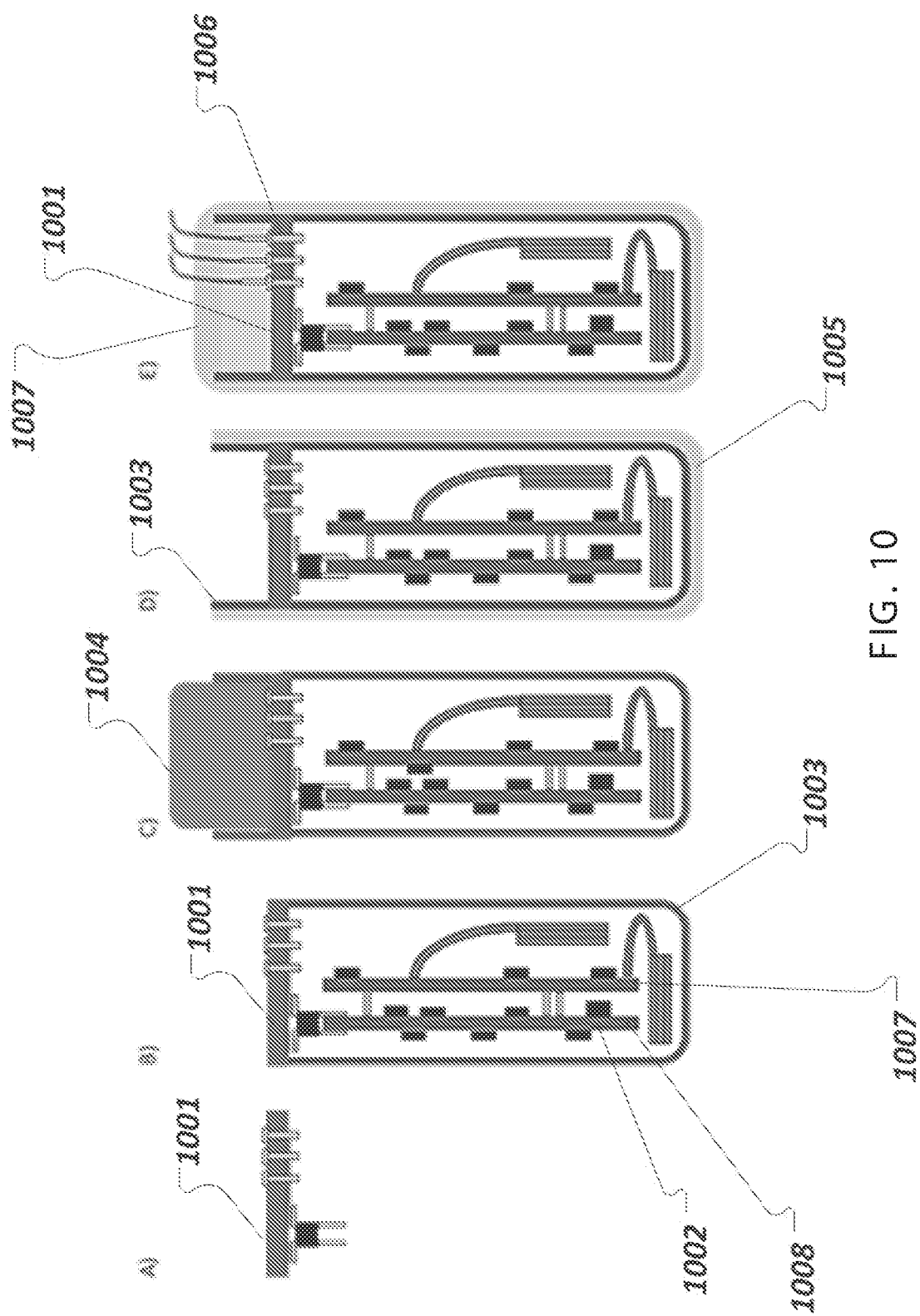
FIG. 10 shows an example of the packaging process of a wireless implantable device, via a cross-sectional view.

FIG. 10 shows an example of the packaging process of a wireless implantable device (the Bionode, also shown in FIGS. 2C and 2D), via a cross-sectional view. In a first stage of the illustrated process, a feedthrough cap 1001 containing receptacles for electrodes (the three receptacles on the right hand side) as well as a connector for the Bionode main board (on the left side of the feedthrough cap 1001) is constructed. Next, the fully assembled Bionode 1002, including its power management board 1007 and main board 1008 in a stacked relationship, are connected to the feedthrough cap, and a case 1003 is attached to the feedthrough cap 1001. Also shown are antennas and power supply lines going from the power management board 1007 to the main board 1008. Subsequently, a plug 1004 is connected to the outside of the feedthrough cap 1001 to insulate the electrode receptacles from epoxy, which is used to create a well above the feedthrough cap 1001. Then, the plug 1004 is removed, and an initial coating of epoxy 1005 is applied around the entire case 1003. Electrode receptacles 1006 are then connected to the electrode receptacles, and the well above the feedthrough cap 1001 is filled with silicone 1007. Once the silicone is cured, the entire implant is coated once again in epoxy which fully encapsulates the implant.

The resulting encapsulated cylindrical bionode package, shown in FIG. 10, can be 3.5 cm long with a diameter of 1.5 cm and weighs 9 grams. This packaging approach illustrated in FIG. 9 can optimize customization and flexibility in the design and test cycle of the implantable device. Changes in the board shape, size, and architecture can be accommodated by quick changes to device casing and feedthrough board layout, providing fast turn-around and implementation. In addition, the interconnects utilized by the feedthrough board can be modified to meet the ever evolving attributes of future devices such as capacitive feed-through systems. Moreover, the materials and tools used in this method are relatively inexpensive and easy to obtain and adopt.

For devices that do not require any adjustments to the Bionode hardware, the top layer of epoxy surrounding the feedthrough well can be removed using a band-saw or rotary tool. Once the epoxy is removed, the silicon and leads can be removed by hand. New leads can then be inserted, the well can be refilled with silicon, and the device can be re-encapsulated in epoxy. For devices needing adjustments to the Bionode hardware (i.e. devices needing different AFE passband values), the casing can be cut below the feedthrough board, and the device can be removed, adjusted, and mounted to a new feedthrough board for repackaging.

Figure 11:
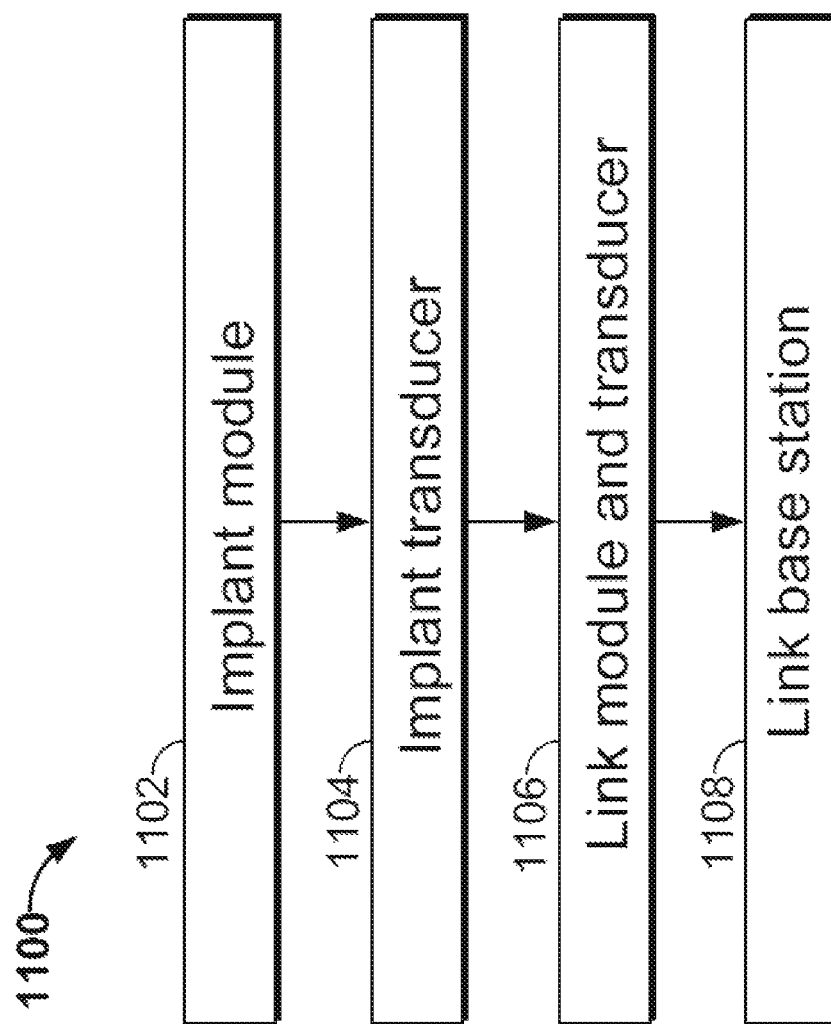
FIG. 11 is a flow chart of an exemplary method of implanting a module (implantable Bionode capsule) in a subject is shown.

Referring to FIG. 11, a flow chart of an exemplary method 1100 of implanting a module (implantable Bionode capsule) in a subject is shown. In some embodiments, the module may have features similar to modules described above with reference to FIGS. 1-10, for example. Method 1100 facilitates implantation of a module within a subject, and communication between the module and other system components.

Exemplary method 1100 includes operation 1102 of implanting a module in a subject. The subject may be a human subject or an animal subject. The module may be implanted in an internal cavity of a subject such that the module is completely within the subject (e.g. completely under the skin of the subject with no part of the module directly exposed to the external environment).

The module may be implanted at a selected anatomical location. For example, operation 1102 may include making an incision proximate a selected implantation location where the module will be secured in the subject, inserting the module through the incision, securing the module (e.g. using one or more sutures to maintain a selected orientation/position), and closing the incision. In one example use scenario involving a human patient, the incision may create an opening proximate the patient's collarbone. The module can be inserted through the incision and secured subcutaneously within the patient at a chest location. In other use scenarios involving a human patient, operation 1102 may include implanting the module elsewhere in the chest, abdominal cavity, pelvic cavity, thoracic cavity, dorsal cavity, cranial cavity, extremities of the body, etc. Similar operation procedures and insertion locations can be used for animals, such as mice.

The anatomical location where the module is implanted may be selected based on the anatomical features the module is configured to interact with. For example, the module may be located proximate to a particular anatomical structure, or between multiple anatomical structures, that the module is intended to monitor or stimulate. Implantation in a subcutaneous region of the chest may facilitate an operation 1102 that is safe and efficient while reducing invasiveness. Implantation in a chest location may be suitable for a range of applications or conditions that the module may be configured to address, and facilitate communication with other system components remotely located within the subject and/or external to the subject.

Method 1100 includes operation 1104 of implanting a transducer proximate an anatomical structure with which the transducer is configured to interact (sense or stimulate, for example). The transducer may be communicatively coupled with the module (wired or wirelessly), such that electrical signals may be communicated between the module and the transducer. In various embodiments, the transducers may include one or more sensors or electrodes configured for impedance monitoring, thermal monitoring, pressure monitoring, optical monitoring and/or one or more outputs, such as outputs configured to provide electrical or optical biomodulation, etc.

Operation 1104 may include securing the transducers to an anatomical structure. The anatomical structure may be selected based on a condition that the module is configured to monitor or stimulate. For example, a transducer may include a pressure sensor located proximate the bladder (e.g. for urinary incontinence applications), an optical sensor configured to measure characteristics of a blood stream (e.g. for measurements of cytokines, hormones, etc.), an electrical sensor and/or output located proximate the vagus nerve, the brain, and sympathetic or tympanic nerves associated with the heart or lungs, etc.

In some embodiments, method 1100 includes operation 1106 of linking the module and the transducer. For example, operation 1106 may include connecting the transducer to the module by a wired lead that physically connect the transducer with the module and allow wired communication between the transducer and the module. The transducer, lead and module may be connected to one another prior to insertion within the subject, and subsequently secured at selected locations within the subject. In other embodiments, the transducers may be connected with the module after the module and/or transducers are implanted within the subject by routing the lead between the transducer and the module.

In some embodiments, the transducers may include one or more wireless communication components that allow wireless transmission between the transducer and the module. Operation 1106 may include communicatively linking the transducer and the module (e.g. after the transducer and module have each been secured in a respective selected location) such that signals from the transducer may be received by the module and/or vice versa. Accordingly, method 1100 may thus include implanting a plurality of wirelessly communicating devices at locations remote from one another within a subject (e.g. a module and one or more transducers in wireless communication with the module).

Operation 1106 includes communicatively linking the module and transducer so that communication and/or processing of transducer outputs may be performed in real-time. For example, a pressure output from a pressure sensor located proximate the bladder may be received and processed by the module located in the chest to determine an appropriate response. The module may in turn send a response to the transducer or send associated information to a base station, as described further herein.

In some embodiments, method 1100 includes operation 1108 of communicatively linking a base station with the module. Operation 1108 may include linking the module and the base station to enable wireless bidirectional telemetry. For example, operation 1108 may allow data received from a transducer to be received and/or processed by the module, and in turn delivered to the base station. Similarly, operation 1108 may allow the base station to deliver data, commands, etc. to the module.

The base station (for example, the base station 130 shown in FIGS. 1A and 1B) may have a form factor selected based on the requirements of a particular application, such as the frequency of communication between the module and base station, and/or the power and processing requirements of the base station. For example, the base station may be configured as a wearable device such as a wristband, bracelet, necklace, earpiece, etc. that may be located proximate a patient's body (e.g. proximate the module) during use. Wearable configurations may facilitate frequent or continuous communication between the module and the base station. In other embodiments, the base station may be fixed or remotely positioned from the patient, and/or configured to communicate intermittently with the module (e.g. once per hour, once per day, etc.). In such configurations, operation 1108 may include linking the module with a base station located at a fixed location (e.g. on a bed-side table, a treatment location, etc.) or location that may frequently be remote from the user during operation.

With particular regards to embodiments of the base station designed for use with animal subjects, the base station may comprise a stationary structure associated with a chamber within which an animal is housed. For example, the base station may be attached to that housing structure, and the wireless power transfer componentry of the base station may include metal components associated with the animal housing.

Figure 12:
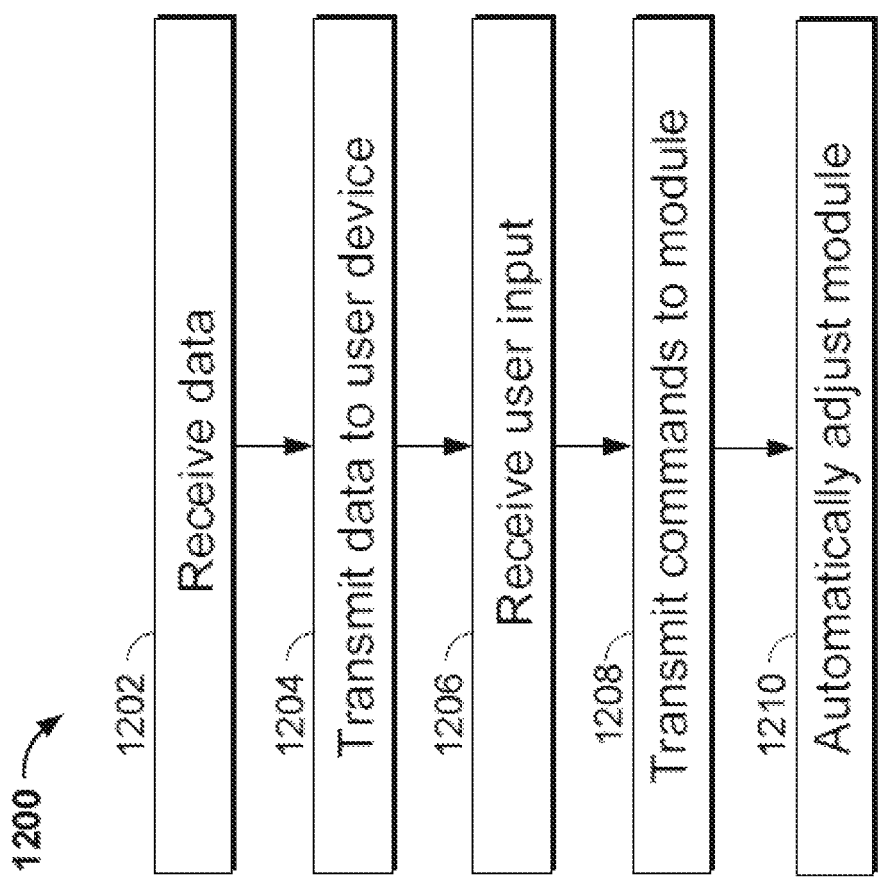
FIG. 12 is a flow chart of an exemplary method of calibrating a module is shown.

Referring to FIG. 12, a flow chart of an exemplary method 1200 of calibrating a module is shown. In some embodiments, the module may have features similar to modules (namely, "implantable Bionodes") described above with reference to FIGS. 1-10, for example. Method 1200 facilitates calibration of operational parameters of the module to customize performance of the module to the anatomical and physiological characteristics of the subject (e.g., human subject or animal).

Method 1200 includes operation 1202 of receiving operational data from an implanted module. The data may include stimulus parameters, patient response data detected by a transducer, and/or associated data. For example, the data may include stimulus parameters including duration, magnitude, profile, etc. of a stimulus delivered to the subject, measured subject response data (e.g. obtained from sensors of one or more transducers), and/or data from which a subject response to the stimulus may be derived. The module may store, process, and/or transmit the data received from one or more transducers. Similarly, an external (non-implanted) base station may receive the data (e.g. from the implanted module) and store, process, and/or transmit the data to another system component.

Method 1200 includes operation 1204 of transmitting the data to an external user device, for example, the computing system 160 shown in FIG. 1 having data acquisition controller software. The data may be transmitted directly to the user device from the external base station, or delivered to the user device via one or more intermediate devices. The user device may process the data to calculate information related to the performance of the treatment. For example, the user device may be programmed to analyze the data to determine optimal or improve stimulus parameters based on the measured patient response to the stimulus.

In an exemplary embodiment, the user device may be a computer, phone, tablet, PDA, etc. that includes a display configured to output the data and/or related information to an operator, such as a physician or medical professional, and an input device to receive input from the operator. The operator may review the stimulus parameters and measured subject response to the stimulus, and make a determination regarding the efficacy of the stimulus parameters based at least in part on the measured subject response to the stimulus. The operator may determine that one or more stimulus parameters should be adjusted to improve patient efficacy, safety, etc. Alternatively, the operator may determine that no changes to the stimulus parameters are necessary (e.g. and that treatment can continue for a predetermined period of time).

Method 1200 includes operation 1206 of receiving user input related to one or more operational parameters of the implanted module. For example, if an operator determines that one or more stimulus parameters should be changed, the operator may provide input instructing the system to adjust one or more stimulus parameters. The operator provides input to the user device. The input may be subsequently transmitted from the user device and received by another system component, such as the base station, module, or other system component.

In an exemplary embodiment in which the base station receives a user input related to one or more stimulus parameters, method 1200 includes operation 1208 of transmitting commands to the implanted module to implement the stimulus parameters instructed by the user. The module may receive the stimulus parameters and operate using the updated stimulus parameters (e.g. for a user selected period of time, for a predetermined period of time, or indefinitely until the stimulus parameters are manually changed). During this period, the system may capture and store patient response data for analysis by the system or an operator. Operations 1204 and 1206 may be repeated to determine whether the stimulus parameters should be maintained or are optimized for the patient on an ongoing basis.

Method 1200 can facilitate calibration (e.g. manual calibration) of system parameters based on measured patient response to actual stimulus applied to the subject. In some embodiments, an initial stimulus may be limited (e.g. in duration, magnitude, profile, etc.) and gradually increased until a particular measured subject response is observed. An operator may identify stimulus parameters by observing the measured subject response in real-time or nearly real-time. Alternatively or in addition, an operator may observe the measured subject responses over a predetermined duration (e.g. an hour, a day, a week, a month, etc.) at one or more intervals to determine whether the stimulus parameters should be modified.

In some exemplary embodiments, method 1200 may include operation 1210 of automatically adjusting stimulus parameters by the system (e.g. automatically generating a command at the implanted module or external base station that adjusts the stimulus parameters) based at least in part on a measured patient response. For example, the system may be configured with a closed-loop control algorithm such that stimulus parameters are adjusted until a desired subject response is attained. If the measured subject response suggests that a stimulus is insufficient to generate the desired subject response, the magnitude, duration, profile, etc. of the stimulus may be increased. Likewise, if the measured subject response suggests that the stimulus is too great (e.g. too close to a safety threshold), the magnitude, duration, profile, etc.), the stimulus may be decreased. In various exemplary embodiments, operations 1206, 1208, and 1210 may be performed individually (e.g. exclusively manual adjustment or exclusively automatic adjustment), together (e.g. sequentially), or in any desired combination.

The system may be programmed to allow automatic adjustments to the stimulus parameters within a particular range and manual adjustments outside of the particular range. For example, the system may automatically refine the stimulus parameters within a relatively narrow range. The external base station may transmit commands to the implanted module to refine the stimulus parameters within a particular range. Relatively larger changes to stimulus parameters may require manual intervention (e.g. at operation 1206). Automatically performing relatively small changes to the stimulus parameters may improve efficacy by calibrating the stimulus parameters to a particular subject with little or no manual intervention. Limiting large changes automatically made by the system to the stimulus parameters may promote overall safety and reliability of the system by requiring manual input from an operator (e.g. a physician or medical professional) in order to make major changes to system operation.

Figure 13:
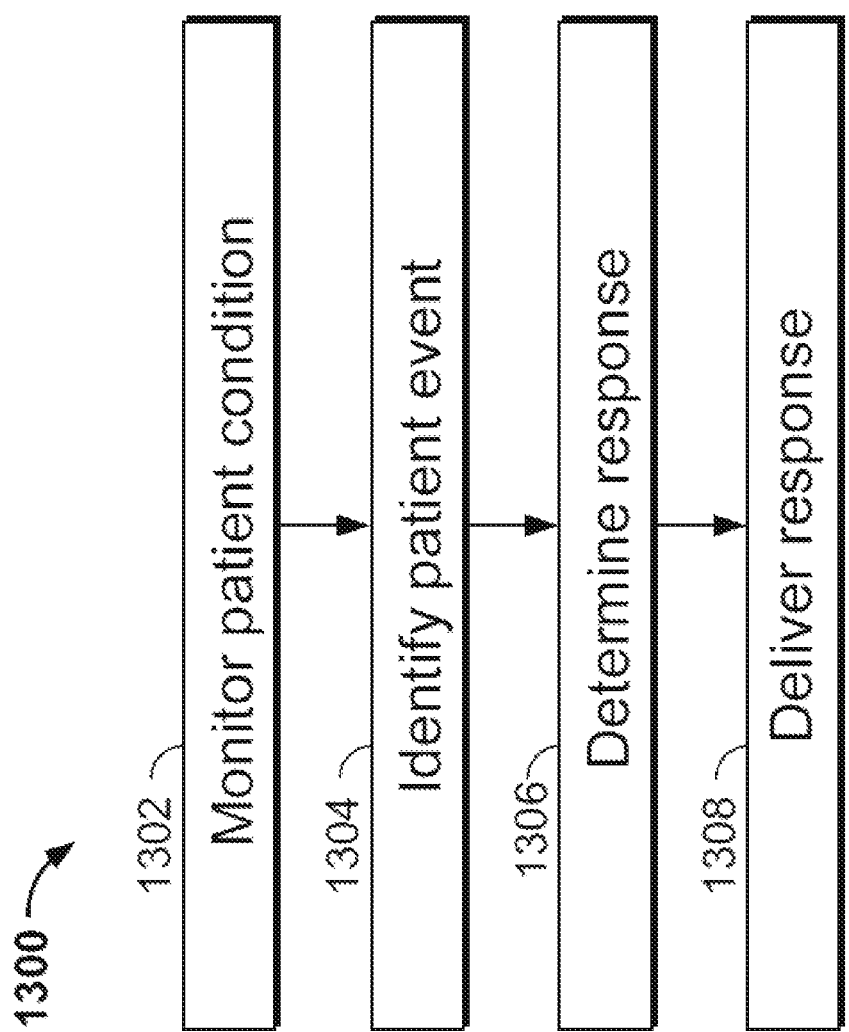
FIG. 13 is a flow chart of an exemplary method of delivering a stimulation to a subject is shown using an implanted module.

Referring to FIG. 13, a flow chart of an exemplary method 1300 of delivering a stimulation to a subject is shown using an implanted module. In some embodiments, the implanted module may have features similar to modules described above with reference to FIGS. 1-10, for example. Method 1300 facilitates subject stimulation in response to a measured condition of the subject.

In an exemplary embodiment, method 1300 includes operation 1302 of monitoring a subject condition (or a patient condition, in the case of a human subject). For example, an implanted transducer may include a sensor for monitoring a condition at an anatomical location, such as a sensor configured for impedance monitoring, thermal monitoring, pressure monitoring, optical monitoring, etc. The transducer may communicate with one or more system components, directly or indirectly, such as the implanted module and/or external base station that receives, processes, and/or stores the measured subject condition. For example, the measured condition may be a pressure proximate a bladder of the subject, electrical activity of a component of the nervous system, or other condition associated with the health condition of a subject.

Method 1300 includes operation 1304 of identifying a subject event based at least in part on the measured subject condition. Data related to the measured subject condition may be communicated from the transducer to the module and/or base station which may, in turn, process the received data to identify whether one or more subject events are occurring or imminent. For example, the measured subject condition, a derivative of the subject condition, or other parameter related to the measured subject condition, may be compared to a threshold value indicative of the subject event.

Comparison to a threshold value, or processing according to a predetermined relationship, the measured subject condition may be used to determine the presence of a subject event. In an exemplary configuration, a transducer is implanted proximate the esophagus and/or larynx, and includes a sensor that outputs a measurement related to an acid level in the esophagus and/or larynx. Operation 1304 may include comparing the acid level measurement to a predetermined acid level threshold considered to be indicative of a reflex that prohibits free breathing. Accordingly, based at least partially on an acid level determined to be greater than the threshold level (e.g. maintained over a particular period of time), the system identifies a subject breathing event. Similarly, such acid levels may be used to identify an underlying cause, such as a seizure, that may be indirectly responsible for the elevated acid levels measured by the transducer.

Operation 1306 includes determining a response to the identified subject condition. The system may identify a responsive stimulation configured to alleviate or reverse the subject event. For example, the system may identify a stimulation for delivery to a particular anatomical location having a selected duration, magnitude, profile, etc. based at least in part on the subject event. After identifying the subject event, the base station determines the appropriate responsive stimulation and delivers a command to the module, which in turn delivers a command to a transducer. Alternatively or in addition, the module may process data related to the subject event to determine the appropriate responsive stimulation and directly command a transducer to deliver the responsive stimulation.

In an exemplary embodiment in which the identified subject event is a breathing event or seizure associated with increased acid levels in the esophagus and/or larynx, the system may determine that the appropriate responsive stimulation is electrical stimulation to nerves connected to the larynx. Such a response stimulation can relax the larynx and remove the reflex associated with high acid levels, promoting free breathing by the subject.

Method 1300 further includes operation 1308 of delivering the response. In an exemplary embodiment, the response is executed by one or more implanted transducers in response to a command transmitted by the implanted module. Upon receiving the command from the implanted module, the transducer delivers the responsive stimulation according to received stimulus parameters.

In some exemplary embodiments, the implanted module automatically sends the command to the implanted transducer. For example, the module and/or base station may automatically carry out operation 1304 of identifying a subject event, operation 1306 of determining a response, and operation 1308 of delivering the response with limited or no manual intervention. Alternatively, one or more operations may require manual intervention, such as by prompting the user for confirmation of a subject event, appropriate response, or delivery of the response. For example, after operation 1304 of identifying a subject event, the system may deliver a prompt to the user (e.g. an audio alert, visual alert, haptic alert, etc.) to acknowledge or confirm the subject event. Similarly, after operation 1306 of determining a response to the identified condition, the system may deliver a prompt to the user to acknowledge or confirm the response, and/or allow the user to manually adjust the suggested response. Likewise, before completing operation 1308 of delivering the response, the system may prompt the user to acknowledge or confirm delivery of the response, and/or allow the user to postpone or adjust the timing of delivery. Accordingly, the system may identify subject event and a recommended responsive stimulation that is only delivered after manual confirmation of the recommendation is received at a user input.

Whether the system automatically delivers a responsive stimulation, or requires manual acknowledgement or confirmation, may be predetermined based on the type and severity of a subject event. For example, operation 1308 of delivering the response may be executed without user input for severe subject events, or subject events that may limit the subject's ability to timely respond to a prompt. Likewise operation 1308 of delivering the response may be postponed until a user confirmation is received for minor subject events, events that do not significantly limit the subject's ability to respond to a prompt, or responsive stimulations that require advanced user awareness.

In some exemplary embodiments, a user may intuitively sense the onset of a subject condition independent of a prompt delivered by the module, base station, user device, or other component of the system that communicates the subject event to the user. For example, an epileptic subject may intuitively sense the onset of a seizure independent of a measured subject condition. Operation 1304 of identifying a subject event may include receiving an input from a user that identifies the onset of a subject event, such as by selecting a subject event from a menu of subject events. The system may then proceed to operation 1306 of determining an appropriate responsive stimulation to the manually identified subject event, and operation 1308 of delivering the response stimulation, as described herein.

Figure 14:
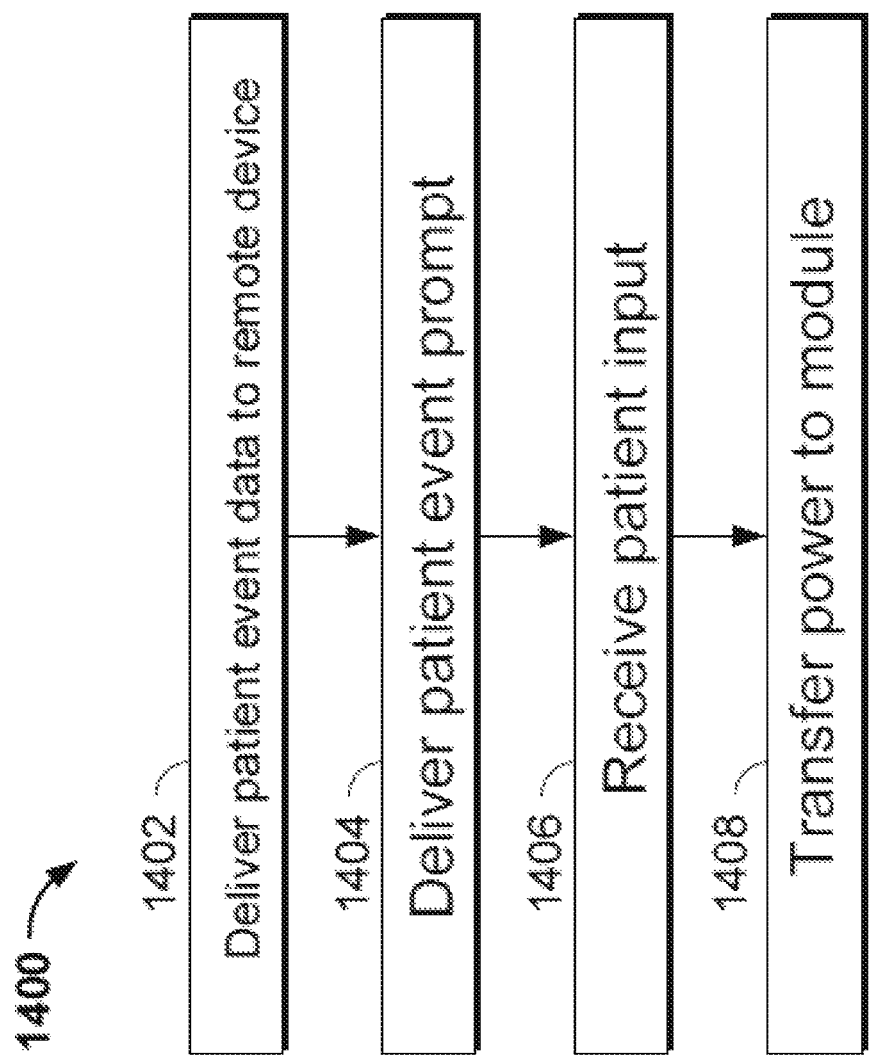
FIG. 14 is a flow chart of an exemplary method of operation of the system including an implantable module and an external base station that obtains patient input is shown.

Referring to FIG. 14, a flow chart of an exemplary method 1400 of operation of the system including an implantable module and an external base station that obtains patient input is shown. In some embodiments, the module and base station may have features similar to implantable modules and base stations described above with reference to FIGS. 1-10, for example. Method 1400 facilitates operation of the implantable module, including communication with one or more external devices that deliver outputs and receive inputs from a user.

Method 1400 includes operation 1402 of delivering patient event data to a remote device external to the patient. The remote device may be the base station or a user device, such as a phone, laptop, wearable device, etc. that includes an output and user input device. In an exemplary embodiment, patient data is wirelessly transmitted from the implanted module to the base station, and from the base station to one or more user devices.

The patient data transmitted to the remote device may include stimulus parameters, measured patient response data, and/or identified patient events, etc. In some exemplary embodiments, the module performs limited or no processing of measured data before forwarding the data to the remote device. The remote device can then process the data to identify a patient event, or manipulate the data into a useful form for observation by the user. Alternatively or in addition, the module may process the measured data to identify a patient event, and the module may transmit a patient event signal to the remote device indicative of the patient event.

Method 1400 includes operation 1404 of delivering a patient event prompt to the user. The patient event prompt notifies the user that a patient event has been identified. In an exemplary embodiment, the patient event prompt includes a visual notification displayed on the remote device. For example, the base station or user device may provide a visual notification indicating that a patient event has been identified, the type of patient event, a recommended response, and/or measured patient data, such as the measured patient data that was used in identifying the patient event. Alternatively or in addition, the patient event prompt may include an audio, tactile, or haptic alert, for example, that may be unique to a particular patent event or category of patient event.

In an exemplary embodiment, such as system used in a urinary incontinence application, a patient event may be identified based on a pressure measurement obtained from a transducer located proximate the patient's bladder. In response to elevated bladder pressure, the remote device may deliver a prompt to the user indicating the user of the elevated bladder pressure.

In some exemplary embodiments, operation 1404 of delivering a patient event prompt to the user may be performed at least partially by the implanted module and transducer. For example, the module may transmit a patient event command signal to a transducer, which in turn generates a patient event stimulation indicative of the patient event. The user senses the stimulation as an indicator of the patient event. Delivering a patient event stimulation may provide a relatively more natural user interaction with the system (e.g. compared to interaction with an external remote device). For example, in an embodiment in which bladder pressure is monitored, the module may transmit a patient event command signal that generates a patient event stimulation that is perceived by the user as a full bladder. For example, the patient event stimulation may generate a sensation that is similar to, or that a user may correlate to, the natural sensation of a full bladder.

Method 1400 includes operation 1406 of receiving patient input in response to the patient event prompt. For example, a visual patient event prompt (e.g. on the display of the base station, phone, or other user device), may include a menu of user responses. The menu may include an acknowledgement input that allows the prompt to be acknowledged and dismissed, or a response input that allows a responsive stimulation to be selected. In an exemplary embodiment, the remote device receives the patient input and transmits the input to the base station and/or module to operate according to the received patient input.

Method 1400 includes operation 1408 of transferring power to the implanted module. In various exemplary embodiments, the implanted module includes a battery configured for periodic wireless recharging. The battery is configured to operate for a predetermined period of time (e.g. a day, a week, a month, a year, etc.), and periodically recharge. Operation 1408 may include charging the battery once a day through inductive charging by positioning the module proximate an appropriate magnetic field. The magnetic field may be generated by the base station or another remote charging device. In this way, the module may be powered while the patient sleeps, for example, or in a manner causing relatively little interference to the patient's activity.

In some embodiments, operation 1408 is conducted during a discrete charging period, such that operations 1402, 1404, and 1406 may be carried out independently from operation 1408 (e.g. operations 1402, 1404, 1406 may be carried out using a stored charge of the battery even when power is not being transferred to the module).

Alternatively or additionally, operation 1408 may include transferring power to the implanted module simultaneously while one or more other operations are being carried out. For example, operation 1408 of transferring power to the module may include inductively powering the module via a circulating magnetic field within a wireless powering transfer chamber. The circulating magnetic field may be generated by the base station or another remote charging device. The module may thus receive power to carry out one or more operations 1402, 1404, 1406, for example, in substantially real time.

Example Use Case #1—Epilepsy

The systems, devices, techniques, protocols, and processes described above and throughout this document can be used in a variety of human and/or animal applications. In one example use case, they can be used to treat patients with epilepsy. Such treatments can include, for example, stimulating the vagus nerve and deep brain stimulation when particular conditions within the body are detected that indicate a seizure is occurring or about to occur, providing patients with warnings, such as on a mobile device (e.g., smartphone, smart watch, other wearable device) and/or base station, stimulating various nerves and/or systems to reduce, stop, or prevent seizures a patient is experiencing, and/or other therapeutic monitoring and/or treatment related to epilepsy.

Example implementations for treating epilepsy are described below with regard to FIGS. 15-19. Some or all of these features can be applied to the treatment of other conditions, as described and/or with modifications, and/or can be applied to the platform more generally. Additionally, some or all of the descriptions with regard to the treatment of other conditions described throughout this document can be applied to epilepsy therapy.

Figure 15:
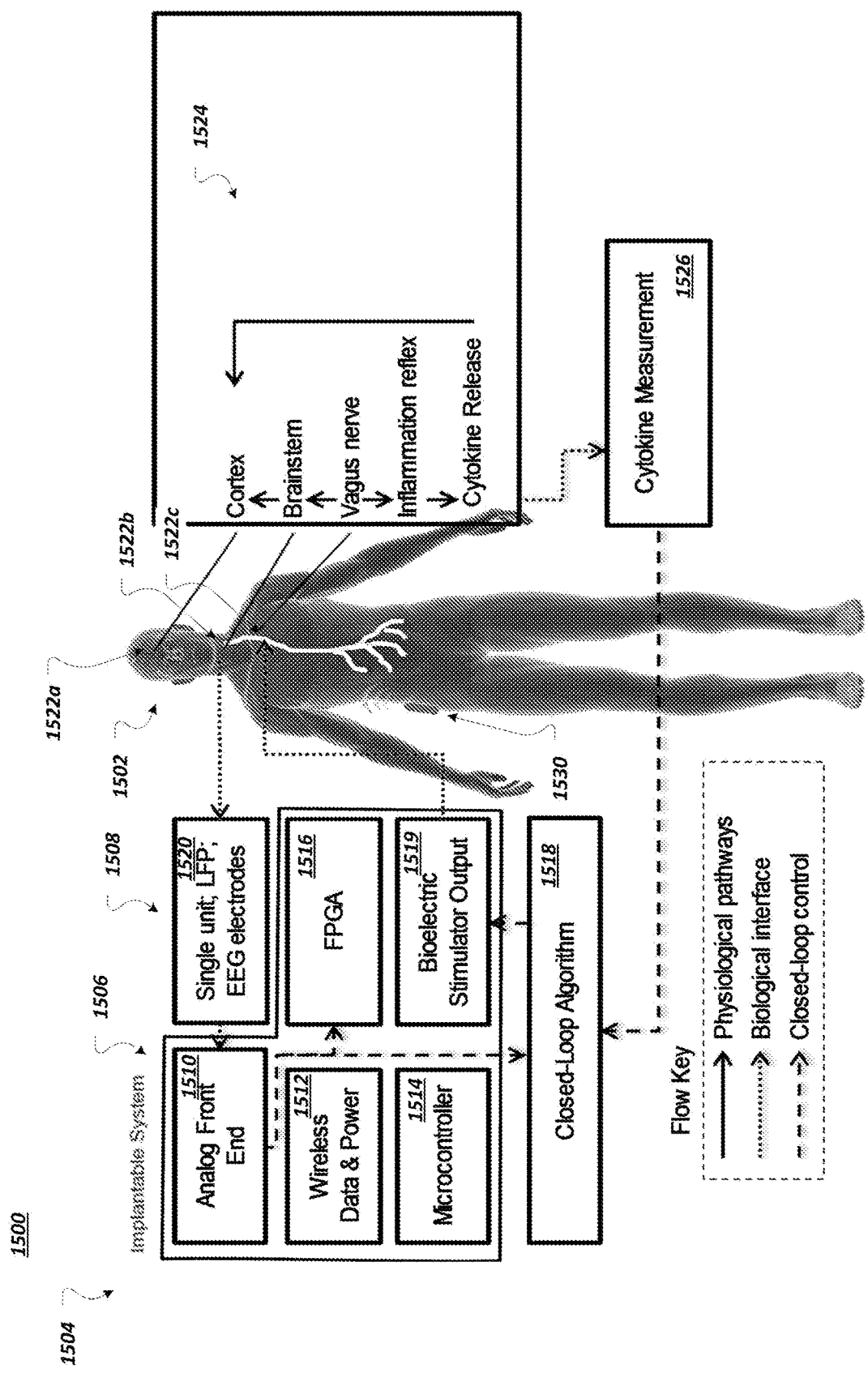
FIGS. 15 and 16 depict an example system in which an implantable system is configured for the treatment of epilepsy in a patient.
Figure 16:
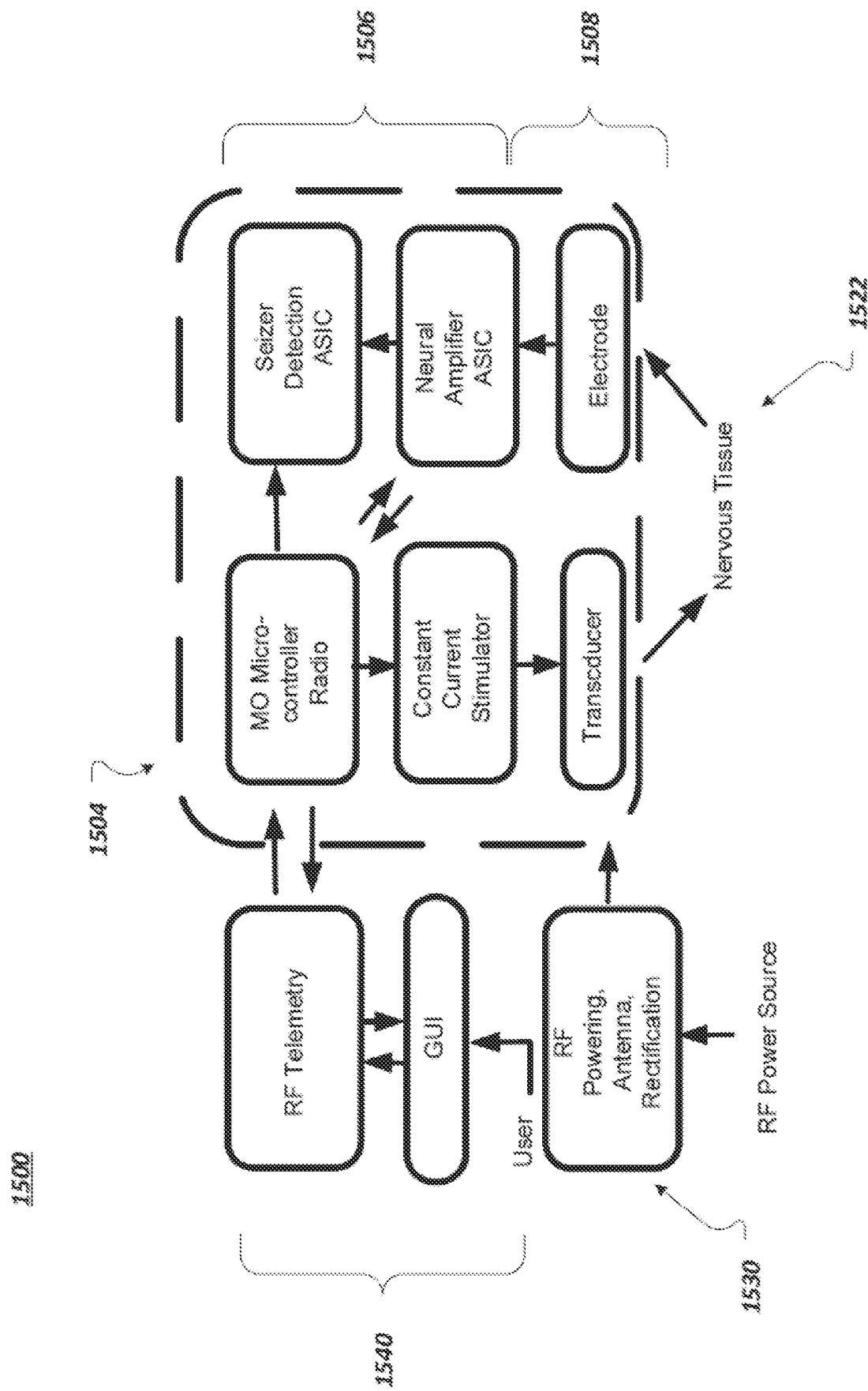

Referring to FIGS. 15 and 16, an example system 1500 is depicted in which an implantable system 1504 is configured for the treatment of epilepsy in a patient 1502. The example implantable system 1504 is similar to the implantable systems described above, and includes an implantable control device 1506 (also referred to as a "bionode") and one or more separate sensing and/or stimulating devices 1508 (e.g., implantable wireless electrodes), which can be wirelessly powered by the control device 1506 (no battery or other locally housed power source in implantable devices 1508), can wirelessly transmit data to the control device 1506, and/or can be wirelessly controlled to discharge therapeutic stimulation to one or more locations on the patient 1502. Alternatively or additionally, the electrodes may be directly connected via leads to the bionode. The system 1500 can provide a toolbox of implantable devices with accompanying base station 1530 for wireless powering and a graphical user interface (GUI) (e.g., provided on a mobile device, like a smartphone or smartwatch) for wireless communication to and from the control device 1506, which can be implanted in the patient's cortex, for example. The devices that are part of the system 1500 have the capacity for multi-channel neural recording, optical and electrical stimulation, wireless telemetry, wireless powering, and embedded algorithms for closed-loop feedback and stimulation. FIG. 16 depicts a schematic view of an example implementation of the system 1500, with examples of the base station 1530, the implantable system 1504, the control device 1506, the implantable sensing and stimulating devices 1508, a user device 1540 providing a GUI and RF telemetry with the control device 1506, and nervous tissue 1522, such as cortical and deep brain tissue to which therapy is applied and/or measurements are taken.

The implantable electrodes 1508 in this example include one or more electrodes 1520 implanted at particular locations 1522a-c in the patient's body, including at the cortex 1522a, the brainstem/deep brain structures 1522b, and the vagus nerve 1522c. The electrodes 1520 can be implanted at depths ranged from 2.0 to 7.0 mm. These electrodes 1520 can take various measurements at one or more of these locations 1522a-c, which can be wireless transmitted to the control device 1506 for analysis. These electrodes 1520 can sense and transmit, for example, single neuron measurements, local field potential (LFP), and electroencephalogram (EEG). These electrodes 1520 can also wirelessly discharge therapeutic stimulation at one or more of these locations 1522a-c when directed to do so by the control device 1506. These stimulations can include, for example, deep brain stimulation (DBS).

In addition to receiving and monitoring conditions related to epilepsy in the patient 1502, determining particular therapeutic stimulation that should be provided to the patient 1502, and wirelessly directing one or more of the electrodes 1520 to deliver the determined therapy, the control device 1506 can include components to provide wireless data and power (1512) that permits the control device 1506 to wirelessly output data to a base station and/or to a mobile device (e.g., smartphone, smart watch), and to be wirelessly powered and/or charged. This output data can include a variety of different patient data, such as patient data, a log of conditions detected and therapies delivered, alerts as to currently detected conditions (e.g., oncoming seizure, seizure currently detected), and/or other data. The control device 1506 can transmit this data wirelessly. The control device 1506 can be powered wirelessly (e.g., via RF signals) and can additionally include a local power source (e.g., battery) that can be charge via the wireless signals and that can power the control device 1506 when the wireless signal is unavailable. The packaging of the control device 1506 can be, for example, glass.

The control device 1506 include an analog front end 1510 that receives wireless signals transmitted by the electrodes 1520. The analog front end 1510 provide the received signals to the signal processing subsystem on the device 1506, which includes a microcontroller 1514 and field-programmable gate array (FPGA) 1516, which is an integrated circuit designed to be configured after manufacturing. Signal processing can be performed on-board or off-board, and can involve using a closed-loop algorithm 1518, which can be used to identify particular physiological conditions within the patient 1502 and can determine, based on the particular detected conditions, whether to provide bioelectric stimulation at one or more of the locations 1522a-c. For example, the closed-loop algorithm 1518 can be performed by the control device 1506, by a device external to the control device 1506 (e.g., mobile device, base station), or by a combination of the two. When a condition is detected that warrants stimulation, the closed-loop algorithm 1518 can direct the bioelectric stimulator output unit 1519 to either directly provide the therapy or to cause one of the electrodes 1520 to deliver the therapy. For example, the control device 1506 can include on-board components to delivery stimulation therapy, and/or can trigger one of more of the electrodes 1520 to deliver the therapy.

The closed-loop algorithm 1518 can use any of a variety of appropriate techniques to learn the particular physiology of the patient 1502 and the patient's particular response to therapy, and can use that information to determine when, how, and under what conditions to provide therapy for the patient 1502. For example, the closed-loop algorithm 1518 can be initially calibrated for the patient by a physician or other trained technician in a clinical setting, which can involve providing various stimulations and recording the physiological response of the patient 1502. After being initially calibrated, the closed-loop algorithm 1518 can continue to learn and adapt over time by analyzing data generated by the electrodes 1520, therapy provided to the patient 1502, and the patient's response to the therapy.

A physiological pathway 1524 that is being monitored as part of the system 1500, which includes the patient's cortex, brainstem, vagus nerve, inflammation reflex, and cytokine release. The closed-loop control that is being implemented by the closed-loop algorithm 1518 is directed toward monitoring and providing therapy related to the physiological pathway 1524, which includes receiving sensor data from electrodes 1520 implanted at the cortex and brainstem, processing those signals, and stimulating the vagus nerve to impact and minimize the inflammation reflex when, for example, a seizure is occurring through a cytokine release. Cytokine measurement 1526 can be taken using the electrodes 1520 (e.g., a optrode, as described in greater detail below with regard to FIG. 33) and used to determine whether the stimulation was sufficient to stop the cytokine release (which can occur in some patients experiencing seizures), and thereby stop/minimize the inflammation reflex. The closed-loop algorithm 1518 can repeatedly monitor the cytokine levels and apply vagus nerve stimulation when appropriate until the patient's inflammation reflex has stopped and/or dropped below a threshold level. The closed-loop algorithm 1518 can be automatically implemented without explicit patient direction.

As indicated by the uppward and downward arrows emanating from the vagus nerve in the physiological pathway 1524, vagus nerve stimulation can provide multiple paths for epilepsy therapy. For example, the upward arrow from the vagus nerve to the brainstem and the cortex indicates that vagus nerve stimulation can evoke a cortical response that can be used to treat patients experiencing seizure (e.g., stop seizures once they are occurring, or prevent them before they begin). The downward arrow from the vagus nerve to the inflammation reflex, the cytokine release, and the cortex indicates that vagus nerve stimulation can evoke a different response via cytokine release modulation. As discussed below with regard to FIGS. 33-34, vagus nerve stimulation can be used to reduce and/or stop the release of cytokine in the patient, which can reduce inflammation. Recent research has suggested that persistent inflammation in patients over a period of time can cause patients to develop epilepsy. For example, patients with traumatic brain injuries (TBIs) can experience increased inflammation caused by increase release of cytokine following the TBI. This may cause, or contribute to, the patients developing epilepsy. By stimulating the vagus nerve, cytokine release can be reduced and inflammation in a patient can be reduced, which can stop, slow, or mitigate the development of epilepsy.

The system 1500 can deliver electrical stimulations to the patient 1502 using appropriate stimulating frequency, waveforms, time delay from detection, stimulus current output, and other parameters to deliver neural therapy to allow for clamping the evoked cortical response so as to stop seizures in patients. Such parameters can be patient-specific, and can be developed through data collected during in-clinic/hospital monitoring of seizure episodes and the patient response to various levels of stimulation therapy. At a behavioral level, wireless closed-loop implantable devices included in the system 1500 can use a range of stimulation parameters will allow for multifactorial modifications to address these complex problems. For example, opsins may be selectively expressed in cell populations within the hippocampus and stimulation paradigms evaluated to stop seizures from progressing.

For closed-loop epilepsy therapy to be successful, the system 1500 and control device 1506 use a reliable seizure detection feedback algorithm. For example, the device 1506 can use a digital ASIC algorithm is ultralow power, reduces the device profile, and is specifically designed for specialized disease applications. Feedback and detection, though, can be used to detect and treat seizures, but can additionally be used to detect and treat other conditions. Through the use of a low power microcontroller (e.g., microcontroller 1514), custom algorithms can be implemented. For instance, additional and/or alternative control algorithms can be implemented for other conditions, such as for psychiatric therapy that can observe correlations between a wide range of longitudinal behaviors, gamma and theta oscillations, and stimulation paradigms to increase or decrease activity of certain neural populations in response to the oscillations.

Referring to FIGS. 17A-C, these figures depict the anatomy and projections of the vagus nerve, and the implant locations of for the system 1500. FIG. 17A depicts example locations for implanting the control device 1506 and the electrodes 1520, which are implanted on the brainstem location 1522b with an example vagal input electrode 1520a and an example vagal output electrode 1520b. FIG. 17B depicts a cross-section of a human brainstem showing the primary sites of vagal input (the nucleus tractus solitarii (NTS), or "solitary tract") and output (the dorsal motor nucleus (DMN), or "dorsal nuc. of X"). FIG. 17C depicts a summary of NTS efferent projections that impart diffuse, nerve activation level and rate-dependent effects on central nervous system (CNS) function.

Referring to these FIGS. 17A-C, the vagal nerves are the largest and most evolved nerves in the human body. They perform mostly sensory and parasympathetic (along with some sympathetic) functions within the autonomic nervous system, using acetylcholine (ACh) as the sole neurotransmitter. The left vagus nerve is a mixed nerve with ~100,000 axons, of which an estimated 65-80% are visceral afferent sensory fibers with sensory receptors located within the aorta, gastrointestinal tract, heart, lungs and esophagus, among others. The anatomy and projections of the vagus nerve is summarized in FIGS. 17A-C. Vagal efferents are myelinated and originate primarily from the dorsal motor nucleus (DMN) of the vagus. The afferent fibers project primarily to the nucleus tractus solitarius (NTS), where diffuse projections convey the visceral (and some somatic) sensory information throughout the CNS, including areas in the limbic system and cortex that regulate emotion. Many of the afferent fibers participate in autonomic reflexes involved in maintaining homeostasis and have myelinated projections from the nodose ganglion to the NTS, DMN, area postrema, nucleus cunneatus and the medial reticular formation (The nodose ganglion comprises the somata of unipolar sensory neurons, with unmyelinated projections inferior to and myelinated projections superior to the nodose ganglion, respectively). The NTS directly communicates with the reticular formation, area postrema and DMN; it also indirectly communicates with the thalamus, hypothalamus, amygdala, cingulate gyrus, and orbitofrontal cortex via the locus coeruleus (LC) and parabrachial nucleus (PB). The NTS projects to the LC, where effective vagus nerve stimulation is believed to excite noradrenergic neurons, resulting in norepinephrine release in several structures of the limbic system and frontal lobe implicated in temporal lobe epilepsy (TLE) and major depressive disorder (MDD). This has also been found to suppress inflammation in the CNS associated with Alzheimer's disease.

The system 1500 can apply stimulation therapy to these brain structures, for example, to address treatment-resistant partial onset seizures, which can help patients with drug-resistant temporal lobe epilepsy (TLE) who can experience significant seizure rate reductions. The system 1500 can also apply stimulation therapy for other disorders as well, such as refractory major depressive disorder (MDD) originated from unexpected patient-reported mood improvements, for example. Such therapy can reduce cingulate activity, the same effect seen from many successful antidepressant therapies, and altered blood flow and metabolism in limbic structures. Other applications of the system 1500 are also possible.

The system 1500 implant procedure can be rather straightforward. Under general anesthesia, the control device 1506 housing can be surgically implanted in the left chest wall, the cortex, the brain stem, or other appropriate structures in the patient 1502. A wireless electrode 1520a (e.g., helical electrode) can then be wrapped around the left cervical vagus nerve and secured to surrounding tissue. The device 1506 may be externally activated and programmed using, for example, a wand-like device placed over the location of insertion. Stimulation can be, for example, intermittent and commonly programmed for 30 seconds of monophasic, constant-current stimulation every five minutes. However, individual parameters may be adjusted on a patient-to-patient basis in order to achieve maximal therapeutic efficacy with minimal side effects. Common side effects, such as dyspnea, cough and hoarseness, can be dependent on the intensity of stimulation, but they may diminish with time. To minimize patient discomfort, the stimulus intensity can be slowly increased over time (e.g., over two week intervals) until a balance is found between the maximum stimulus intensity and the patients' willingness to accept any side effects. The control method of parameter optimization can be complex and time consuming for the patient and physician. Table CHA (below) summarizes an example protocol for stimulus parameter adjustments after implantation. Various device and therapy parameters, as discussed above, can be adjusted according to this protocol on a per-patient basis.

TABLE CHA

Suggested stimulus parameter adjustment protocol

| To increase efficacy | To manage side effects |
| --- | --- |
| 1. ≥2 weeks after implant, increase output current by 0.25-0.5 mA at 2-week intervals to maximum tolerated level, typically 1.0-2.0 mA.<br>2. If no response after 1-3 months at maximum tolerated output current, gradually increase duty cycle (increase ON time, decrease OFF time) | 1. Reduce, output current<br>2. Reduce pulse width<br>3. Reduce frequency<br>4. Reduce ON time |

Vagus nerve stimulation (VNS) therapy with the system 1500 can impart antiepileptic and anti-depressive effects through activation of vagal afferent fibers. This is a logical conclusion, because 1) the device is intended to treat neuronal network-level disorders in the CNS, 2) vagal afferent fibers primarily project to the NTS and onward to the LC, where a chemical lesion was shown to significantly attenuate VNS-mediated anticonvulsive activity, and 3) evoked potentials from VNS have been repeatedly observed in neural recording/imaging studies. However, the conclusion that VNS works by activating unmyelinated Group C nerve fibers of the vagus nerve is not settled, because 1) destruction of C fibers does not destroy the antiepileptic effect of VNS and 2) stimuli found to be effective in epilepsy are of insufficient strength to activate the unmyelinated, afferent C fibers. Table CHB below provides an overview of the VNS stimulation parameter settings that can be used with the system 1500.

TABLE CHB

| Overview of available VNS stimulus parameter settings | | | | |
| --- | --- | --- | --- | --- |
| Stimulation parameters | Programmable range | Programming steps | Recommended initial values | Typical target values |
| Output current | 0-3.5 mA | 0.25 mA | 0.25 mA | 1.0-2 mA |
| Frequency | 1-30 Hz[1] | 1, 2, 5, 10, 15, 20, 25, 30 Hz | 20 Hz[2]<br>30 Hz[3] | 20-30 Hz |
| Pulse width | 130-1000 µs | 130, 250, 500, 750, 1000 µs | 250-500 µs | 250-500 µs |
| Duty cycle | 10-100%[4] | Function of signal ON, OFF times | 10% | 10% |
| Signal ON time | 7-60 s | 7, 14, 21, 30, 60 s | 30 s | 30 s |

TABLE CHB-continued

Overview of available VNS stimulus parameter settings

| Stimulation parameters | Programmable range | Programming steps | Recommended initial values | Typical target values |
|---|---|---|---|---|
| Signal OFF time | 0.2-180 min[5] | 5-60 min, 5-min steps<br>60-180 min, 30-min steps | 5 min | 5 min |

[1] Values below 5 Hz should be avoided.
[2] In depression.
[3] In epilepsy.
[4] Duty cycles greater than 50% have resulted in nerve damage in laboratory animals (26).
[5] Setting OFF time to 0.0 min turns off the pulse generator.

If the effects of VNS are due to activation of specific nerve fiber groups within the vagus nerve, then knowledge of the type, level and rate of nerve fiber activation can be used for advancing the field of VNS therapy and for discovering candidate symptom- or disorder-linked biomarkers suitable for use in closed-loop biomodulation devices, such as the system 1500. Rather than reporting applied stimulus parameters and the associated effects on symptom severity in VNS studies, the nerve fiber activation levels in response to the applied stimulus parameters can be reported and used in closed-loop biomodulation by the system 1500. If the nerve fiber activation level is held constant, then it can serve as a pseudo-independent variable so that researchers can investigate the mechanisms of action of VNS in a standardized manner (e.g., biomarker response data can be more easily interpreted and compared across studies or therapy can be dosed in a standardized manner).

Maintaining a fixed nerve activation level can be especially useful for quantifying any symptom- or disorder-linked biomarker level changes in response to fixed levels of nerve fiber activation for use by the system 1500. Graded cortical responses in response to VNS at different stimulus intensities provide indications of relationships between nerve activation levels and biomarker responses. For example, observed cortical responses with respect to VNS intensity, instead of nerve activation level, indicate that the relationship may be patient-specific and cannot be adequately quantified or compared to analogous relationships observed in different subjects (due to differing nerve activation properties). If the nerve fiber activation level is maintained with respect to the maximal level of nerve fiber activation in each subject (e.g., when all fibers are activated), then quantitative analyses and comparisons of data from VNS studies becomes feasible. Furthermore, if fixed nerve activation levels can be maintained, then the stimulus parameter adjustment/optimization period required of all VNS device recipients is hypothesized to become more efficient and effective.

An automated strength-duration curve-mapping algorithm, known as the Closed Loop Control System, has been developed as a tool for standardizing study/data reporting methods and therapy. Closed loop control and its related functionality are disclosed in US Pub 2014/0243714 entitled "Method and Apparatus for Closed-Loop Control of Nerve Activation," the entire contents of which is hereby incorporated by reference as if set forth in its entirety herein. The Closed Loop Control System rapidly determines all stimulus pulse durations and amplitudes within the programmable range that yield a compound action potential (CAP) response of fixed magnitude relative to the maximal CAP response that occurs when all fibers of a given type are activated. The magnitude of a peak in a CAP response is directly proportional to the number of activated nerve fibers with similar activation and conduction properties; given the natural variation in fiber diameters and degrees of myelination, distinct fiber groups can be identified based on the measured conduction velocity of individual CAP response peaks. When the error between the desired CAP magnitude (i.e., desired percent maximal activation) and the observed CAP magnitude (i.e., actual percent maximal activation) is used as negative feedback to adjust the amplitude or duration of the next applied pulse, then the nerve activation property-mapping algorithm becomes a nerve activation clamp. In the latter implementation, the Closed Loop Control System clamps a nerve fiber group of interest to any desired level of activation between minimal and maximal activation for research or therapeutic purposes.

Using this approach, patient-specific parameters can be identified by examining the VNS efficacy as a function of therapy delivered to the patient as measured by the CAP. This is in contrast with all previous approaches, which quantify efficacy as a function of current delivered. There is an enormous variability in fiber recruitment, as observed in the CAP, from an identical current stimulus from patient to patient. For example, measurements of the current therapy being delivered to human patients implanted with the VNS device can be taken by varying the stimulus parameters to maintain varying degrees of constant CAP activation of A, B, and C fibers. This can permit simultaneous exploration of the mechanism of action for VNS therapy and improve the clinical efficacy obtained from that therapy. These mappings can be programmed into, for example, the microcontroller 1514 and/or the FPGA 1516.

VNS for control of epileptic seizures was approved for clinical use in 1997 using a device manufactured by Cyberonics, Inc. Despite 15 years of investigative efforts, the exact mechanism of action have been largely undefined. As discussed above, the vagus nerve is composed of both myelinated and unmyelinated fibers and one of the specific unknown factors is precisely which elements of the nerve are activated by stimulation with various parameter settings of the stimulator. The knowledge of specific response patterns of the nerve elicited by various stimulator settings would be very beneficial in helping to assess mechanisms of VNS efficacy. Stimulation of a peripheral or cranial nerve with a mixed fiber population generates a nerve compound action potential (CAP) with components from various nerve fiber populations, conducted at different rates. The electrical response due to these different populations can then be separated by certain recording techniques. These techniques have been used in the electrophysiological evaluation of peripheral nerves but their extension to cranial nerves such as the vagus has been limited due to anatomical inaccessibility and problems of signal-to-noise ratio.

The system 1500 provides a platform to record and analyze compound actions potentials from the vagus nerve to identify mechanism of action of VNS in seizure suppression, which can be patient-specific. Furthermore, the system 1500 can be applied in other clinical settings in which it would be useful to evaluate the physiological integrity of the vagus nerve, or deliver other therapies via cranial nerve stimulation (e.g. depression or atrial fibrillation). Accordingly, the system 1500 provides a reliable and patient-acceptable method of recording stimulus-induced action potentials from the human vagus nerve of patients and provides software tools to reliably extract the CAP signal from background noise and estimate the proportion of neurons of each fiber type (i.e. A, B, and C fibers) within the vagus nerve that fire in response to stimulation from the implanted VNS pulse generator.

Patient-specific responses can be analyzed using data recorded in response to applied stimulations. For example, a learning algorithm (e.g., closed loop algorithm 1518) can estimates the type and proportion of neurons within the vagal nerve that 'fire' each time the implanted pulse generator turns on, yielding insight into which neurons are important for effective therapy. This technique can also predict the neurons that will fire when more or less intense stimuli are applied, but only the former software function will be tested. To perform the former function, the learning algorithm locates, aligns, and averages the individual compound action potential responses to stimulation to enhance the quality of the signal. Specific peaks within the signal are then located, measured and classified along with the implanted pulse generator settings. This information is compared to data from other patients or data taken from the same patient to determine the type and proportion of neurons that 'fire' each time the stimulator turns on. The pulse generator settings will not be altered in any way during the measurement and signal processing routines. In this manner, data and mappings can be generated showing:

Variability in therapy as measured by the CAP rather than stimulator current output, delivered to patients currently implanted Correlation between therapy delivered, relative A, B, and C *fiber* recruitments as a result of existing stimulus parameters, and reported efficacy over time Referring to FIG. 18, which depicts a cardiocentric view of the autonomic neuronal hierarchy that coordinates regional cardiac indexes as they related to the CNS. Anatomically, the heart is innervated by diverse nerve plexi, such as sensory, motor (sympathetic and parasympathetic efferent) and interconnecting nerves to communicate with extracardiac and intracardiac ganglia. FIG. 18 shows a conceptual diagram of a hierarchical neural structure based on more than a century of study on cardiac neural regulations. As shown in the figure, the intrathoracic extracardiac ganglia contain not only cardiac sympathetic efferent postganglionic neurons but also cardiac afferent neurons and local circuit neurons. Similarly, Intrinsic cardiac ganglia contain sensory and local circuit neurons as well as sympathetic and parasympathetic efferent postganglionic neurons. These neurons and their interactions are under the tonic influence of central (medullary and spinal cord) neurons. The functional implication of such a complex interconnection has only been studied with limited capability, largely due to a prior inability to study neural function in its working state. In addition to controlling normal physiology, cardiac autonomic nerves also play roles in arrhythmogenesis. For example, pulmonary veins have muscle sleeves that extend from the left atrium, along with projections from the vagus nerve. The pulmonary vein and left atrial junction are richly innervated by both sympathetic and parasympathetic fibers, and these two branches of the autonomic nervous system are highly co-located. These cardiac autonomic nerves could be identified by specific immunohistochemical staining, such as tyrosine hydroxylase for sympathetic nerves and cholineacetyltransferase for parasympathetic nerves. Acetylcholine-mediated atrial fibrillation (AF) can be facilitated by isoproterenol infusion, which decreases the acetylcholine concentration for AF induction and increased AF duration.

Sympathetic nerves primarily originate from the upper fourth and fifth segments of thoracic spinal cord and innervate the heart by passing through the superior cervical ganglion, the middle cervical ganglion, and the stellate ganglion. The sympathetic nerves from the superior cervical ganglia and the stellate ganglia communicate primarily with C1-3 and C7-8 and T1-2, respectively. The superior, middle and inferior cardiac nerves follow along large vessels such as the brachiocephalic trunk, common carotid and subclavian arteries. They join with cardiac branches from the vagus nerve and form the cardiac plexus. The parasympathetic nerves innervating the heart originate from the vagus nerve. The cardiac branches of the vagus nerve converge with ganglion cells in the cardiac plexus or intracardiac ganglia within epicardial fat pads. Intracardiac ganglionated plexi are a complex of intrinsic cardiac neurons connecting with extracardiac nerve structures and atrial and ventricular tissue. They function as final coordinator influencing cardiac mechanical and electrical indices. For example, the right atrial ganglionated plexus (RAGP) innervates the sinoatrial node and the inferior right ganglionated plexi innervates the AV node. The function of these two GPs as "integration centers" for an extrinsic autonomic nervous system to modulate SA node and AV node, respectively. Also, ablation of these GPs could eliminate effective refractory period shortening and reduce AF inducibility during sympathovagal co-stimulation. GP stimulation using the system 1500, for example, can facilitate converting pulmonary vein firing into AF. The superior left ganglionated plexi (SLGP) located between pulmonary vein and the left atrial appendage, is another intrinsic nerve structure known to contain both sympathetic and parasympathetic nerves. The ligament of Marshall (LOM) derives from the embryonic left superior vena cava and is known to contain both nerve and muscle fibers. Sympathetic nerves from the middle cervical and stellate ganglia passes along the LOM to innervate the left ventricle. Parasympathetic nerve fibers from vagus nerve traverse LOM to innervate left atrium, left pulmonary veins, coronary sinus and posterior LA fat pads.

Neural control of cardiac function has been studied for over a century. However, the fact that cardiac autonomic regulation involves, in addition to central commands, peripheral autonomic activity was understood only recently. The system 1500 can be used to generate further insights into these effects. In order to understand the nerve traffic, high-definition methods, such as those described above and below with regard to 1500, capable of simultaneous recording from multiple distributed sites can be used. For example, the system 1500 can be used to simultaneously monitor multiple locations to understand the activation and propagation of these nerve activities, and to associate the nerve activities with AF vulnerability. These high-definition measurement will allow testing of the hypothesis that sympathovagal co-activation involves a feedback mechanism between the stellate ganglion and the middle cervical ganglion, and based on the results, stimulation and therapeutic applications via the system 1500. The feedback can be provided through the neural connections between the stellate and the middle cervical ganglia. Such evaluation can include, for example:

Increasing the number of observation sites to allow better characterization of the neural activities and neural traffic from different areas of origin.

Increasing the bandwidth and sampling rate of nerve signals to allow deconvolution of nerve bundle and ganglion local field potentials into more functionally homogeneous groups.

Modulating recruitment of vagus nerve fibers during VNS therapy to decrease the incidence of atrial fibrillation.

The system 1500 permits integrating signal processing and feature extraction algorithms on-board implantable medical devices, such as the control device 1506. This eliminates or reduces the need for wireless transfer of data outside the patient. Effective prediction or detection algorithms can be used to implement closed-loop treatment devices that deliver electrical, optical, or pharmacological stimulus upon detection of a physiological event of interest.

In the context of therapeutic devices, such as the system 1500, signal processing allows for integrating responsive detection or prediction algorithms to analyze recorded physiological data and apply interventional therapy in a temporally specific manner. While there have been a number of different approaches proposed to both predict and detect events, barely a handful of these algorithms are employed in portable computing devices, whether implantable (e.g., 1506) or hand-held (e.g., 1540).

The system 1500 can implement control algorithms that, responsive stimulation of the descending vagus nerve fibers, can modulate atrial fibrillation and other conditions (e.g., seizure), and can dramatically reduce hospitalizations in the US and worldwide.

The system 1500 and the control device 1506 can implement event detection algorithms to make them feasible in implantable applications, such as through low-power digital design techniques allowing for customizable digital designs to implement the detection algorithms at a cost several times lower than employing standard micro-controllers or digital signal processors. For example, the system 1500 can use a custom feature extraction processor to transmit relevant markers of events, which can reduce the amount of time a wireless transmitter would need to be powered and can improve the power when feature extraction was applied. The RF components of the system 1500 can consume the most power when operated—sometimes an order of magnitude more than the rest of the system. With the need to transmit through longer distances and through skin and tissue, RF transmission schemes may need to be more robust while still remaining low-power. For neural prostheses as part of the system 1500, integrating event detection and/or prediction algorithms on board the implant 1506 eliminates the need to transmit any data outside of the implant besides programming and housekeeping information during startup.

Two general methods can be used as part of the system 1500 to extract meaningful information from neural data-analog and digital. Traditionally, analog schemes are thought of to be more power hungry, although there have been low-power implementations of analog feature extraction circuits proposed lately. Analog circuit techniques do not require an ADC to accurately digitize neural signals—a challenging design given the dynamic range of neural signals.

FIG. 19 shows a block diagram of the possible feature extraction schemes that can be applied to implantable medical devices, such as part of the system 1500. The system 1500 can use an analog signal encoding scheme, for example, that uses a one-bit comparator to threshold (spike detect) data, reducing the neural signal to digital spike or threshold-crossings. The value of the chosen amplitude threshold is critical in deciding the efficacy of this technique. This simple digitization scheme is justified by the fact that most neuroprosthetic applications only require timing information from spikes (action potentials) accurate to about 1-ms. Additional and/or alternative encoding and detection schemes can be used.

Digital schemes included with the system 1500 can be implemented at low hardware costs and can integrate maximal functionality per unit silicon area occupied especially with scaled technologies. Given that medical implants normally do not demand high clock-speed performance, the digital designs of the system 1500 can also allow for severe voltage scaling operating in near to sub-threshold regions of operation. For example, a computationally efficient digital implementation of an event-based detection algorithm for the system 1500 can be operated at a voltage as low as 300-mV with less than 350-nW of power consumption per channel. The selection of features for the system 1500 and the control device 1506 for implementing an algorithm can be suitable for wirelessly-powered devices and/or battery-powered devices.

Using these approached in a manner similar to our prior work in seizure detection, this same techniques and system components can be applied to lower the mortality rate of SUDEP, and reducing the number of hospitalizations from atrial fibrillation, as described below.

Example Use Case #2—Sudden Unexpected Death in Epilepsy (SUDEP)

The systems, devices, techniques, protocols, and processes described above and throughout this document can be used in a variety of human and/or animal applications. In one example use case, they can be used to treat patients with epilepsy to prevent SUDEP, which is a fatal complication of epilepsy defined as the sudden and unexpected, non-traumatic and non-drowning death of a person with epilepsy, without a toxicological or anatomical cause of death detected during the post-mortem examination. The specific causes of SUDEP are not precisely known, but appear to be multifactorial and include respiratory, cardiac and cerebral factors, as well as the severity of epilepsy and seizures. Possible pathophysiological mechanisms of SUDEP include seizure-induced cardiac and respiratory arrests. Treatments to prevent SUDEP in patients can include, for example, stimulating the vagus nerve when particular conditions within the body are detected that indicate a possible SUDEP condition, providing patients with warnings, such as on a mobile device (e.g., smartphone, smart watch, other wearable device) and/or base station, stimulating various nerves and/or systems to reduce the incident of acid reflux that may occur while a patient is experiencing a seizure, and/or other therapeutic monitoring and/or treatment related to epilepsy.

Example implementations for preventing SUDEP are described below with regard to FIG. 20. Some or all of these features can be applied to the treatment of other conditions, as described and/or with modifications, and/or can be applied to the platform more generally. Additionally, some or all of the descriptions with regard to the treatment of other conditions described throughout this document can be applied epilepsy therapy.

Referring to FIG. 20, an example system 2000 is depicted in which an implantable system 2004 is configured for the treatment of epilepsy in a patient 2002. The example implantable system 2004 is similar to the implantable systems described above, and includes an implantable control device 2006 (also referred to as a "bionode") and one or more separate sensing and/or stimulating devices 2008 (e.g., implantable wireless electrodes), which can be wirelessly powered by the control device 2006 (no battery or other locally housed power source in implantable devices 2008), can wirelessly transmit data to the control device 2006, and/or can be wirelessly controlled to discharge therapeutic stimulation to one or more locations on the patient 2002. The system 2000 can provide a toolbox of implantable devices with accompanying base station 2030 for wireless powering and a graphical user interface (GUI) (e.g., provided on a mobile device, like a smartphone or smartwatch) for wireless communication to and from the control device 2006.

The implantable electrodes 2008 in this example include one or more electrodes 2020 implanted at particular locations 2022a-c in the patient's body, including at the cortex 2022a, the brainstem 2022b, the vagus nerve 2022c, the respiratory system 2022d, and/or other locations. For example, the electrodes 2020 can be implanted in the brainstem 2022b (e.g., hippocampus, pre-Botzinger, nucleus ambiguus, nucleus tractus solitarius, and rostral and caudal ventral-lateral medulla (VLM)) to detect local field potential and single and multiunit activity for evidence of seizures propagating into, or silencing, brainstem structures. These electrodes 2020 can take various measurements at one or more of these locations 2022a-c, which can be wired and/or wireless transmitted to the control device 2006 for analysis. These electrodes 2020 can sense and transmit, for example, electric physiological conditions including single neuron measurements, LFP, EEG, electrocardiogram (ECG), and electromyogram (EMG). These electrodes 2020 can also wirelessly discharge therapeutic stimulation at one or more of these locations 2022a-c when directed to do so by the control device 2006. This stimulations can include, for example, deep brain stimulation (DBS) and/or nerve stimulation.

In addition to measuring electric physiological conditions using the electrodes 2020, the implant system 2006 can use one or more sensors 2016 to measure mechanical and/or chemical conditions within the patient 2002. For example, the sensors 2016 can measure and provide data on mechanical physiological conditions including respiratory conditions (e.g., rate of respiration) and patient temperature. The sensors 2016 can also measure and transmit chemical conditions including pH in the patient's body. The sensors 2016 can be, for example, transducers. Such sensors 2016 can be either directly or indirectly (via leads) connected to particular physiological structures in the patient's body, such as ECG leads on the chest wall; EMG leads to diaphragm or other muscle; and/or thermocouple implanted in the nasal passage.

In addition to receiving and monitoring conditions related to SUDEP in the patient 2002, determining particular therapeutic stimulation that should be provided to the patient 2002, and wirelessly directing one or more of the electrodes 2020 to deliver the determined therapy, the control device 2006 can include components to provide wireless data and power (2012) that permits the control device 2006 to wirelessly output data to a base station and/or to a mobile device (e.g., smartphone, smart watch), and to be wirelessly powered and/or charged. This output data can include a variety of different patient data, such as patient data, a log of conditions detected and therapies delivered, alerts as to currently detected conditions (e.g., oncoming seizure, seizure currently detected), and/or other data. The control device 2006 can transmit this data wirelessly. The control device 2006 can be powered wirelessly (e.g., via RF signals) and can additionally include a local power source (e.g., battery) that can be charge via the wireless signals and that can power the control device 2006 when the wireless signal is unavailable. The packaging of the control device 2006 can be, for example, glass.

The control device 2006 includes an analog front end 2010 that receives wireless signals transmitted by the electrodes 2020. The analog front end 2010 provide the received signals to the signal processing subsystem on the device 2006, which includes a microcontroller 2014 and a FPGA. Signal processing can be performed on-board or off-board, and can involve using a closed-loop algorithm 2018, which can be used to identify particular physiological conditions within the patient 2002 and can determine, based on the particular detected conditions, whether to provide bioelectric stimulation at one or more of the locations 2022a-c. For example, the closed-loop algorithm 2018 can be performed by the control device 2006, by a device external to the control device 2006 (e.g., mobile device, base station), or by a combination of the two. When a condition is detected that warrants stimulation, the closed-loop algorithm 2018 can direct the bioelectric stimulator output unit 2018 to either directly provide the therapy or to cause one of the electrodes 2020 to deliver the therapy. For example, the control device 2006 can include on-board components to delivery stimulation therapy, and/or can trigger one of more of the electrodes 2020 to deliver the therapy.

The closed-loop algorithm 2018 can use any of a variety of appropriate techniques to learn the particular physiology of the patient 2002 and the patient's particular response to therapy, and can use that information to determine when, how, and under what conditions to provide therapy for the patient 2002. For example, the closed-loop algorithm 2018 can be initially calibrated for the patient by a physician or other trained technician in a clinical setting, which can involve providing various stimulations and recording the physiological response of the patient 2002. After being initially calibrated, the closed-loop algorithm 2018 can continue to learn and adapt over time by analyzing data generated by the electrodes 2020, therapy provided to the patient 2002, and the patient's response to the therapy.

A physiological pathway 2024 that is being monitored as part of the system 2000, which includes the patient's cortex, brainstem, vagus nerve, upper esophageal sphincter (UES) and/or larynx, and laryngospasm. The closed-loop control that is being implemented by the closed-loop algorithm 2018 is directed toward monitoring and providing therapy related to the physiological pathway 2024, which includes receiving sensor data from electrodes 2020 implanted at the cortex and brainstem and the electrodes 2016 positioned to measure respiratory and temperature information, processing those signals, and stimulating the vagus nerve to impact and minimize the inflammation reflex when, for example, possible SUDEP conditions are detected. Measurements can be taken by the electrodes 2016 and 2020, and can be used to determine whether the stimulation was sufficient to mitigate the detected condition (which can occur in some patients experiencing seizures), and thereby stop/minimize the condition that may indicate the onset of SUDEP, such as an inflammation reflex the closes the UES and/or larynx. The closed-loop algorithm 2018 can repeatedly monitor patient data and apply vagus nerve stimulation when appropriate until the patient's SUDEP condition (e.g., UES inflammation reflex) has stopped and/or dropped below a threshold level. The closed-loop algorithm 2018 can be automatically implemented without explicit patient direction.

The closed-loop VNS therapy provided by the system 2000 in response to, for example, alterations in cardiac or respiratory rate has the potential to reduce the incidence of SUDEP. Other factors and alterations in other factors can additionally and/or alternatively be used to identify the onset of SUDEP and to prevent SUDEP in a patient by, for example, reducing the UES inflammation reflex via stimulation.

The system 2000 take a variety of patient factors into account as part of the closed-loop algorithm, including biological factors of sex and correlations with strain on seizures and their consequences. Strain and/or sex in subjects (e.g., animals) may have an impact on SUDEP, factors which can be evaluated separately and/or using an epilepsy model (kainic acid and TeNT). Seizure number and duration can be covariates of SUDEP, and primary measurements can be of the extent and duration of postictal changes in heart rate and postictal changes in respiration. Statistical analysis can assess the impact on the measurements of time after injection, and of numbers, durations and semiologies of seizures. SUDEP risk associated with these factors can be evaluated by examining whether SUDEP incidents are distributed randomly amongst the factors (strain and sex). In another example, the latter analysis can include EMG and nasal temperature as indicators of obstructive apnea. Given the substantial difference in seizure durations in the acute kainic acid status model and chronic experimental epilepsy, other mechanisms, including interactions of cardiac and respiratory dysfunctions can be evaluated as the cause of SUDEP.

The system 2000 can additionally and/or alternatively evaluate the cardiac and respiratory consequences of intrahippocampal injection of tetanus toxin and kainic acid when identifying SUDEP conditions. The TeNT model may not cause status epilepticus at induction and results in little or no neuronal loss in >70% of cases. The kainic acid model may not cause status epilepticus in subject (e.g., animals) at induction and reliably results in gross neuronal loss in the hippocampus. This can provide for reliable induction of chronic epilepsy in the kainic acid model and works well for the tetanus toxin model too. It has the advantages of avoiding residual effects of general anesthesia with isoflurane, and can provide baseline pre-induction data and therefore reduce the between-animal sources of variation. Outcome measures can include the extent and duration of postictal tachycardia, arrhythmias, hyperventilation, apneas and sudden deaths.

The system 2000 can provide a platform to identify unit and local field potentials associated with seizure-related changes in heart rate, respiration, arrhythmias and apneas. Temporal relationships between unit activity and postictal cardio-respiratory changes will shed light on mechanism. E.g., tachycardia continuing long after cessation of postictal changes in neuronal activity in cardiac centers (notably VLM) would implicate an endocrine component. To be able to detect any seizure-like activity propagating into the brainstem, recordings will be made wider band than is conventional for unit recordings. Off-line filtering can be implemented to help isolate unit activity.

Example Use Case #3—Urinary Incontinence

The systems, devices, techniques, protocols, and processes described above and throughout this document can be used in a variety of human and/or animal applications. In one example use case, they can be used to treat patients with urinary incontinence by stimulating the pelvic nerve. For example, since micturition can be evoked in response to exogenous bladder filling, urodynamic measurements can be made and pelvic nerve stimulation can be tracked to identify relevant functional responses, including urinary voiding. A variety of configurations are possible to identify such voiding conditions, including using balloon pressure sensors into the uterus and colon, recording EMG activity from the abdominal wall to investigate the possibility of off-target effects of pelvic nerve stimulation, measuring temperature in the nerve bundle during prolonged periods of high frequency stimulation, and/or others, as well as combinations thereof.

Example implementations for urinary incontinence are described below with regard to FIGS. 21-32. Some or all of these features can be applied to the treatment of other conditions, as described and/or with modifications, and/or can be applied to the platform more generally. Additionally, some or all of the descriptions with regard to the treatment of other conditions described throughout this document can be applied urinary incontinence therapy.

Referring to FIG. 21, an example system 2100 is depicted in which an implantable system 2104 is configured for the treatment of urinary incontinence in a patient 2102. The example implantable system 2104 is similar to the implantable systems described above, and includes an implantable control device 2106 (also referred to as a "bionode") and one or more separate sensing and/or stimulating devices 2108 (e.g., implantable wireless electrodes), which can be wirelessly powered by the control device 2106 (no battery or other locally housed power source in implantable devices 2108), can wirelessly transmit data to the control device 2106, and/or can be wirelessly controlled to discharge therapeutic stimulation to one or more locations on the patient 2102. The system 2100 can provide a toolbox of implantable devices with accompanying base station 2130 for wireless powering and a graphical user interface (GUI) (e.g., provided on a mobile device, like a smartphone or smartwatch) for wireless communication to and from the control device 2106, which can be implanted in at one or more locations in the patient's body, for example. The devices that are part of the system 2100 have the capacity for multi-channel neural recording, optical and electrical stimulation, wireless telemetry, wireless powering, and embedded algorithms for closed-loop feedback and stimulation.

The implantable electrodes 2108 in this example include a cuff electrode or single neuron electrodes implanted at a location 2122a that corresponds to the patient's pelvic nerve, a pressure and/or temperature sensor implanted at a location 2122b corresponding to the patient's bladder, and/or other electrodes and transducers implanted at or around the locations 2122a-b, such as external urethral sphincter (EUS) EMG electrodes, a urine drop counter, and/or other electrodes. The control device 2106 can be implanted at any of a variety of locations, such as the locations 2122a-b and/or the location 2122c corresponding to the patient's PAG. The control device 2106 includes an on-board compound nerve action potential (CNAP) device that can simultaneously record as a bioelectric input analog front end 2116 and can provide nerve stimulation as a bioelectric stimulator output 2119.

The electrodes 2120 can take various measurements at the locations 2122a-b, which can be wireless transmitted to the control device 2106 for analysis. The electrodes 2120 can sense and transmit, for example, bladder response to pelvic nerve stimulation, which can also receive the CNAP input from the on-board bioelectric input analog front end 2116.

In addition to receiving and monitoring conditions related to urinary incontinence in the patient 2102, determining particular therapeutic stimulation that should be provided to the patient 2102, and wirelessly directing one or more of the electrodes 2120 and/or the bioelectric stimulator output 2119 to deliver the determined therapy, the control device 2106 can include components to provide wireless data and power (3322) that permits the control device 2106 to wirelessly output data to a base station and/or to a mobile device (e.g., smartphone, smart watch), and to be wirelessly powered and/or charged. This output data can include a variety of different patient data, such as patient data, a log of conditions detected and therapies delivered, alerts as to currently detected conditions (e.g., oncoming inflammation, inflammation reflex currently detected), and/or other data. The control device 2106 can transmit this data wirelessly. The control device 2106 can be powered wirelessly (e.g., via RF signals) and can additionally include a local power source (e.g., battery) that can be charge via the wireless signals and that can power the control device 2106 when the wireless signal is unavailable. The packaging of the control device 2106 can be, for example, glass.

The control device 2106 includes an analog front end 2110 that receives wireless signals transmitted by the electrodes 2120. The analog front end 2110 provide the received signals to the signal processing subsystem on the device 2106, which can include a microcontroller 2114. Signal processing can be performed on-board or off-board, and can involve using a closed-loop algorithm 2118, which can be used to identify particular physiological conditions within the patient 2102 and can determine, based on the particular detected conditions, whether to provide bioelectric stimulation of the pelvic nerve (location 2122*a*). For example, the closed-loop algorithm 2118 can be performed by the control device 2106, by a device external to the control device 2106 (e.g., mobile device, base station), or by a combination of the two. When a condition is detected that warrants stimulation, the closed-loop algorithm 2118 can direct the bioelectric stimulator output unit 2119 to either directly provide the therapy or to cause one of the electrodes 2120 to deliver the therapy to the pelvic nerve. For example, the control device 2106 can include on-board components to delivery stimulation therapy (CNAP device 2119), and/or can trigger one of more of the electrodes 2120 to deliver the therapy.

The closed-loop algorithm 2118 can use any of a variety of appropriate techniques to learn the particular physiology of the patient 2102 and the patient's particular response to therapy, and can use that information to determine when, how, and under what conditions to provide therapy for the patient 2102. For example, the closed-loop algorithm 2118 can be initially calibrated for the patient by a physician or other trained technician in a clinical setting, which can involve providing various stimulations and recording the physiological response of the patient 2102. After being initially calibrated, the closed-loop algorithm 2118 can continue to learn and adapt over time by analyzing data generated by the electrodes 2120, therapy provided to the patient 2102, and the patient's response to the therapy.

A physiological pathway 2124 that is being monitored as part of the system 2100, which includes micturition center, PAG, bladder, the pelvic nerve, the lower GI, and urinary voiding. The closed-loop control that is being implemented by the closed-loop algorithm 2118 is directed toward monitoring and providing therapy related to the physiological pathway 2124, which includes receiving sensor data from electrode 2120 implanted at bladder, processing those signals in combination with the CNAP signals, and stimulating the pelvic nerve to minimize instances of urinary incontinence, for example, when the patient 102 is experiencing involuntary urinary voiding. The closed-loop algorithm 2118 can repeatedly monitor the urinary flow measurements 2126 and can apply pelvic nerve stimulation when appropriate until the patient's urinary voiding has subsided and/or dropped below a threshold level. The closed-loop algorithm 2118 can be automatically and repeatedly implemented without explicit patient direction.

The system 2100 can deliver electrical stimulations to the patient 2102 using appropriate stimulating frequency, waveforms, time delay from detection, stimulus current output, and other parameters to deliver neural therapy to allow for clamping the urinary tract response so as to modify the patient's urinary incontinence symptoms. Such parameters can be patient-specific, and can be developed through data collected during in-clinic/hospital monitoring of seizure episodes and the patient response to various levels of stimulation therapy.

FIG. 22 shows in more detail, the anatomical relationship between pelvic nerve and bladder and the localization of sensors and electrodes placed in the bladder, external urethral sphincter and pelvic nerve.

FIG. 23 show example silver hook electrode assemblies used for stimulation and recording from the pelvic nerve, which can allow for a determination of the bladder response to pelvic nerve stimulation and can provide a benchmark against which to compare cuff electrodes, as depicted in FIG. 24. For example, bipolar cuff electrodes (platinum iridium wire with cobalt core in silicone epoxy) can be used on the pelvic nerve routinely in both acute experiments and for chronic implantation in conscious patients. Cuffs can be implanted, for example, onto the preganglionic nerve trunk with leads tunneled subcutaneously and exteriorized to the nape of the neck for tethered stimulation.

In preclinical testing, it was found that stimulation of the pelvic nerve unilaterally using rectangular pulses evoked graded increases in bladder pressure (FIG. 25). In preliminary experiments (n=3) the effectiveness of low frequency pelvic nerve stimulation was tested in order to assess the functional integrity of the nerve-bladder projection following surgery. In line with data from others, brief trains (10 s) of low frequency stimulation evoked a phasic increase in bladder pressure reflecting contraction of the detrusor (FIG. 25). The effect was dependent on both the intensity (FIG. 25*b*) and the duration (FIG. 25). At low intensities (1-2V), each pulse evoked a twitch-like response in the EUS EMG (latency=16-18 ms) (FIG. 25*d*). As the stimulation intensity increased, twitch responses were superimposed on tonic EMG activity (FIG. 25*e* and FIG. 25*f*). Tonic EMG activation was not secondary to increased bladder pressure (FIG. 25*e* and FIG. 25*f*). Occasionally, a single drop of urine was expelled from the urethra during low frequency stimulation but co-ordinated voids (see below) were never evoked by this procedure.

Figure 26B:
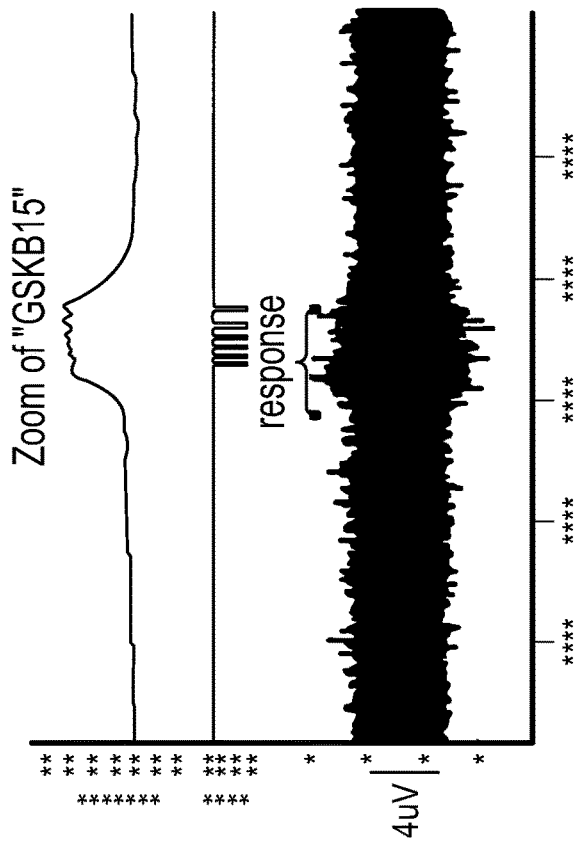

Multi-unit activity was recorded from postganglionic nerve bundles during voiding evoked by infusion of saline into the bladder. When recording from the whole nerve bundle the signal to noise ratio during was not usually great enough to enable clear distinction of spike activity (FIG. 26). However, by carefully splitting the nerve, clear voiding-related activity could be recorded from some fibre bundles (FIGS. 26B and C and FIG. 27). In some cases, a clear linear relationship between bladder pressure and nerve activity was present (FIG. 28). In other cases nerve activity was time locked to the contraction phase of the void rather than bladder pressure per se—firing ceased at the time of the sharp drop in pressure as the bladder started to relax.

During preclinical testing, saline was infused continuously into the bladder to evoke repeated voiding. During the filling phase bladder pressure rose slowly until a threshold pressure was reached, upon which time bladder pressure rose steeply, signalling in imminent void. During this time tonic activity in the external urethral sphincter (EUS) increased significantly (FIG. 29a) and then switched to a bursting pattern (approx. 8 Hz, FIG. 29b) during which time urine was expelled. During the expulsion phase 'ripples' could be seen on the bladder pressure trace, in phase with rhythmic sphincter activity, reflecting back pressure transmitted to the bladder as the detrusor contracts against the intermittently closed sphincter.

Figure 29D:
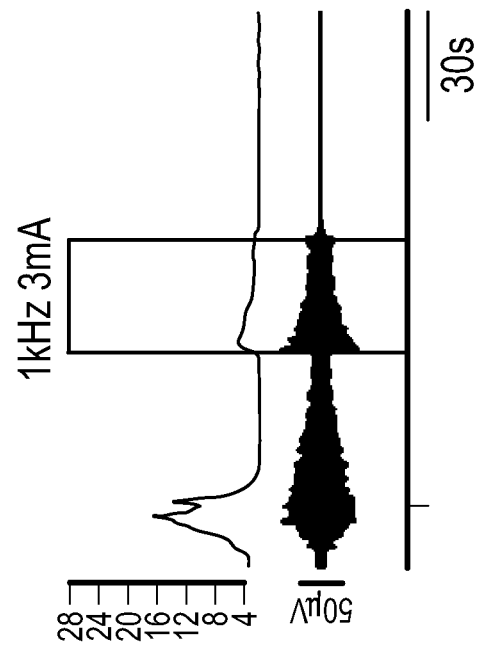
Figure 29C:
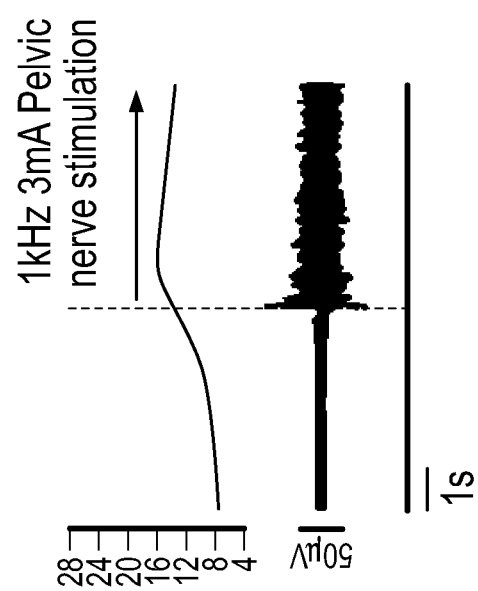

Stimulation of the pelvic nerve (preganglionic bundle) using high frequency charge balanced alternating current (sine) initiated within 1-2 s of the steep rise in bladder pressure signaling an imminent void was able to suppress urine output completely (FIG. 29a-c). The effect was readily reversible and voiding resumed within a few minutes of terminating pelvic nerve stimulation (FIG. 29a). The bladder contraction was aborted and tonic activity in the EUS increased (FIG. 29c). Stimulation during the filling phase in between voids (FIG. 29d) had no effect on bladder pressure but evoked tonic activity in the EUS. The effect of pelvic nerve stimulation on voiding was frequency dependent. In different animals optimal suppression of voiding occurred at frequencies between 1 and 3 kHz. There was a non-monotonic relationship between frequency and efficacy of inhibiting voiding (FIG. 30). At sub-optimal stimulation parameters, voiding was sometimes suppressed incompletely or alternatively, a void occurred but was deferred until late on in the 60 s stimulation period.

The effect of pelvic nerve stimulation on voiding was frequency dependent. In different animals optimal suppression of voiding occurred at frequencies between 1 and 3 kHz. There was a non-monotonic relationship between frequency and efficacy of inhibiting voiding (FIG. 30). At sub-optimal stimulation parameters, voiding was sometimes suppressed incompletely or alternatively, a void occurred but was deferred until late on in the 60 s stimulation period. Stimulation of either the right or left pelvic nerve appeared to be equally effective. Bilateral stimulation was no more effective than stimulating the pelvic nerve on one side.

Figure 31D:
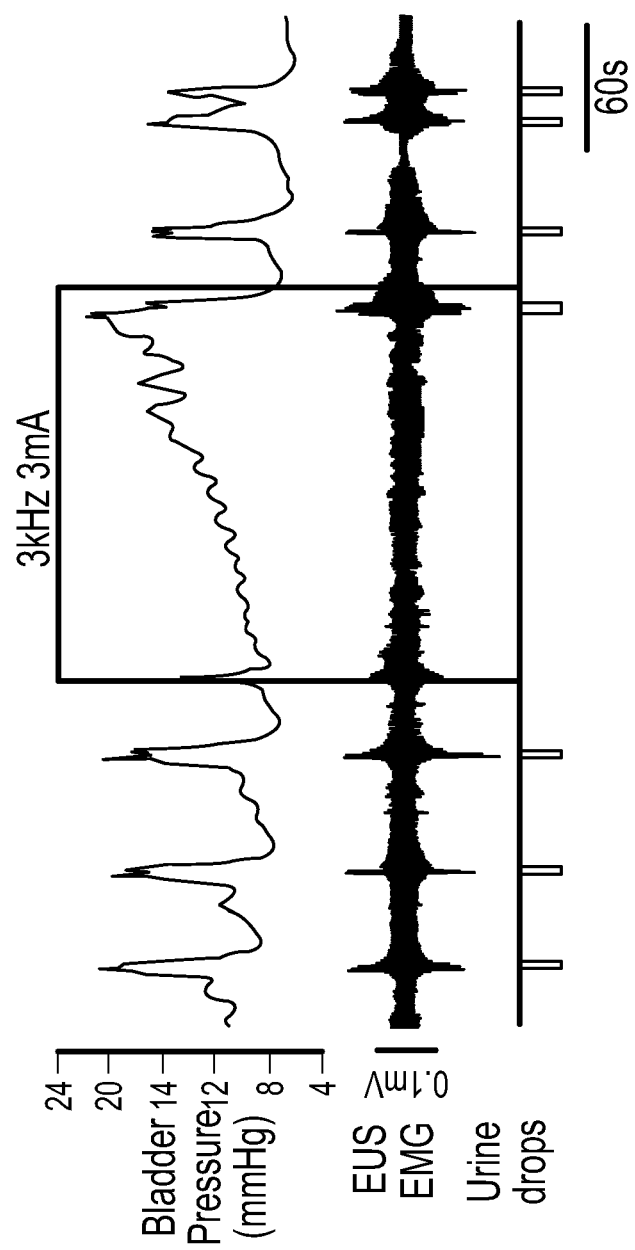
Figure 31E:
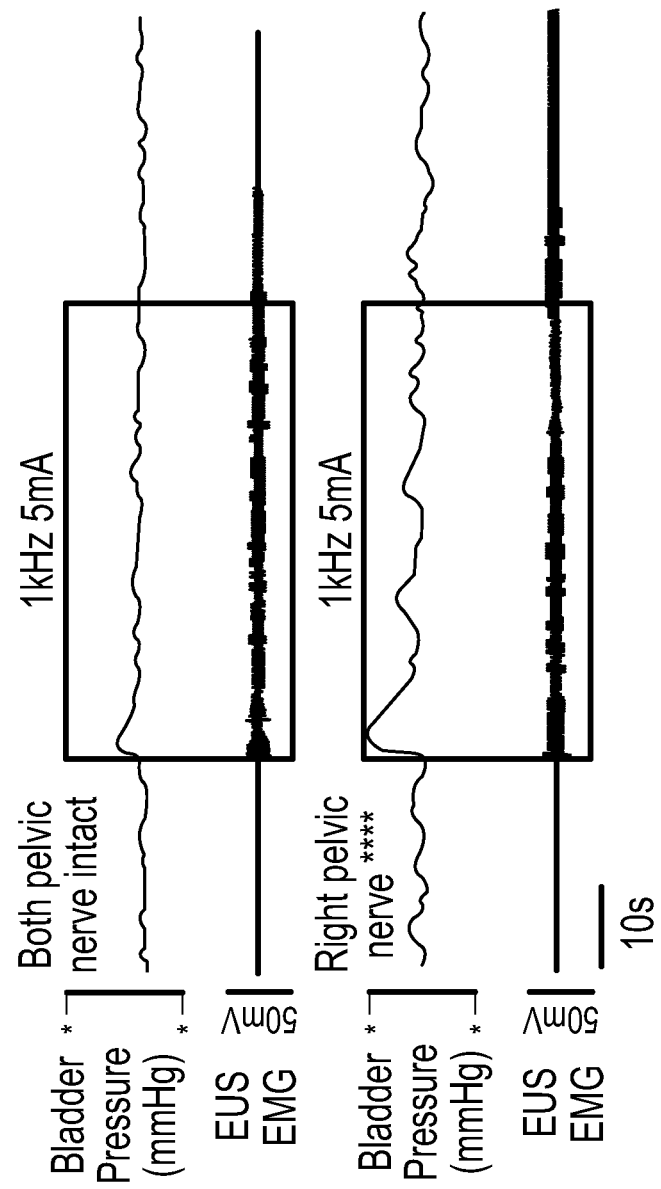

In evaluating the mechanism underlying pelvic nerve-evoked suppression of voiding, cutting the pelvic nerve contralateral to the stimulated side (FIG. 31a) did not suppress repeated voiding evoked by infusion of saline into the bladder (FIG. 31b,c). Neither did it prevent the suppression of voiding evoked by stimulation of the ipsilateral nerve (FIG. 31d). When stimulation was carried out during the filling phase in between voids, tonic activity in the EUS and the transient on-response in bladder pressure persisted (FIG. 31e).

Figure 32B:
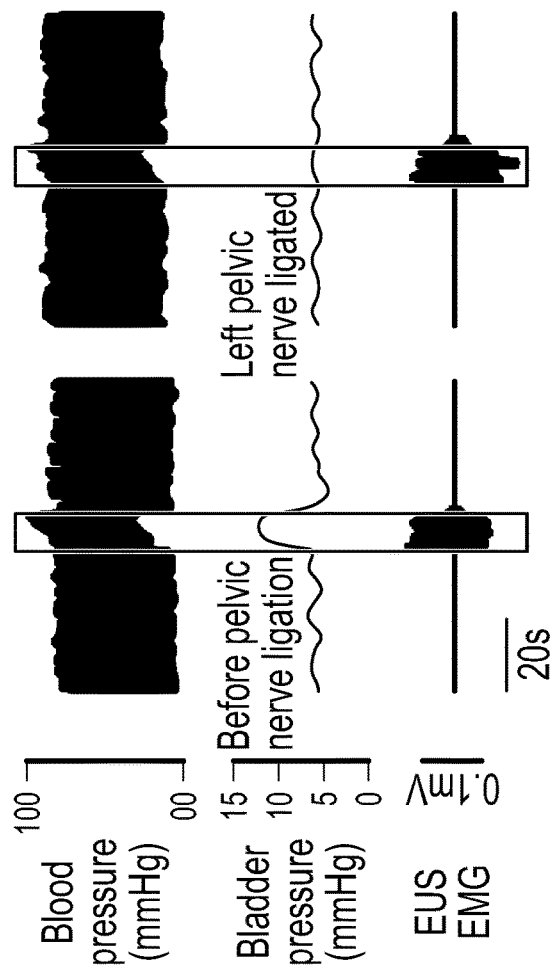
Figure 32A:
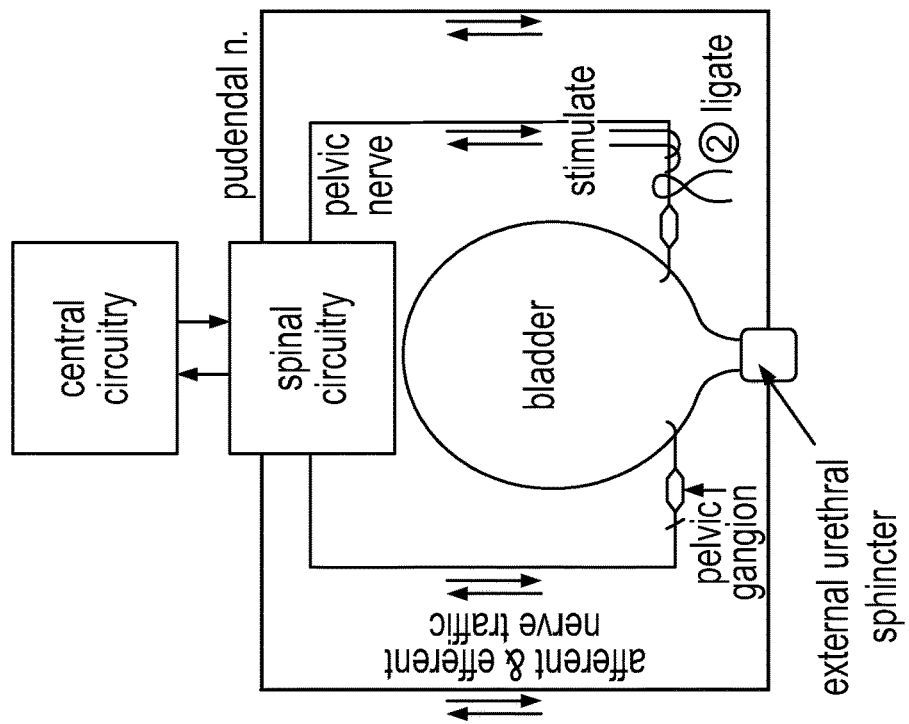
Figure 32C:
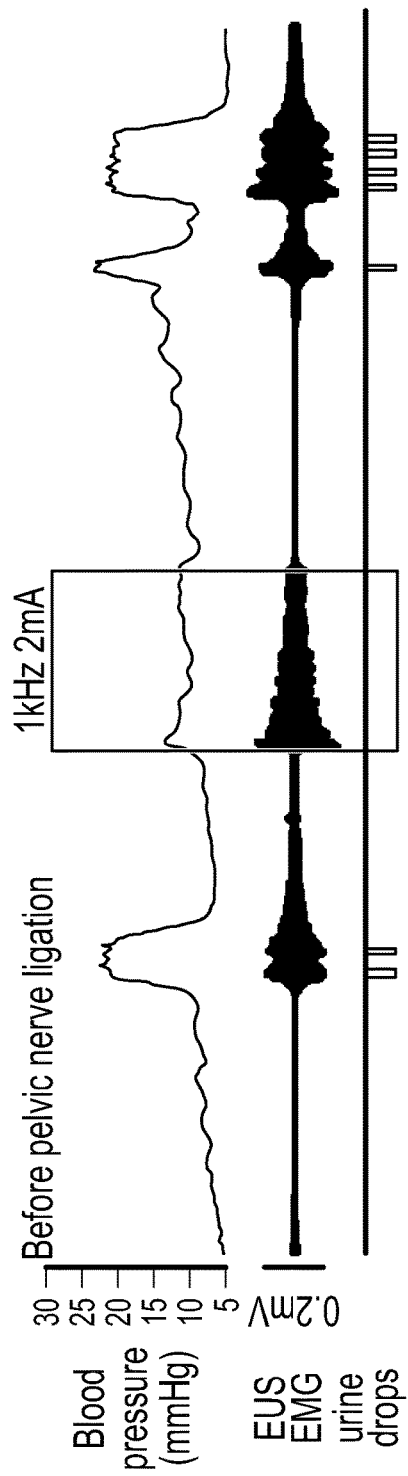
Figure 32D:
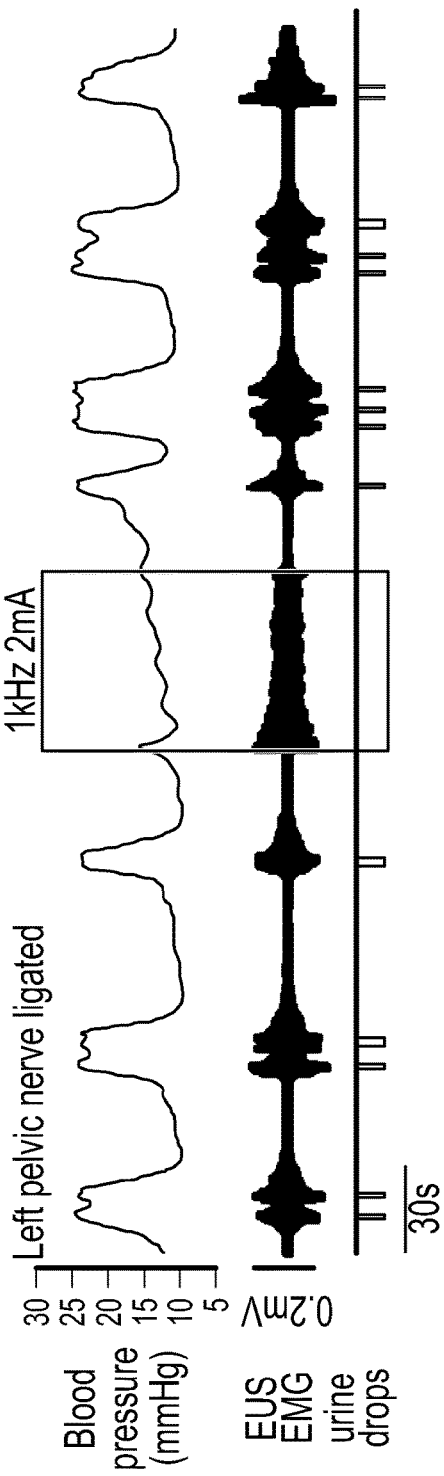
Figure 32F:
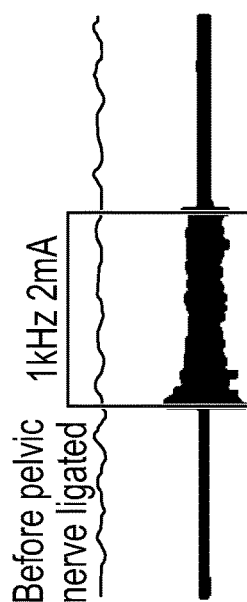
Figure 32E:
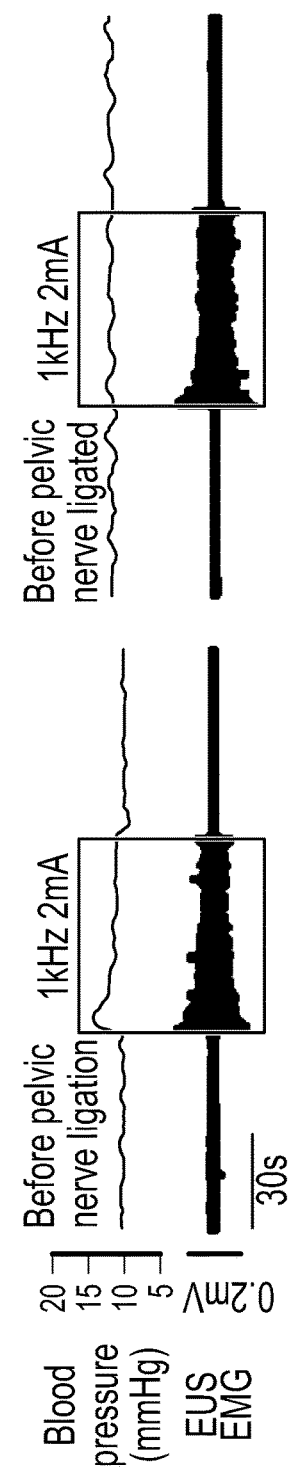

In another series of experiments, the pelvic nerve distal to the stimulating electrode was ligated (FIG. 32a). Ligation rather than section was preferred since cutting the nerve inevitably lead to movement of the central end relative to the nerve cuff electrode. This procedure blocked the on response to high frequency ipsilateral nerve stimulation but not the increase in tonic activity in the EUS (FIG. 32b). These effects are consistent with activation of pelvic nerve afferents to evoke reflex responses in the EUS whilst interrupting nerve transmission past the distal ligature. Following ipsilateral nerve ligation, repeated voiding continued in response to infusion of saline into the bladder (FIG. 32d). Moreover, stimulation of the pelvic nerve was still able to suppress imminent voids (FIG. 32d).

Example Use Case #4—Inflammation

The systems, devices, techniques, protocols, and processes described above and throughout this document can be used in a variety of human and/or animal applications. In one example use case, they can be used to treat patients with an inflammatory reflex associated with the spleen releasing inflammatory cytokines by splenic macrophages into the blood stream, which is often associated with conditions like depression and anxiety. Treatment of inflammatory reflexes can involve stimulating the vagus nerve to reduce the release of inflammatory cytokines (i.e., trapped T cells originating in the GI tract) to cause a vagally mediated reduction in lymphocyte release from the post-synaptic sites of vagus nerve innervation in the gastrointestinal tract. Vagus nerve stimulation can be performed when particular conditions within the body are detected that indicate an inflammatory reflex is occurring or is about to occur, providing patients with warnings, such as on a mobile device (e.g., smartphone, smart watch, other wearable device) and/or base station, stimulating various nerves and/or systems to reduce, stop, or prevent the inflammatory reflex a patient is experiencing, and/or other therapeutic monitoring and/or treatment related to inflammation reflexes.

Example implementations for treating inflammation are described below with regard to FIGS. 33-34. Some or all of these features can be applied to the treatment of other conditions, as described and/or with modifications, and/or can be applied to the platform more generally. Additionally, some or all of the descriptions with regard to the treatment of other conditions described throughout this document can be applied inflammation reflex therapy.

Referring to FIG. 33, an example system 3300 is depicted in which an implantable system 3304 is configured for the treatment of inflammation reflex in a patient 3302. The example implantable system 3304 is similar to the implantable systems described above, and includes an implantable control device 3306 (also referred to as a "bionode") and one or more separate sensing and/or stimulating devices 3308 (e.g., implantable wireless electrodes), which can be wirelessly powered by the control device 3306 (no battery or other locally housed power source in implantable devices 3308), can wirelessly transmit data to the control device 3306, and/or can be wirelessly controlled to discharge therapeutic stimulation to one or more locations on the patient 3302. The system 3300 can provide a toolbox of implantable devices with accompanying base station 3330 for wireless powering and a graphical user interface (GUI) (e.g., provided on a mobile device, like a smartphone or smartwatch) for wireless communication to and from the control device 3306, which can be implanted in at one or more locations in the patient's body, for example. The devices that are part of the system 3300 have the capacity for multi-channel neural recording, optical and electrical stimulation, wireless telemetry, wireless powering, and embedded algorithms for closed-loop feedback and stimulation.

The implantable electrodes 3308 in this example include one or more cytokine optrode 3320 (hybrid opto-electrode to measure real-time cytokine tracking) implanted at a location 3322a that corresponds to the patient's spleen. The control device 3306 is implanted at a location 3322b that corresponds to the patient's vagus nerve. The control device 3306 includes an on-board compound nerve action potential (CNAP) device that can simultaneously record as a bioelectric input analog front end 3316 and can provide nerve stimulation as a bioelectric stimulator output 3319.

The implantable optical biosensors 3320 (i.e. optrodes) can provide continuous monitoring of cytokines (e.g. TNF-alpha) in the spleen, blood, and brain by building cytokine sensitive micro-optrodes on an implantable optical bionode. These autonomous implantable sensors 3320 can measure cytokine output in response to VNS stimulation to map and quantitatively define the neuro-inflammatory circuit and control loop as a dynamical system. The biosensors 3320 can be calibrated and validated against blood and plasma cytokine levels measured by cytometric gold standard methods, for example, using both experimental and reference samples. The implantable optical biosensor 3320 measurements can complement the cytometric measurements, by providing a dynamic cytokine time course and serve as the first existing prototype for therapeutic closed-loop control of neuro-inflammation. Together these sets of output data can provide a more complete data set for defining the control system 3300.

The electrodes 3320 can take various measurements at the locations 3322a, which can be wireless transmitted to the control device 3306 for analysis. The electrodes 3320 can sense and transmit, for example, cytokine measurements from the patient's spleen to the control device 3306, which can also receive the CNAP input from the on-board bioelectric input analog front end 3316.

In addition to receiving and monitoring conditions related to inflammation in the patient 3302, determining particular therapeutic stimulation that should be provided to the patient 3302, and wirelessly directing one or more of the electrodes 3320 and/or the bioelectric stimulator output 3319 to deliver the determined therapy, the control device 3306 can include components to provide wireless data and power (3322) that permits the control device 3306 to wirelessly output data to a base station and/or to a mobile device (e.g., smartphone, smart watch), and to be wirelessly powered and/or charged. This output data can include a variety of different patient data, such as patient data, a log of conditions detected and therapies delivered, alerts as to currently detected conditions (e.g., oncoming inflammation, inflammation reflex currently detected), and/or other data. The control device 3306 can transmit this data wirelessly. The control device 3306 can be powered wirelessly (e.g., via RF signals) and can additionally include a local power source (e.g., battery) that can be charge via the wireless signals and that can power the control device 3306 when the wireless signal is unavailable. The packaging of the control device 3306 can be, for example, a 3D print polymer.

The control device 3306 includes an analog front end 3310 that receives wireless signals transmitted by the electrodes 3320. The analog front end 3310 provide the received signals to the signal processing subsystem on the device 3306, which can include a microcontroller 3314 and field-programmable gate array (FPGA). Signal processing can be performed on-board or off-board, and can involve using a closed-loop algorithm 3318, which can be used to identify particular physiological conditions within the patient 3302 and can determine, based on the particular detected conditions, whether to provide bioelectric stimulation at one or more of the vagus nerve (location 3322b). For example, the closed-loop algorithm 3318 can be performed by the control device 3306, by a device external to the control device 3306 (e.g., mobile device, base station), or by a combination of the two. When a condition is detected that warrants stimulation, the closed-loop algorithm 3318 can direct the bioelectric stimulator output unit 3319 to either directly provide the therapy or to cause one of the electrodes 3320 to deliver the therapy. For example, the control device 3306 can include on-board components to delivery stimulation therapy (CNAP device 3319), and/or can trigger one of more of the electrodes 3320 to deliver the therapy.

The closed-loop algorithm 3318 can use any of a variety of appropriate techniques to learn the particular physiology of the patient 3302 and the patient's particular response to therapy, and can use that information to determine when, how, and under what conditions to provide therapy for the patient 3302. For example, the closed-loop algorithm 3318 can be initially calibrated for the patient by a physician or other trained technician in a clinical setting, which can involve providing various stimulations and recording the physiological response of the patient 3302. After being initially calibrated, the closed-loop algorithm 3318 can continue to learn and adapt over time by analyzing data generated by the electrodes 3320, therapy provided to the patient 3302, and the patient's response to the therapy.

A physiological pathway 3324 that is being monitored as part of the system 3300, which includes behavioral modifications (e.g., onset and/or alleviation of depression, anxiety, etc.), vagus nerve (including a functional map and anatomical map of the vagus nerve to physiological responses and structures), gut, T-lymphocyte release, lymphocyte trapping (spleen), and cytokine release. The closed-loop control that is being implemented by the closed-loop algorithm 3318 is directed toward monitoring and providing therapy related to the physiological pathway 3324, which includes receiving sensor data from electrode 3320 implanted at the spleen, processing those signals in combination with the CNAP signals, and stimulating the vagus nerve to impact and minimize the inflammation reflex when, for example, the patient 102 is experiencing depressions and/or anxiety as caused by a cytokine release. Cytokine measurement 3326 can be taken using the cytokine optrode 3320 and used to determine whether the stimulation was sufficient to stop the cytokine release (which can occur in some patients experiencing behavioral changes), and thereby stop/minimize the inflammation reflex. The closed-loop algorithm 3318 can repeatedly monitor the cytokine levels and apply vagus nerve stimulation when appropriate until the patient's inflammation reflex has stopped and/or dropped below a threshold level. The closed-loop algorithm 3318 can be automatically implemented without explicit patient direction.

The system 3300 can deliver electrical stimulations to the patient 3302 using appropriate stimulating frequency, waveforms, time delay from detection, stimulus current output, and other parameters to deliver neural therapy to allow for clamping the evoked cytokine response so as to modify the patient's behavior (e.g., alleviate feelings of depression and anxiety). Such parameters can be patient-specific, and can be developed through data collected during in-clinic/hospital monitoring of seizure episodes and the patient response to various levels of stimulation therapy.

A closed loop control can be used to implement the closed loop algorithm 3318, which can determine therapeutic doses based on indirect measures that are likely to affect a patient's response to a given treatment. For example, the degree of neural activation in response to a given dose of stimulus varies greatly from patient to patient (e.g., as a result of genetics, tissue/immune response to the implant, or environmental factors), and changes over time in individual patients. This response variability can be especially problematic when electrical nerve stimulation is used to treat a biological dysfunction (i.e., electroceuticals as an electrical correlate of pharmaceuticals).

Within safe limits, a physician does not care what the dose of therapy is, so much as the amount of evoked biomarker response. It follows that a better way of delivering therapy is to track and maintain a constant biomarker response, allowing the strength of electrical stimulation to vary freely according to objective, quantifiable patient and disease characteristics. This approach, implemented in the mathematical modeling underlying the closed loop control algorithm (e.g., closed loop algorithm 3318), provides advantages, including improved and more consistent patient therapy. Closed loop control is a self-optimizing pairing of custom software (described with regard to FIG. 34) and hardware (i.e. the system 3304) that adapts electrical stimulation parameters on the fly to the measured response of each nerve and neuron type stimulated. Through closed-loop biological feedback control, closed loop control maintains a constant dose of neural activation rather than stimulation. Using closed loop control, a prescribed dose of neural activation, ranging from 0 to 100%, can be maintained in the same manner, independently for each fiber type, across patients and within the same patient over time. In this way it serves as a tool automatically identify relationships between the degree and pattern of neural activation and therapeutic efficacy. Moreover, it allows for the rapid if not immediate deployment of stimulus parameters that are optimized for each patient, nerve and neuron type.

Referring to FIG. 34, an example system 3400 is depicted in which the control device 3306 provides simultaneous stimulation and readings (e.g., using the CNAP device) on a nerve 3402 (e.g., vagus nerve) as part of a closed loop control algorithm 3410, which can provide constant-voltage stimulation.

The closed loop control 3410 program is loaded/modified (3412), it receives and conditions nerve activation (3424) at the electrode 3404 mounted to the nerve 3402 (3414). The closed loop control 3410 then deconstructs stimulus-evoked compound nerve action potential (CNAP) responses (3416), recorded at a fixed distance from the stimulating cathode, to estimate the level and type of nerve fiber activation, for example. Conduction velocity is used to identify distinct nerve fiber groups (i.e., neuron populations), referred to as A (fast, myelinated fibers), B (slow, myelinated fibers), or C (slow, unmyelinated fibers). When recording at a fixed, known distance from the stimulating cathode, the CNAP response waveform peaks can be separated in time due to the differing conduction velocities of A, B and C fibers. The maximal CNAP response, otherwise referred to as maximal activation, is the CNAP response magnitude at which an increase in stimulus intensity does not produce an increase in response. By individually deriving stimulus-response relationships for A, B and C fibers, the effect of any stimulus pulse on nerve activity is directly measurable. The resulting model (3418), known as a nerve activation profile, describes the sensitivity and dynamic range of each fiber type that can be identified in a CNAP. The closed loop control algorithm 3410 constructs it from measured data in under a minute, for example. The 3306 running the closed loop control 3410 can further continuously update the activation profile (3418) to improve its prediction accuracy over time and adapt to the variety of factors that influence the efficacy of stimulation. The updated profile can then be used to make decisions regarding stimulation therapy (3420) and, based on the decisions, to apply personalized stimulus adjustments of the nerve 3402 by activating 3426 the electrode attachment 3406.

Example Use Case #5—Alcoholism

In another example use case, the systems, devices, techniques, protocols, and processes described above and throughout this document can be used can be used to treat patients with alcoholism. Such treatments can include, for example, deep brain stimulation at targeted locations to reduce alcohol intake, providing patients with warnings, such as on a mobile device (e.g., smartphone, smart watch, other wearable device) and/or base station, and/or other therapeutic monitoring (e.g. monitoring dopamine transmission) and/or treatment related to chronic alcoholic intake.

Example implementations for treating alcoholism are described below with regard to FIG. 35. Some or all of these features can be applied to the treatment of other conditions, as described and/or with modifications, and/or can be applied to the platform more generally. Additionally, some or all of the descriptions with regard to the treatment of other conditions described throughout this document can be applied alcoholism therapy.

Referring to FIG. 35, an example system 3500 is depicted in which an implantable system 3504 is configured for the treatment of alcoholism in a patient 3502. The example implantable system 3504 is similar to the implantable systems described above, and includes an implantable control device 3506 (also referred to as a "bionode") and one or more separate sensing and/or stimulating devices 3508 (e.g., implantable wireless electrodes), which can be wirelessly powered by the control device 3506 (e.g. no battery or other locally housed power source in implantable devices 3508), can wirelessly transmit data to the control device 3506, and/or can be wirelessly controlled to discharge therapeutic stimulation to one or more locations on the patient 3502.

The implantable electrodes 3508 in this example include one or more electrodes implanted at particular locations in the patient's body, including at the cortex. These electrodes 3520 can take various measurements at the cortex and/or one or more of these locations, which can be wireless transmitted to the control device 3506 for analysis. In some embodiments, the electrodes 3520 can sense and transmit, for example, single neuron measurements, local field potential (LFP), and electroencephalogram (EEG). The electrodes 3520 can also wirelessly discharge therapeutic stimulation at the cortex and/or one or more of these locations when directed to do so by the control device 3506. This stimulations can include, for example, deep brain stimulation (DBS).

In addition to receiving and monitoring conditions in the patient 3502, determining particular therapeutic stimulation that should be provided to the patient 3502, and wirelessly directing one or more of the electrodes 3508 to deliver the determined therapy, the control device 3506 can include components to provide wireless data and power (3512) that permits the control device 3506 to wirelessly output data to a base station and/or to a mobile device (e.g., smartphone, smart watch), and to be wirelessly powered and/or charged. This output data can include a variety of different patient data, such as patient data, a log of conditions detected and therapies delivered, alerts as to currently detected conditions, and/or other data. The control device 3506 can transmit this data wirelessly. The control device 3506 can be powered wirelessly (e.g., via RF signals) and/or can additionally include a local power source (e.g., battery) that can be charged via the wireless signals and that can power the control device 3506 when the wireless signal is unavailable.

The control device 3506 can receive wireless signals transmitted by the electrodes 3508. For example, an analog front end can provide the received signals to the signal processing subsystem on the device 3506, which includes a microcontroller 3514. Signal processing can be performed on-board or off-board, and can involve using a closed-loop algorithm, which can be used to identify particular physiological conditions within the patient 3502 and can determine, based on the particular detected conditions, whether to provide bioelectric stimulation. For example, a closed-loop algorithm can be performed by the control device 3506, by a device external to the control device 3506 (e.g., mobile device, base station), or by a combination of the two. When a condition is detected that warrants stimulation, the closed-loop algorithm can direct the bioelectric stimulator output unit to either directly provide the therapy or to cause one of the electrodes 3508 to deliver the therapy. For example, the control device 3506 can include on-board components to delivery stimulation therapy, and/or can trigger one of more of the electrodes 3520 to deliver the therapy.

A physiological pathway 3524 can be monitored as part of the system 3500. In an example embodiment, the patient's cortex is monitored, including the patient's response to deep brain stimulation delivered by the electrode 3508. Closed-loop control may be implemented to monitor and provide therapy related to the physiological pathway 3524, and may include receiving sensor data from electrode 3508 implanted at the cortex, processing the data, and stimulating the cortex to impact neural activity in the cortex (or in the nucleus accumbens shell, for example). The closed-loop control may result in stimulus delivered by electrode 3508 based on detected patient conditions. Alternatively or in addition, stimulus may be delivered at predetermined intervals or according to a predetermined pattern.

In an example embodiment, system 3500 is configured to regulate the mesocorticolimbic system. One or more electrodes may be positioned to deliver deep brain stimulation of the nucleus accumbens shell (AcbSh). The AcbSh is a neuroanatomical substrate that can have reinforcing effects of alcohol. Reversible inactivation of the AcbSh has been found to regulate chronic alcohol intake. Alternatively or in addition, one or more electrodes 3508 may be positioned to monitor and/or deliver stimulus proximate throughout the midbrain dopaminergic system, such as the ventral tegmental area, nucleus accumbens, olfactory tubercle, frontal cortex, and amygdala. In an example embodiment, unilateral deep brain stimulation is delivered (e.g. only to the left AcbSh). Alternatively or in additional, bilateral deep brain stimulation may be delivered (e.g. to both the left and right AcbSh). Deep brain stimulation delivered to patient 3502 by system 3500 may at least partially normalize an otherwise deficient dopaminergic system through alterations in dopamine and dopamine related enzyme levels. Alternatively or in addition, system 3500 may alter neurophysiological interactions, such as abnormal neuronal discharge and excessive synchrony that may otherwise occur in and/or between cortical and subcortical sites (e.g. in diseases related to dopamine depletion).

Electrodes 3508 are configured to deliver a stimulus that provides an at least partial inactivation of a target brain location, such as that of various subjects (e.g., animals, like rats, humans). In an example embodiment, the stimulus is delivered as a biphasic, anode-leading, rectangular pulse with no interphasic delay, a pulse frequency of between about 50 Hz and 500 Hz (e.g. about 150 Hz), a pulse width between 1 μsec and 1000 μsec (e.g. about 100 μsec), and current intensities between 25 μA and 1000 μA (e.g. 100 μA (n=3) or 200 μA (n=4)).

Deep brain stimulation may be delivered by system 3500 according to a predetermined schedule. For example, electrodes 3508 may be instructed to deliver stimulation during a predetermined period (e.g. a predetermined period each hour, each day, each week, etc.). Deep brain stimulation may be delivered during a one-hour period each day for a period of days.

Example Use Case #6—Parkinson's

Referring now to FIG. 36, the systems, devices, techniques, protocols, and processes described above and throughout this document can be used for preclinical trials of subjects with Parkinson's disease. Such preclinical tirals can include, for example, stimulating the target areas of the brain (e.g. cortical and subcortical structures) of subjects with Parkinson's.

Example implementations for preclinical trials related to Parkinson's disease are described herein with regard to FIG. 36. Some or all of these features can be applied to the treatment of other conditions, as described and/or with modifications, and/or can be applied to the platform more generally. Additionally, some or all of the descriptions with regard to the treatment of other conditions described throughout this document can be applied to Parkinson's disease studies.

Referring to FIG. 36, an example system 3600 is depicted in which an implantable system 3604 is configured for preclinical trials related to subjects with Parkinson's disease in a patient 3602. The example implantable system 3604 is similar to the implantable systems described above, and includes an implantable control device 3606 (also referred to as a "bionode") and one or more separate sensing and/or stimulating devices 3608 (e.g., implantable wireless electrodes), which can be wirelessly powered by the control device 3606 (e.g., no battery or other locally housed power source in implantable devices 3608), can wirelessly transmit data to the control device 3606, and/or can be wirelessly controlled to discharge therapeutic stimulation to one or more locations on the patient 3602.

The implantable electrodes 3608 in this example include one or more electrodes 3620 implanted at particular locations 922a in the patient's body, including at the cortex 922a. These electrodes 3620 can take various measurements at one or more of these locations, which can be wireless transmitted to the control device 3606 for analysis. These electrodes 3620 can sense and transmit, for example, single neuron measurements, local field potential (LFP), and electroencephalogram (EEG). These electrodes 3620 can also wirelessly discharge therapeutic stimulation at one or more of these locations when directed to do so by the control device 3606. This stimulation can include, for example, deep brain stimulation (DBS).

In addition to receiving and monitoring conditions related to Parkinson's disease in the patient 3602, determining particular therapeutic stimulation that should be provided to the patient 3602, and wirelessly directing one or more of the electrodes 3620 to deliver the determined therapy, the control device 3606 can include components to provide wireless data and power (3622) that permits the control device 3606 to wirelessly output data to a base station and/or to a mobile device (e.g., smartphone, smart watch), and to be wirelessly powered and/or charged. This output data can include a variety of different patient data, such as patient data, a log of conditions detected and therapies delivered, alerts as to currently detected conditions (e.g., oncoming seizure, seizure currently detected), and/or other data. The control device 3606 can transmit this data wirelessly. The control device 3606 can be powered wirelessly (e.g., via RF signals) and can additionally include a local power source (e.g., battery) that can be charge via the wireless signals and that can power the control device 3606 when the wireless signal is unavailable.

In some embodiments, the implantable system 3604 includes features similar to the implantable system 3604 described above. The control device 3606 includes an analog front end 3610 that receives wireless signals transmitted by the electrodes 3620. The analog front end 3610 provide the received signals to the signal processing subsystem on the device 3606, which includes a microcontroller 3614 and field-programmable gate array (FPGA) 3616, which is an integrated circuit designed to be configured after manufacturing.

Signal processing can be performed on-board or off-board, and can involve using a closed-loop algorithm 3618, which can be used to identify particular physiological conditions within the patient 3602 and can determine, based on the particular detected conditions, whether to provide bioelectric stimulation at one or more locations, such as location 3622. For example, the closed-loop algorithm 3618 can be performed by the control device 3606, by a device external to the control device 3606 (e.g., mobile device, base station), or by a combination of the two. When a condition is detected that warrants stimulation (e.g. based on cortical activity), the closed-loop algorithm 3618 can direct the bioelectric stimulator output unit 3618 to either directly provide the therapy or to cause one of the electrodes 920 to deliver the therapy. For example, the control device 3606 can include on-board components to delivery stimulation therapy, and/or can trigger one of more of the electrodes 3620 to deliver the therapy. Implementation using an embedded FPGA-based algorithm can reduce telemetry burden and allow a longer battery life.

The closed-loop algorithm 3618 can use any of a variety of appropriate techniques to learn the particular physiology of the patient 3602 and the patient's particular response to therapy, and can use that information to determine when, how, and under what conditions to provide therapy for the patient 3602. For example, the closed-loop algorithm 3618 can be initially calibrated for the patient by a physician or other trained technician in a clinical setting, which can involve providing various stimulations and recording the physiological response of the patient 3602. After being initially calibrated, the closed-loop algorithm 3618 can continue to learn and adapt over time by analyzing data generated by the electrodes 3620, therapy provided to the patient 3602, and the patient's response to the therapy.

System 3600 may monitor one or more physiological pathways 3624, which includes monitoring cortical activity of patient 3602. The closed-loop control implemented by the closed-loop algorithm 3618 is directed toward monitoring and providing therapy related to the physiological pathway 3624, which includes receiving sensor data from electrodes 3620 implanted at the cortex, for example.

In an example embodiment, system 3600 is configured to regulate excessive beta-band oscillation synchrony in the basal ganglia and other structures. For example, electrodes 3620 are configured to delivery stimulation to subcortical structures, including structures within the basal ganglia-thalmocortical loop, according to the closed-loop control 3618. One or more electrodes 3620 may be configured to stimulate the subthalamic nucleaus.

The closed-loop control 3618 may use cortical neural activity, at least in part, for feedback. Cortical neural activity has been found to be stable and relatively easy to measure, and can provide an accurate indicator of basal ganglia activity. For example, cortical activity may be measured by EEG or subcranial electrodes, and stimulation delivered by electrodes 3620 based on the detected cortical activity.

The stimulus parameters may be configured to improve treatment efficacy while reducing power requirements and ensuring patient safety. In some example embodiments, the waveform of the stimulation delivered by electrode 3620 may have a relatively small amplitude while targeted to reduce the pathological activity which results in primary symptoms. Such a waveform may provide enhanced suppression of symptoms with reduced sized affects, while also reducing power consumption. Similarly, high-frequency pulse shaping can increase fiber recruitment, reduces power consumption, and enhances selectivity.

Example Use Case #7—Gastric Disorders

Referring now to FIG. 37, the systems, devices, techniques, protocols, and processes described above and throughout this document can be used to treat gastric disorders. Such treatments can include, for example, stimulating the vagus nerve when particular conditions within the body are detected, providing patients with warnings, such as on a mobile device (e.g., smartphone, smart watch, other wearable device) and/or base station, stimulating various nerves and/or systems to ameliorate gastric conditions, and/or other therapeutic monitoring and/or treatment related to the stomach.

An example implementation for treating gastric disorders are described below with regard to FIG. 37. Some or all of these features can be applied to the treatment of other conditions, as described and/or with modifications, and/or can be applied to the platform more generally. Additionally, some or all of the descriptions with regard to the treatment of other conditions described throughout this document can be applied to gastric therapy.

Referring to FIG. 37, an example system 3700 is depicted in which an implantable system 3704 is configured for the treatment of gastric disorders in a patient 3702. The example implantable system 3704 is similar to the implantable systems described above, and includes an implantable control device 3706 (also referred to as a "bionode") and one or more separate sensing and/or stimulating devices 3708 (e.g., hormone optrodes, implantable wireless electrodes), which can be wirelessly powered by the control device 3706 (e.g., no battery or other locally housed power source in implantable devices 3708), can wirelessly transmit data to the control device 3706, and/or can be wirelessly controlled to discharge therapeutic stimulation to one or more locations on the patient 3702. The system 3700 can provide a toolbox of implantable devices with accompanying base station 3730 for wireless powering and a graphical user interface (GUI) (e.g., provided on a mobile device, like a smartphone or smartwatch) for wireless communication to and from the control device 3706, which can be implanted in the vagus-stomach neural circuitry, for example. The devices that are part of the system 3700 have the capacity for multi-channel neural recording, optical and electrical stimulation, wireless telemetry, wireless powering, and embedded algorithms for closed-loop feedback and stimulation. FIG. 37 depicts a schematic view of an example implementation of the system 3700, with examples of the base station 3730, the implantable system 3704, the control device 3706, the implantable sensing and stimulating devices 3708, and nervous tissue 3722, such as the vagus nerve to which therapy is applied and/or measurements are taken.

The implantable electrodes 3708 in this example include one or more electrodes 3720 implanted at particular locations in the patient's body, including at one or more locations of the vagus nerve 3722a, and/or gut 3722b. These electrodes 3720 can take various measurements at one or more of these locations 3722a, 3722b, which can be wireless transmitted to the control device 3706 for analysis. These electrodes 3720 may include one or more hormone optrodes that can sense and transmit, for example, levels of ghrelin, PYY, somatostatin, gastrin, nesfatin, leptin and 5-HT (e.g. in the stomach), and/or CCK, secretin, 5-HT, GIP, GLP-1, PYY and neurotensin (e.g. in the duodenum). Alternatively or in addition, various electrodes 3720 can be included that sense and transmit, for example, single neuron measurements, local field potential (LFP), and electroencephalogram (EEG). These electrodes 3720 can also wirelessly discharge therapeutic stimulation at one or more of these locations 3722a, 3722b when directed to do so by the control device 3706.

In addition to receiving and monitoring conditions related to gastric disease in the patient 3702, determining particular therapeutic stimulation that should be provided to the patient 3702, and wirelessly directing one or more of the electrodes 3720 to deliver the determined therapy, the control device 3706 can include components to provide wireless data and power that permits the control device 3706 to wirelessly output data to a base station and/or to a mobile device (e.g., smartphone, smart watch), and to be wirelessly powered and/or charged. This output data can include a variety of different patient data, such as patient data, a log of conditions detected and therapies delivered, alerts as to currently detected conditions (e.g., related to appetite), and/or other data. The control device 3706 can transmit this data wirelessly. The control device 3706 can be powered wirelessly (e.g., via RF signals) and can additionally include a local power source (e.g., battery) that can be charge via the wireless signals and that can power the control device 3706 when the wireless signal is unavailable. The packaging of the control device 3706 can be, for example, glass.

The control device 3706 include an optical analog front end 3710 that receives wireless signals transmitted by the electrodes 3720. The optical analog front end 3710 provide the received signals to the signal processing subsystem on the device 3706, which includes a microcontroller 3714 and field-programmable gate array (FPGA) 3716, which is an integrated circuit designed to be configured after manufacturing. Signal processing can be performed on-board or off-board, and can involve using a closed-loop algorithm 3718, which can be used to identify particular physiological conditions within the patient 3702 and can determine, based on the particular detected conditions, whether to provide bioelectric stimulation at one or more of the locations 3722a, 3722b. For example, the closed-loop algorithm 3718 can be performed by the control device 3706, by a device external to the control device 3706 (e.g., mobile device, base station), or by a combination of the two. When a condition is detected that warrants stimulation, the closed-loop algorithm 3718 can direct the bioelectric stimulator output unit 3719 to either directly provide the therapy or to cause one of the electrodes 3720 to deliver the therapy. For example, the control device 3706 can include on-board components to delivery stimulation therapy, and/or can trigger one or more of the electrodes 3720 to deliver the therapy.

The closed-loop algorithm 3718 can use any of a variety of appropriate techniques to learn the particular physiology of the patient 3702 and the patient's particular response to therapy, and can use that information to determine when, how, and under what conditions to provide therapy for the patient 3702. For example, the closed-loop algorithm 3718 can be initially calibrated for the patient by a physician or other trained technician in a clinical setting, which can involve providing various stimulations and recording the physiological response of the patient 3702. After being initially calibrated, the closed-loop algorithm 3718 can continue to learn and adapt over time by analyzing data generated by the electrodes 3720, therapy provided to the patient 3702, and the patient's response to the therapy.

In an example embodiment, a physiological pathway 3724 monitored as part of the system 3700 can include the vagus nerve (e.g., branches of the vagus nerve associated with the stomach, its sphincters (lower esophageal sphincter; pylorus), and neighboring segments of the GI tract (distal esophagus; proximal duodenum)). The closed-loop control implemented by the closed-loop algorithm 3718 is directed toward monitoring and providing therapy related to the physiological pathway 3724, which includes receiving sensor data from electrodes 3720 and stimulating the vagus to engage vago-vagal reflexes. In an example embodiment, the closed-loop control includes monitoring of compound action potentials, smooth muscle activity, coordinated gastric emptying, reflux, hormone release, CNS activations, and control of meals ingested.

Hormone measurement 3726 can be taken using the electrodes 3720 (e.g., hormone optrodes) and used to analysis the efficacy of the stimulation. The closed-loop algorithm 3718 can repeatedly monitor hormone levels and apply vagus nerve stimulation when appropriate until the desired gastric system response is achieved. The closed-loop algorithm 3718 can be automatically implemented without explicit patient direction, continuously monitoring and adjusting delivery of stimulation to the vagus nerve.

The system 3700 can deliver electrical stimulations to the patient 3702 using appropriate stimulating frequency, waveforms, time delay from detection, stimulus current output, and other parameters to deliver neural therapy. Such parameters can be patient-specific, and can be developed through data collected during in-clinic/hospital monitoring of gastric response to various levels of stimulation therapy. At a behavioral level, wireless closed-loop implantable devices included in the system 3700 can use a range of stimulation parameters to allow for multifactorial modifications to address these complex problems.

A reliable gastric response feedback algorithm facilitates successful closed-loop therapy of system 3700. Similar to other use cases described herein, the device 3706 can use a digital ASIC algorithm that is ultralow power, reduces the device profile, and is specifically designed for specialized gastric disease applications. Through the use of a low power microcontroller (e.g., microcontroller 1514), custom algorithms can be implemented. For instance, additional and/or alternative control algorithms can be implemented for other conditions, such as for psychiatric therapy that can observe correlations between a wide range of longitudinal behaviors, gamma and theta oscillations, and stimulation paradigms to increase or decrease activity of certain neural populations in response to the oscillations (e.g. related to appetite or other parameters of the gastric system).

In various exemplary embodiments, biomodulation protocols of system 3700 are configured to bioelectronically ameliorate and monitor gastric disorders such as gastroparesis (e.g., modulating nausea and vomiting in patients receiving gastric stimulation for diabetic gastroparesis), obesity, tachygastria, motility problems, reflux disorders such as gastroesophageal reflux disease (GERD) disease, and eating disorders. The stomach has been found to be appropriate and accessible for biomodulation delivered by system 3700 (e.g., via electrodes 3720) because the vagus nerve provides multiple candidate sites for electrode access. Electrodes 3720 may be located at one or more electrode-accessible vagal branches that innervate regions of the stomach, for example.

System 3700 may be configured for focal biomodulation of afferent concentrations (e.g., without stimulation of entire branches or trunks of the vagus. Increasing or decreasing the activity of afferents (e.g., putative stretch receptors of the vagal afferent intramuscular arrays (IMAs)) have been found to be a more natural mode of engaging vago-vagal reflexes. Stimulation of afferent concentrations may generate activity that engages the more programmed elements of the reflex arcs.

In an example embodiment, electrodes 3720 are configured to monitor compound nerve action potential (CNAP) from vagus or electrogastrogram (EGG) from the antrum and other compartments of the stomach. The measured signals are buffered, filtered, and differentially amplified and converted to a single-ended output in an instrumentation amplifier. A band-pass filter removes physiological and extraneous (e.g., high-frequency monitor or dc drift) noise above 5 kHz or below 1 Hz, while passing the signals of interest between those cutoffs. A second amplifier stage can have a selectable gain of 100-1,000 (e.g., programmable) to place the expected input amplitude range in the 0-1 V dynamic range of the analog-to-digital converter. Simulation from the bioelectric stimulator output unit 3719 is delivered constant current with 1 μA resolution, 12 V headroom, and up to 1 mA peak current, for example.

During operation of system 3700, gastric hormones may be optically sensed by hormone optrodes of electrodes 3720. For example, an example hormone optrode may be a micro-optrode grown by photopolymerization of a polyethylene glycol (PEG) diacrylate and silica composite material, which has been optimized for biomolecule based biosensing. The PEG hydrogel maintains sensor biomolecule stability and controls the material porosity for good temporal response. The acrylate provides the light controlled growth to modify the tip geometry for the implant site. The porous silica provides stability, structural integrity, and good adhesion to the optical fiber. The micro-optrode may be grown on the tip of an optical fiber (e.g. a 100 um optical fiber) that is connected to the internal microoptics and microelectronics (e.g., that communicate with components of implantable system 3704).

Example Use Case #8—Addiction

The systems, devices, techniques, protocols, and processes described above and throughout this document can be used in a variety of human and/or animal applications. In one example use case, they can be used to treat patients with addiction. Addiction is a chronic disease of brain reward, motivation, memory and related circuitry. Dysfunction in these circuits leads to characteristic biological, psychological, social and spiritual manifestations. This is reflected in an individual pathologically pursuing reward and/or relief by substance use and other behaviors. Addiction is characterized by inability to consistently abstain, impairment in behavioral control, craving, diminished recognition of significant problems with one's behaviors and interpersonal relationships, and a dysfunctional emotional response. Like other chronic diseases, addiction often involves cycles of relapse and remission. Without treatment or engagement in recovery activities, addiction is progressive and can result in disability or premature death. Treatments to treat patients can include, for example, stimulating the vagus nerve when particular conditions within the body are detected that indicate a possible neurological condition associated with addiction, providing patients with controls and/or indications, such as on a mobile device (e.g., smartphone, smart watch, other wearable device) and/or base station, stimulating various nerves and/or systems to reduce the incident of changes in the function of multiple brain circuits that control pleasures/reward, stress, decision-making, impulse control, learning and memory, and other functions, and/or other therapeutic monitoring and/or treatment related to addiction.

Example implementations for therapeutic stimulation of addiction are described below with regard to FIG. 38. Some or all of these features can be applied to the treatment of other conditions, as described and/or with modifications, and/or can be applied to the platform more generally. Additionally, some or all of the descriptions with regard to the treatment of other conditions described throughout this document can be applied to addiction therapy.

Referring to FIG. 38, an example system 3800 is depicted in which an implantable system 3804 is configured for the treatment of addiction in a patient 3802. The example implantable system 3804 is similar to the implantable systems described above, and includes an implantable control device 3806 (also referred to as a "bionode") and one or more separate sensing and/or stimulating devices 3808 (e.g., implantable wireless electrodes), which can be wirelessly powered by the control device 3806 (no battery or other locally housed power source in implantable devices 3808), can wirelessly transmit data to the control device 3806, and/or can be wirelessly controlled to discharge therapeutic stimulation to one or more locations on the patient 3802. The system 3800 can provide a toolbox of implantable devices with accompanying base station 3830 for wireless powering and a graphical user interface (GUI) (e.g., provided on a mobile device, like a smartphone or smartwatch) for wireless communication to and from the control device 3806.

The implantable electrodes 3808 in this example include one or more electrodes 3820 implanted at particular locations 3822a-e in the patient's body, including at the cortex 3822a, the brainstem 3822b, the vagus nerve 3822c, the phrenic nerves 3822d, diaphragm/intercostals 3822e and/or other locations. For example, the electrodes 3820 can be implanted in the brainstem 3822b (e.g., hippocampus, pre-Botzinger, nucleus *ambiguus*, nucleus tractus solitarius, and rostral and caudal ventral-lateral medulla (VLM)). Also, the electrodes 3829 can be implanted in various locations associated with the sympathetic nervous system (e.g., vagus, phrenic) which activates what is often termed the fight or flight response, and is often associated with addiction. As an example, the electrodes 3829 can detect to local field potential and single and multiunit activity for evidence of excitation of the sympathetic nervous system, which may be indicative of addiction. These electrodes 3820 can take various measurements at one or more of these locations 3822a-e, which can be wired and/or wireless transmitted to the control device 3806 for analysis. These electrodes 3820 can sense and transmit, for example, electric physiological conditions including single neuron measurements, LFP, EEG, electrocardiogram (ECG), and electromyogram (EMG). These electrodes 3820 can also wirelessly discharge therapeutic stimulation at one or more of these locations 3822a-e when directed to do so by the control device 3806.

This stimulation can include, for example, deep brain stimulation (DBS) and/or nerve stimulation.

In addition to measuring electric physiological conditions using the electrodes 3820, the implant system 3806 can use one or more sensors 3816 to measure mechanical and/or chemical conditions within the patient 3802. For example, the sensors 3816 can measure and provide data on mechanical physiological conditions including respiratory conditions (e.g., rate of respiration) and patient temperature. The sensors 3816 can also measure and transmit chemical conditions including aptamer in the patient's body. The sensors 3816 can be, for example, transducers. Such sensors 3816 can be either directly or indirectly (via leads) connected to particular physiological structures in the patient's body, such as ECG leads on the chest wall; EMG leads to diaphragm or other muscle; and/or thermocouple implanted in the nasal passage.

In addition to receiving and monitoring conditions related to addiction in the patient 3802, determining particular therapeutic stimulation that should be provided to the patient 3802, and wirelessly directing one or more of the electrodes 3820 to deliver the determined therapy, the control device 3806 can include components to provide wireless data and power (3812) that permits the control device 3806 to wirelessly output data to a base station and/or to a mobile device (e.g., smartphone, smart watch), and to be wirelessly powered and/or charged. This output data can include a variety of different patient data, such as patient data, a log of conditions detected and therapies delivered, alerts as to currently detected conditions (e.g., sympathetic), and/or other data. The control device 3806 can transmit this data wirelessly. The control device 3806 can be powered wirelessly (e.g., via RF signals) and can additionally include a local power source (e.g., battery) that can be charge via the wireless signals and that can power the control device 3806 when the wireless signal is unavailable. The packaging of the control device 3806 can be, for example, glass.

The control device 3806 includes an analog front end 3810 that receives wireless signals transmitted by the electrodes 3820. The analog front end 3810 provide the received signals to the signal processing subsystem on the device 3806, which includes a microcontroller 3814 and a FPGA. Signal processing can be performed on-board or off-board, and can involve using a closed-loop algorithm 3818, which can be used to identify particular physiological conditions within the patient 3802 and can determine, based on the particular detected conditions, whether to provide bioelectric stimulation at one or more of the locations 3822a-e. For example, the closed-loop algorithm 3818 can be performed by the control device 3806, by a device external to the control device 3806 (e.g., mobile device, base station), or by a combination of the two. When a condition is detected that warrants stimulation, the closed-loop algorithm 3818 can direct the bioelectric stimulator output unit 3818 to either directly provide the therapy or to cause one of the electrodes 3320 to deliver the therapy. For example, the control device 3806 can include on-board components to delivery stimulation therapy, and/or can trigger one of more of the electrodes 3820 to deliver the therapy.

The closed-loop algorithm 3818 can use any of a variety of appropriate techniques to learn the particular physiology of the patient 3802 and the patient's particular response to therapy, and can use that information to determine when, how, and under what conditions to provide therapy for the patient 3802. For example, the closed-loop algorithm 3818 can be initially calibrated for the patient by a physician or other trained technician in a clinical setting, which can involve providing various stimulations and recording the physiological response of the patient 3802. After being initially calibrated, the closed-loop algorithm 3818 can continue to learn and adapt over time by analyzing data generated by the electrodes 3820, therapy provided to the patient 3802, and the patient's response to the therapy.

A physiological pathway 3824 that is being monitored as part of the system 3800, which includes the patient's cortex, brainstem, vagus nerve, phrenic nerve, and diaphragm/intercostals. The closed-loop control that is being implemented by the closed-loop algorithm 3818 is directed toward monitoring and providing therapy related to the physiological pathway 3824, which includes receiving sensor data from electrodes 3320 implanted at the cortex and brainstem and the electrodes 3816 positioned to measure respiratory and temperature information, processing those signals, and stimulating the vagus nerve. Measurements can be taken by the electrodes 3816 and 3820, and can be used to determine whether the stimulation was sufficient to mitigate the detected condition (which can occur in some patients experiencing seizures), and thereby stop/minimize the condition that may indicate the onset of and overdose. The closed-loop algorithm 3818 can repeatedly monitor patient data and apply vagus nerve stimulation when appropriate until the patient's additive condition (e.g., overdose) has stopped and/or dropped below a threshold level. The closed-loop algorithm 3818 can be automatically implemented without explicit patient direction.

The closed-loop VNS therapy provided by the system 3800 in response to, for example, alterations in cardiac or respiratory rate has the potential to reduce the incidence of conditions related to addiction. Other factors and alterations in other factors can additionally and/or alternatively be used to identify the onset of potentially harmful or fatal addictive conditions and via stimulation. For instance, increases in certain levels of chemicals, or neurotransmitters, in the brain, can be indicative of an overdose situation, which results in levels that can harm the central nervous system (the brain and spinal cord). The system 3800 can be configured to prevent damage to nerves from the brain stem caused by the overdose, which untreated can cause opthalmoplegia (weakness of the muscle that controls the eyes), induce delirium or seizures.

The system 3800 take a variety of patient factors into account as part of the closed-loop algorithm, including biological factors, environmental stimulants, stress, diet, and overall health and correlations and their consequences. Moreover, aspects related to SUDEP can be utilized in application involving addiction. Thus, the system 3800 can provide a platform to identify unit and local field potentials associated with seizures, overdose, and/or addiction related changes in heart rate, respiration, arrhythmias and apneas. Temporal relationships between unit activity and postictal cardio-respiratory changes will shed light on mechanism. E.g., tachycardia continuing long after cessation of postictal changes in neuronal activity in cardiac centers (notably VLM) would implicate an endocrine component. To be able to detect any seizure-like activity propagating into the brainstem, recordings will be made wider band than is conventional for unit recordings. Off-line filtering can be implemented to help isolate unit activity.

For the example use cases #1-8 described above, absent an explicit discussion on the location other the implantable control device, the implantable control device can be inserted in any of a variety of locations within the patient's body, such as in or near the point of stimulation, in or near the point of monitoring, in one or more cavities within the body, and/or other appropriate locations for transmitting and receiving wireless signals.

Pressure Monitoring Chip

The pressure monitoring chips, devices, systems, assemblies, and techniques described below can be used in combination with the systems, devices, chips, assemblies, and techniques described above.

Biological pressure measurement is a common diagnostic procedure conducted by physicians. For example, a blood pressure measurement is performed routinely in the physician's office along with other vital signs. In addition to the diseases diagnosis, biological pressure monitoring enables a necessary framework required to study the progression of complex diseases and disorders. Urinary incontinence (UI) is an example of such progressive diseases. The loss of bladder sensation or control due to a high bladder pressure imposes serious health risks to the patients suffering from UI.

Since the bladder pressure has diurnal variations, continuous monitoring is highly desirable. However, the currently available methods are not adequate to provide continuous biological pressure monitoring. For bladder pressure measurement, a catheter-based pressure sensing device is commonly utilized. In this technique catheter tubes are directly inserted into the bladder through the urethra to measure the bladder pressure. The catheter-based procedure is not feasible for long-term bladder pressure monitoring and presents a urinary tract infection risk to the patients. Additionally, catheter disturbances produce errors in the pressure measurements.

Recent advances in low power integrated circuit (IC) design, minuscule biosensors, and wireless power transfer (WPT) have laid the foundation for fully wireless, miniaturized implantable microsystems that can be utilized in many biomedical applications including pressure sensing. An unprecedented level of miniaturization is possible with such microsystems which make them an ideal candidate for biological pressure sensing applications. FIG. 39A shows the target implant location for bladder pressure monitor systems. FIG. 39B is a conceptual diagram of a microsystem implant that comprises a pressure sensor, a readout IC, a powering coil and an antenna. The use of a pressure sensor for bladder may be employed with any mammalian patient, including humans and animals (e.g. rodents).

The design of uninterrupted pressure sensing monitors presents a number of design challenges, with size constraint and power consumption being the most important ones. As depicted in FIG. 39, due to the small implant site, the diameter and thickness of the receive coil for energy harvesting should preferably not exceed more than 2.6 mm and 100 µm, respectively. This area restriction limits the energy efficiency of the WPT and thus the instantaneous power consumption of the chip. The size constraint for the implant also limits the combined dimensions of the pressure sensor and readout IC to 750 µm×750 µm×300 µm. Table 4.1 illustrates the size specifications for pressure sensing microsystems.

Specifications for Pressure Monitoring Microsystem

| Parameters | Specifications |
| --- | --- |
| ASIC dimensions | <750 µm × 750 µm × 250 µm |
| Sensor dimensions | <700 µm × 500 µm × 50 µm |
| Telemetry antenna diameter | <2.4 mm |
| Powering coil size | <2.6 mm; <100 µm thick |
| ASIC peak power consumption | <500 µW |

State-of-the-art commercial capacitive pressure sensors (E1.3N, microFAB Bremen) are often employed in pressure sensing applications in humans, however, it cannot be used for animal studies due to its large size. A push forward in piezoresistive pressure sensor fabrication technology yields micro-scale sensors (700 µm×100 µm×50 µm) and thus make them ideal candidates for this application. Apart from its smaller size, the piezoresistive pressure sensor also offers better linearity than capacitive sensors.

This disclosure presents a sub-cubic millimeter (sub-mm3) sized continuous pressure monitoring microsystem that includes a piezoresistive differential pressure sensor, a fully wireless CMOS read-out ASIC, a loop antenna for data transmission, and a receiver powering coil. The readout ASIC is highly integrated and senses the change in differential resistance with applied pressure and provides a resistance-to-digital (R-D) conversion. The chip also includes a 2.45 GHz ISM band active transmitter (TX) to wirelessly transmit the raw sensing data. The system is batteryless thereby increasing the life span of the implant and is wirelessly powered by exciting a cavity resonator at 340 MHz.

The main goal for the system is to provide all the necessary functionality to the implant by designing a highly integrated system-on-chip (SoC), without using any external components, in the given size limit. Having features such as, on-chip first order calibration, data processing, active transmission and signal conditioning remove the need for a constant nearby external device to perform these tasks, which is essential in a scenario where the experiments are done on a freely moving animal. A simple base station, such as a smartphone, kept a few tens of centimeters away, is all we need to demodulate and display the pressure data in real time.

FIG. 40 shows the block diagram of a pressure sensing SoC that comprises four major blocks: energy harvesting (EH) and power management, resistance-to-frequency converter (R-F) front-end circuit, a digital core that finally provides a resistance-to-digital (R-D) conversion, and a 2.45 GHz ISM band TX. Also shown in the figure is a three-terminal differential piezoresistive pressure sensor, consisting of two resistive elements $R_{S1}$ and $R_{S2}$, which senses the applied pressure P by increasing the resistance of $R_{S1}$ and decreasing the resistance of $R_{S2}$ by the same amount $\Delta RS$ (for $R_{S2} > R_{S1}$). The change in differential resistance $R_{DIFF}$ is given by:

$$R_{DIFF} = [R_{S2} - \Delta R_S] - [R_{S1} + \Delta R_S]$$

$$R_{DIFF} = (R_{S2} - R_{S1}) - 2\Delta R_S; (R_{S2} > R_{S1})$$

where, $2\Delta RS$ is the change in the differential sense resistance with the applied pressure P. The resistance of both the elements increases with the temperature, thereby canceling out the temperature variation in a differential measurement. The R-F front-end circuit measures the change $2\Delta RS$ and hence the applied pressure.

For WPT for rodents, 340 MHz RF energy is utilized to excite the resonance cavity. The use of a high value of frequency allows the implant to harvest the energy with a very small, two-turn receive coil (100 µm thickness, and 2.6 mm diameter) and the on-chip adaptive matching network. The EH section of the SoC utilizes two capacitors for the matching network, as can be seen in the FIG. 41. The drop-in power transfer efficiency (PTE) due to the coil misalignment and other factors is addressed by an efficiency tracking loop that maximizes PTE under various operating conditions by automatically tuning the capacitor bank in the matching network. In addition, a sub-1V bandgap reference (BGR) circuit is designed to provide the pseudo-differential reference and common mode voltages for the R-F front-end circuit. The BGR also generates bias currents for the entire chip. Two on-chip n+ diffusion base resistances (RB1 and RB2) were implemented with the values close to the sensor resistances for calibration purposes.

A binary-counter based digital core logic provides the frequency to digital conversion and packetizes the data for wireless transmission. Finally, the data packets are transmitted by an On-Off-Key (OOK) modulated ISM band TX at 2.45 GHz. The TX consists of a voltage controlled power oscillator (VCPO) utilizing a LC resonant circuit to generate its carrier frequency in the 2.45 GHz ISM band. An off-chip loop antenna (2.4 mm diameter) is employed for the TX that also acts as a high-Q inductive element L for the LC resonator thereby minimizing both power consumption and the overall size of the system by eliminating the matching network between the TX and the antenna. The use of an active TX also eliminates the "self-jamming" problem associated with the passive backscattering based transmitters.

FIG. 41 depicts the energy harvesting (EH) and power management subsystem. In this work, the WPT leverages the cavity resonance based near field method due to its high PTE and ability to deliver large amounts of power to the implant. The cavity is excited by a 340-MHz RF source. An on-chip 4-stage rectifier provides an AC-DC conversion by multiplying the voltage induced on the receive coil. High efficiency and low leakage Schottky diodes with forward voltage drop of <200 mV are used to implement the rectifier. The unregulated voltage $V_{RECT}$ at the output of the rectifier acts as a supply voltage for the rest of the power management circuits. Although the orientation of the coil remains fixed once the device is implanted, an ultra-low power energy efficiency loop is employed that tracks the $V_{RECT}$ and tunes the capacitor bank in the on-chip matching network.

FIG. 42 shows the sub-1V and sub-1 µW BGR, which generates the pseudo differential voltages for the R-F circuit, and reference voltages and the 100 nA bias currents for the entire chip. The BGR generates a total of seven precise reference voltages from 100 mV to 700 mV in steps of 100 mV. The pseudo differential voltage of 100 mV is ensured by using three reference voltages (VR7=700 mV, VR6=600 mV, and VR5=500 mV) and using VR6 as a common mode voltage. The difference value of a precise 100 mV voltage (i.e., (VR7−VR6) and (VR6−VR5) is provided by the R-F circuit (section 4.5). The output reference voltage for the BGR is given by:

$$V_{RN} = \frac{R_N}{R_X} V_{R,Conv}$$

where, N is from 1 to 7 in the output resistor ladder, and $V_{R,Conv}$ is the conventional bandgap voltage of 1.25 V. As shown in the equation above, the generation of multiple reference voltages with a precise step of 100 mV, in the presence of process variations, requires the multiple degrees of matching between the resistors in the BGR circuit. In order to accomplish the task, first, we match the resistors R5, R6 and R7 with each other by treating R6 as a "common-mode" resistor. Second, we match the combination of (R5+R6+R7) with the resistors R1, R2, R3, and R4. Finally, we match all the resistors RX, RZ and (RO=R1+ . . . +R7) in the BGR with each other. The matching is achieved by utilizing common centroid and symmetrical layout techniques. We used high density but well-matched poly resistors to implement all the resistors in the BGR circuit. A power-on-reset (POR) circuit pulls the gate of the PMOS current sources (M1-M4) down during startup. As a result, the PMOS current sources inject a finite amount of current into the BGR core during startup to ensure a stable operating point for the BGR.

The linear voltage regulators are implemented to provide a clean supply voltage to various blocks of the chip by regulating the unstable output voltage of the rectifier $V_{RECT}$. In order to decouple the supply domains of various circuit blocks, four separate linear voltage regulators are employed. FIG. 43 depicts the schematic diagram of the voltage regulator and the supply voltage domains of the circuit blocks. Since an external capacitor is not available, the regulator is internally compensated with a minimum phase margin of 57 degrees. An NMOS pass transistor is utilized to ensure the stability across the variable load conditions with a good power supply rejection ratio (PSRR). The reference voltage divider in the regulators consists of two identical PMOS transistors operating in the weak threshold region. These transistors provide extremely high on-chip resistance (~22 MΩ each) and thus consume a negligible amount of quiescent current.

A differential resistance-to-frequency (R-F) conversion is performed in two steps: first, resistance-to-current (R-I) conversion, and second, current-to-frequency (I-F) conversion. Two separate R-F converters were implemented in this work for the comparison purposes. FIG. 44 shows a concept diagram for an R-F converter, where an R-I circuit senses the differential change in the sensor resistance and provides an output current $I_{OUT}$. The current $I_{OUT}$ is then fed to the I-F converter consisting of a current control oscillator (CCO). The CCO changes its frequency by sensing the current $I_{OUT}$ and thereby providing an I-F and hence R-F conversion.

There are two major challenges in the design of an R-I converter: linearity, and low power operation. FIG. 45 illustrates the schematic diagram of a conventional linear R-I converter. A negative feedback loop consisting of an op-amp, an NMOS transistor, and a sensing resistor element, forces the voltage drop across the sense resistor to be equal to the constant reference voltage from BGR. The current generated in this manner is highly linear and inversely proportional to the sense resistance ($I_R=V_{REF}/R_S$). This current is then copied to the subsequent CCO through current mirrors (M2-M3). The power consumption of the circuit is dependent on the absolute values of $R_S$ and $V_{REF}$. Since the absolute base value of $R_S$ is fixed, a low value of $V_{REF}$ can be generated by the BGR to minimize power consumption. However, the minimum value of $V_{REF}$ is limited by the dynamic range of the circuit. Thus, the power consumption of the R-I converter is mainly limited by the absolute value of the sense resistor and the required sensitivity.

The principle of an R-I converter depicted in FIG. 45 can also be extended to differential measurements. FIG. 46 shows the schematic diagram of the first differential R-I converter (R-I1). The difference in current $I_{RS1}(=V_{REF}/R_{S1})$ and $I_{RS2}(=V_{REF}/R_{S2})$ is given by:

$$I_D = I_{RS1} - I_{RS2} = \frac{V_{REF}}{R_{S1}} - \frac{V_{REF}}{R_{S2}}; (R_{S2} > R_{S1})$$

where, $R_{S1}$ and $R_{S2}$ are the base values of the sensor resistors at atmospheric pressure and their values are known a priori. If $\Delta RS$ is the change in the sensor resistance with applied pressure P, then the equation 4.3 can be rearranged in accordance with equation 4.1 as:

$$I_D = \frac{V_{REF}}{R_{S1} + \Delta R_S} - \frac{V_{REF}}{R_{S2} - \Delta R_S}$$

$$I_D = V_{REF}\left[\frac{(R_{S2} - R_{S1}) - 2\Delta R_S}{(R_{S1} + \Delta R_S)(R_{S2} - \Delta R_S)}\right]$$

The term ($R_{S2}$–$R_{S1}$) is a constant difference between the base values of the sensor resistances, when the pressure is not applied. The change in resistance $\Delta R_S$ with applied pressure is small compared to the absolute base values of the sense resistors (i.e. $\Delta R_S \ll R_{S1,2}$). Moreover, the absolute values of the sense resistances are close to each other and are of the same order. For instance, the approximate values of the Volcano pressure sensor used in this work has $R_{S2}$=3.6KΩ and $R_S$=3.3KΩ at atmospheric pressure. The maximum change in differential resistance $\Delta R_S$ is 12Ω across the IOP range (0-60 mmHg). Therefore, the equation can be written as:

$$I_D = V_{REF}\left[\frac{(R_{S2} - R_{S1}) - 2\Delta R_S}{R_{S1}R_{S2}}\right]$$

$$I_D = I_{DS,Const} - \Delta I_{DS}$$

Here, the difference current ID has two parts: a constant current $I_{D,Const}$ and the change in the current $\Delta I_{DS}$ with the change in sensor resistance with applied pressure. These two parts are given as: $I_{DS,Const}=V_{REF}[(R_{S2}-R_S)/R_{S2}R_{S1}]$, and $\Delta I_{DS}=V_{REF}[2\Delta R_S/R_{S2}R_{S1}]$.

Both of the operational transconductance amplifiers (OTA) in the R-I1 converter were identical with a high open loop gain of 100 dB. A two-stage miller-compensated OTA was designed for very low power, noise, and offset. Both of the OTAs were matched together to further reduce the effect of an offset between two current branches. A 100-mV reference voltage $V_{REF}$ is chosen as a tradeoff between minimum power consumption and maximum dynamic range across the pressure range. A full scale dynamic range of 70 nA is achieved in the $\Delta I_D$.

Since an R-$I_1$ converter uses two current branches to sense differential resistance, high power consumption is inevitable with such a structure. A 50% power saving can be achieved with the use of only one sensing current branch to measure the differential current. To accomplish the task, a second R-$I_2$ converter is proposed in this work. The schematic of the R-I2 converter is depicted in FIG. 47.

Three negative feedback loops are introduced in the R-$I_2$ converter. A pseudo-differential reference voltage $V_{REF}$ of 100 mV is generated by the BGR as explained earlier ($V_{REF}=VR_7-VR_6=VR_6-VR_5$). The first and second feedback loop (depicted as 1 and 2 in the FIG. 47) set the reference voltages of VR7=700 mV and VR5=500 mV at the nodes "X" and "Y", respectively, and are designed with a high loop gain (>95 dB). The third feedback loop sets the common-mode reference voltage of VR6=600 mV at node "N". As a result, each resistor in the sensor sees a voltage drop of 100 mV across it. The difference current ΔID flows through the transistors M3 and M4, which is copied via current mirrors M4-M5. Since the third feedback loop sees both first and second loops as a load, it has a lower loop gain (>70 dB) compared to the other two feedbacks. The first and second feedback loops are designed with lower settling time than the third feedback loop, to ensure accurate startup and stability. All of the OTAs are matched with each other in a single block to reduce the effect of offset voltages. In the calibration mode, the on-chip base resistors (RB1,2) are switched to the feedback loop via the analog multiplexers and the sensor resistor elements are switched to the ground.

The I-F converter consists of a wide tuning range ring oscillator as depicted in FIG. 48. A current starved inverter and a transmission gate constitute a single-stage of the ring oscillator. The bias voltage (VBP and VBN) generated by the R-I converter controls the oscillation frequency of the ring oscillator by regulating the resistance of the transmission gate (RT). The oscillation frequency $f_{osc}$ for the wide tuning range N-stage ring oscillator is given by:

$$f_{OSC} = \frac{g_m}{2NC_P(1 + g_m R_T)}$$

where, $g_m$ is the total effective transconductance of a single stage inverter, N is the total number of stages, and $C_P$ is the total parasitic capacitance at the gate of a single stage inverter that consists of the total gate capacitance of the PMOS and NMOS transistors and the wiring capacitance.

For $g_m R_T \gg 1$, the prior equation can be rearranged as:

$$f_{OSC} = \frac{1}{2NC_P R_T}$$

The average value of $V_{ds}/I_T$ provides the effective resistance of the transmission gate $R_T$, where $V_{ds}$ and $I_T$ are the voltage drop and current across the transmission gate, respectively. For $V_{dsat} < V_{DD}/2$, $I_T$ remains constant when a step-input rises from $V_{DD}/2$ to $V_{DD}$ and $R_T$ can be approximated as:

$$R_T = \frac{2\ln2}{V_{DD}} \int_{V_{DD}/2}^{V_{DD}} \frac{V}{I_T} dV \frac{3\ln2}{4} \frac{V_{DD}}{I_T} \approx \frac{V_{DD}}{2I_T}$$

By combining equations, the oscillation frequency $f_{osc}$ of the I-F converter is given by:

$$f_{OSC} = \frac{I_T}{NC_P V_{DD}}$$

Since the current through the transmission gate $I_T$ is controlled by the bias voltages VBP and VBN, generated by the R-I converter, $f_{osc}$ is a linear function of the difference current $I_D$ ($I_T=I_D$). In order to make this function extremely linear, the inverters in the conventional wide tuning ring oscillators are made current starved with the current ID. This also minimizes the crowbar current of the inverters, and hence reduces the voltage droop in the output of a capacitor-less voltage regulator, which provides a clean supply to the oscillator. High-VTH transistors were used for the inverters, which further reduces its crowbar current.

Although the temperature effect is canceled out in the differential current due to the sensor properties, it can change the absolute base value of the oscillation frequency. Similarly, the supply variation in the regulated output can alter the oscillation frequency and therefore the accuracy of the measurement. Temperature variation for the bladder pressure monitor system is not a concern, since the temperature inside the bladder remains virtually constant.

If implanted in a physical environment with varying temperature, the impact can be combatted or mitigated by using two on-chip base resistors ($R_{B1}$ and $R_{B2}$), with values close to the absolute base values of the sense resistors and with the same initial resistance difference, are implemented with n+ diffusion resistors. The n+ diffusion resistor has a positive temperature coefficient very close to the sense resistor in the temperature range of interest. Since both the resistors values are close to each other, a near perfect matching is achieved by laying them out in a common centroid fashion. The difference current in the base resistance sensing mode depends only on the temperature and supply variations and is utilized to calibrate the variations in the pressure sensing mode. Since the resistances of both the sensor resistors change by the same amount with a temperature change, a difference current is given by setting $\Delta R_S$ equal to zero in equation:

$$I_D = I_{DS,Const} = V_{REF}\left[\frac{R_{S2} - R_{S1}}{R_{S2}R_{S1}}\right]$$

Similarly, a difference currant in the base sensing mode is given by:

$$I_D = I_{DB,Const} = V_{REF}\left[\frac{R_{B2} - R_{B1}}{R_{B2}R_{B1}}\right]$$

By dividing equation 4.12 by equation 4.13, we get:

$$\frac{I_{DS,Const}}{I_{DB,Const}} = \left(\frac{R_{S2} - R_{S1}}{R_{B2} - R_{B1}}\right)\frac{R_{B2}R_{B1}}{R_{S2}R_{S1}} = \frac{f_{osc,S}}{f_{osc,B}}$$

The resistances in the above equations are absolute base values and their values are known a priori. Since the sensor and base resistors share the same oscillator for R-F conversion, the ratio of their frequencies $f_{osc,S}/f_{osc,B}$ is independent of $V_{DD}$, as suggested by equation 4.11. Therefore, an initial calibration for temperature and supply voltage variation can be easily achieved by having a separate time slot for the on-chip differential base resistance sensing mode. A differential sensing and an on-chip base resistor calibration method in this work enable accurate pressure measurements without having an extra temperature, voltage and current sensing mode.

The values of the sensor and base resistors frequencies are calculated by the counter-based digital core logic, operating at a constant reference frequency $f_{REF}$. A similar oscillator to the one being used in the I-F conversion but with more stages, is employed to generate a much lower reference frequency ($f_{REF}$=1.5 KHz). A temperature independent constant bias current is utilized for the reference oscillator. The much lower clock speed ($f_{REF}$) for the digital core minimizes its dynamic power consumption and reduces the OOK data rate for the TX.

FIG. 49(a) shows the block diagram of the digital core which provides frequency-to-digital (F-D) conversion and encodes the resulting data for a burst transmission. The F-D converter in FIG. 49(b) consists of two counters $CNT_{SEN}$ and $CNT_{REF}$. When receiving the Start signal from the timer, both counters are reset and start counting upward. Once $CNT_{REF}$ reaches 350 cycles, the conversion is completed with an end-of conversion (EoC) pulse stopping both counters and the value of $CNT_{SEN}$ (Data) is read out, which guarantees a minimum frequency resolution of (1 bit)/(5 Hz) at a reference clock ($CLK_{REF}$) frequency of 1.5 KHz. The $CNT_{REF}$ and $CNT_{SEN}$ are designed for 10 and 18 bits, respectively, to avoid overflow in both the counters at maximum input clock ($CLK_{IN}$) frequency.

FIGS. 49 (c) and (d) show the block and state diagram of the encoder (ENC), respectively. Initially in the SLEEP state, the output of the encoder PKTO is fixed at logic "0" to turn off the TX. When receiving an EoC pulse, the encoder latches data from the F-D converter and proceeds to the next state based on the input signals DIFRS and SELRS, as indicated in FIG. 49 (d). In the SAMP RB and SAMP RS state, in which the digital outputs generated from the reference base resistor (RB) and sensing resistor (RS), respectively are recorded, the data from the F-D converter is directly stored into the sampling parallel-to-serial register (P 2SR SAMP) with 18-bit precision. While in the DIF F RS state, where only the RS difference is stored, the P 2SR SAMP is disabled from writing to hold the value stored in SAMP RS states. Meanwhile, the RS difference is calculated by subtracting the data with the previously recorded RS and stored into the differential parallel-to-serial register (P 2SR DIFF). Considering a 10-kHz dynamic range of CLKIN, the precision of the P 2SR DIFF is set to 12 bits. The flip-bit generator (FB Gen) counts the number of logic "1" in all the three states via bitwise summing of the parallel data DatP. If the summed value is greater than a threshold value, set at 9 for 18-bit digital data and 6 for 12-bit difference, each bit of DatP is reversed and the flip-bit register (FB) is updated to logic "1". In the next cycles, the encoder enters either the SRL PKSAMP state where the data stored in P 2SR SAMP is serially outputted in sample packets (PKSAMP), or the SRL PKSAMP state where the RS difference stored in P 2SR DIFF is serially outputted in differential packets (PKSAMP). At the same time, a 3-bit cyclic redundant check (CRC) code is also derived from the DatS. The encoder returns to the SLEEP state after the formation of the data packet and waits for the next EoC pulse.

FIG. 50 illustrates the timing diagram of the digital core and structures for both the sample packet (PKSAMP) and the differential packet (PKDIFF). The PKSAMP consists of a 4-bit header (HB) indicating the starting of a specific packet, a flip bit (FB), 18-bit data, a 3-bit CRC code, and a 4-bit tail (T B) indicating the ending of a packet transmission. The structure of the PKDIF F is similar to that of the PKSAMP except having a 12-bit RS difference data instead of 18-bits. The headers of PKSAMP transmitting the data from RB and RS are set as "1001" and "1010", respectively, and that of PKDIF F is set as "1100". The timer of the digital core is implemented with a packet counter, which, upon receiving an EoC pulse, is incremented by 1 and reset when its value is equal to (NPKC−1), where NPKC is the number of packets per cycle and is set to be equal to 10. As shown in FIG. 50, the Start pulse for the F-D launches two CLKREF cycles after both EoC and reset-digital-core (RSTDC) pulses, allowing CLKIN of the F-D converter to stabilize before the conversion starts. Both the SELRS and the DIFRS signals are disabled when the packet counter is reset, and become active high when the value of the packet counter is greater than 0 and 1, respectively. As a result, among the NPKC packet outputs (PKTO), the 1st and 2nd ones are PKSAMP recording the digital data converted from RB and RS, and the rest of the 8 packets are PKDIF F recording RS differences, each of which is separated by 352 CLKREF cycles. At the receiver, the exact values of RS can be recovered at 18-bit precision by summing RS differences with the Data obtained from the 2nd PKSAMP. Therefore, by applying differential encoding and bit-flipping strategies to data from the slow-varying IOP and bladder pressure signals, the number of bit "1" in data packets and hence the switching-ON rate of OOK TX can be minimized without degrading the sampling rate and data precision, saving overall power dissipation dominated by the TX during the data transmission phase.

Real-time pressure monitoring with a limited amount of harvested wireless energy requires a very low, both instantaneous and average, power consumption for the transmitter. In this work, an OOK modulated, 2.45 GHz ISM band, transmitter was designed for wireless transmission of the data packets. FIG. 51 shows the schematic of the transmitter that comprises a LC voltage controlled power oscillator (VCPO). The design of the TX is inspired by the recent works published in [150], [151]. However, in these studies, especially in [151], the TX was aggressively optimized for extremely low data rate (~1 bps) applications, where the minimization of the leakage current and the supply voltage scaling are the two major design criteria. In this work, the design of the TX was mainly aimed towards the reduction of both instantaneous and average power consumption. A 2.45 GHz ISM band was chosen for the carrier frequency as a trade-off between power dissipation, antenna efficiency, and tissue losses. An off-chip loop antenna, with a diameter of 2.4 mm, is fabricated on the printed circuit board (PCB) that connects directly to the VCPO at nodes X and Y. Since the circumference of the loop antenna is much smaller than its transmitting wavelength at 2.45 GHz, it considered an electrically small antenna. The equivalent lumped circuit model of an electrically small loop can be represented as a series combination of an inductor (LA) and a small resistor (RA) as can be seen in FIG. 52. Therefore, an off-chip electrically small loop can effectively be utilized as the inductive element for the LC tank circuit of the VCPO. The self-resonance frequency of the loop antenna is typically much higher than the resonance frequency of the LC tank and can be modeled by adding a parallel capacitor CSRF.

The design of the antenna is optimized to maximize its radiation efficiency and minimize the tissue losses in an implantable environment for the given size constraints (Table 4.1). It is a well-known fact that the radiation efficiency of an antenna increases with its physical size or carrier frequency (since the carrier wavelength approaches the physical dimension of the antenna). However, tissue conductivity also increases with frequency, resulting in higher tissue losses. In order to efficiently utilize the space available for the implant, a diameter of 2.4 mm was chosen for the loop antenna. A carrier frequency of 2.45 GHz offers a good balance between the radiation efficiency and tissue losses. The antenna was designed and optimized using the full-wave 3-D electromagnetic simulation software ANSYS High Frequency Structural Simulator (HFSS). The antenna parameters with HFSS simulations are listed in Table 4.2.

TABLE 4.2

HFSS simulation and calculation results for the loop antenna

| Simulations @ 2.45 GHz | L (nH) | L with wirebond (nH) | Antenna Gain (dB) | Calculated Efficiency (%) | Q |
|---|---|---|---|---|---|
| 20 μm thick Parylene substrate with 20 μm Parylene coating layer | 4.87 | 6.4 | −21.57 | 1.47 | 121 |
| Gold trace on 20 μm Parylene substrate with a coating layer | 4.88 | 6.41 | −22.86 | 1.27 | 91 |
| FR-4 board (Air) | 4.75 | 6.27 | −19.9 | 1.47 | 172 |

Figure 53A:
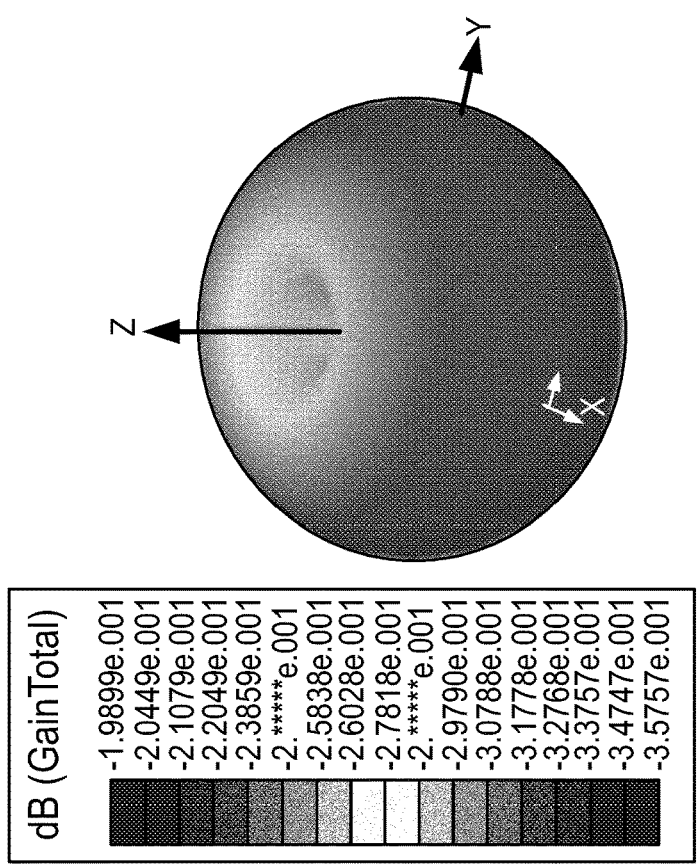

FIGS. 53(a) and (b) show the simulated radiation pattern for the loop antenna, designed on a FR-4 PCB and a parylene substrate, respectively.

FIG. 51 shows the schematic diagram of the VCPO. The core of the oscillator consists of the NMOS (M1-M2) and PMOS (M3-M4) cross-connected transistor pairs, an LC tank circuit, and a tail current source NMOS transistor M5. Having both the PMOS and NMOS cross-couple pairs increases the effective transconductance of the VCPO, thereby reducing the startup current required for the VCPO to ensure oscillations. This configuration also discards a need for center tapping the loop antenna to bias the VCPO, thereby simplifying final device packaging which is essential in the IOP monitor system. The sizes of the transistors M1-M4 are designed carefully to minimize the phase noise, while ensuring an acceptable start-up condition for the VCPO [152]. Additional power saving during startup is achieved by using a high-Q inductive element for the LC tank circuit, which is implemented by an off-chip loop antenna.

The data packets from the digital core directly OOK modulate the TX by dynamically switching the tail current source transistor M5. The size of the transistor M5 is chosen such that the VCPO delivers 80 μW (−11 dBm) of instantaneous power to the loop antenna. The TX is operated at a regulated supply voltage of 1.2 V. The TX was simulated with extracted layout parasitics and extracted s-parameters of the antenna from HFSS simulations. With no on-chip tuning capacitor, the maximum frequency of the VCPO is limited by the parasitic capacitances at node X and Y (mainly due to the bond-pad and device capacitances). The extracted simulations in the Cadence R Spectre R RF result in the maximum VCPO oscillation frequency of 3.4 GHz without the tuning capacitors. Thus, a Metal-Insulator-Metal (MIM) capacitor was introduced in the LC tank circuit to obtain a carrier frequency at 2.45 GHz ISM Band (2.4 GHZ-2.5 GHz).

Since the TX design is extremely power efficient, it can be useful in various other short-range biomedical communication applications, such as a wireless body area network (WBAN). Therefore, the design of this TX is also optimized as a separate stand-alone structure. A 5-bit capacitive MIM DAC is implemented to provide a tuning range from 2.3 GHz-2.7 GHz, as depicted in FIG. 54. This tuning range would also cover a 2360 MHz-2400 MHz frequency band allocated for WBAN (IEEE 802.15.6) [153]. Unlike the digital switch implemented in [151], this work utilizes a resistor based switch biasing scheme [154] that provides a definite off-state negative gate-to-source voltage Vgs for the NMOS switch depicted in FIG. 54. A frequency-shift-keying (FSK) modulation with variable bandwidth is also possible by dynamically switching the DAC tuning capacitors via data packets. In order to reconfigure the output power delivered, seven tail current sources M5<6:0> with binary weighted sizes are employed.

The pressure sensing readout ASIC is implemented and fabricated in a standard 0.18 μm CMOS process. The chip occupies 750 μm×750 μm of silicon area, including bond pads. The microphotograph of the chip is illustrated in FIG. 55. Since the full system SoC has a limited number of testing bond pads due to the size restriction, separate test structure dies were fabricated to characterize the individual circuit blocks. First, the DC testing of the individual circuit blocks was performed. The pressure sensor resistor is placed in the pressure chamber to carry out the measurements. The pressure in the chamber is varied from 0 mmHg to 60 mmHg and the variation in difference current ID is measured for both R-I1 and R-I2 circuit blocks (FIG. 56). The dynamic range of ID was measured to be 105 nA across the pressure range of 0-60 mmHg, which is very close to the simulated value. FIG. 57 (a) illustrates the pseudo-differential reference voltage across the sensor resistor terminals for the R-I2 converter. The voltage drop across both the sensing elements was precise and measured to be 100 mV, as can be seen in Figure. Similarly, the voltage drop across the sensing elements in R-I1 converter was accurately measured to be 100 mV (FIG. 57 (b)).

The output voltages of the all four voltage regulators are measured to be within ±3% of the designed values across multiple dies. The measured bias current of the chip is 97 nA, which is very close to the designed value of 100 nA.

A TX test structure allowing frequency and current tuning is used to characterize its performance. A loop antenna with 2.4 mm diameter is fabricated on a FR4 printed circuit board (PCB). The TX die is directly wire-bonded to the antenna trace in order to minimize the effect of parasitics. Since the loop antenna is directly connected to the nodes X and Y of the VCPO (FIG. 51) and no buffers or PA were implemented, a direct probing of the TX output was not possible. Therefore, all the measurements for the TX are done in a wireless test setup. A horn antenna with a gain 8 dBi is placed approximately 20 cm away from the TX chip. The horn antenna is connected to the Agilent E4404B spectrum analyzer, which receives the transmitted data. A value −52 dBm of the peak power was received with this setup. With the help of the well-known Friis transmission formula for the received power, the peak output power of the TX is calculated to be −33.76 dBm. The VCPO power consumption for this setup was measured to be 69.8 μW (=−11.56 dBm), providing loop antenna gain of −22.2 dB.

FIG. 58 depicts the output spectrum of the TX, OOK modulated by a pseudo-random-binary-sequence (PRBS) at 1 Mbps, 5 Mbps and 10 Mbps data rates. Although the TX is not designed to provide a FSK modulation, the future revision of this design can easily accommodate a sub-DAC capacitive array to enable FSK modulation along with the course tuning array which is already implemented in this chip. To demonstrate the possibility of FSK modulation, the minimum capacitor of 43 fF in the tuning DAC array is switched with a 1 Mbps PRBS data, resulting in a wide-band FSK spectrum depicted in FIG. 59. The transmitter consumes 140 μW in this mode. The VCPO achieves a phase noise of −115 dBc/Hz at an offset of 1 MHz from the carrier frequency.

Next, full system testing is carried out by placing the sensing element in a pressure chamber. The sensing element is connected to the R-I converter of the chip. The full system SoC employs the R-I2 converter due to its low power feature. The digital core sends the Sel RS signal to the R-I2 converter to select either the sensing element or the on-chip base resistor (Sel RS=0 selects the sensing element and Sel RS=1 selects base resistance). The measured output frequency of the R-F circuit corresponding to the on-chip base resistance was 360 KHz. FIG. 60 shows the measured periodic Sel RS signal, R-F converter output, reference oscillator clock, and digital data packets at a constant pressure. The measured data packets for the base frequency (30 bits), sensing element frequency (30 bits), and difference frequency (24 bits) are illustrated in FIG. 61. The header bits (HB) are different for all three types of packets for decoding purposes, as can be seen in the figure.

FIG. 62 depicts the measured sensor and base frequencies within the pressure range of interest. The sensor frequency ranges from 390.7 KHz to 379.9 KHz, resulting in the resolution of 0.024 mmHg/LSB with the digital core counter conversion time of 350 reference clock cycles at 1.5 KHz. However, the actual sensor resolution is limited by the thermal-noise. The thermal noise of the op-amps in the R-I converter circuit is the dominant noise source in the readout chip due to their low power dissipation. The noise simulation of the R-I converter suggests an rms error of 0.31 (mmHg)rms in the pressure readout. The measured value of the average base resistor frequency remains constant at 360 KHz.

A sensing resistance dynamic range of 12Ω was measured with the Agilent 4284A Precision LCR meter for the pressure range of 0-60 mmHg. Maximum non-linearity is measured to be 87 mΩ with the two-point calibration, resulting in the readout sensitivity of 0.44 mmHg. The measured sensing resistance linearity is depicted in FIG. 63 for the nominal difference in sensor resistances (RS1-RS2) of 312Ω. This sensitivity is enough to accommodate both the IOP and the bladder pressure range. The rms error can be reduced by either increasing the conversion time or averaging the multiple data samples taken at each pressure point. FIG. 64 shows the improvement in the measured sensitivity when the number of data samples to be averaged are increased.

Next, the SoC was measured in a wireless setup. A 2-turn, 100 μm thick, receive powering coil of 2.6 mm diameter is connected in front of the on-chip matching network. The sensor is placed in the pressure chamber and the system is kept in a cavity resonator which is excited by a 340 MHz RF source. The data is received by a spectrum analyzer and demodulated by the base-station comprises of commercial-off-the-shelf (COTS) components. FIG. 65 depicts the output power spectrum of the received data packets. Demodulated data packets are then fed to a FPGA board which has an UART interface to a computer. The received data packets are decoded real-time in the matlab software. FIG. 66 shows the received data by a spectrum analyzer and corresponding digital packets, demonstrating correct packet reception.

Since the sensitivity of the pressure sensing chip is mainly limited by noise, it is important to characterize it in a wireless setup. FIG. 67 shows deviation due to noise in the wirelessly measured data at a constant pressure. A total of 60 data packets were averaged for each noise measurement. FIG. 68 depicts the resulting histogram for wirelessly measured noise. The standard deviation (1σ) is measured to be 429.12 ppm, or 133.9 mΩ for a nominal difference in sensor resistances of 312Ω, resulting in a pressure sensitivity of 0.67 mmHg. FIG. 69 depicts the wirelessly measured pressure with time and compares it with a reference sensor. After the 2-point calibration, the maximum measured error in the pressure reading was 0.81 mmHg with a standard deviation of 0.63 mmHg.

Temperature effects on the sensing and base frequencies were also characterized and the results are depicted in FIG. 70. The maximum error in the recorded pressure due to temperature variation was measured to be 0.54 mmHg, after performing a 2-point calibration in the temperature range of 30° C. to 38° C. With a 3-point calibration, the error in the pressure measurement due to temperature is further reduced to 0.39 mmHg.

Thanks to the burst data transmission, the chip consumes 61.4 µW from the harvested energy. Table 4.3 illustrates the measured performance summary of the ASIC.

TABLE 4.3

Performance Summary

| | |
|---|---|
| Process node | 0.18 µm |
| Unregulated supply | 1.35 V |
| Power consumption | 61.4 µW |
| Rectifier Efficiency | 15.35% |
| Power Transfer Efficiency (PTE) | 4.3% |
| Difference resistance resolution | 133.9 mΩ (1σ) |
| Pressure resolution | 0.67 mmHg (1σ) |

The performance comparison of the ASIC with the previously published pressure monitor systems is presented in Table 4.4.

TABLE 4.4

Comparison with previous work

| | This Work | [127] JSSC'11 | [42] TbioCAS'10 | [108] TCAS1'13 | [41] JSSC'01 |
|---|---|---|---|---|---|
| Unregulated Supply Voltage | 1.35 V | 1.5 V | >1.5 V | — | >3 V |
| Regulated Supply Voltage | 1.2 V, 1 V | | 1.5 V | 3.6 V | 3 V |
| Energy Harvesting Source | MRC/Cavity Resonator | RF | RF | Battery | Inductive |
| Energy Harvesting Frequency | 340 MHz-434 MHz | 2.4 GHz | 3.65 GHz | — | 13.56 MHz |
| Sensor | Resistive (differential) | Capacitive | Capacitive | Capacitive | Capacitive |
| Full System (Wireless) | ✓ | ✓ | ✓ | x | ✓ |
| TX Frequency | 2.45 GHz | 2.4 GHz | 2.4 GHz | — | 13.56 MHz |
| TX P$_{out}$ | −33.8 dBm | N/A | −45 dBm | — | N/A |
| TX Data Rate | 1.5 Kbps/ 103 bps (Burst) | 21-25 kbps | 8 Mbps | — | 26.5 kbps |
| Modulation | OOK | Backscatter | OOK | FSK | Backscatter |
| Pressure Resolution | 0.67 mmHg | 0.9 mmHg | 1.27 mmHg | 0.5 mmHg‡ | 0.73 mmHg* (9-bit) |
| Power  Power Management | 2.1 µA | 1.041 µW | 39.38 µW | 116.9 nW | N/A |
| Readout Front End | 39.37 µA | 1.19 µW | 158.91 µW | 7 µW | N/A |
| TX | 5.4 µW (6.86%) | — | 1.1506 mW | 47 mW | — |
| Total Power | 61.4 µW | 2.3 µW | 1.3533 mW | N/A | 210 µW† |
| CMOS Technology | 0.18 µm | 0.13 µm | 0.13 µm | 0.18 µm | 1.2 µm |
| Chip Area | 0.75 × 0.75 mm² | 1 × 0.7 mm² | 0.7 × 0.7 mm² | 1.8 mm² | 6.76 mm² |
| Micro-system Volume | 0.78 mm³†† | N/A | N/A | 1.5 mm³ | N/A |

‡Resolution is not measured for fully wireless system.
*Converted to mmHg from given pressure range and resolution of 9-bits,
†power consumption from regulated supply,
††After the chip back-lapping process.

Finally, the ASIC performance was evaluated in the in-vivo rodent experiment. The bladder pressure was recorded from an anesthetized rat. Since the pressure sensor die was packaged with three long leads connected to it, implantation of the entire microsystem inside the rat's bladder was not possible in this experiment. Therefore, the pressure sensor was implanted inside the bladder and connected to the ASIC microsystem that is kept outside the animal. However, in future, the microsystem can be fully implanted, when the lead-less bare dies will available for the pressure sensor. FIG. 71 (a) illustrates the experimental setup. The pressure response of the bladder to infusion of saline into the bladder, at a constant rate of 4 ml/Hour, is recorded and depicted in FIG. 71 (b).

Through the aspects described herein, a low-power, sub-mm3 IOP and bladder pressure monitoring microsystem is presented in this disclosure. The microsystem can be implanted in any of a variety of anatomical setting suitable for pressure measurements, including but not limited to the bladder of a mammalian subject. The microsystem integrates a pressure sensor, a powering coil, a loop antenna and a low-power wireless pressure readout ASIC in a given space of 2.6 mm diameter. Thanks to the low power pressure sensing front-end, power management, and transmitter circuitry, the power consumption of the chip is only 61.4 µW, while harvesting the energy wirelessly form a 340 MHz RF source through a cavity resonator.

Cavity Resonator

FIG. 72 illustrates a cavity resonator forming part of the wireless power transfer system for use with pre-clinical studies involving certain non-human mammals (e.g. rats, pigs, rabbits, etc. . . . ), such as is common in the field of medical research. The cavity resonator described with regard to FIGS. 72-74 can be used in combination with the devices, systems, assemblies, methods, and techniques described throughout this document. The resonant cavity is sized and dimensioned to receive one or more such mammals (e.g. the rat shown in FIG. 72) after it has been surgically implanted with a Bionode at a given location for a given topic of study (e.g. epilepsy, etc. . . . ). In use, the resonant cavity is excited in TM110 mode characterized by circulating magnetic fields (red=high; blue=low). An untethered animal with an implanted, packaged Bionode device is housed within the cavity volume. A bi-axial arranged receive coil system on the Bionode device is utilized to achieve orientation insensitivity for continuous power coupling.

FIG. 73 illustrates a constructed cavity resonator and fully assembled device with Bionode microelectronics platform, power management board, and receive coil assembly according to the present disclosure. In this arrangement, the magnetic field source is the cavity itself, which is constructed from any of a variety of suitable metallic materials (e.g. aluminum). Optimal impedance matching is used to tune the system and attain maximum power transfer efficiency to the Bionode implanted within the untethered animals in or near the resonant cavity. The cavity may have any suitable dimension, but in one example was constructed with cavity dimensions of 60 cm×60 cm×30 cm, providing a large operating volumetric space (~1e5 cm3). A biaxial receive coil system (disposed in the implanted Bionode) includes two copper coils with any suitable dimension, such as (but not limited to) diameters of 5 mm and 7 mm.

The resonant cavity system described herein boasted greater than 90% continuous device powering of 6 freely behaving, untethered rats, with a peak power transfer efficiency of 14.3%. The resonant cavity system maintains sufficient wireless power transfer performance to a freely-behaving rodent in a large operational volume. The resonant cavity system achieves a power transfer efficiency (PTE) level sufficient to safely operate a power-demanding (>40 mW), multi-featured implantable device. FIG. 74 illustrates a comparison of the wireless power transfer performance of the resonant cavity system relative to other types of wireless power transfer.

Based on these collective features, the resonant cavity system of this disclosure provides significant promise for the field of pre-clinical testing involving the use of non-human mammals, such as described herein. By providing the wireless power transfer to untethered animals, industry may maximize the efficiency and scale of biomedical research involving implanted Bionodes. This, in turn, may hasten the adoption and proliferation of Bionodes for the treatment in human or veterinary patients of a host of diseases or pathologies that would otherwise rely primarily (and oftentimes exclusively) on pharmacologic treatment options.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented using one or more modules of computer program instructions encoded on a computer-readable medium for execution by, or to control the operation of, data processing apparatus. The computer-readable medium can be a manufactured product, such as hard drive in a computer system or an optical disc sold through retail channels, or an embedded system. The computer-readable medium can be acquired separately and later encoded with the one or more modules of computer program instructions, such as by delivery of the one or more modules of computer program instructions over a wired or wireless network. The computer-readable medium can be a machine-readable storage device, a machine-readable storage substrate, a memory device, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, a runtime environment, or a combination of one or more of them. In addition, the apparatus can employ various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM (Erasable Programmable Read-Only Memory), EEPROM (Electrically Erasable Programmable Read-Only Memory), and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., LCD (liquid crystal display), OLED (organic light emitting diode) or other monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The computing system can include clients and servers. A client and server are generally remote from each other and typically interact through a communication network. The relationship of client and server arises by virtue of computer programs running on the respective computers and having a client-server relationship to each other. Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described is this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

While this specification contains many implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. In addition, the actions recited in the claims can be performed in a different order and still achieve desirable results.

What is claimed is:

1. A biomodulation system comprising:
    a non-implantable assembly configured to be worn by a subject, the non-implantable assembly comprising:
        a power amplifier module configured to generate a wireless power signal;
        a communication module configured to provide at least one communication channel between an implantable assembly and an external computing device;
    the implantable assembly comprising:
        a control module operably connected to the at least one communication channel and at least one stimulation output, the control module comprising:
            acquisition circuitry configured to acquire information sensed via the at least one communication channel,
            stimulation circuitry configured to generate an electrical stimulation signal associated with the least one stimulation output, and
            a processor unit to process the information acquired by the acquisition circuitry and, upon determining a condition exists, instruct the stimulation circuitry to trigger generation of the electric stimulation signal;
    one or more sensors located within a subject to obtain biomodulation data indicating one or more of a pH level, a temperature, a neurotransmitter, and a respiratory condition of the subject;
    a first electrode configured to deliver the electric stimulation signal to a location within the subject based at least in part on the biomodulation data, wherein the electric stimulation signal is configured to affect a reflex; and
    a power management module configured to provide power signals to the control module, the power management module comprising (i) one or more receiving coils to receive the wireless power signal from the non-implantable assembly and (ii) a voltage regulator to process the wireless power signal and (a) generate a first supply voltage for a first signal provided to the acquisition circuitry and the processor unit and to (b) generate a second supply voltage for a second signal provided to the stimulation circuitry.

2. The biomodulation system of claim 1, wherein the electrical stimulation signal comprises deep brain stimulation (DBS).

3. The biomodulation system of claim 1, wherein the external computing device is configured to provide a user interface for receiving user input to control the implantable assembly.

4. The biomodulation system of claim 1, wherein the wireless power signal is generated based on magnetic resonance coupling.

5. The biomodulation system of claim 1, wherein the wireless power signal is generated based on near-field magnetic inductive coupling.

6. The biomodulation system of claim 1, wherein the reflex comprises a laryngospasm and the electric stimulation signal is configured to prevent at least one of sudden unexplained death from epilepsy (SUDEP) or sudden infant death syndrome (SIDS) due, at least in part, to the laryngospasm.

7. A method of biomodulation, comprising:

providing a wireless power signal to an implantable assembly, wherein:
the wireless power signal is generated by a non-implantable assembly that is worn by a subject,
the non-implantable assembly comprises:
a power amplifier module configured to generate the wireless power signal,
a communication module configured to provide at least one communication channel between the implantable assembly and an external computing device, and
wherein the implantable assembly comprises:
a control module operably connected to the at least one communication channel and at least one stimulation output, the control module comprising:
acquisition circuitry configured to acquire information sensed via the at least one communication channel,
stimulation circuitry configured to generate an electrical stimulation signal associated with the least one stimulation output, and
a processor unit to process the information acquired by the acquisition circuitry and, upon determining a condition exists, instruct the stimulation circuitry to trigger generation of the electric stimulation signal;
a power management module comprising (i) one or more receiving coils to receive the wireless power signal from the non-implantable assembly and (ii) a voltage regulator to process the wireless power signal and to generate first and second supply voltages from the wireless power signal, the first supply voltage selected at a first voltage level for a first signal provided to the acquisition circuitry and the processor unit, and the second supply voltage selected at a second voltage level for a second signal provided to the stimulation circuitry, the first voltage level generated by the voltage regulator different from the second voltage level;
monitoring biomodulation data generated by an electrode of the implantable assembly, the biomodulation data indicating one or more of a pH level, a temperature, a neurotransmitter, and a respiratory condition of the subject;
wirelessly transmitting the biomodulation data to the control module, the control module implanted within the subject and remote from the electrode and operably connected to the at least one communication channel configured to receive the biomodulation data;
determining a condition exists based at least in part on the biomodulation data; and
delivering the electrical stimulation signal to an electrode at a location within the subject, wherein the electrical stimulation signal is configured to affect a reflex.

8. The method of claim 7, comprising:
wirelessly transferring the biomodulation data to the non-implantable assembly;
processing the biomodulation data by the non-implantable assembly; and
transmitting a command to the implantable assembly to generate an output to deliver the electrical stimulation signal.

9. The method of claim 7, wherein providing the wireless power signal to the implantable assembly by charging, based on the wireless power signal, a rechargeable battery of the implantable assembly.

10. The method of claim 9, wherein the wireless power signal is sufficient for the electrode to generate the electrical stimulation signal.

11. The method of claim 7, wherein the at least one communication channel comprises a wired lead.

12. The method of claim 7, wherein the at least one communication channel comprises a wireless communication channel.

13. The method of claim 7, wherein the reflex comprises a laryngospasm and the electrical stimulation signal is configured to prevent at least one of sudden unexplained death from epilepsy (SUDEP) or sudden infant death syndrome (SIDS) due, at least in part, to the laryngospasm.

* * * * *

UNITED STATES PATENT AND TRADEMARK OFFICE
CERTIFICATE OF CORRECTION

| | | |
|---|---|---|
| PATENT NO. | : 11,524,161 B2 | |
| APPLICATION NO. | : 16/308355 | |
| DATED | : December 13, 2022 | |
| INVENTOR(S) | : Pedro Irazoqui et al. | |

It is certified that error appears in the above-identified patent and that said Letters Patent is hereby corrected as shown below:

In the Claims

In Column 96, Line 29, In Claim 1, after the insert -- at --;

In Column 96, Line 34, In Claim 1, delete "electric" and insert -- electrical --;

In Column 96, Line 40, In Claim 1, delete "electric" and insert -- electrical --;

In Column 96, Line 43, In Claim 1, delete "electric" and insert -- electrical --;

In Column 97, Line 2, In Claim 6, delete "electric" and insert -- electrical --;

In Column 97, Line 29, In Claim 7, before least insert -- at --;

In Column 97, Line 34, In Claim 7, delete "electric" and insert -- electrical --.

Signed and Sealed this
Twenty-eighth Day of February, 2023

Katherine Kelly Vidal
*Director of the United States Patent and Trademark Office*